United States Patent
Pastor Fernández et al.

(10) Patent No.: US 9,453,031 B2
(45) Date of Patent: Sep. 27, 2016

(54) CHEMICAL ENTITIES

(71) Applicant: Fundación Centro Nacional de Investigaciones Oncológicas Carlos III, Madrid (ES)

(72) Inventors: Joaquín Pastor Fernández, Madrid (ES); Oscar Fernández-Capetillo Ruiz, Madrid (ES); Sonia Martínez González, Madrid (ES); Carmen Blanco Aparicio, Madrid (ES); María del Rosario Rico Ferreira, Madrid (ES); Luis Ignacio Toledo Lázaro, Zaragoza (ES); Sonsoles Rodríguez Arístegui, Madrid (ES); Matilde Murga Costa, Madrid (ES); Carmen Varela Busto, Madrid (ES); Andrés Joaquín Lopez Contreras, Molina de Segura (ES); Oliver Renner, Madrid (ES); María Nieto Soler, Barcelona (ES); David Alvaro Cebrián Muñoz, Madrid (ES)

(73) Assignee: Fundación Centro Nacional de Investigaciones Oncológicas Carlos III, Madrid (ES)

( * ) Notice: Subject to any disclaimer, the term of this patent is extended or adjusted under 35 U.S.C. 154(b) by 0 days.

(21) Appl. No.: 14/774,294

(22) PCT Filed: Mar. 14, 2014

(86) PCT No.: PCT/GB2014/050825
§ 371 (c)(1),
(2) Date: Sep. 10, 2015

(87) PCT Pub. No.: WO2014/140644
PCT Pub. Date: Sep. 18, 2014

(65) Prior Publication Data
US 2016/0024112 A1    Jan. 28, 2016

(30) Foreign Application Priority Data

Mar. 15, 2013    (EP) .................................. 13382089

(51) Int. Cl.
| | | |
|---|---|---|
| C07D 498/14 | (2006.01) | |
| C07D 519/00 | (2006.01) | |
| A61K 45/06 | (2006.01) | |
| A61K 31/553 | (2006.01) | |
| A61K 31/5383 | (2006.01) | |

(52) U.S. Cl.
CPC ......... *C07D 498/14* (2013.01); *A61K 31/5383* (2013.01); *A61K 31/553* (2013.01); *A61K 45/06* (2013.01); *C07D 519/00* (2013.01)

(58) Field of Classification Search
CPC ........................... C07D 498/14; C07D 519/00
See application file for complete search history.

(56) References Cited

U.S. PATENT DOCUMENTS

| 5,583,024 A | 12/1996 | McElroy et al. |
| 5,674,713 A | 10/1997 | McElroy et al. |
| 5,700,670 A | 12/1997 | Yamagishi et al. |
| 6,602,677 B1 | 8/2003 | Wood et al. |

FOREIGN PATENT DOCUMENTS

| WO | 98/35985 A1 | 8/1998 | |
| WO | 99/02166 A1 | 1/1999 | |
| WO | 00/40529 A1 | 7/2000 | |
| WO | 00/41669 A2 | 7/2000 | |
| WO | 00/47212 A1 | 8/2000 | |
| WO | 01/32651 A1 | 5/2001 | |
| WO | 01/60814 A2 | 8/2001 | |
| WO | 01/92224 A1 | 12/2001 | |
| WO | 01/94341 A1 | 12/2001 | |
| WO | 02/04434 A1 | 1/2002 | |
| WO | 02/08213 | 1/2002 | |
| WO | 2012082997 A1 | 6/2012 | |
| WO | WO 2012082997 A1 * | 6/2012 | ........... C07D 487/14 |

OTHER PUBLICATIONS

Wagner et al. Pharmaceuticals (2010), 3, p. 1311-1334.*

(Continued)

*Primary Examiner* — Yong Chu
(74) *Attorney, Agent, or Firm* — McCarter & English, LLP; Steven G. Davis; Wei Song

(57) ABSTRACT

Provided are chemical entities selected from compounds of formula (I), wherein $R_1$, $R_2$ and m have meanings given in the description, and pharmaceutically acceptable salts, solvates and stereoisomers thereof, which are inhibitors of ATR and are potentially useful in the treatment of cancer. Further provided are pharmaceutical compositions of the chemical entities, combination products containing the chemical entities, the use of the compositions as therapeutic agents, and methods of treatment using these compositions.

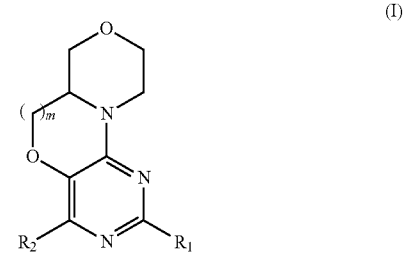

(I)

17 Claims, 17 Drawing Sheets

(56) References Cited

OTHER PUBLICATIONS

Blanco-Aparicio, et al. Cancer Lett. 2011, 300(2), 145-153.
Cree et al. (1995) AntiCancer Drugs 6:398-404.
Crouch et al. (1993) J. Immunol. Meth.160:81-88.
Lombardo et al., J. Med. Chem. 2004, 47, 6658-6661.
Lopez-Contreras, A.J. et al., DNA Repair 9, 1249-1255 (2010).
Lopez-Contreras, A.J. et al., J. Exp. Med. (2012) vol. 209, No. 3, 455-461.
Piper, et al. Assay & Drug Dev. Tech. 6, 213 (2008).
Toledo, L.I., et al Genes Dev. 22, 297-302 (2008).
Toledo et al., "A cell-based screen identifies ATR inhibitors with synthetic lethal properties for cancer-associated mutations", Nature Structural & Molecular Biology, vol. 18, No. 6, pp. 721-727 (2011).
Ward et al., "UV-induced Ataxia-telangiectasia-mutated and Rad3-related (ATR) Activation Requires Replication Stress", Journal of Biological Chemistry, vol. 279, No. 11, pp. 9677-9680 (2004).
Sultana et al., "Ataxia Telangiectasia Mutated and Rad3 Related (ATR) Protein Kinase Inhibition is Synthetically Lethal in XRCC1 Deficient Ovarian Cancer Cells", PLOS One, vol. 8, Issue 2, e57098 (2013).

* cited by examiner

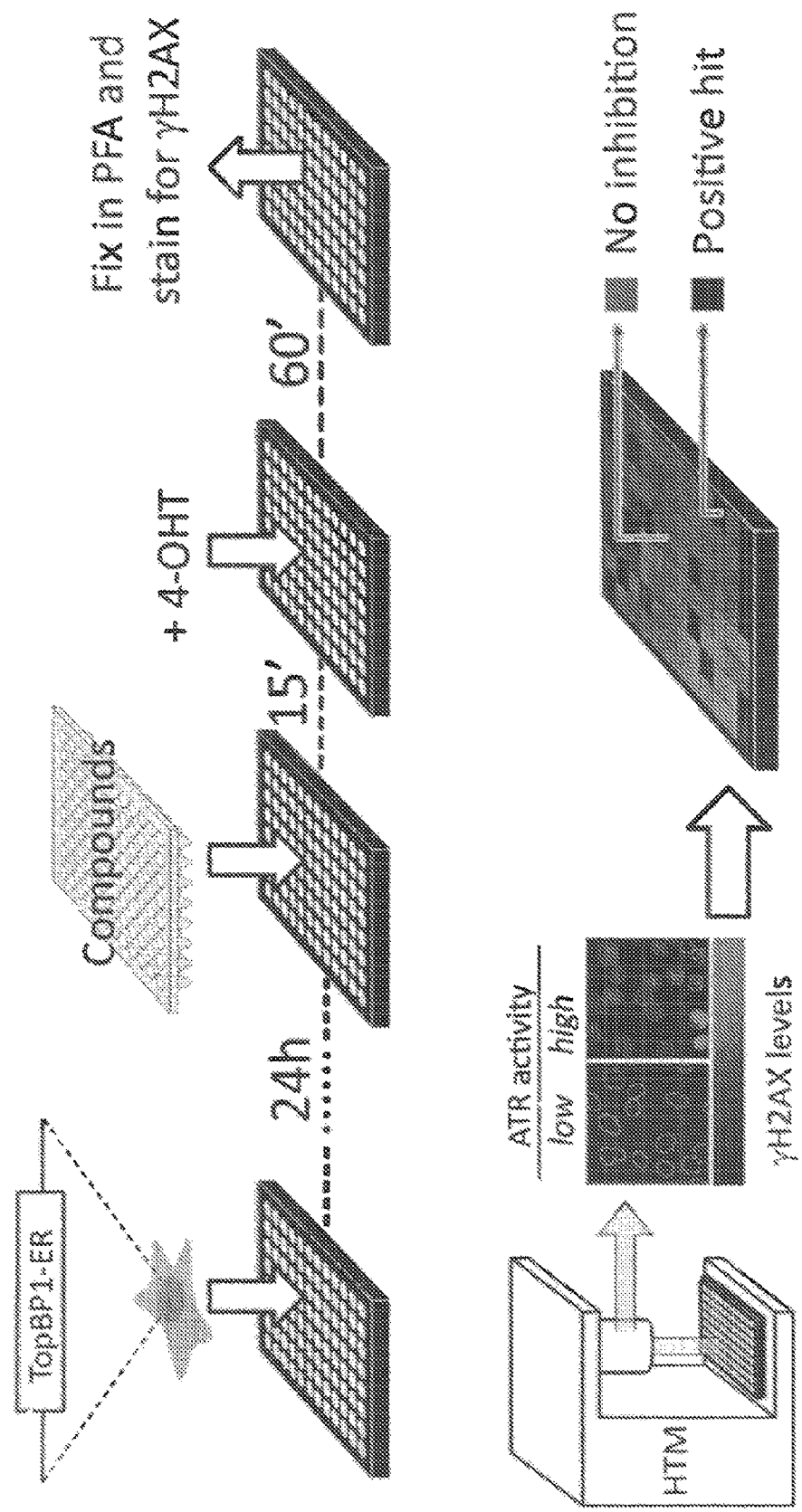

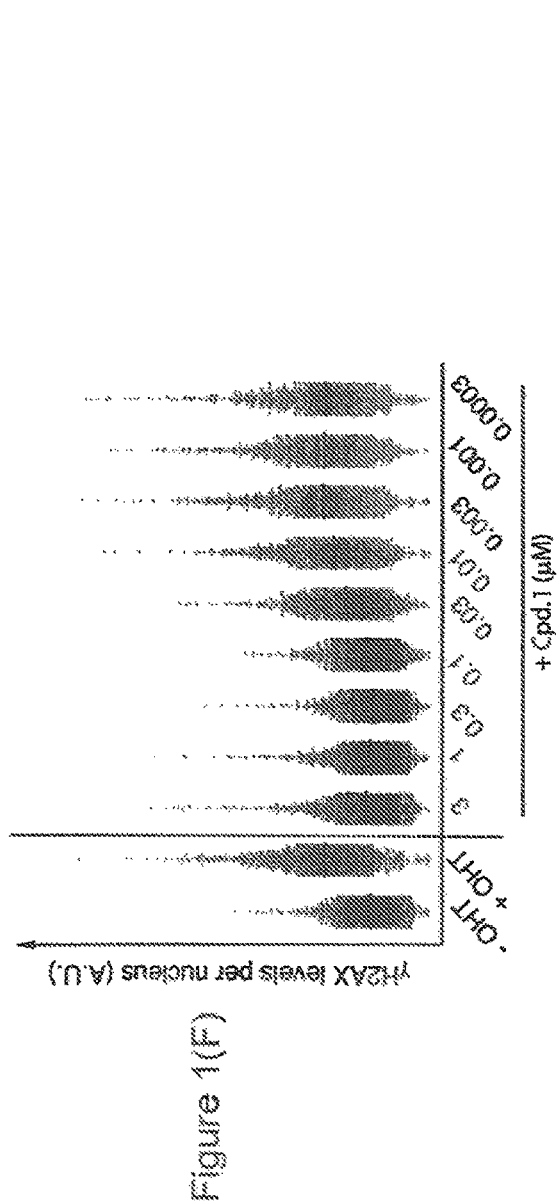
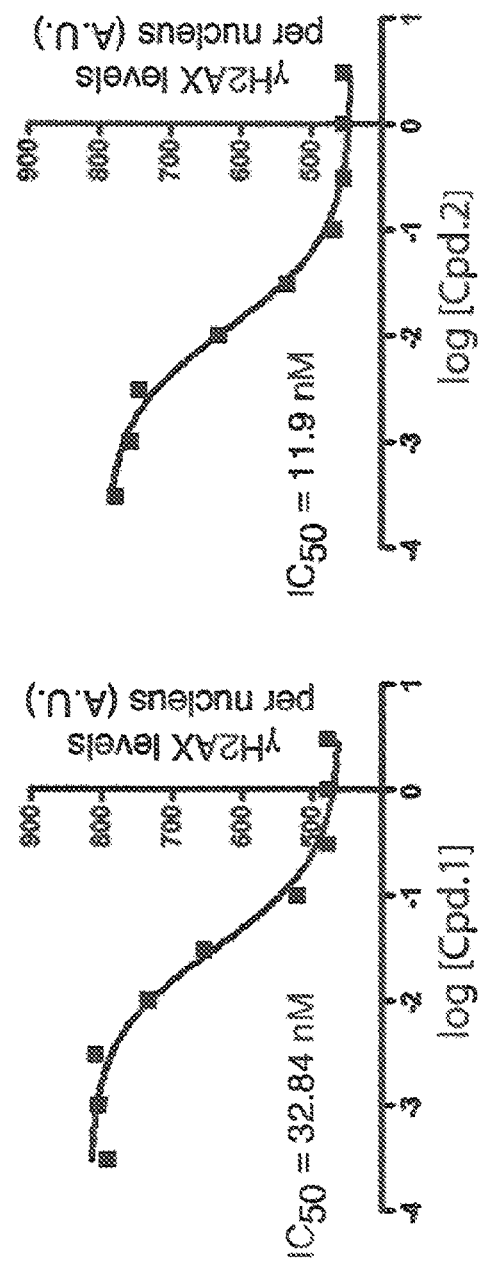
Figure 1(F)
Figure 1(G)

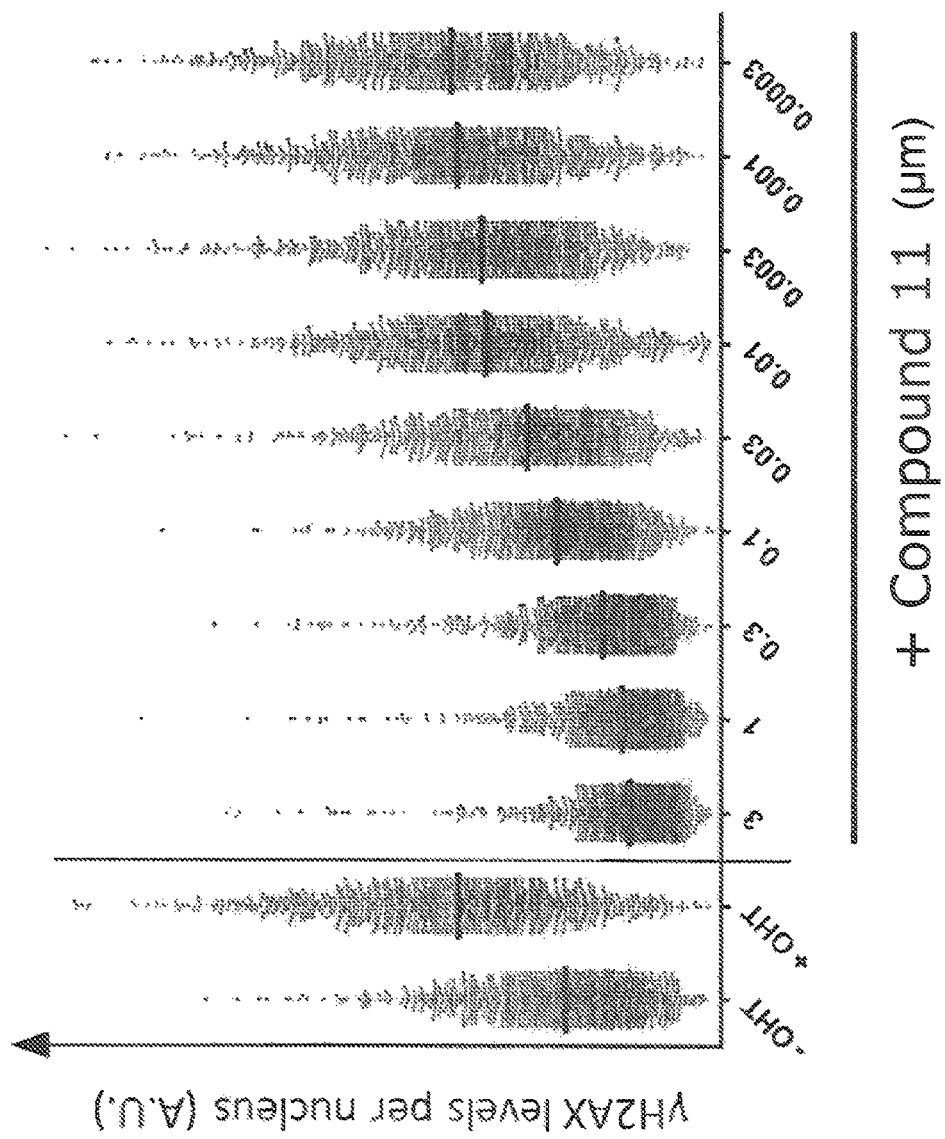

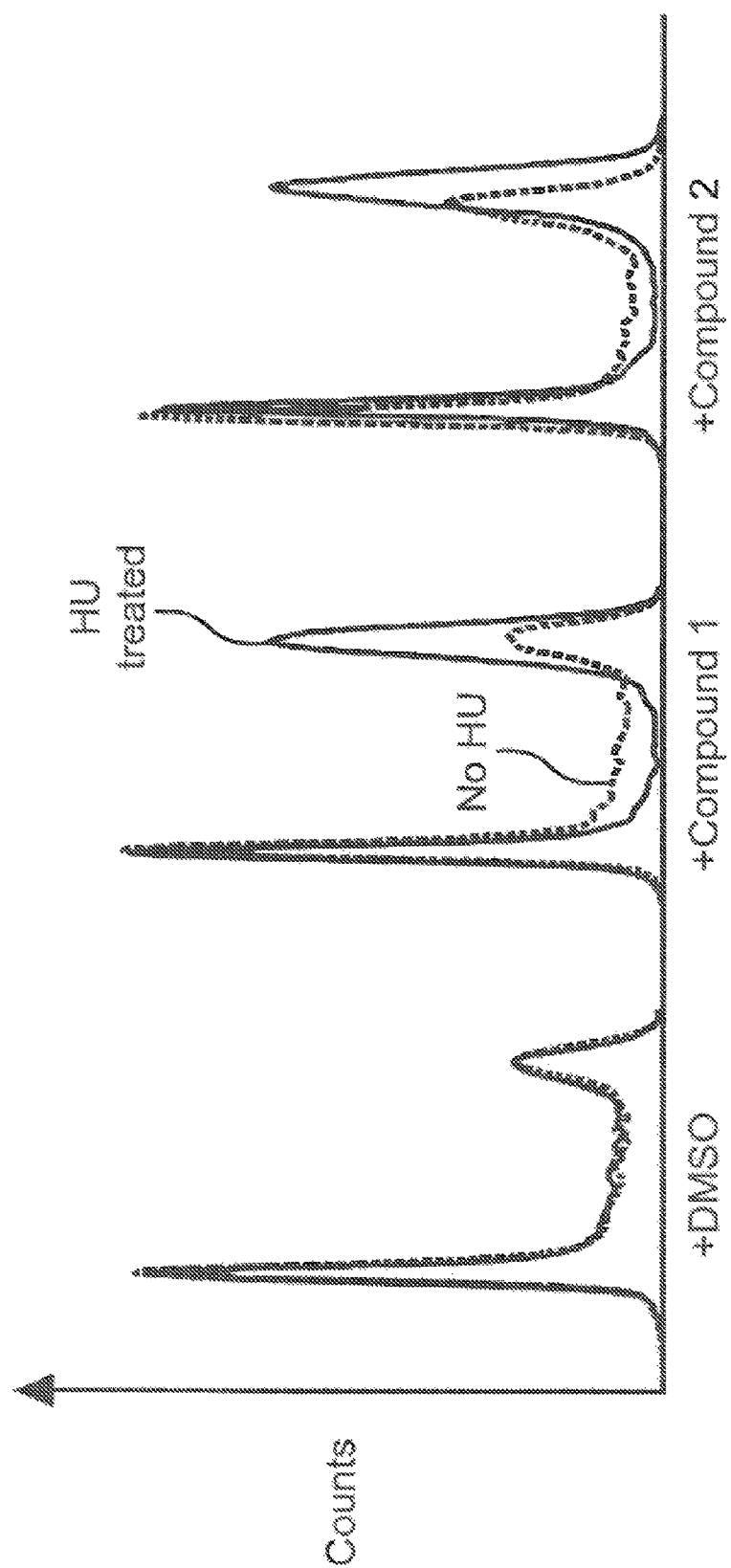

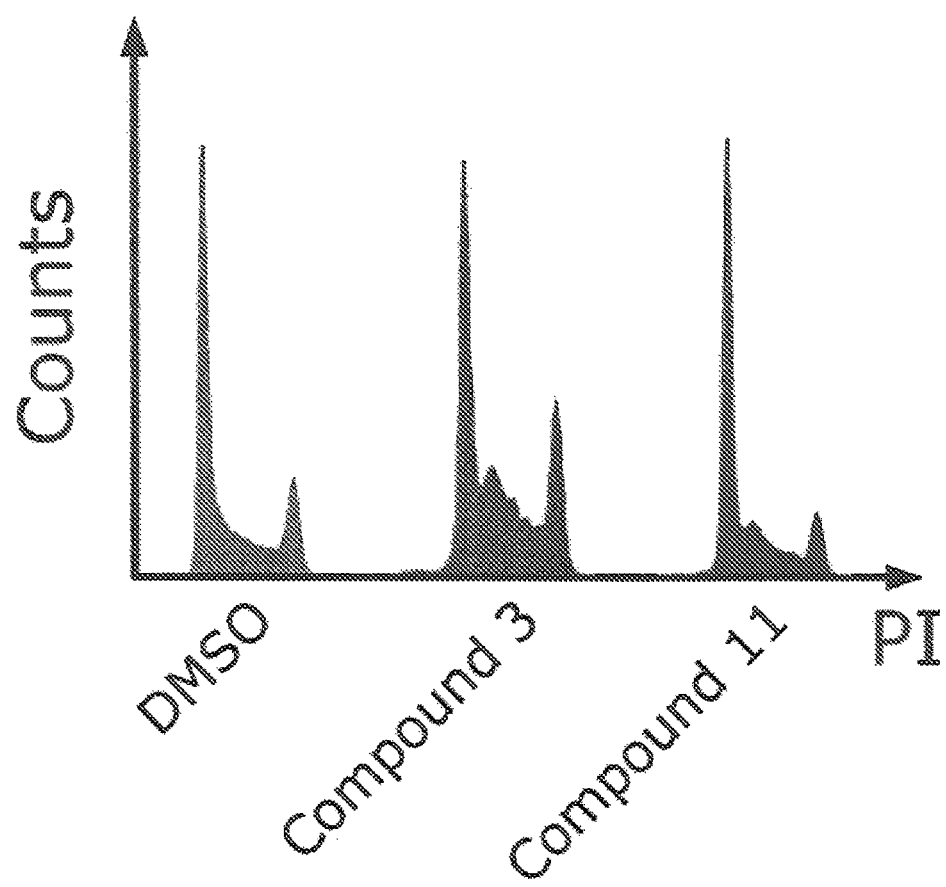

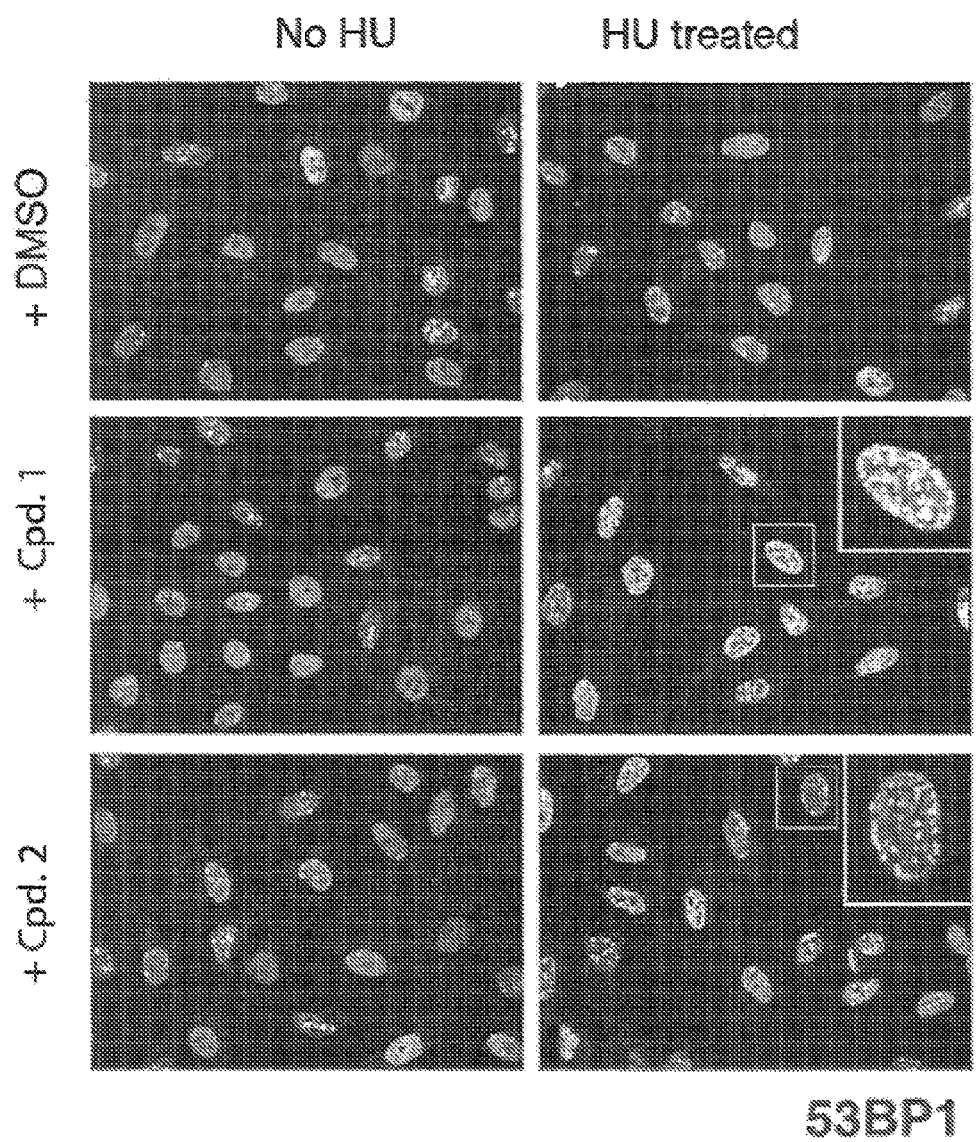

CHEMICAL ENTITIES

CROSS-REFERENCE TO RELATED APPLICATIONS

This application is a 35 U.S.C. §371 national stage filing of International Application No. PCT/GB2014/050825, filed Mar. 14, 2014, which claims priority to European Patent Application No. 13382089.4, filed Mar. 15, 2013. The entire contents of each of the aforementioned applications are incorporated herein by reference.

This invention relates to chemical entities with anticancer activity, and more specifically to chemical entities that inhibit ATR (Ataxia telangiectasia mutated and Rad3-related kinase). This invention also relates to pharmaceutical compositions containing, and the uses of, such chemical entities.

BACKGROUND TO THE INVENTION

The tricyclic chemical entities of the present invention are inhibitors of ATR and have a number of therapeutic applications, particularly in the treatment of cancer.

Cancers are the consequence of uncontrolled cell growth of a wide variety of different tissues. In many cases the new cells penetrate into existing tissue, or they metastasize into remote organs. Cancers occur in a wide variety of organs and often progress in a manner specific to the tissue. The term "cancer" as a generic term therefore describes a large group of defined diseases of different organs, tissue and cell types.

In 2008, over 12 million people worldwide were diagnosed with cancer. In the same year, approx. 7.5 million deaths were assumed to be a consequence of these diseases (Globocan 2008 Report). In the USA alone, in 2012, more than 1.6 million new cases and more than 500 000 deaths were predicted from cancers. The majority of these new cases relate to cancers of the colon (~100 000), lung (~230 000), breast (~230 000) and prostate (~240 000) (American Cancer Society, Cancer Facts and Figures 2012).

Many current cancer treatments, including chemotherapeutic agents and ionizing radiation, induce DNA damage and replication fork stalling, thereby activating cell cycle checkpoint pathways and leading to cell cycle arrest. A variety of studies have shown that this response is an important mechanism that helps cancer cells survive the treatments. These findings have prompted the development of agents targeting DNA damage response signalling pathways.

ATR is a member of phosphatidylinositol kinase-related kinase (PIKK) protein family, and is activated by a wide variety of DNA damage events. In particular, ATR is essential to coordinate the response to replicative stress (RS), which stands for the pathological accumulation of single stranded DNA (ssDNA). The recombinogenic nature of ssDNA leads to chromosomal rearrangements that are a hallmark of cancer. In response to RS, ATR triggers arrest of the cell cycle in the S and G2/M stages by phosphorylation of CHK1.

ATR can prevent cancer development, as the ATR checkpoint response might limit the expansion of precancerous cells undergoing RS as a result of oncogene activation. Moreover, because the ATR-CHK1 checkpoint pathway serves to ensure cell survival after RS, a normal and robust ATR-CHK1 checkpoint may be a mechanism of resistance to chemotherapy and may allow cancer cells to survive with high endogenous levels of RS.

Inhibition of ATR-CHK1 pathway components could potentially enhance the effectiveness of replication inhibitors. In addition, ATR inhibition may be particularly toxic for cells with high levels of RS, such as those expressing oncogenes or lacking tumour suppressors. In these cells, strong limitation of ATR activity (for example, by use of an ATR inhibitor) would generate lethal amounts of RS leading to cell death.

A potential advantage of sensitizing cells in this way would be the capacity to lower the doses of the replication inhibitors. This would result in reduced toxicity to haematological and gastrointestinal organ systems among others, if the normal cells are not sensitized to the same extent. Specificity of the replication inhibitor for causing cancer cell death may be assisted by the fact that untransformed cells have more robust S and G2 checkpoints than tumour cells. For example, many cancers have mutations in p53 or other components of the p53 pathway, leading to reliance on the S and G2 checkpoints to arrest the cell cycle and provide for repair and survival. Inhibition of the S and G2 checkpoints may then preferentially kill these p53 deficient tumour cells.

The listing or discussion of an apparently prior-published document in this specification should not necessarily be taken as an acknowledgement that the document is part of the state of the art or is common general knowledge.

There is a lack of potent inhibitors of ATR. Therefore, a need exists for chemical entities that selectively inhibit ATR for clinical use or for further study of the ATR response.

SUMMARY OF THE INVENTION

The present invention relates to a series of tricyclic chemical entities that are inhibitors of ATR. These chemical entities demonstrate good selectivity for ATR and are potentially useful in the treatment of cancer. The invention further relates to pharmaceutical compositions of the chemical entities, to the use of the compositions as therapeutic agents, and to methods of treatment using these compositions.

In an aspect, the present invention provides chemical entities selected from compounds of formula (I)

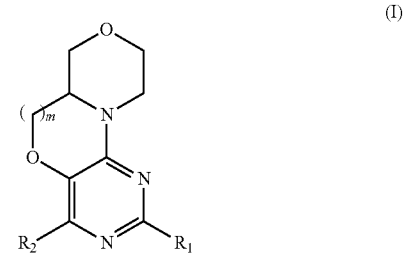

wherein
$R_1$ is selected from aryl and heteroaryl;
$R_2$ is selected from $NR_3SO_2R_3$, alkyl, cycloalkyl, aryl and heteroaryl;
wherein $R_3$ is independently selected at each occurrence from H, alkyl, cycloalkyl and heterocycloalkyl; and m is 1 or 2;
alkyl is a linear saturated hydrocarbon having up to 10 carbon atoms ($C_1$-$C_{10}$) or a branched saturated hydrocarbon of from 3 to 10 (i.e. between 3 and 10) carbon atoms ($C_3$-$C_{10}$);
cycloalkyl is a mono- or bi-cyclic saturated $C_3$-$C_{10}$ hydrocarbon, which may optionally be fused to an aryl group; or cycloalkyl is adamantyl;

heterocycloalkyl is a C-linked or N-linked 3-10 membered saturated mono- or bi-cyclic ring, which contains 1, 2, 3 or 4 ring heteroatoms independently selected from N, S and O, wherein an N or S atom in the ring may be substituted with oxygen to form an N-oxide, sulfoxide or sulfone group;

aryl is phenyl, biphenyl or naphthyl; and heteroaryl is a 5, 6, 9 or 10, 12, 13 or 14 membered mono-, bi- or tri-cyclic aromatic ring, which may contain 1, 2, 3 or 4 ring heteroatoms independently selected from N, S and O;

and pharmaceutically acceptable salts, solvates and stereoisomers thereof.

Where any of $R_1$, $R_2$ and $R_3$ is selected from alkyl, cycloalkyl, heterocycloalkyl, aryl and heteroaryl, in accordance with formula (I) as defined above, then that group may be substituted or unsubstituted. Where substituted, there will generally be 1 to 5 substituents present, preferably 1, 2 or 3 substituents.

Substituents for said alkyl, heterocycloalkyl, cycloalkyl, unless otherwise stated, may be independently selected from halo, OH, CN, $COOR_4$, $CF_3$, $NR_4R_4$, $NR_4COR_4$, $(NR_4)_nSO_2R_4$, wherein n is 0 or 1, alkyl optionally substituted by 1, 2 or 3 halo atoms, cycloalkyl optionally substituted by 1, 2 or 3 halo atoms, and O-alkyl optionally substituted by 1, 2 or 3 halo atoms, or two substituents on a single atom may be taken together with the atom to which they are attached to form a cyclic structure selected from cycloalkyl and heterocycloalkyl optionally substituted by 1, 2 or 3 groups selected from halo, $C(O)C_1$-$C_4$ alkyl, $C(O)O$—($C_1$-$C_4$ alkyl) and $C_1$-$C_4$ alkyl optionally substituted with 1, 2 or 3 halo atoms; and wherein $R_4$ is independently selected at each occurrence from H, alkyl, aryl, heteroaryl, cycloalkyl and heterocycloalkyl, wherein alkyl, aryl, heteroaryl, cycloalkyl and heterocycloalkyl is optionally substituted by 1, 2 or 3 substituents selected from halo, alkyl, O-alkyl, $N(C_1$-$C_4alkyl)_2$, $N(C_1$-$C_4alkyl)COC_1$-$C_4alkyl$, or two $R_4$ groups in a substituent are taken together with the atom(s) to which they are attached to form a heterocycloalkyl optionally substituted by 1, 2 or 3 halo atoms, or, where a substituent comprising an $R_4$ group is present on an alkyl, cycloalkyl or heterocycloalkyl, the $R_4$ group is taken together with a substituent on that alkyl, cycloalkyl or heterocycloalkyl to form a heterocycloalkyl optionally substituted by 1, 2 or 3 halo atoms.

Substituents for said aryl and heteroaryl may be independently selected from halo, OH, CN, $COOR_4$, $CF_3$, $NR_4R_4$, $NR_4COR_4$, $(NR_4)_nSO_2R_4$, wherein n is 0 or 1, $NHR_5$, alkyl optionally substituted by 1, 2 or 3 halo atoms, O-alkyl optionally substituted by 1, 2 or 3 halo atoms, cycloalkyl optionally substituted by 1, 2 or 3 halo atoms, and heterocycloalkyl optionally substituted by 1, 2 or 3 halo atoms;

wherein $R_5$ is independently selected from COalkyl, COaryl or COheteroaryl.

In an embodiment of the present invention, substituents for said alkyl, heterocycloalkyl, cycloalkyl, unless otherwise stated, may be independently selected from halo, OH, CN, $COOR_4$, $CF_3$, $NR_4R_4$, $NR_4COR_4$, $(NR_4)_nSO_2R_4$, wherein n is 0 or 1, alkyl optionally substituted by 1, 2 or 3 halo atoms, cycloalkyl optionally substituted by 1, 2 or 3 halo atoms, and O-alkyl optionally substituted by 1, 2 or 3 halo atoms, or two substituents on a single atom may be taken together with the atom to which they are attached to form a cyclic structure selected from cycloalkyl and heterocycloalkyl optionally substituted by 1, 2 or 3 groups selected from halo and $C_1$-$C_4$ alkyl optionally substituted with 1, 2 or 3 halo atoms.

The present invention encompasses all tautomers, isomers, stereoisomers (including enantiomers, diastereoisomers and racemic and scalemic mixtures) thereof of compounds of formula (I) as herein defined and pharmaceutically acceptable salts and prodrugs thereof.

In yet another aspect the present invention provides an N-oxide of a compound of formula (I) as herein defined, and tautomers, isomers, stereoisomers (including enantiomers, diastereoisomers and racemic and scalemic mixtures) thereof, and pharmaceutically acceptable salts and prodrugs thereof.

It will be understood that certain chemical entities of the present invention may exist in solvated, for example hydrated, as well as unsolvated forms. It is to be understood that the present invention encompasses all such solvated forms.

The present invention also comprises the following aspects, alternatives and combinations thereof. Preferences and options for a given aspect, feature or parameter of the invention should, unless the context indicates otherwise, be regarded as having been disclosed in combination with any and all preferences and options for all other aspects, features and parameters of the invention. For example, particular definitions for the $R_1$ group defined here may be combined with particular definitions for the $R_2$ group.

In an aspect of the invention, $R_1$ is heteroaryl. In particular, $R_1$ is bicyclic heteroaryl.

In an aspect of the invention, $R_1$ is selected from:

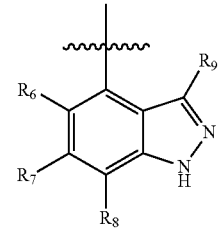

and particularly

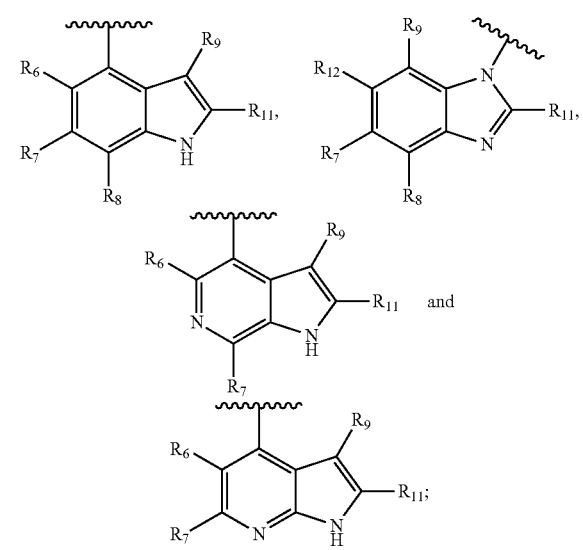

wherein each of $R_6$, $R_7$, $R_8$, $R_9$, $R_{11}$ and $R_{12}$ is independently selected from H, halo, cycloalkyl, OH, CN, $COOR_4$, $CF_3$, $NR_4R_4$, $NR_4COR_4$, $R_{10}$ and $OR_{10}$, wherein $R_{10}$ is $(C_1-C_6)$alkyl optionally substituted with 1, 2 or 3 halo atoms.

Preferably, $R_6$ is selected from halo or H, more preferably, F or H.

Preferably, $R_7$, $R_8$ and $R_9$ are each independently selected from CN or particularly H, halo, $R_{10}$, and $OR_{10}$, more preferably, from H, halo and $R_{10}$.

Preferably, $R_7$ is selected from halo, $(C_1-C_6)$alkyl, and $O(C_1-C_6)$alkyl, particularly from halo and $O(C_1-C_6)$alkyl, more particularly from halo and OMe, more particularly from F and OMe.

Preferably, $R_7$ is selected from halo, CN, $O(C_1-C_6)$alkyl and $(C_1-C_6)$alkyl optionally substituted by 1 to 3 halo atoms, particularly from halo, CN, $O(C_1-C_4)$alkyl and $(C_1-C_4)$ alkyl optionally substituted by 1 to 3 halo atoms, more particularly from halo, CN, Me, $CF_3$ and OMe, more particularly from Cl, F, CN, Me, $CF_3$ and OMe.

Preferably, $R_{11}$ is selected from H, $R_{10}$, $NR_4R_4$ and $NR_4COR_4$, for example, from morpholinyl, $N(C_{1-4}$alkyl$)C_{1-4}$alkyl, or particularly H, $(C_1-C_6)$alkyl, $NH_2$, $NHC_{1-4}$alkyl and $NHCOC_{1-4}$alkyl, more particularly, H, Me, NHMe, $N(Me)_2$, NHEt, NH(iso-propyl), NH(n-propyl), $NH_2$, and morpholin-4-yl. More preferably, $R_{11}$ is selected from $(C_1-C_6)$alkyl, $NR_4R_4$ and $NR_4COR_4$, more preferably, $NR_4R_4$, in particular, NHMe, $N(Me)_2$, NHEt, NH(iso-propyl), NH(n-propyl), $NH_2$, and morpholin-4-yl.

Preferably, $R_{12}$ is selected from H, halo, $R_{10}$ or $OR_{10}$, particularly from H, halo or $R_{10}$, or more particularly from H or $R_{10}$.

In particular, $R_6$ and $R_9$ may each independently be selected from F or H;

$R_7$ and $R_8$ may each independently be selected from H, halo, $R_{10}$, and $OR_{10}$;

$R_{11}$ may be selected from H, $R_{10}$, $NR_4R_4$ and $NR_4COR_4$; and $R_{12}$ is selected from H, halo, $R_{10}$ or $OR_{10}$.

Alternatively, $R_6$ and $R_9$ may each independently be selected from F or H;

$R_7$ and $R_8$ may each independently be selected from H, halo, CN, $R_{10}$, and $OR_{10}$;

$R_{11}$ may be selected from H, $R_{10}$, $NR_4R_4$ and $NR_4COR_4$; and $R_{12}$ is selected from H, halo, $R_{10}$ or $OR_{10}$.

Alternatively, $R_6$ may be selected from halo or H, in particular, F or H;

$R_7$, $R_8$ and $R_9$ may be each independently selected from H, halo, $R_{10}$, and $OR_{10}$;

$R_{11}$ may be selected from H, $R_{10}$, $NR_4R_4$ and $NR_4COR_4$;

wherein $R_4$ is independently selected at each occurrence from H or alkyl optionally substituted by 1, 2 or 3 halo atoms, or the $R_4$ groups are taken together with the atom to which they are attached to form heterocycloalkyl, optionally substituted by 1, 2 or 3 halo atoms; and $R_{12}$ may be selected from H or $R_{10}$.

In another alternative, $R_6$ may be selected from halo or H, in particular, F or H;

$R_7$, $R_8$ and $R_9$ may be each independently selected from H, halo, CN, $R_{10}$, and $OR_{10}$;

$R_{11}$ may be selected from H, $R_{10}$, $NR_4R_4$ and $NR_4COR_4$;

wherein $R_4$ is independently selected at each occurrence from H or alkyl optionally substituted by 1, 2 or 3 halo atoms, or the $R_4$ groups are taken together with the atom to which they are attached to form heterocycloalkyl, optionally substituted by 1, 2 or 3 halo atoms; and $R_{12}$ may be selected from H, halo or $R_{10}$.

In particular, $R_6$ may be selected from halo or H, in particular, F or H;

$R_7$, $R_8$ and $R_9$ may be each independently selected from H, halo, $(C_{1-6})$alkyl, and $O(C_{1-6})$alkyl;

$R_{11}$ may be selected from H, $(C_{1-6})$alkyl, $NR_4R_4$ and $NR_4COR_4$;

wherein $R_4$ is independently selected at each occurrence from H or alkyl optionally substituted by 1, 2 or 3 halo atoms, or the $R_4$ groups are taken together with the atom(s) to which they are attached to form heterocycloalkyl, optionally substituted by 1, 2 or 3 halo atoms; and $R_{12}$ may be selected from H, $(C_{1-6})$alkyl or $O(C_{1-6})$alkyl.

Alternatively, $R_6$ may be selected from halo or H, in particular, F or H;

$R_7$, $R_8$ and $R_9$ may be each independently selected from H, halo, CN, $O(C_{1-6})$alkyl and $(C_{1-6})$alkyl optionally substituted by 1, 2 or 3 halo atoms;

$R_{11}$ may be selected from H, $(C_{1-6})$alkyl, $NR_4R_4$ and $NR_4COR_4$;

wherein $R_4$ is independently selected at each occurrence from H or alkyl optionally substituted by 1, 2 or 3 halo atoms, or the $R_4$ groups are taken together with the atom(s) to which they are attached to form heterocycloalkyl, optionally substituted by 1, 2 or 3 halo atoms; and $R_{12}$ may be selected from H, halo, $(C_{1-6})$alkyl or $O(C_{1-6})$alkyl.

In particular, $R_6$ may be selected from halo or H, in particular, F or H;

$R_7$, $R_8$ and $R_9$ may be each independently selected from H, halo, $(C_{1-6})$alkyl and $O(C_{1-6})$alkyl;

$R_{11}$ may be selected from H, $(C_1-C_6)$alkyl, $NH_2$, $NHC_{1-4}$alkyl and $NHCO(C_{1-4})$alkyl; and $R_{12}$ may be selected from H or $R_{10}$.

Alternatively, $R_6$ may be selected from halo or H, in particular, F or H;

$R_7$, $R_8$ and $R_9$ may be each independently selected from H, halo, CN, $O(C_{1-6})$alkyl and $(C_{1-6})$alkyl optionally substituted by 1, 2 or 3 halo atoms;

$R_{11}$ may be selected from H, $(C_1-C_6)$alkyl, $NH_2$, $NHC_{1-4}$alkyl, $N(C_{1-4}$alkyl$)_2$, morpholinyl and $NHCO(C_{1-4})$alkyl; and $R_{12}$ may be selected from H halo or $R_{10}$.

Alternatively, $R_6$, $R_7$, $R_8$, $R_9$ and $R_{12}$ may be H; and $R_{11}$ may be selected from $(C_1-C_6)$alkyl, $NR_4R_4$ and $NR_4COR_4$, particularly $NR_4R_4$, more particularly NHMe, $N(Me)_2$, NHEt, NH(iso-propyl), NH(n-propyl), $NH_2$, and morpholin-4-yl, more particularly NHMe;

wherein $R_4$ is independently selected at each occurrence from H or alkyl optionally substituted by 1, 2 or 3 halo atoms, or the $R_4$ groups are taken together with the atom to which they are attached to form heterocycloalkyl, optionally substituted by 1, 2 or 3 halo atoms.

Alternatively, $R_{11}$ may be selected from $(C_1-C_6)$alkyl, $NR_4R_4$ and $NR_4COR_4$; one of $R_6$, $R_7$, $R_8$, $R_9$ and $R_{12}$ is present and is not H; and the remainder of $R_6$, $R_7$, $R_8$, $R_9$ and $R_{12}$ if present are H.

Alternatively, $R_6$, $R_8$, $R_9$, $R_{11}$ and $R_{12}$ may be H; and $R_7$ may be selected from halo, $(C_1-C_6)$alkyl, and $O(C_1-C_6)$alkyl, particularly from halo and $O(C_1-C_6)$alkyl, more particularly from halo and OMe.

In another alternative, $R_6$, $R_8$, $R_9$, $R_{11}$ and $R_{12}$ may be H; and $R_7$ may be selected from halo, CN, $O(C_1-C_6)$alkyl and $(C_1-C_6)$alkyl optionally substituted by 1, 2 or 3 halo atoms, particularly from halo, CN, Me, $CF_3$ and OMe.

Alternatively, $R_6$, $R_7$, $R_8$, $R_9$, $R_{11}$ and $R_{12}$ may all be H.

In an aspect of the invention, $R_2$ is selected from $NR_4SO_2R_4$, alkyl, cycloalkyl, aryl and heterocycloalkyl,
  wherein alkyl and cycloalkyl are optionally substituted with 1, 2 or 3 substituents selected from 1, 2 or 3 substituents selected from $(NR_4)_nSO_2R_4$, OH and CN, and further optionally substituted with 1 or 2 substituents independently selected from halo, $(C_1-C_6)$alkyl optionally substituted by 1, 2 or 3 halo atoms, cycloalkyl optionally substituted by 1, 2 or 3 halo atoms, and $O(C_1-C_6)$alkyl optionally substituted by 1, 2 or 3 halo atoms, and further still optionally substituted with (i) 2 substituents on a single atom that are taken together with the atom to which they are attached to form a cyclic structure selected from cycloalkyl optionally substituted by 1, 2 or 3 groups selected from halo and $C_1-C_4$ alkyl, or with (ii) a substituent that is taken together with one of the $R_4$ groups to form a heterocycloalkyl optionally substituted by 1, 2 or 3 halo atoms;
  and wherein aryl and heterocycloalkyl are optionally substituted with 1, 2 or 3 substituents selected from 1, 2 or 3 substituents selected from $(NR_4)_nSO_2R_4$, OH and CN, and further optionally substituted with 1 or 2 substituents independently selected from halo, $(C_1-C_6)$alkyl optionally substituted by 1, 2 or 3 halo atoms, cycloalkyl optionally substituted by 1, 2 or 3 halo atoms, and $O(C_1-C_6)$alkyl optionally substituted by 1, 2 or 3 halo atoms.

In another aspect of the invention, $R_2$ is selected from $NR_3SO_2R_3$, alkyl, cycloalkyl, aryl and heteroaryl,
  wherein alkyl and cycloalkyl are optionally substituted with 1, 2 or 3 substituents selected from $(NR_4)_nSO_2R_4$, OH and CN, and further optionally substituted with 1 or 2 substituents independently selected from halo, $(C_1-C_6)$alkyl optionally substituted by 1, 2 or 3 halo atoms, cycloalkyl optionally substituted by 1, 2 or 3 halo atoms, and $O(C_1-C_6)$alkyl optionally substituted by 1, 2 or 3 halo atoms, and further still optionally substituted with (i) 2 substituents on a single atom that are taken together with the atom to which they are attached to form a cyclic structure selected from cycloalkyl and heterocycloalkyl both of which are optionally substituted by 1, 2 or 3 groups selected from halo, $C_1-C_4$ alkyl, $C(O)C_1-C_4$ alkyl and $C(O)O-C_1-C_4$ alkyl, or with (ii) a substituent that is taken together with one of the $R_4$ groups (if present) to form a heterocycloalkyl optionally substituted by 1, 2 or 3 halo atoms;
  and wherein aryl and heteroaryl are optionally substituted with 1, 2 or 3 substituents selected from $(NR_4)_nSO_2R_4$, OH and CN, and further optionally substituted with 1 or 2 substituents independently selected from halo, $(C_1-C_6)$alkyl optionally substituted by 1, 2 or 3 halo atoms, cycloalkyl optionally substituted by 1, 2 or 3 halo atoms, and $O(C_1-C_6)$alkyl optionally substituted by 1, 2 or 3 halo atoms.

In particular, $R_2$ is selected from $NR_4SO_2R_4$, alkyl and cycloalkyl, wherein alkyl and cycloalkyl are optionally substituted as described in the preceding paragraph;
  in particular, wherein alkyl and cycloalkyl is substituted with at least one substituent selected from $(NR_4)_nSO_2R_4$, wherein n is 0 or 1, OH and CN, and wherein alkyl and cycloalkyl is further optionally substituted with 1 or 2 substituents independently selected from halo, CN, $COOR_4$, $CF_3$, $(C_1-C_6)$alkyl optionally substituted by 1, 2 or 3 halo atoms, cycloalkyl optionally substituted by 1, 2 or 3 halo atoms, and $O(C_1-C_6)$alkyl optionally substituted by 1, 2 or 3 halo atoms, or with 2 substituents on a single atom that are taken together with the atom to which they are attached to form a cyclic structure selected from cycloalkyl and heterocycloalkyl optionally substituted by 1, 2 or 3 groups selected from halo and $C_1-C_4$ alkyl.

In particular, $R_2$ is selected from $NR_3SO_2R_3$, alkyl and cycloalkyl, wherein alkyl and cycloalkyl are optionally substituted as described in the preceding paragraph;
  in particular, wherein alkyl and cycloalkyl is substituted with at least one substituent selected from $(NR_4)_nSO_2R_4$, wherein n is 0 or 1, OH and CN, and wherein alkyl and cycloalkyl is further optionally substituted with 1 or 2 substituents independently selected from halo, CN, $COOR_4$, $CF_3$, $(C_1-C_6)$alkyl optionally substituted by 1, 2 or 3 halo atoms, cycloalkyl optionally substituted by 1, 2 or 3 halo atoms, and $O(C_1-C_6)$alkyl optionally substituted by 1, 2 or 3 halo atoms, or with 2 substituents on a single atom that are taken together with the atom to which they are attached to form a cyclic structure selected from cycloalkyl and heterocycloalkyl optionally substituted by 1, 2 or 3 groups selected from halo, $C_1-C_4$ alkyl, $C(O)C_1-C_4$ alkyl and $C(O)O-C_1-C_4$ alkyl.

In particular, $R_2$ may be alkyl substituted with at least one substituent selected from $(NR_4)_nSO_2R_4$, OH and CN, and further optionally substituted with 1 or 2 substituents independently selected from halo, $(C_1-C_6)$alkyl optionally substituted by 1, 2 or 3 halo atoms, cycloalkyl optionally substituted by 1, 2 or 3 halo atoms, and $O(C_1-C_6)$alkyl optionally substituted by 1, 2 or 3 halo atoms, and further still optionally substituted with (i) 2 substituents on a single atom that are taken together with the atom to which they are attached to form a cyclic structure selected from cycloalkyl optionally substituted by 1, 2 or 3 groups selected from halo and $C_1-C_4$ alkyl, or with (ii) a substituent that is taken together with one of the $R_4$ groups to form a heterocycloalkyl optionally substituted by 1, 2 or 3 halo atoms.

In particular, $R_2$ may be alkyl substituted with at least one substituent selected from $(NR_4)_nSO_2R_4$, OH and CN, and further optionally substituted with 1 or 2 substituents independently selected from halo, $(C_1-C_6)$alkyl optionally substituted by 1, 2 or 3 halo atoms, cycloalkyl optionally substituted by 1, 2 or 3 halo atoms, and $O(C_1-C_6)$alkyl optionally substituted by 1, 2 or 3 halo atoms, and further still optionally substituted with (i) 2 substituents on a single atom that are taken together with the atom to which they are attached to form a cyclic structure selected from cycloalkyl and heterocycloalkyl both of which are optionally substituted by 1, 2 or 3 groups selected from halo, $C_1-C_4$ alkyl, $C(O)C_1-C_4$ alkyl and $C(O)O-C_1-C_4$ alkyl, or with (ii) a substituent that is taken together with one of the $R_4$ groups (if present) to form a heterocycloalkyl optionally substituted by 1, 2 or 3 halo atoms.

In particular, $R_2$ may be $(CH_2)_pC(R_{13})_2(CH_2)_qQ$, wherein Q is $(NR_4)_nSO_2R_4$, OH or CN, in particular, wherein Q is $SO_2R_4$, wherein p and q are independently 0, 1 or 2, and wherein (i) $R_{13}$ is independently selected from the group consisting of H and $(C_1-C_4)$alkyl, in particular, wherein both $R_{13}$ groups are H, wherein both $R_{13}$ groups are methyl, or (ii) one $R_{13}$ is selected from the group consisting of H and $(C_1-C_4)$alkyl and the other $R_{13}$ is taken together with $R_4$, if present, to form a 3-6 membered heterocycloalkyl optionally substituted by 1, 2 or 3 groups selected from halo and $C_1-C_4$ alkyl, or (iii) the $R_{13}$ groups are taken together with the atom to which they are attached to form a cyclic structure selected from $(C_3-C_6)$cycloalkyl and 3-6 membered heterocycloalkyl optionally substituted by 1, 2 or 3 groups selected from halo and $C_1$-$C_4$ alkyl, in particular cyclopropanyl, tetrahydropyranyl, piperidinyl or N-methylpiperidinyl.

In particular, $R_2$ may be $(CH_2)_pC(R_{13})_2(CH_2)_qQ$, wherein Q is $(NR_4)_nSO_2R_4$, OH or CN, in particular, wherein Q is $SO_2R_4$, wherein p and q are independently 0, 1 or 2, and wherein (i) $R_{13}$ is independently selected from the group consisting of H and $(C_1$-$C_4)$alkyl, in particular, wherein both $R_{13}$ groups are H, wherein both $R_{13}$ groups are methyl, or (ii) one $R_{13}$ is selected from the group consisting of H and $(C_1$-$C_4)$alkyl and the other $R_{13}$ is taken together with $R_4$, if present, to form a 3-6 membered heterocycloalkyl optionally substituted by 1, 2 or 3 halo atoms, or (iii) the $R_{13}$ groups are taken together with the atom to which they are attached to form a cyclic structure selected from $(C_3$-$C_6)$cycloalkyl and 3-6 membered heterocycloalkyl optionally substituted by 1, 2 or 3 groups selected from halo, $C_1$-$C_4$ alkyl, $C(O)C_1$-$C_4$ alkyl and $C(O)O$—$C_1$-$C_4$ alkyl, in particular cyclopropanyl, cyclobutyl, tetrahydropyranyl, piperidinyl, N-methylpiperidinyl, or N-ethoxycarbonylpiperidinyl.

Alternatively, $R_2$ may be selected from $NR_3SO_2R_3$.

In this and other aspects of the invention, $R_3$ may be H or $(C_1$-$C_4)$alkyl optionally substituted by 1, 2 or 3 halo atoms, particularly H or $(C_1$-$C_4)$alkyl, more particularly H or Me.

In some aspects of the invention, $R_4$ may be $(C_1$-$C_4)$alkyl optionally substituted by 1, 2 or 3 halo atoms or $(C_3$-$C_6)$ cycloalkyl optionally substituted by 1, 2 or 3 halo atoms. In particular, $R_4$ may be methyl, cyclopropyl or trifluoromethyl.

In a further aspect of the invention, $R_2$ is selected from $(NR_4)_nSO_2R_4$, alkyl, cycloalkyl, aryl and heteroaryl, wherein alkyl, cycloalkyl, aryl and heteroaryl is substituted with $(NR_4)_nSO_2R_4$, and wherein alkyl and cycloalkyl is further optionally substituted with 1 or 2 substituents independently selected from halo, CN, $COOR_4$, $CF_3$, $(C_1$-$C_6)$ alkyl optionally substituted by 1, 2 or 3 halo atoms, cycloalkyl optionally substituted by 1, 2 or 3 halo atoms, and $O(C_1$-$C_6)$alkyl optionally substituted by 1, 2 or 3 halo atoms, or with two substituents on a single atom that are taken together with the carbon to which they are attached to form cycloalkyl optionally substituted by 1, 2 or 3 groups selected from halo and $C_1$-$C_4$ alkyl, and wherein aryl and heteroaryl is further optionally substituted with 1 or 2 substituents independently selected from halo, CN, $COOR_4$, $CF_3$, $(C_1$-$C_6)$alkyl optionally substituted by 1, 2 or 3 halo atoms, cycloalkyl optionally substituted by 1, 2 or 3 halo atoms, and $O(C_1$-$C_6)$alkyl optionally substituted by 1, 2 or 3 halo atoms.

In a further aspect of the invention, $R_2$ is selected from $NR_3SO_2R_3$, alkyl, cycloalkyl, aryl and heteroaryl, wherein alkyl, cycloalkyl, aryl and heteroaryl is substituted with $(NR_4)_nSO_2R_4$, and wherein alkyl and cycloalkyl is further optionally substituted with 1 or 2 substituents independently selected from halo, CN, $COOR_4$, $CF_3$, $(C_1$-$C_6)$alkyl optionally substituted by 1, 2 or 3 halo atoms, cycloalkyl optionally substituted by 1, 2 or 3 halo atoms, and $O(C_1$-$C_6)$alkyl optionally substituted by 1, 2 or 3 halo atoms, or with two substituents on a single atom that are taken together with the carbon to which they are attached to form cycloalkyl or heterocycloalkyl both of which are optionally substituted by 1, 2 or 3 groups selected from halo, $C_1$-$C_4$ alkyl, $C(O)C_1$-$C_4$ alkyl and $C(O)O$—$C_1$-$C_4$ alkyl, and wherein aryl and heteroaryl is further optionally substituted with 1 or 2 substituents independently selected from halo, CN, $COOR_4$, $CF_3$, $(C_1$-$C_6)$alkyl optionally substituted by 1, 2 or 3 halo atoms, cycloalkyl optionally substituted by 1, 2 or 3 halo atoms, and $O(C_1$-$C_6)$alkyl optionally substituted by 1, 2 or 3 halo atoms.

For example, $R_2$ may be selected from $NR_3SO_2R_3$, alkyl, cycloalkyl, aryl and heteroaryl, wherein alkyl, cycloalkyl, aryl and heteroaryl is substituted with $(NR_4)_nSO_2R_4$, and wherein alkyl, cycloalkyl, aryl and heteroaryl is further optionally substituted with 1 or 2 substituents independently selected from halo, CN, $CF_3$, $(C_1$-$C_6)$ alkyl optionally substituted by 1, 2 or 3 halo atoms and $O(C_1$-$C_6)$alkyl optionally substituted by 1, 2 or 3 halo atoms.

The stereochemical configuration about the mandatory chiral centre in the chemical entity of formula (I) (i.e. the chiral centre adjacent to the —(CH)$_m$— group) may be S. In particular, when n is 1 the stereochemical configuration about the chiral centre may be S. More particularly, when m is 1 the stereochemical configuration about the chiral centre may be S.

The stereochemical configuration about the chiral centre may be R. In particular, when n is 2 the stereochemical configuration about the chiral centre may be R. More particularly, when m is 2 the stereochemical configuration about the chiral centre may be R.

In an aspect, the invention comprises a compound selected from the group consisting of:

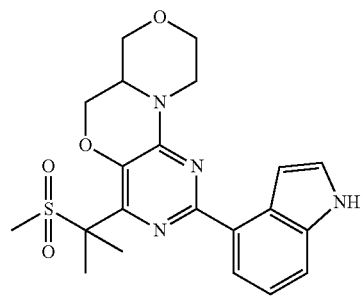

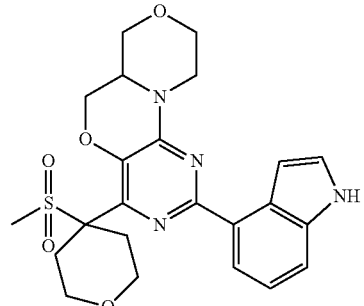

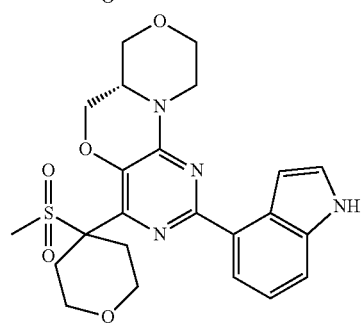

-continued
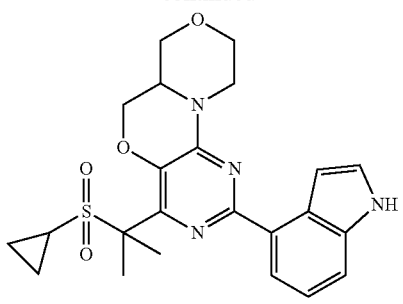
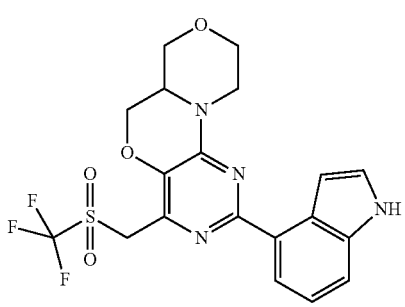
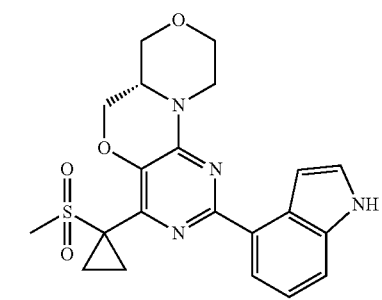
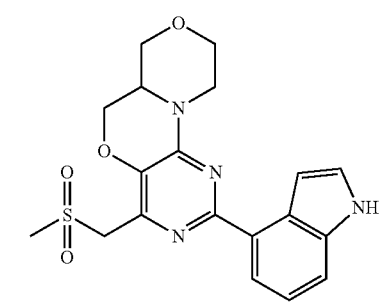
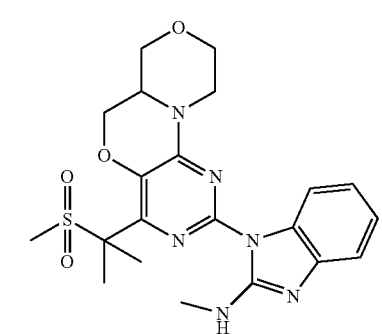
-continued
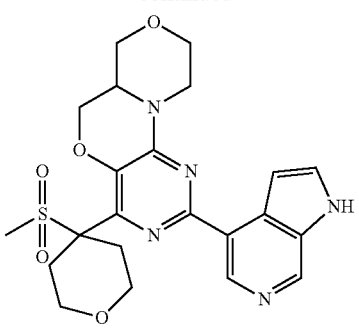
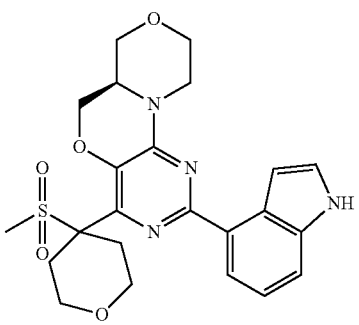
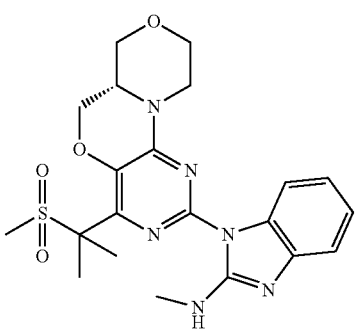
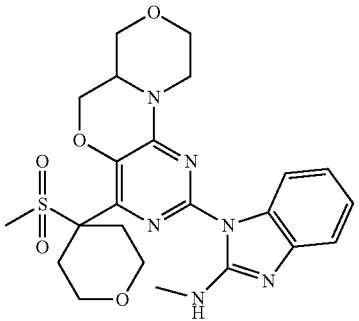
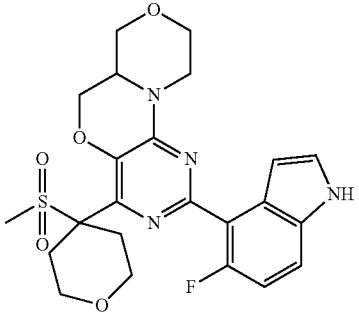

-continued
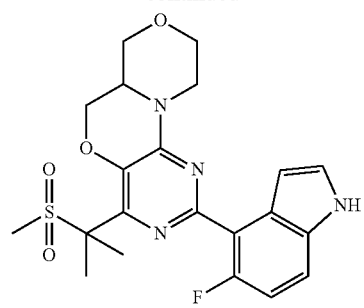
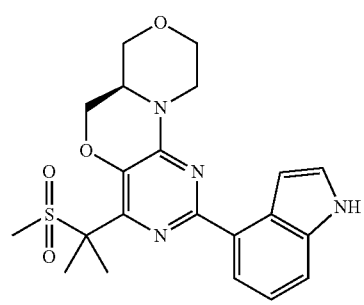
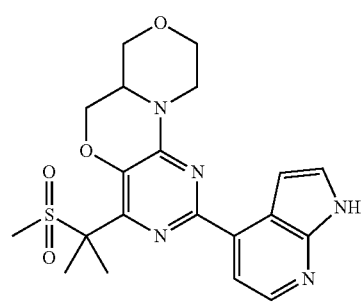
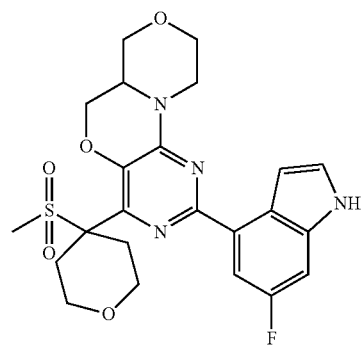
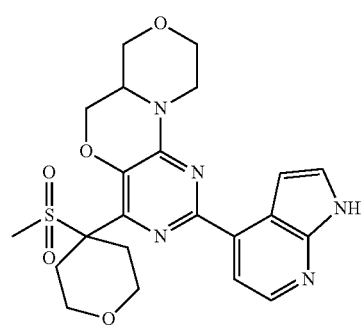
-continued
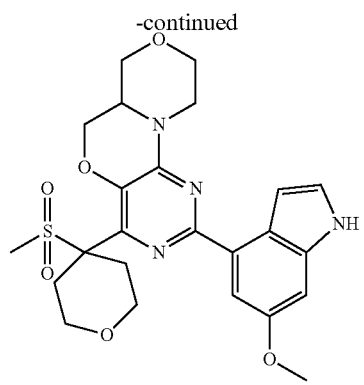
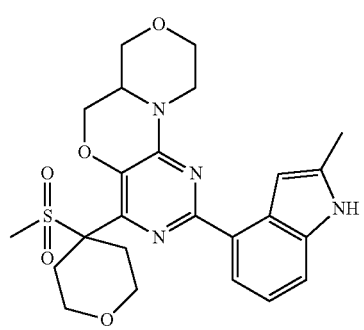
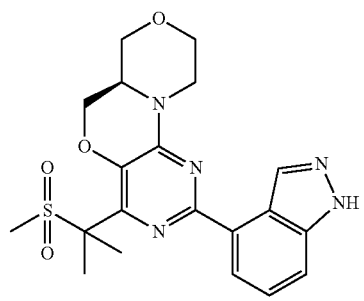
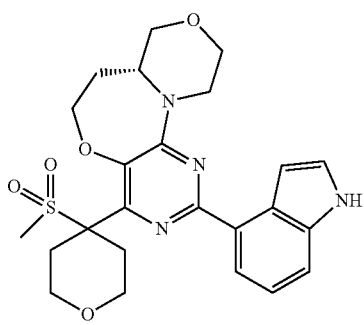
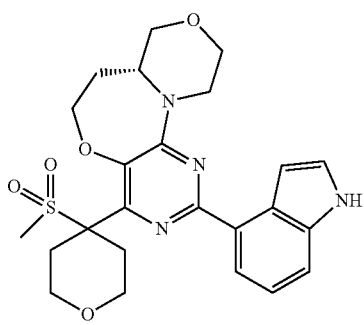

-continued
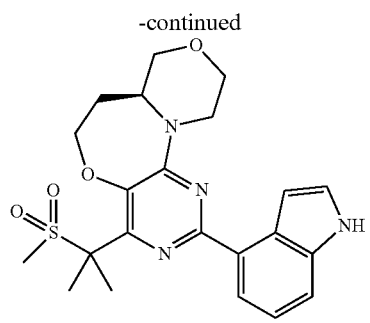
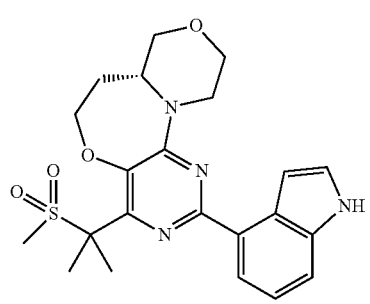
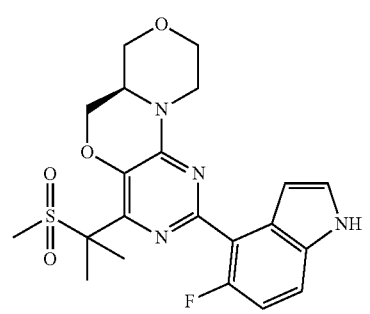
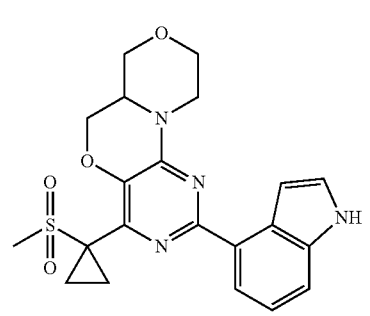
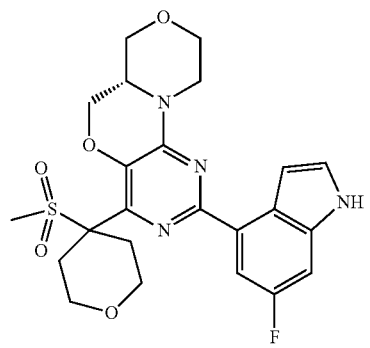
-continued
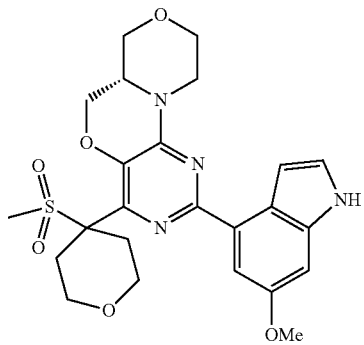
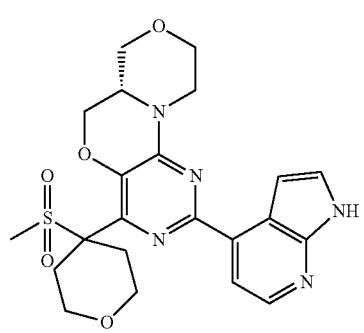
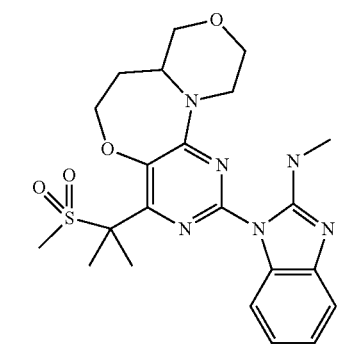
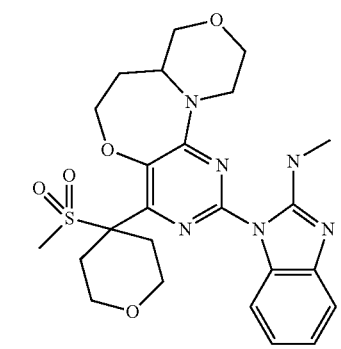
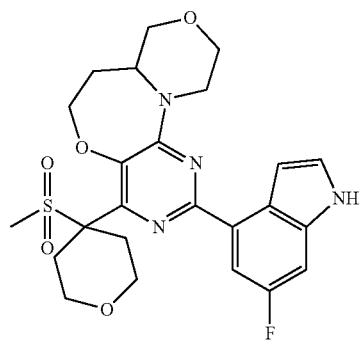

-continued
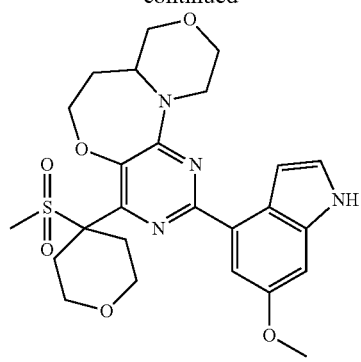
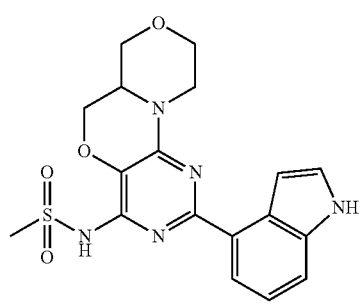
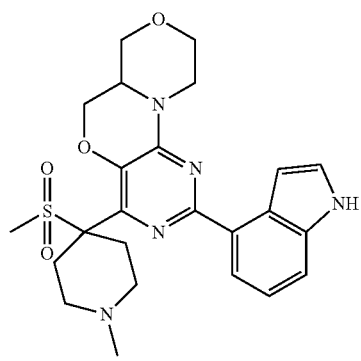
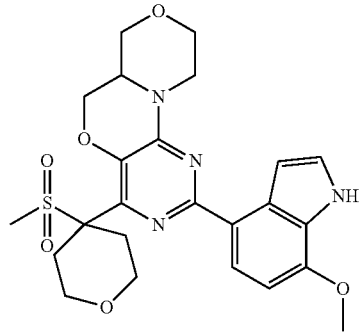
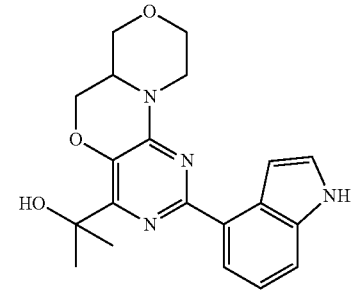
-continued
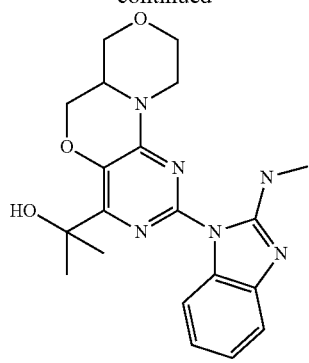
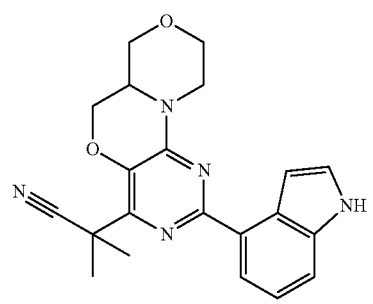
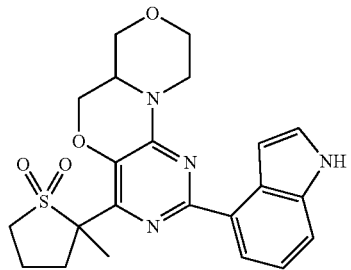
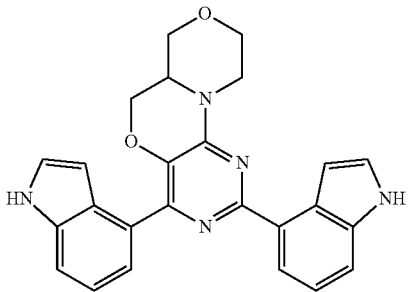
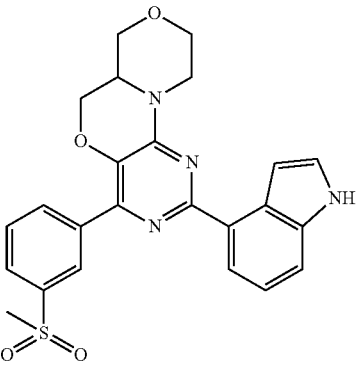

-continued
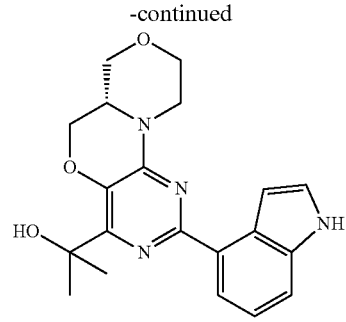
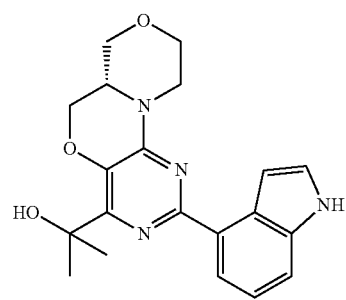
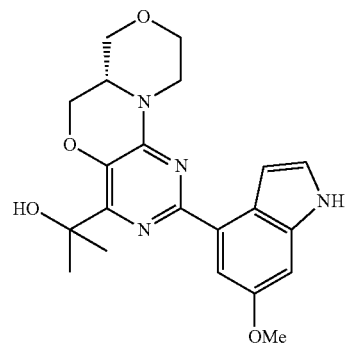
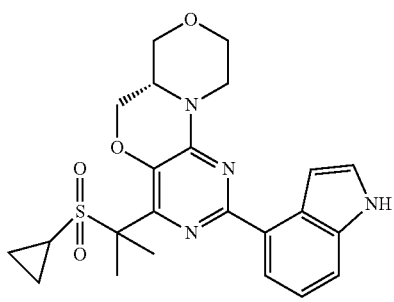
-continued
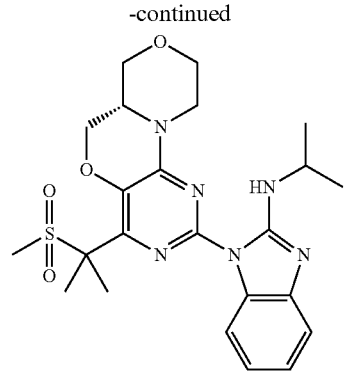
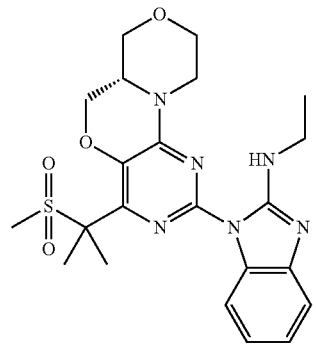
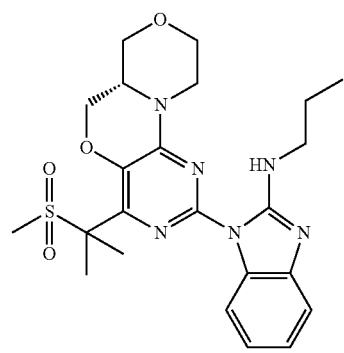
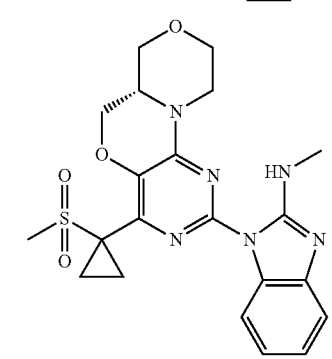
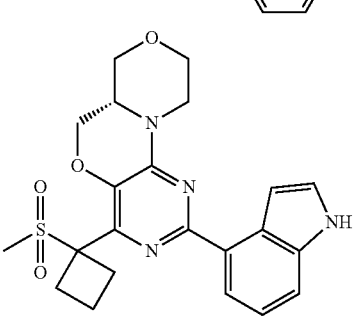

-continued
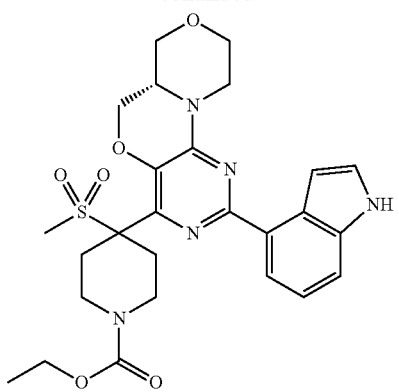
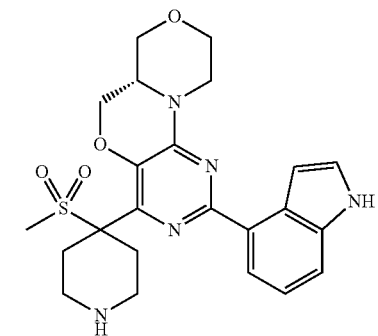
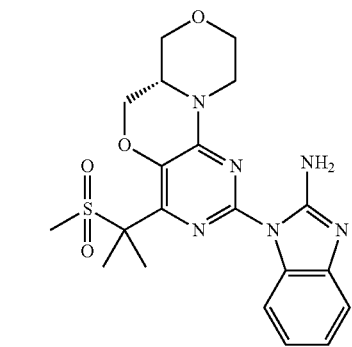
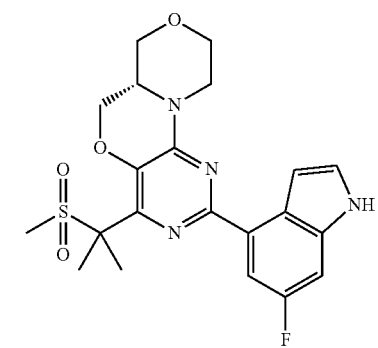
-continued
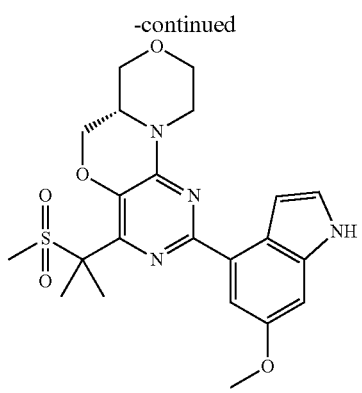
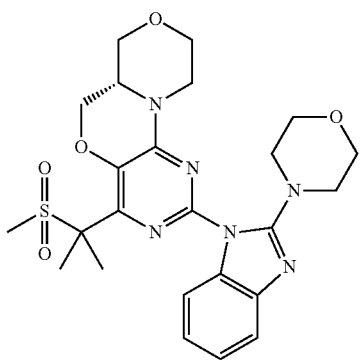
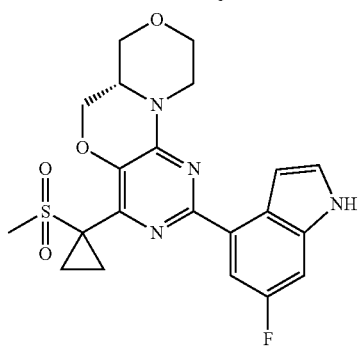
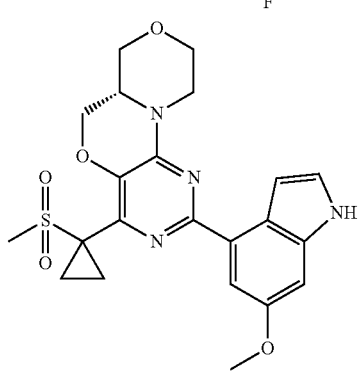
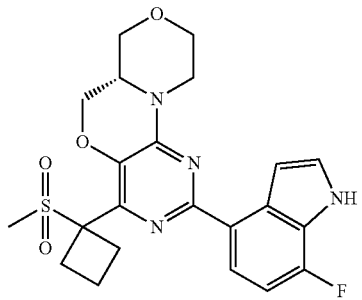

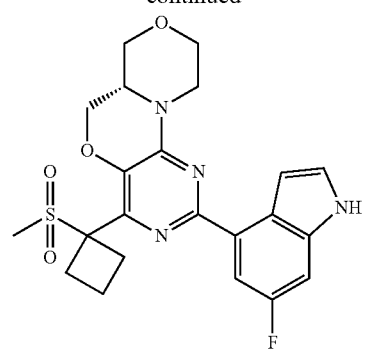
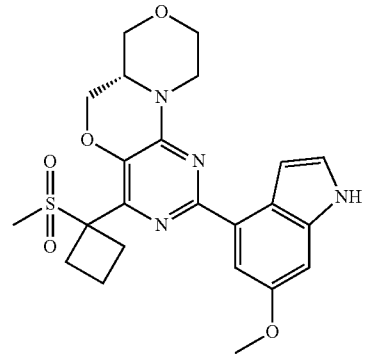
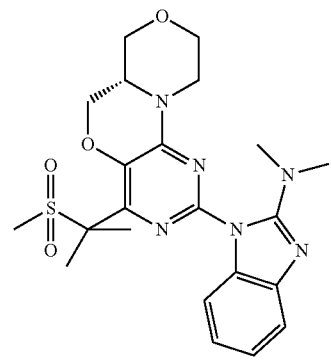
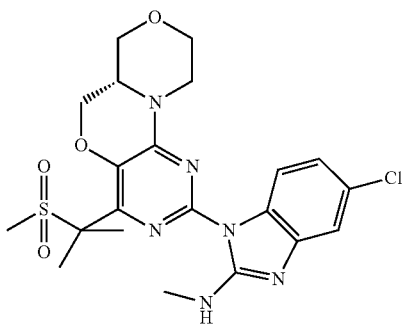
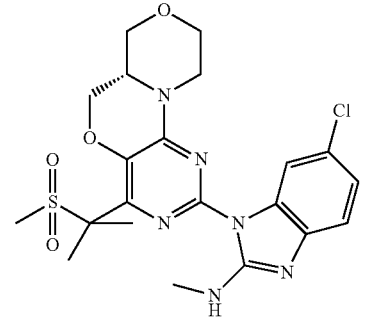
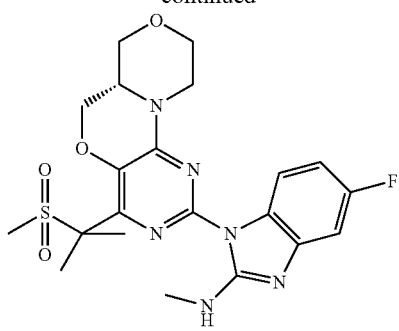
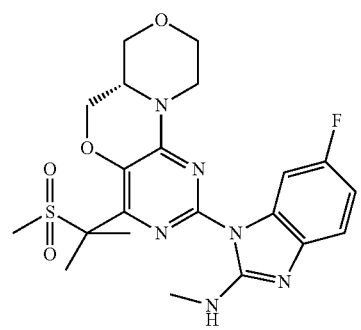
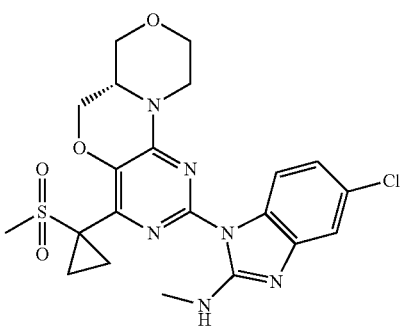
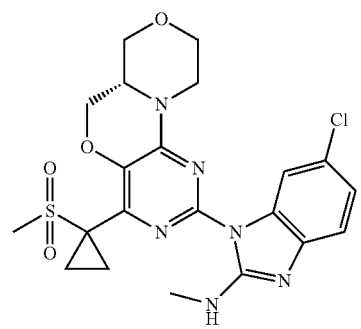
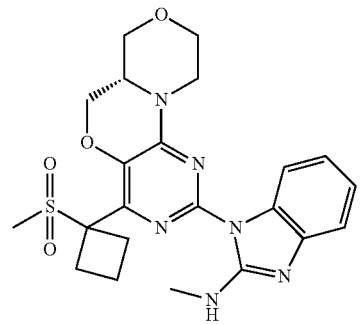

-continued
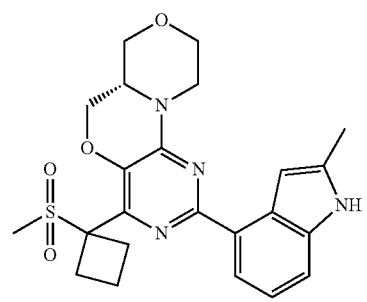
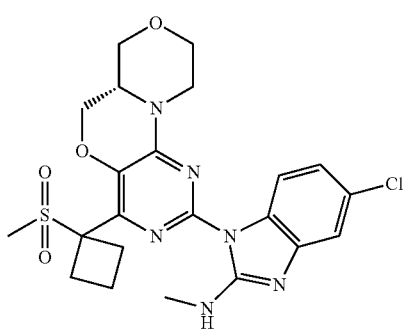
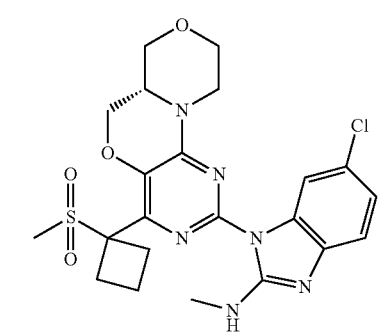
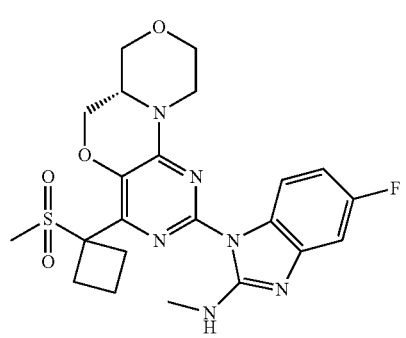
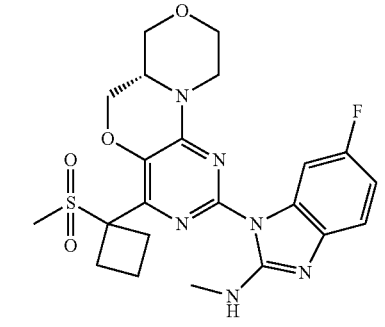
-continued
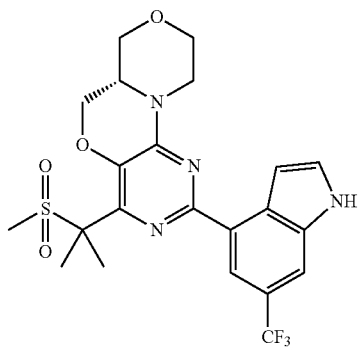
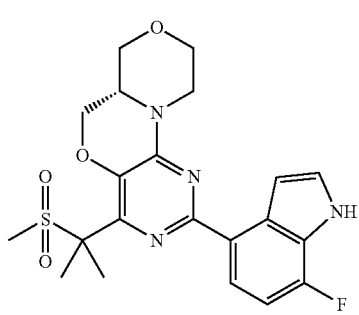
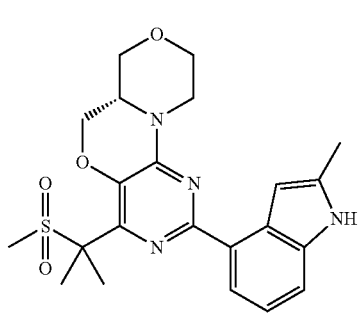
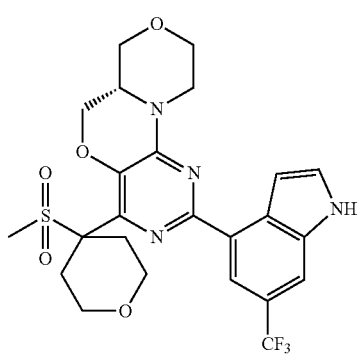
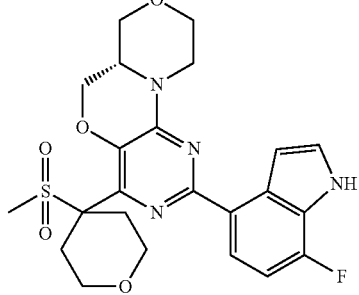

-continued

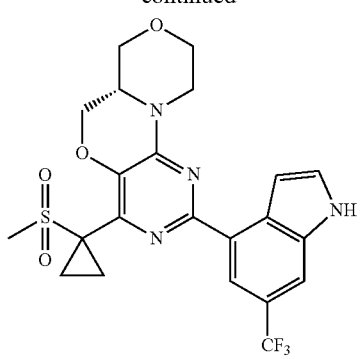

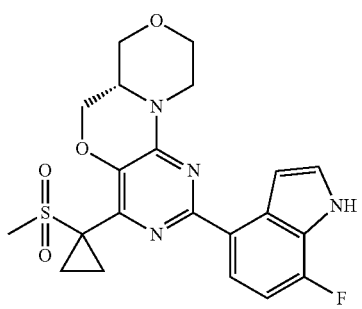

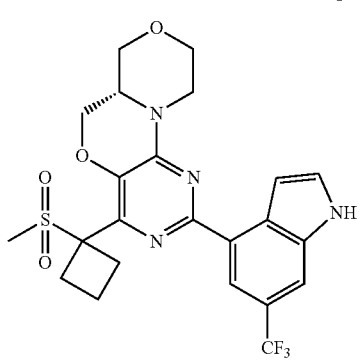

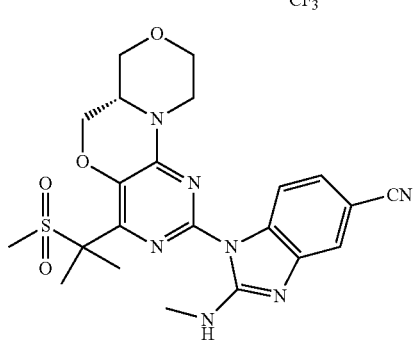

-continued

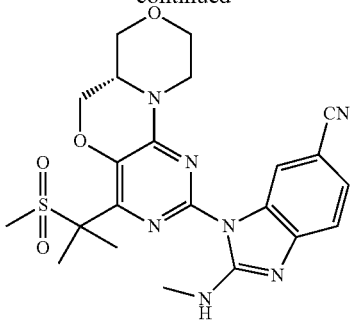

and tautomers, pharmaceutically acceptable salts, solvates and stereoisomers thereof.

Therapeutic Applications

As previously mentioned, the chemical entities of the present invention are potent and selective inhibitors of ATR. They are therefore useful in the treatment of disease conditions for which over-activity of ATR is a causative factor or where ATR activity is particularly necessary for the survival of the unhealthy cells.

Accordingly, the present invention provides a compound of formula (I) for use in medicine.

The present invention also provides for the use of a compound of formula (I) in the manufacture of a medicament for the treatment or prevention of a disease or condition in which ATR activity is implicated.

The present invention also provides a compound of formula (I) for use in the treatment or prevention of a disease or condition in which ATR activity is implicated.

The present invention also provides a method of treatment of a disease or condition in which ATR activity is implicated comprising administration to a subject in need thereof a therapeutically effective amount of a compound of formula (I).

In one aspect, the disease or condition in which ATR activity is implicated is cancer.

In one aspect, the disease or condition in which ATR activity is implicated is lung cancer, prostate cancer, melanoma, ovarian cancer, breast cancer, endometrial cancer, kidney cancer, gastric cancer, sarcomas, head and neck cancers, tumours of the central nervous system and their metastases, and also for the treatment of patients with acute myeloid leukaemia.

Other diseases or conditions in which ATR activity is implicated include, but are not limited to, haematological malignancies such as leukaemia, multiple myeloma, lymphomas such as Hodgkin's disease, non-Hodgkin's lymphomas (including mantle cell lymphoma), and myelodysplastic syndromes, and also solid tumours and their metastases such as breast cancer, lung cancer (non-small cell lung cancer (NSCLC), small cell lung cancer (SCLC), squamous cell carcinoma), endometrial cancer, tumours of the central nervous system such as gliomas, dysembryoplastic neuroepithelial tumour, glioblastoma multiforme, mixed gliomas, medulloblastoma, retinoblastoma, neuroblastoma, germinoma and teratoma, cancers of the gastrointestinal tract such as gastric cancer, oesophagal cancer, hepatocellular (liver) carcinoma, cholangiocarcinomas, colon and rectal carcinomas, cancers of the small intestine, pancreatic cancers, cancers of the skin such as melanomas (in particular metastatic melanoma), thyroid cancers, cancers of the head and neck and cancers of the salivary glands, prostate, testis, ovary, cervix, uterus, vulva, bladder, kidney (including renal cell carcinoma, clear cell and renal oncocytoma), squamous cell carcinomas, sarcomas such as osteosarcoma, chondrosarcoma, leiomyosarcoma, soft tissue sarcoma, Ewing's sarcoma, gastrointestinal stromal tumour (GIST), Kaposi's sarcoma, and paediatric cancers such as rhabdomyosarcomas and neuroblastomas.

The chemical entities of the present invention may be administered in combination with other therapeutic agents. In particular, chemical entities of the present invention may be administered in combination with cytotoxic agents. When combination therapy is employed, the chemical entities of the present invention and said combination agents may exist in the same or different pharmaceutical compositions, and may be administered separately, sequentially or simultaneously. The chemical entities of the present invention, and the other therapeutic agents may be present in a combination in any proportions For example, the combination product may contain from 0.01 wt % to 99.99 wt % of the chemical entities of the present invention, and may similarly contain from 0.01 wt % to 99.99 wt % of the other therapeutic agents.

Suitable agents to be used in combination include the following:

(i) antiproliferative/antineoplastic drugs and combinations thereof, as used in medical oncology such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem. 2004, 47, 6658-6661), and metalloproteinase inhibitors like marimastat and inhibitors of urokinase plasminogen activator receptor function);

(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD 1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or through the PI3K, mTOR and AKT kinases pathway;

(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SUI 1248 (sunitinib; WO 01/60814), and compounds that work by other mechanisms (for example linomide, inhibitors of integrin αvβ3 function and angiostatin)];

(vi) vascular damaging agents such as combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense agent;

(viii) gene therapy approaches, including approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapeutic approaches, including ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies; and (x) chromatin modifying agents that allow reversal of epigenetic alterations involved in carcinogenesis, for example, DNA demethylating agents such as 5' azacytidine and decitabine (5-aza-2'deoxycytidine, dezocitidine) and deacetylase inhibitors such as vorinostat (suberoylanilide hydroxamic acid, Zolinza) and depsipeptide (romidepsin, lstodax).

According to a further aspect of the invention, there is provided a combination product comprising:

(A) a compound of formula (I), or a pharmaceutically acceptable salt, solvate or stereoisomer thereof, as hereinbefore defined; and (B) another therapeutic agent that is useful in the treatment of cancer and/or a proliferative disease, wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:

(1) a pharmaceutical formulation including a compound of formula (I), or a pharmaceutically acceptable salt, solvate or stereoisomer thereof, as hereinbefore defined, another therapeutic agent that is useful in the treatment of cancer and/or a proliferative disease, and a pharmaceutically-acceptable adjuvant, diluent or carrier; and (2) a kit of parts comprising components:

(a) a pharmaceutical formulation including a compound of formula (I), or a pharmaceutically acceptable salt, solvate or stereoisomer thereof, as hereinbefore defined, in admixture with a pharmaceutically-acceptable adjuvant, diluent or carrier; and (b) a pharmaceutical formulation including another therapeutic agent that is useful in the treatment of cancer and/or a proliferative disease in admixture with a pharmaceutically-acceptable adjuvant, diluent or carrier, which components (a) and (b) are each provided in a form that is suitable for administration in conjunction with the other.

The invention further provides a process for the preparation of a combination product as hereinbefore defined, which process comprises bringing into association a compound of formula (I), or a pharmaceutically acceptable salt, solvate or stereoisomer thereof, as hereinbefore defined, with the other therapeutic agent that is useful in the treatment of cancer and/or a proliferative disease, and at least one pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

DEFINITIONS

The term "alkyl" includes saturated hydrocarbon residues including:

linear groups of 1 to 10 carbon atoms ($C_1$-$C_{10}$), or of 1 to 6 carbon atoms ($C_1$-$C_6$), or of 1 to 4 carbon atoms ($C_1$-$C_4$). Examples of such alkyl groups include, but are not limited, to $C_1$ (methyl), $C_2$ (ethyl), $C_3$ (propyl) and $C_4$ (butyl).

branched groups of from 3 to 10 (i.e. between 3 and 10) carbon atoms ($C_3$-$C_{10}$), or of up to 7 carbon atoms ($C_3$-$C_7$), or of up to 4 carbon atoms ($C_3$-$C_4$). Examples of such alkyl groups include, but are not limited to, $C_3$ (1-methylethyl), $C_4$ (1-methylpropyl, 2-methylpropyl, 1,1-dimethylethyl) and $C_5$—(1,1-dimethylpropyl, 2,2-dimethylpropyl, 3-methylbutyl, pentan-2-yl, pentan-3-yl).

each optionally substituted as stated above.

Unless otherwise stated, halo is selected from F, Cl, Br and I; in particular, halo is F.

Cycloalkyl is as defined above. Cycloalkyl groups may contain from 3 to 10 carbon atoms, or from 4 to 10 carbon atoms, or from 5 to 10 carbon atoms, or from 3 to 6 carbon atoms. Examples of suitable monocyclic cycloalkyl groups include cyclopropyl, cyclobutyl, cyclopentyl, cyclohexyl and cycloheptyl. Examples of suitable bicyclic cycloalkyl groups include decahydronaphthalene and octahydro-1H-indene. Cycloalkyl may be fused with aryl. Examples of suitable cycloalkyl groups, when fused with aryl, include indanyl and 1,2,3,4-tetrahydronaphthyl.

Heterocycloalkyl is a C-linked or N-linked 3 to 10 membered saturated, mono- or bi-cyclic ring, wherein said heterocycloalkyl ring may contain 1, 2, 3 or 4 heteroatoms independently selected from S, N and O, wherein an N or S atom in the ring may be substituted with oxygen to form an N-oxide, sulfoxide or sulfone group. Examples of suitable heterocycloalkyl groups include tetrahydrothiophene and, particularly, oxiranyl, aziridinyl, azetidinyl, tetrahydrofuranyl, pyrrolidinyl, tetrahydropyranyl, piperidinyl, N-methylpiperidinyl, morpholinyl, N-methyl morpholinyl, piperazinyl, N-methylpiperazinyl, azepanyl, oxazepanyl and diazepanyl.

Aryl is as defined above. Typically, aryl will be optionally substituted with 1, 2 or 3 substituents. Optional substituents are selected from those stated above. Examples of suitable aryl groups include phenyl and naphthyl (each optionally substituted as stated above).

Heteroaryl is as defined above. Typically, heteroaryl groups contain 5, 6, 9, 10, 12, 13 or 14 ring members wherein 1, 2, 3 or 4 ring members are independently selected from O, S and N. In one embodiment, a heteroaryl group may be 5, 6, 9 or 10 membered, e.g. 5-membered monocyclic, 6-membered monocyclic, 9-membered fused-ring bicyclic or 10-membered fused-ring bicyclic.

Monocyclic heteroaromatic groups include heteroaromatic groups containing 5-6 ring members wherein 1, 2, 3 or 4 ring members are independently selected from O, S and N.

Examples of suitable heteroaryl groups include indazolyl, pyrrolopyridinyl and, particularly, thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above).

The term "C-linked", such as in "C-linked heterocycloalkyl", means that the heterocycloalkyl group is joined to the remainder of the molecule via a ring carbon atom.

The term "N-linked", such as in "N-linked heterocycloalkyl", means that the heterocycloalkyl group is joined to the remainder of the molecule via a ring nitrogen atom.

The term "O-linked", such as in "O-linked hydrocarbon residue", means that the hydrocarbon residue is joined to the remainder of the molecule via an oxygen atom.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, succinates, oxalates, phosphates, esylates, tosylates, benzenesulfonates, naphthalenedisulphonates, maleates, adipates, fumarates, hippurates, camphorates, xinafoates, p-acetamidobenzoates, dihydroxybenzoates, hydroxynaphthoates, succinates, ascorbates, oleates, bisulfates and the like.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming pro-drugs are described in The Practice of Medicinal Chemistry, $2^{nd}$ Ed. pp 561-585 (2003) and in F. J. Leinweber, *Drug Metab. Res.*, 1987, 18, 379.

The chemical entities of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where chemical entities of the invention exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallization techniques). Where appropriate such isomers can be prepared by the application or adaptation of known methods (e.g. asymmetric synthesis).

In the context of the present invention, references herein to "treatment" include references to curative, palliative and prophylactic treatment.

General Methods

The chemical entities of formula (I) should be assessed for their biopharmaceutical properties, such as solubility and solution stability (across pH), permeability, etc., in order to select the most appropriate dosage form and route of administration for treatment of the proposed indication. They may be administered alone or in combination with one or more other chemical entities of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

Chemical entities of the invention intended for pharmaceutical use may be administered as a solid or liquid, such as a tablet, capsule or solution. Pharmaceutical compositions suitable for the delivery of chemical entities of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Accordingly, the present invention provides a pharmaceutical composition comprising a compound of formula (I) and a pharmaceutically acceptable carrier, diluent or excipient. The compound of formula (I) (or pharmaceutically acceptable salt, solvate or stereoisomer thereof), and the pharmaceutically acceptable carrier, diluent or excipient may be present in the composition in any proportions For example, the pharmaceutical composition may contain from 0.01 wt % to 99.99 wt % of the compound of formula (I), and may similarly contain from 0.01 wt % to 99.99 wt % of the pharmaceutically acceptable carrier, diluent or excipient. Where m is 1, the (S) enantiomer of the compound of formula (I) may be present in the composition at 90% enantiomeric excess or greater, preferably, at 95% enantiomeric excess or greater. Where m is 2, the (R) enantiomer of the compound of formula (I) may be present in the composition at 90% enantiomeric excess or greater, preferably, at 95% enantiomeric excess or greater.

The chemical entities of the invention may also be administered directly into the blood stream, into subcutaneous tissue, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous or oily solutions. Where the solution is aqueous, excipients such as sugars (including but not restricted to glucose, manitol, sorbitol, etc.), salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Parenteral formulations may include implants derived from degradable polymers such as polyesters (i.e., polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilization, may readily be accomplished using standard pharmaceutical techniques well known to those skilled in the art.

The solubility of chemical entities of formula (I) used in the preparation of parenteral solutions may be increased by the use of appropriate formulation techniques, such as the incorporation of co-solvents and/or solubility-enhancing agents such as surfactants, micelle structures and cyclodextrins.

In one embodiment, the chemical entities of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the chemical entities of the invention in an immediate release manner or in a rate-sustaining manner, wherein the release profile can be delayed, pulsed, controlled, sustained, or delayed and sustained or modified in such a manner which optimizes the therapeutic efficacy of the said chemical entities. Means to deliver chemical entities in a rate-sustaining manner are known in the art and include slow release polymers that can be formulated with the said chemical entities to control their release.

Examples of rate-sustaining polymers include degradable and non-degradable polymers that can be used to release the said chemical entities by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The chemical entities of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

For administration to human patients, the total daily dose of the chemical entities of the invention is typically in the range of from 0.01 mg and 1000 mg, or from 0.1 mg and 250 mg, or from 1 mg and 50 mg depending, of course, on the mode of administration.

The total dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Synthetic Methods

The chemical entities of the present invention can be prepared according to the procedures of the following schemes and examples, using appropriate materials, and are further exemplified by the specific examples provided herein below. Moreover, by utilizing the procedures described herein, one of ordinary skill in the art can readily prepare additional chemical entities that fall within the scope of the present invention claimed herein. The chemical entities illustrated in the examples are not, however, to be construed as forming the only genus that is considered as the invention. The examples further illustrate details for the preparation of the chemical entities of the present invention. Those skilled in the art will readily understand that known variations of the conditions and processes of the following preparative procedures can be used to prepare these chemical entities.

The chemical entities of the invention may be isolated in the form of their pharmaceutically acceptable salts, such as those described previously herein above.

It may be necessary to protect reactive functional groups (e.g. hydroxy, amino, thio or carboxy) in intermediates used in the preparation of chemical entities of the invention to avoid their unwanted participation in a reaction leading to the formation of the chemical entities. Conventional protecting groups, for example those described by T. W. Greene and P. G. M. Wuts in "Protective groups in organic chemistry" John Wiley and Sons, 4th Edition, 2006, may be used. For example, a common amino protecting group suitable for use herein is tert-butoxy carbonyl (Boc), which is readily removed by treatment with an acid such as trifluoroacetic acid or hydrogen chloride in an organic solvent such as dichloromethane. Alternatively the amino protecting group may be a benzyloxycarbonyl (Z) group which can be removed by hydrogenation with a palladium catalyst under a hydrogen atmosphere or 9-fluorenylmethyloxycarbonyl (Fmoc) group which can be removed by solutions of secondary organic amines such as diethylamine or piperidine in an organic solvents. Carboxyl groups are typically protected as esters such as methyl, ethyl, benzyl or tert-butyl which can all be removed by hydrolysis in the presence of bases such as lithium or sodium hydroxide. Benzyl protecting groups can also be removed by hydrogenation with a palladium catalyst under a hydrogen atmosphere whilst tert-butyl groups can also be removed by trifluoroacetic acid. Alternatively a trichloroethyl ester protecting group is removed with zinc in acetic acid. A common hydroxy protecting group suitable for use herein is a methyl ether, deprotection conditions comprise refluxing in 48% aqueous HBr for 1-24 hours, or by stirring with borane tribromide in dichloromethane for 1-24 hours. Alternatively where a hydroxy group is protected as a benzyl ether, deprotection conditions comprise hydrogenation with a palladium catalyst under a hydrogen atmosphere.

The chemical entities according to general formula (I) can be prepared using conventional synthetic methods for example, but not limited to, the routes outlined in Scheme 1.

Scheme 1
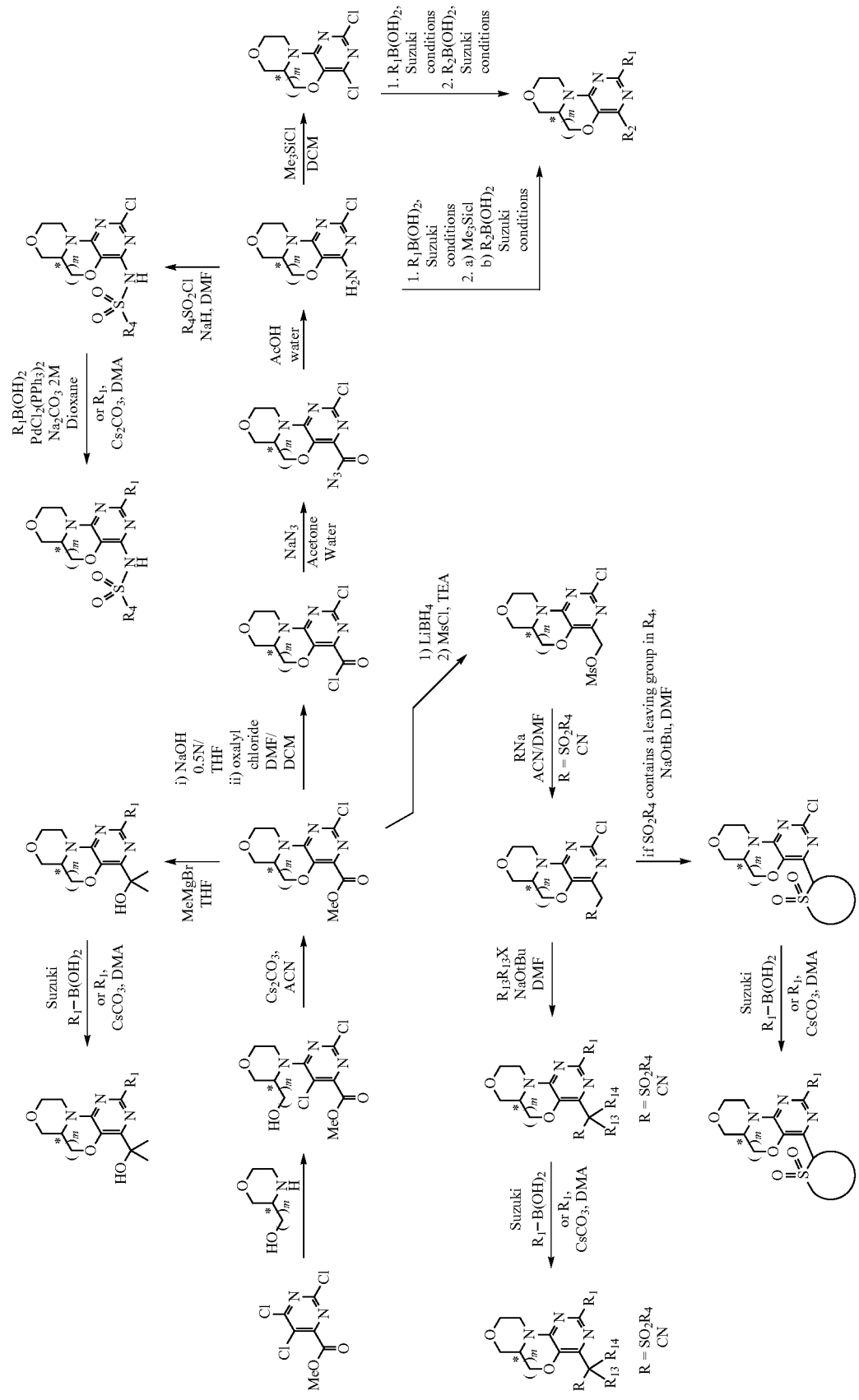

In scheme 1, * indicates a chiral centre.

Methods of making other compounds according to Formula (I) will be apparent to the person skilled in the art.

BRIEF DESCRIPTION OF DRAWINGS

FIG. 3(A) shows the effect of chemical entities Example 1 and Example 2, alone or in combination with HU, on the progression of cells through the G2/M checkpoint. FIG. 3(B) shows the effect of chemical entities Example 3 and Example 11 on the progression of cells through the S phase.

FIG. 4(A) shows the effect of chemical entities Example 1 and Example 2, alone or in combination with HU, on the formation of nuclear foci of the DNA repair protein 53BP1.

EXAMPLES

Figure 1A:
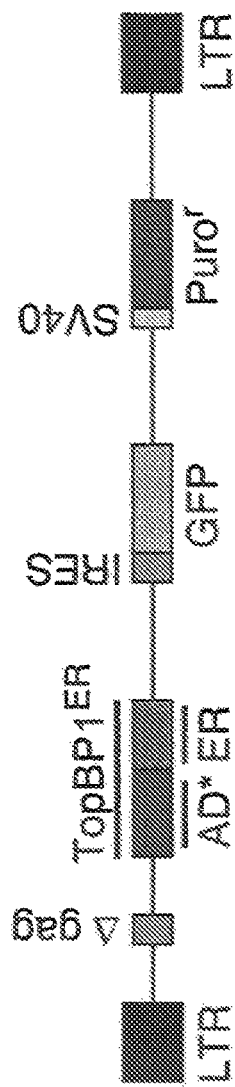
FIG. 1 shows the inhibition of ATR in living cells by chemical entities Example 1, Example 2, Example 3 and Example 11 and the effect of caffeine, an ATR inhibitor.
Figure 1B:
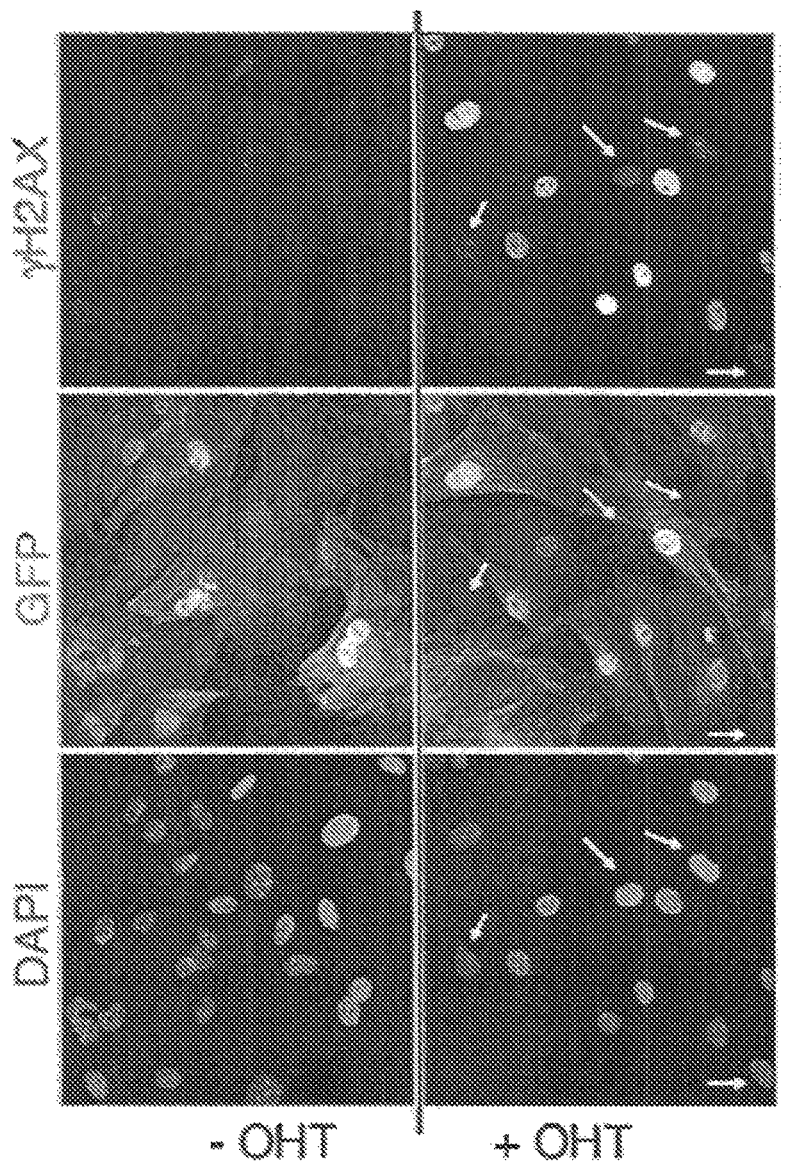
Figures 1D, 1E:
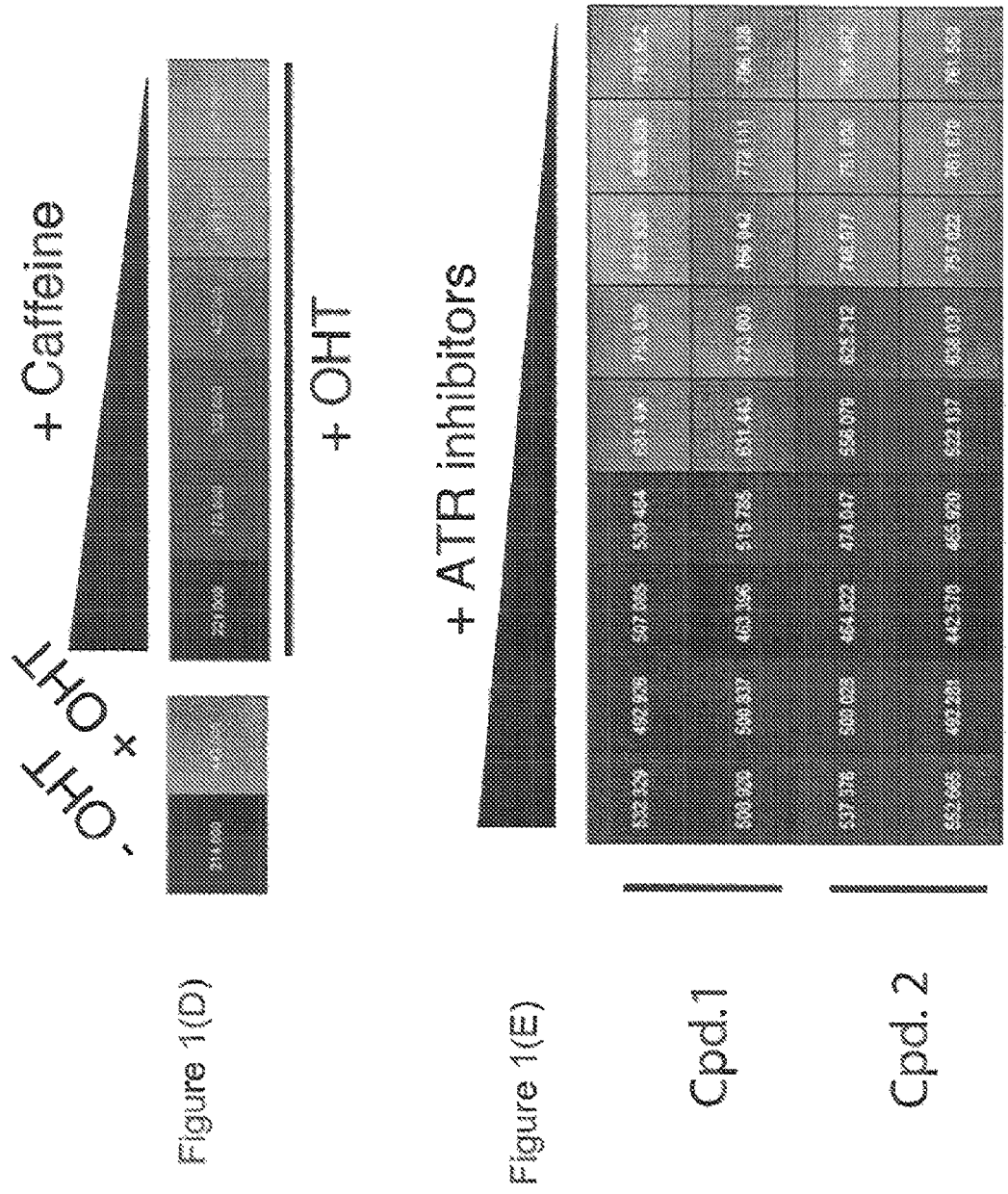
Figure 1H:
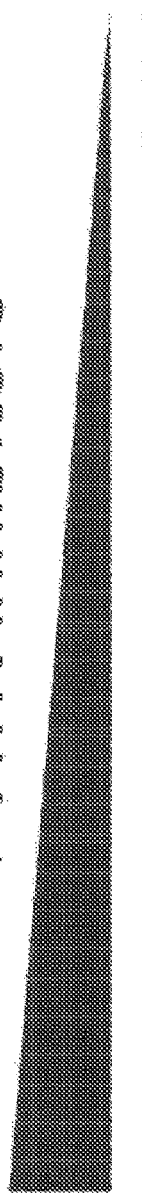
Figure 1K:
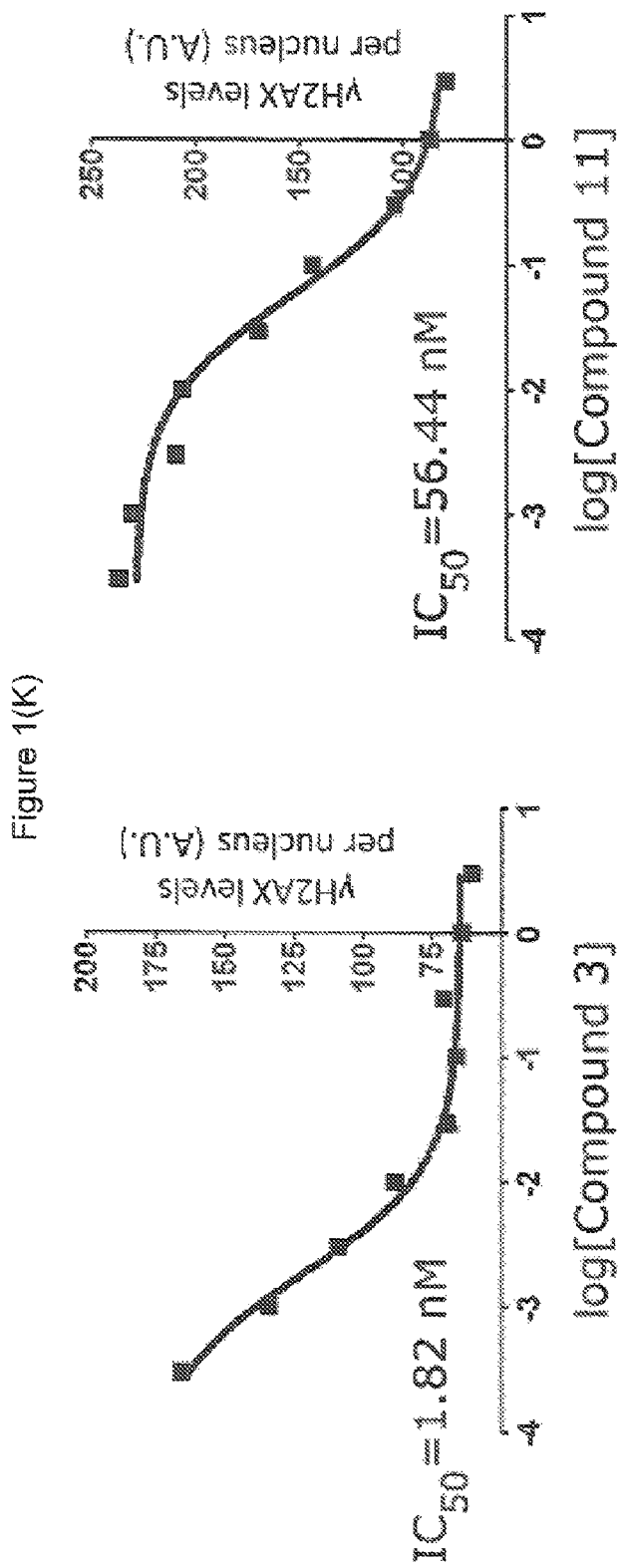

The invention is illustrated by the following non-limiting examples of synthesis, characterization and biological testing, in which the following abbreviations and definitions are used:

Herein after, the term "DCM" means dichloromethane, "CHCl$_3$" means chloroform, "MeOH" means methanol, "EtOH" means ethanol, "EtOAc" means ethyl acetate, "THF" means tetrahydrofuran, "AcCN" means acetonitrile, "DMAP" means 4-dimethylaminopyridine, "DIPEA" means diisopropylethylamine, "DMF" means dimethylformamide, "DME" means dimetoxyethane, "DMA" means dimethylacetamide, "DMSO" means dimethylsulfoxide, "Et$_2$O" means diethyl ether, "Hex" means hexane, "EtOAc" means ethyl acetate, "BA/BE" means boronic acid/ester, "Pd(PPh$_3$)$_4$" means tetrakis(triphenylphosphine)palladium, "Pd(Ph$_3$P)$_2$Cl$_2$" means dichlorobis(triphenylphosphine)palladium(II), "Pd(dppf)Cl$_2$.DCM" means 1,1'-bis(diphenylphosphino)ferrocenepalladium(II) dichloride, dichloromethane complex, "CDI" means carbonyldiimidazol, "Na$_2$SO$_4$" means disodium sulphate, "MgSO$_4$" means magnesium sulphate, "K$_2$CO$_3$" means dipotassium carbonate, "Na$_2$CO$_3$" means disodium carbonate, "NaHCO$_3$" means sodium bicarbonate, "NaH" means sodium hydride, "TEA" means triethylamine, "POCl$_3$" means phosphorus oxychloride, "TFA" means trifluoroacetic acid, "TBAF" means tetrabutylammonium fluoride, "sat." means saturated, "aq." means aqueous, "Ar" means argon, "HPLC" means high performance liquid chromatography, "t$_R$" means retention time, "MS" means mass spectrometry, "TLC" means thin layer chromatography, "R$_f$" means retardation factor, "g" means gram(s), "mmol" means millimole(s), "eq" means equivalent(s), "mL" means milliliter(s), "min" means minute(s), "h" means hour(s), "rt" means room temperature.

Characterization

NMR spectra were recorded on a Bruker Avance II 300 spectrometer and Bruker Avance II 700 spectrometer fitted with 5 mm QXI 700 S4 inverse phase, Z-gradient unit and variable temperature controller.

The HPLC measurements were performed using a HP 1100 from Agilent Technologies comprising a pump (binary) with degasser, an autosampler, a column oven, a diode-array detector (DAD) and a column as specified in the respective methods below. Flow from the column was split to a MS spectrometer. The MS detector was configured with an electrospray ionization source or API/APCI. Nitrogen was used as the nebulizer gas. Data acquisition was performed with ChemStation LC/MSD quad, software.

HPLC Method 1 (LC-MS1):

Reversed phase HPLC was carried out on a Gemini-NX C18 (100×2.0 mm; 5 um), Solvent A: water with 0.1% formic acid; Solvent B: acetonitrile with 0.1% formic acid. Gradient: 5% of B to 100% of B within 8 min at 50° C., DAD.

HPLC Method 2 (LC-MS2):

Reversed phase HPLC was carried out on a Gemini-NX C18 (100×2.0 mm; 5 um), Solvent A: water with 0.1% formic acid; Solvent B: acetonitrile with 0.1% formic acid. Gradient: 50% of B to 100% of B within 8 min at 50° C., DAD.

HPLC Method 3 (LC-MS3):

Reversed phase HPLC was carried out on a Gemini-NX C18 (100×2.0 mm; 5 um), Solvent A: water with 0.1% formic acid; Solvent B: acetonitrile with 0.1% formic acid. Gradient: 5% of B to 40% of B within 8 min at 50° C., DAD.

HPLC Method 4 (LC-MS4):

Reversed phase HPLC was carried out on a Gemini C18 column (50×2 mm, 3 um); Solvent A: water with 0.1% formic acid; Solvent B: acetonitrile with 0.1% formic acid. Gradient: 10-95% of B within 4 min at a flow rate of 0.5 mL/min followed by 2 min of 100% of B at 0.8 mL/min, controlled temperature at 50° C., DAD.

HPLC Method 5 (LC-MS5):

Reversed phase HPLC was carried out on a Gemini C18 column (50×2 mm, 3 um); Solvent A: water with 10 mM ammonium bicarbonate; Solvent B: acetonitrile. Gradient: 20-100% of B within 3 min at a flow rate of 0.5 mL/min followed by 2 min of 100% of B at 0.8 mL/min, controlled temperature at 40° C., DAD.

HPLC Method 6 (LC-MS6):

Reversed phase HPLC was carried out on a Gemini-NX C18 (100×2.0 mm; 5 um), Solvent A: water with 0.1% formic acid; Solvent B: acetonitrile with 0.1% formic acid. Gradient: 0% of B to 30% of B within 8 min at 50° C., DAD.

"Found mass" refers to the most abundant isotope detected in the HPLC-MS.

Optical Value: The optical value was measured in a digital Perkin Elmer 241 with a cell of 1 dm of length.

Example 1

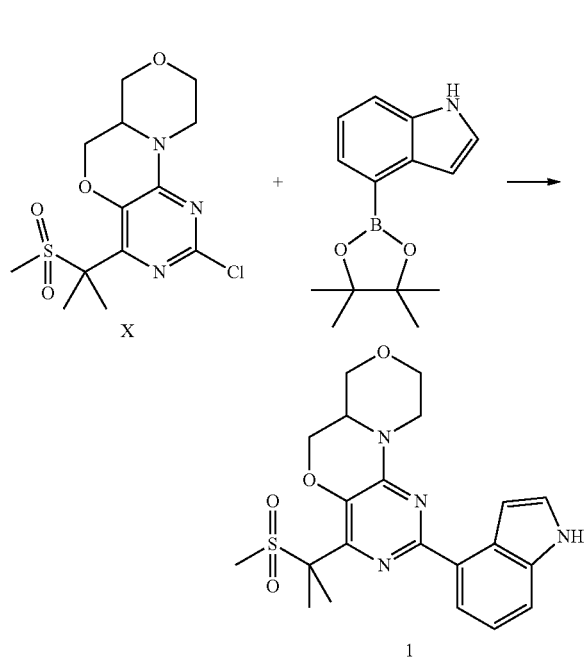

A mixture of intermediate X (100 mg, 0.30 mmol) with indole-4-boronic acid pinacol ester (90 mg, 0.37 mmol), dichlorobis(triphenylphosphine)palladium(ii) (40 mg) and a 2M aqueous solution of $Na_2CO_3$ (0.4 mL) in dioxane (2 mL), was heated in a high pressure tube for 3 h. The dark mixture was cooled down to rt, diluted with water (20 mL) and extracted with EtOAc (2×15 mL). The organic layers were washed with brine, dried over $Na_2SO_4$ and concentrated in vacuo. The crude was purified first by flash column chromatography (Isolute Si II 5 g) eluting with a solvent system of EtOAc/cyclohexane (from 50% to 100% on EtOAc) and then with $NH_3$ 7 M in MeOH/DCM (from 0% to 10% on $NH_3$). Required product was recovered as cream solid that was tritured several times with diethylether to obtain 12 mg of Example 1.

1H NMR (300 MHz, DMSO) δ 7.89 (d, J=7.4 Hz, 1H), 7.44 (d, J=8.0 Hz, 1H), 7.36 (d, J=2.8 Hz, 1H), 7.24 (d, J=2.8 Hz, 1H), 7.11 (t, J=7.8 Hz, 1H), 4.53 (d, J=12.6 Hz, 1H), 4.33 (d, J=10.9 Hz, 1H), 4.00 (d, J=11.4 Hz, 1H), 3.89-3.82 (m, 2H), 3.70 (d, J=9.8 Hz, 1H), 3.50 (t, J=10.6 Hz, 1H), 3.19-3.02 (m, 2H), 2.89 (s, 3H), 1.83 (s, 3H), 1.81 (s, 3H).

LC-MS1: tR=4.88 min, M+1=429.0.

Intermediate X

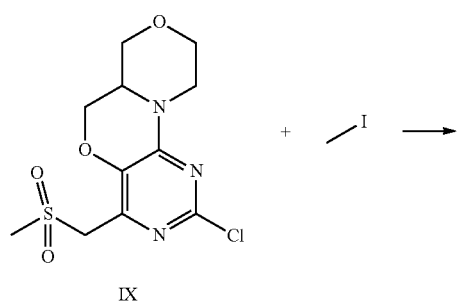

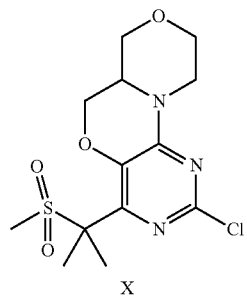

To a cooled (−5° C.) solution of intermediate IX (100 mg, 0.3 mmol) in DMF (1 mL) was added sodium tert-butoxide (35 mg, 0.3 mmol) and MeI (20 μL, 0.3 mmol). After 10 min stirring more sodium tert-butoxide (35 mg, 0.3 mmol) and MeI (35 μL, 0.3 mmol) were added. The resulting mixture was stirred at 0° C. for 1 h and at it for 3 h. The mixture was diluted with DCM (5 mL), washed with 1 M aqueous solution of HCl (2×15 mL). The combined organic layers were washed with brine, dried over $Na_2SO_4$ and concentrated in vacuo. The yellow residue recovered resulted required product X that was used further without additional purification (75 mg).

Intermediate IX

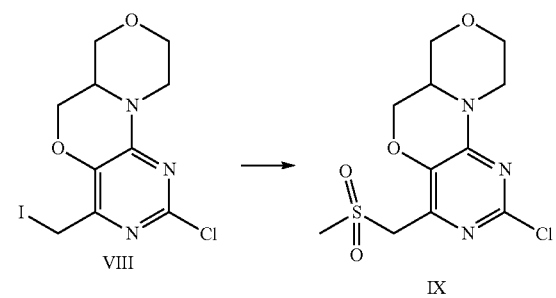

A mixture of intermediate VIII (800 mg, 2.1 mmol) and sodium methanesulfinate (200 mg, 3.8 mmol) in DMF (8 mL) was stirred at rt for 2 h. The mixture was quenched by addition of aqueous 1 M solution of $Na_2SO_3$. The mixture was extracted with DCM (3×25 mL). The combined organic layers were dried over $Na_2SO_4$ and concentrated in vacuo, leaving required product as cream solid, intermediate IX (550 mg).

Intermediate IX can be also synthesized directly from intermediate VI and VII. A mixture of VI and VII (400 mg) with sodium methanesulfinate (150 mg, 1.4 mmol) in AcCN/DMF (10 mL, 4:1) was heated at 80° C. for 18 h. The reaction mixture was quenched by the addition of sat. aq. $Na_2S_2O_3$ and extracted three times with DCM (3×20 mL). The combined organic layers were dried over $Na_2SO_4$ and concentrated in vacuo. The cream solid, intermediate IX was used into next step without additional purification, 320 mg.

Intermediate VIII

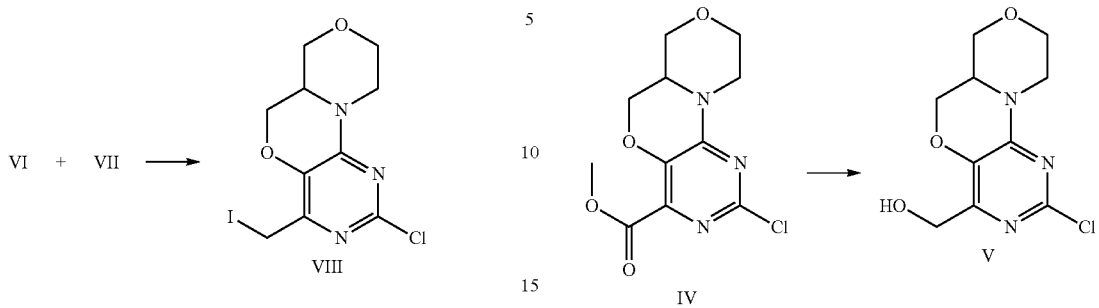

A mixture of mixture VI, VII (800 mg) and lithium iodide (730 mg, 5.4 mmol) in dioxane (6 mL) was heated at reflux for 3 h. The mixture was cooled down to rt and water and brine were added. The mixture was extracted with EtOAc (3×20 mL). The combined organic layers were washed with brine, dried over $Na_2SO_4$, and concentrated in vacuo. The product obtained was used further without additional purification, as intermediate VIII (1 g, quantitative).

Intermediate VI and VII

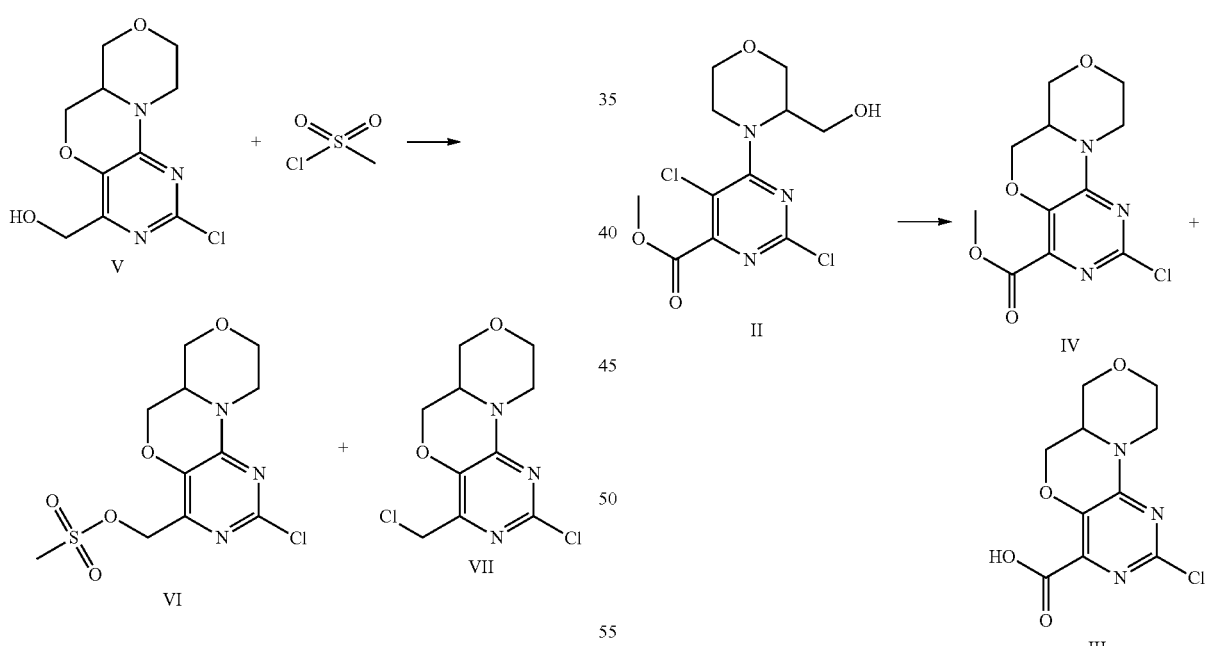

To a solution of intermediate V (800 mg) in DCM (20 mL) with TEA (0.650 mL, 4.6 mmol) was added dropwise methanesulfonyl chloride (0.290 mL, 3.7 mmol). The resulting mixture was stirred at rt for 1 h and quenched by addition of sat. $NaHCO_3$. The different layers were separated, and the aqueous layer was extracted with DCM (3×15 mL). The combined organic layers were washed with brine (30 mL), dried over $Na_2SO_4$ and concentrated, in vacuo. The residue obtained (800 mg) was a mixture of intermediate VI and VII, but it was used further into next step without additional purification.

Intermediate V

To two solutions of intermediate IV (400 mg, 1.4 mmol) in THF (40 mL) cooled to 0° C. was added a solution of lithium borohydride 2 M in THF (1 mL). The resulting mixtures were stirred at 0° C. for 15 min and at rt for 1 h. The two mixtures were quenched by addition of water, mixed and extracted with EtOAc (3×50 mL). The combining organic layers were washed with brine, dried over $Na_2SO_4$ and concentrated in vacuo. Required product was obtained as white solid, intermediate V (800 mg) and used into next step without additional purification.

Intermediate III, IV

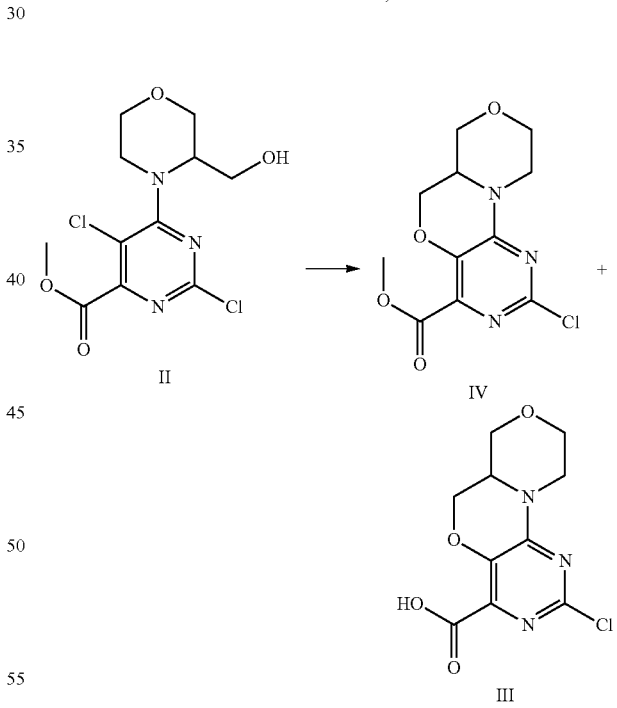

To a solution of intermediate II (1.860 g, 5.7 mmol) in THF (280 mL) was added in one pot NaH (60% suspension on mineral oil, 276 mg). The resulting mixture was stirred at 60° C. for 5 h, more NaH (60 mg) was added continuing the heating for 3 h. The mixture was cooled down to rt, quenched by addition of water/ice and solvents removed partially in the rotavap. The mixture was diluted with some water and extracted with EtOAc (3×20 mL). The combined organic layer were washed with brine, dried over $Na_2SO_4$ and concentrated in vacuo.

The crude was triturated with MeOH, filtered out and the filtrate was concentrated in vacuo. The filtrate was purified by flash column chromatography eluting with a solvent system of EtOAc/cychlohexane (from 25% to 100% on EtOAc), but very small amount of required product IV (30 mg) was recovered.

The aqueous layer was acidified and extracted with DCM (3×50 mL). The combined organic layers were dried over $Na_2SO_4$ and concentrated in vacuo, leaving a white solid, that resulted intermediate III (1.2 g).

To a suspension of Intermediate III (500 mg) in MeOH (25 mL) was added a solution of (trimethylsilyl)diazomethane 2 M in THF (3 mL). The resulting mixtures were stirred at it for 3 h, and more trimethylsilyldiazomethane 2 M in THF (2.5 mL) was added. The stirring at it continued for 5 h. The reactions were quenched by addition of water, combined and extracted with EtOAc (2×50 mL). The combined organic layers were washed with brine (20 mL), dried over $Na_2SO_4$ and concentrated in vacuo, leaving the required product as intermediate IV, light cream solid (740 mg, 70%).

Intermediate IV can be synthesized also from intermediate II using cesium carbonate as base in AcCN under heating till completion of the reaction.

Intermediate II

Intermediate I

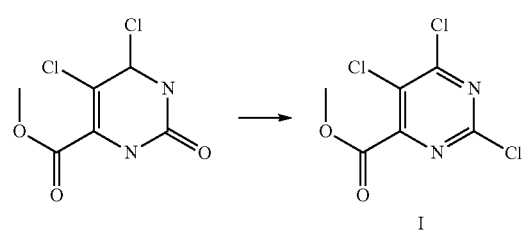

Phosphorus oxychloride (150 mL) were added dropwise to methyl 5-chloro-2,6-dioxo-3h-pyrimidine-4-carboxylate (5 g, 24 mmol) using a compensation pression funnel for 30 min at 0° C. After N,N-diethylaniline (5 mL, 32 mmol) was added. The resulting mixture was warmed to room temperature and heated at reflux for 18 h. The brown mixture was cooled down to it and excess of $POCl_3$ was removed under reduced pressure. The oily residue was poured onto ice/water and extracted with diethyl ether (3×20 mL). The combined organic layers were washed with brine, dried over $Na_2SO_4$ and concentrated in vacuo. The brown solid was triturated with cyclohexane, leaving a brown-pink solid, as intermediate I (4 g, 78%).

Example 2

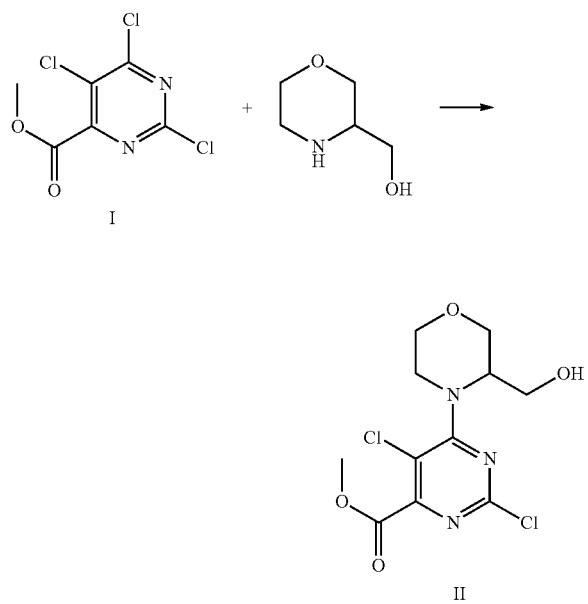

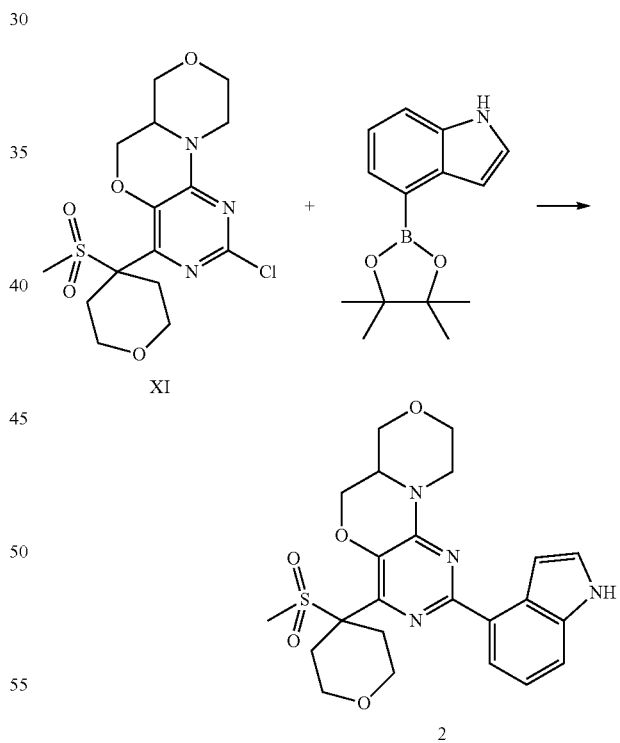

A mixture of I (1.5 g, 6.2 mmol) and (rac) 3-hydroxymethylmorpholine (875 mg, 7.4 mmol) with DIPEA (1.6 mL, 9.3 mmol) in EtOH (30 mL) was heated at 75° C. for 1 h 30 min. The mixture was cooled down to rt and solvents were removed in vacuo. The oily residue was redissolved in DCM (20 mL), washed with sat. solution of $NaHCO_3$ (3×20 mL), brine (30 mL), dried over $Na_2SO_4$ and concentrated in vacuo. Required product, intermediate II (1.860 g, 93%) was used further without additional purifications.

Example 2 was synthesized following a similar protocol to Example 1 by coupling of intermediate XI with indole-4-boronic acid pinacol ester.

1H NMR (300 MHz, DMSO) δ 7.88 (d, J=7.4 Hz, 1H), 7.44 (d, J=8.0 Hz, 1H), 7.35 (d, J=3.0 Hz, 1H), 7.24-7.03 (m, 2H), 4.56 (d, J=12.3 Hz, 1H), 4.31 (dd, J=10.8, 3.1 Hz, 1H), 4.00 (d, J=11.3 Hz, 1H), 3.85-3.78 (m, 5H), 3.52-3.58 (m, 1H), 3.31-3.02 (m, 6H), 2.89 (s, 3H) 2.10-2.02 (m, 2H).

LC-MS1: tR=4.54 min, M+1=471.0

Intermediate XI

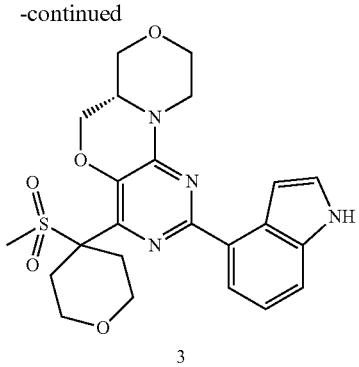

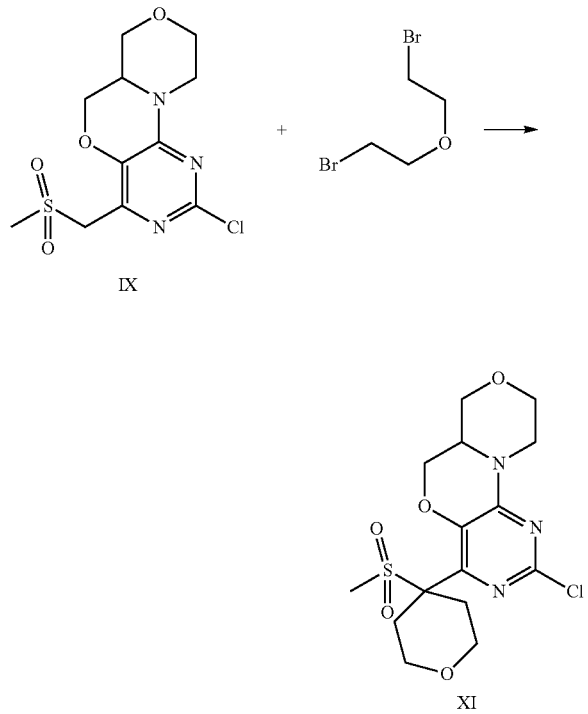

To a cooled (0° C.) solution of intermediate IX (75 mg, mmol) in DMF (3 mL) with bis(2-bromoethyl) ether (75 μL, mmol) was added $^t$BuONa (55 mg) in one pot. The resulting mixture was stirred at rt for 5 h. More $^t$BuONa (25 mg) was added stirring at rt for 22 h. The mixture was diluted with EtOAc and water. The organic layer was separated and washed with water (3×10 mL), dried over Na$_2$SO$_4$ and concentrated in vacuo. The crude, intermediate XI (100 mg) was used further into next step without additional purifications.

Example 3

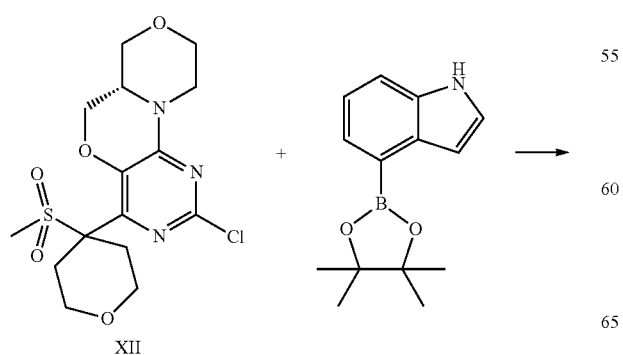

Example 3 was synthesized following a similar protocol to the one used for Example 1 by coupling of intermediate XII with indole-4-boronic acid pinacol ester.

1H NMR (300 MHz, DMSO) δ 11.14 (s, 1H), 7.87 (d, J=7.5 Hz, 1H), 7.44 (d, J=7.5 Hz, 1H), 7.42 (bs, 1H), 7.23 (bs, 1H), 7.16 (d, t=7.8 Hz, 1H), 4.55 (d, J=12.9 Hz, 1H), 4.31 (dd, J=10.7, 3.2 Hz, 1H), 4.00 (d, J=11.2 Hz, 1H), 3.93-3.62 (m, 5H), 3.51 (t, J=10.6 Hz, 1H), 3.23-3.05 (m, 5H), 2.79 (s, 3H), 2.11-2.05 (m, 2H).

LC-MS1: tR=4.55 min, M+1=471.0.

$[α]_D$=+40 (c 0.273, CHCl$_3$/MeOH 9:1).

Intermediate XII

Intermediate XII was synthesized following a similar synthetic protocol than the one used for the synthesis of intermediate XI, but using in step 1, 3(R)-hydroxymethyl-morpholine hydrochloride. Intermediate XIV, $[α]_D$=+29 (c 0.52, CHCl$_3$/MeOH 9:1).

Example 4

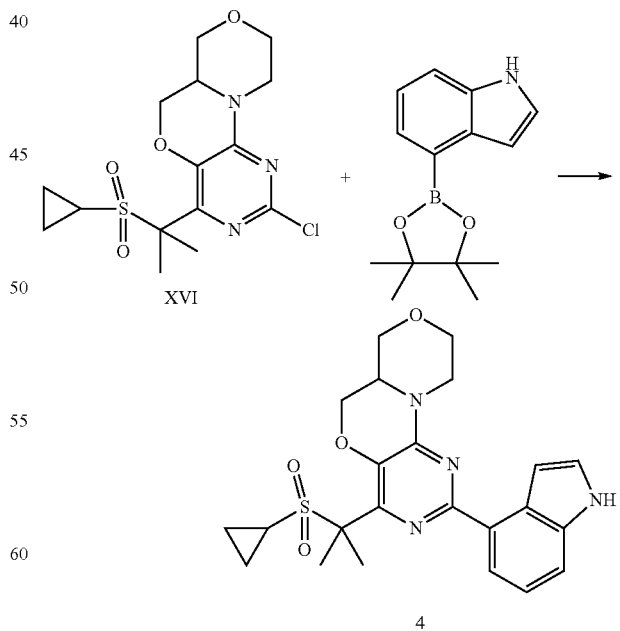

Example 4 was synthesized following a similar protocol to the one used for Example 1 by coupling of intermediate XVI with indole-4-boronic acid pinacol ester.

1H NMR (300 MHz, DMSO) δ 11.12 (s, 1H), 7.91 (d, J=7.6 Hz, 1H), 7.41 (d, J=7.9 Hz, 1H), 7.35 (bs, 1H), 7.27 (bs, 1H), 7.09 (t, J=7.8 Hz, 1H), 4.53 (d, J=12.1 Hz, 1H), 4.32 (dd, J=11.0, 3.3 Hz, 1H), 3.98 (d, J=8.0 Hz, 1H), 3.92-3.74 (m, 2H), 3.69-3.65 (m, 1H), 3.49-3.44 (m, 1H), 3.21-2.96 (m, 2H), 2.65-2.60 (m, 1H), 1.88 (s, 6H), 0.92-0.67 (m, 4H).

LC-MS1: tR=5.18 min, M+1=455.0.

Intermediate XVI

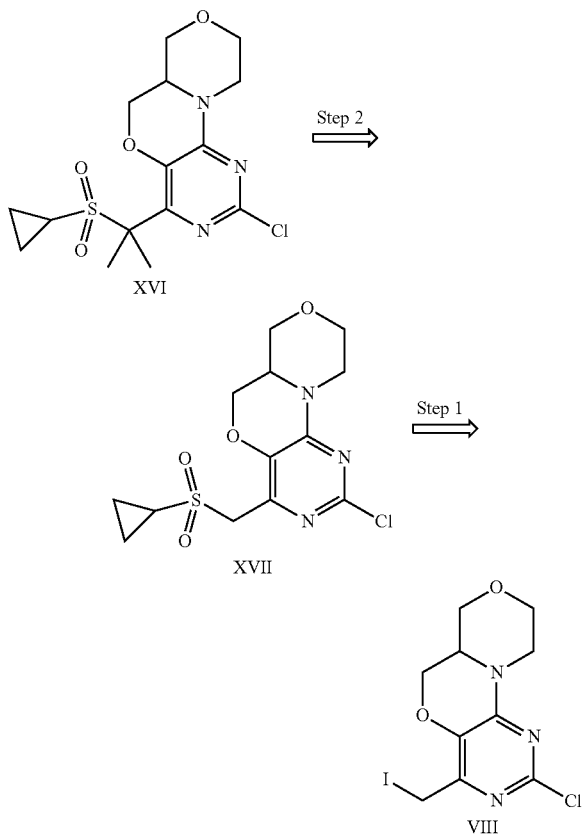

Intermediate XVI was synthesized following a similar protocol to the one used for Intermediate X by alkylation reaction with methyl iodide of intermediate XVII.

Intermediate XVII was synthesized following a similar protocol to the one used for Intermediate IX by reaction of VIII with sodium cyclopropanesulfinate.

Example 5

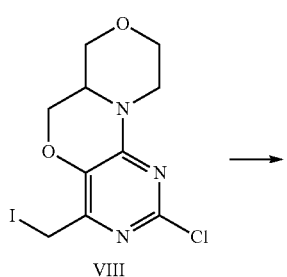

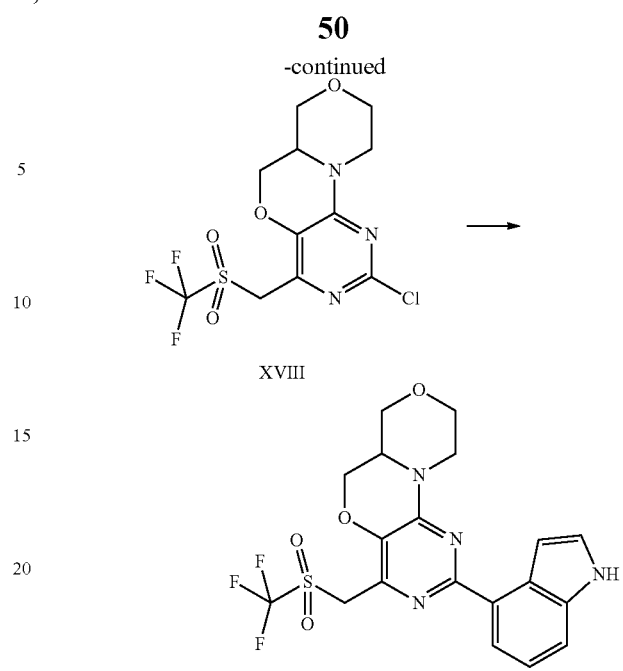

Compound 5 was synthesized following a similar protocol to the one used for Product 1 by coupling of intermediate XVIII with indole-4-boronic acid pinacol ester.

1H NMR (300 MHz, DMSO) δ 7.93 (d, J=7.4 Hz, 1H), 7.45 (d, J=7.9 Hz, 1H), 7.39-7.32 (m, 2H), 7.12 (t, J=7.8 Hz, 1H), 4.58-4.35 (m, 2H), 4.01 (d, J=8.5 Hz, 1H), 3.89-3.84 (m, 2H), 3.74-3.70 (m, 1H), 3.65-3.55 (m, 2H), 3.53-3.50 (m, 1H), 3.27-3.02 (m, 2H).

LC-MS1: tR=5.29 min, M+1=455.0

Intermediate XVIII was prepared by reaction of intermediate VIII with sodium trifluoromethanesulfinate in DMF at 80° C. for 2 h.

Example 6

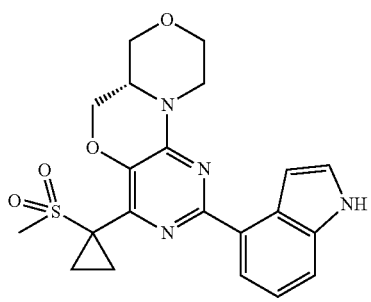 [SMILES: CS(=O)(=O)C1(c2nc(-c3cccc4[nH]ccc34)nc3c2OC[C@@H]2COCCN32)CC1]

Example 6 was synthesized following a similar synthetic route to the one used for example 27, using as precursor 3(R)-hydroxymethylmorpholine.

LC-MS1: tR=4.77 min, M+1=427.1.

¹H NMR (300 MHz, DMSO) δ 11.21 (s, 1H), 7.98 (d, J=7.4 Hz, 1H), 7.48 (d, J=7.9 Hz, 1H), 7.45-7.31 (m, 2H), 7.16 (t, J=7.8 Hz, 1H), 4.53 (m, 1H), 4.43 (m, 1H), 4.06 (m, 1H), 4.05-3.90 (m, 2H), 3.74 (m, 1H), 3.56 (m, 1H), 3.29-3.11 (m, 2H), 3.09 (s, 3H), 1.71 (m, 2H), 1.43 (m, 2H).

Example 7

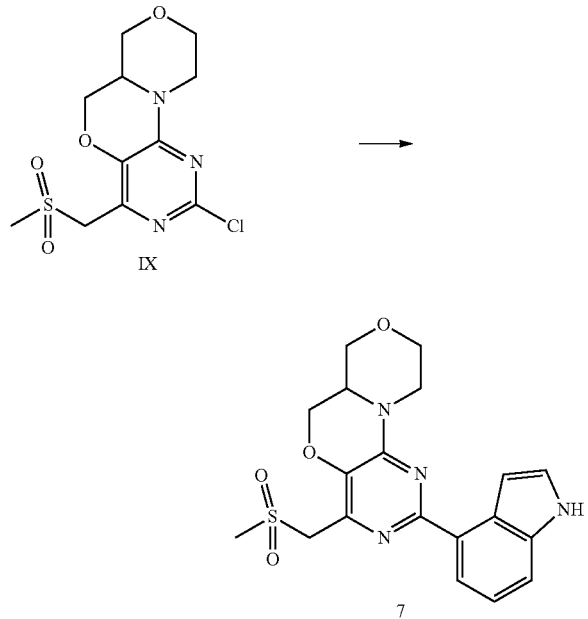

Example 7 was synthesized following a similar protocol to the one used for Example 1 by coupling of intermediate IX with indole-4-boronic acid pinacol ester.

1H NMR (300 MHz, DMSO) δ 7.96 (d, J=7.4 Hz, 1H), 7.49 (d, J=8.0 Hz, 1H), 7.39 (d, J=3.0 Hz, 1H), 7.35 (d, J=3.0 Hz, 1H), 7.16 (t, J=7.8 Hz, 1H), 4.64-4.31 (m, 4 H), 4.11-4.00 (m, 1H), 4.02-3.84 (m, 2H), 3.77-3.74 (m, 1H), 3.57 (t, J=11.7 Hz, 1H), 3.22 (t, J=10.9 Hz, 1H), 3.15 (s, 3H), 3.13-3.03 (m, 1H).

LC-MS1: tR=3.64 min, M+1=401.2

Example 8

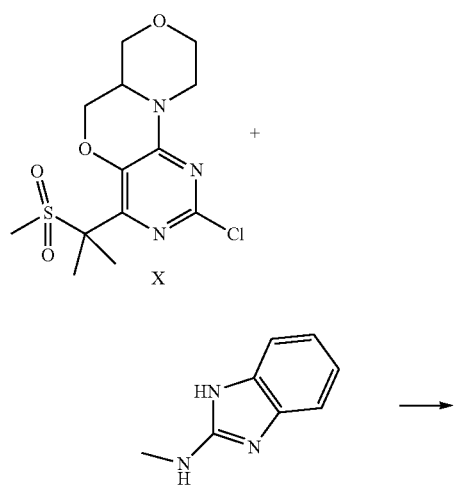

A mixture of intermediate X (50 mg, 0.14 mmol) and N-methyl-1H-1,3-benzodiazol-2-amine (45 mg, 0.28 mmol) with $Cs_2CO_3$ (140 mg, 0.43 mmol) in DMA (2 mL) was heated in a high pressure tube for 7 days. The mixture was cooled down to rt filtered and concentrated in vacuo. The oily residue was redissolved in EtOAc (25 mL) washed with water (3×20 mL) and brine (30 mL). The organic layer was dried over $Na_2SO_4$ and concentrated in vacuo.

The crude was purified by flash column chromatography (Isolute Si II 5 g) eluting with a solvent system of EtOAc/cyclohexane (from 50% to 100% on EtOAc). Example 8 was recovered clean, (10 mg, 15%).

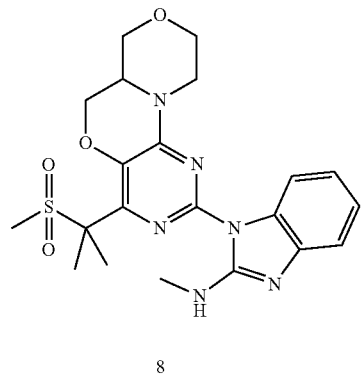

1H NMR (300 MHz, DMSO) δ 8.14 (q, J=4.8 Hz, 1H), 8.00 (d, J=7.8 Hz, 1H), 7.25 (d, J=7.7 Hz, 1H), 7.07 (t, J=7.5 Hz, 1H), 6.98 (t, J=7.7 Hz, 1H), 4.44-4.38 (m, 2H), 4.15-3.77 (m, 4H), 3.57 (t, J=10.8 Hz, 1H), 3.23 (t, J=10.8 Hz, 2H3.03 (s, 3H), 3.02 (d, J=5.0 Hz, 3H), 1.83 (s, 3H), 1.82 (s, 3H).

LC-MS1: tR=3.03 min, M+1=459.0.

Example 9

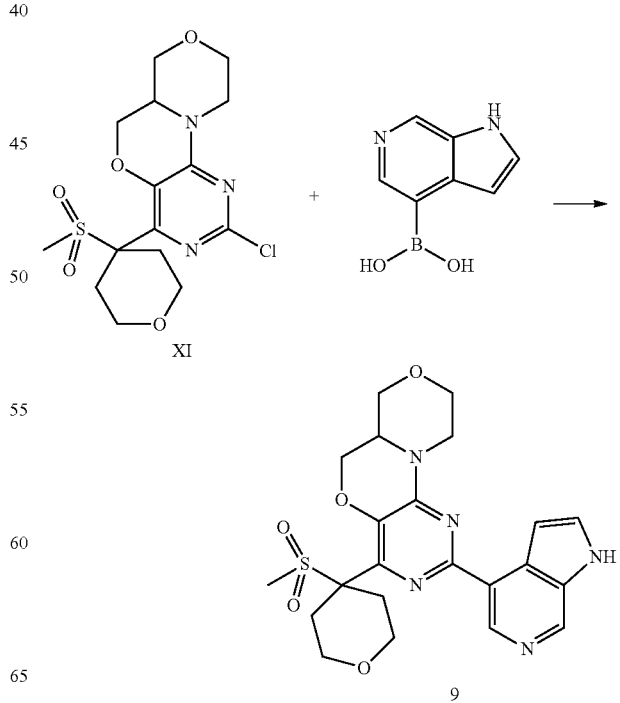

Example 9 (formate salt) was synthesized following a similar protocol to the one used for Example 1 by coupling of intermediate XI with B-1H-pyrrolo[2,3-c]pyridin-4-ylboronic acid (cas1312368-90-3).

1H NMR (300 MHz, DMSO) δ 11.68 (s, 1H), 8.90 (s, 1H), 8.72 (s, 1H), 8.30 (s, 1H, HCOOH), 7.62 (s, 1H), 7.12 (s, 1H), 4.63 (d, J=13.0 Hz, 1H), 4.43-4.37 (m, 1H), 4.09-3.53 (m, 7H), 3.33-3.15 (m, 6H), 2.87 (s, 3H), 2.18-1.95 (m, 2H).

LC-MS1: tR=2.36 min, M+1=472.1

Example 10

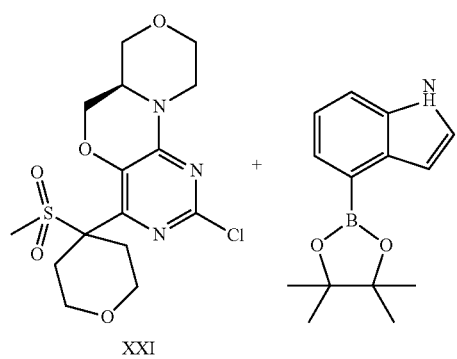

XXI

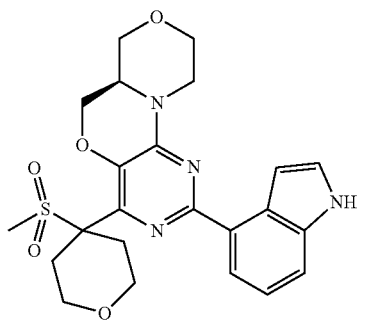

10

Example 10 was synthesized following a similar protocol to the one used for Example 1 by coupling of intermediate XXI with indole-4-boronic acid pinacol ester.

Intermediate XXI was synthesized following a similar synthetic protocol to the one used for the synthesis of intermediate XII, but using in step 1, 3(S)-hydroxymethylmorpholine.

1H NMR (300 MHz, DMSO) δ 11.21 (s, 1H), 7.94 (d, J=7.3 Hz, 1H), 7.48 (d, J=8.0 Hz, 1H), 7.42 (s, 1H), 7.23 (s, 1H), 7.16 (t, J=7.8 Hz, 1H), 4.63 (d, J=12.8 Hz, 1H), 4.38 (dd, J=10.7, 3.1 Hz, 1H), 4.07 (d, J=11.4 Hz, 1H), 3.99-3.68 (m, 5H), 3.58 (t, J=10.7 Hz, 1H), 3.30-3.07 (m, 6H), 2.86 (s, 3H), 2.23-2.04 (m, 2H).

LC-MS1: tR=4.58 min, M+1=471.3.

[α]$_D$=−36 (c 0.32, CHCl$_3$/MeOH 9:1)

Optical value of one of the precursors in the synthesis:

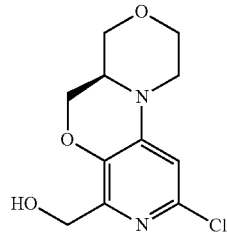

[α]$_D$ = -28(c 0.43, CHCl$_3$/MeOH 9:1).

Example 11

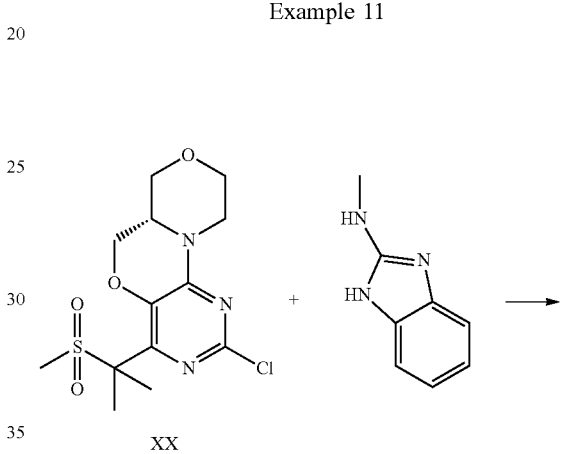

XX

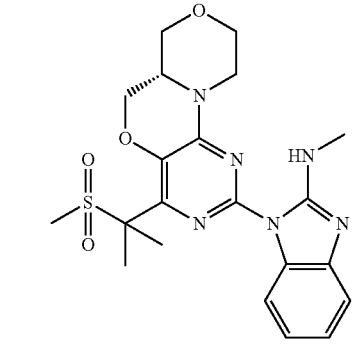

11

Example 11 was synthesized following a similar protocol to the one used for Example 8 from intermediate XX in DMF.

1H NMR (300 MHz, DMSO) δ 8.14 (q, J=4.8 Hz, 1H), 8.00 (d, J=7.8 Hz, 1H), 7.25 (d, J=7.7 Hz, 1H), 7.07 (t, J=7.5 Hz, 1H), 6.98 (t, J=7.7 Hz, 1H), 4.44-4.38 (m, 2H), 4.15-3.77 (m, 4H), 3.57 (t, J=10.8 Hz, 1H), 3.23 (t, J=10.8 Hz, 2H), 3.03 (s, 3H), 3.02 (d, J=5.0 Hz, 3H), 1.83 (s, 3H), 1.82 (s, 3H).

LC-MS1: tR=2.95 min, M+1=459.1.

[α]$_D$=+49 (c 0.233, CHCl$_3$/MeOH 9:1).

Intermediate XX was synthesized following synthetic routes described here and using as precursor 3(R)-hydroxymethylmorpholine hydrochloride.

Example 12

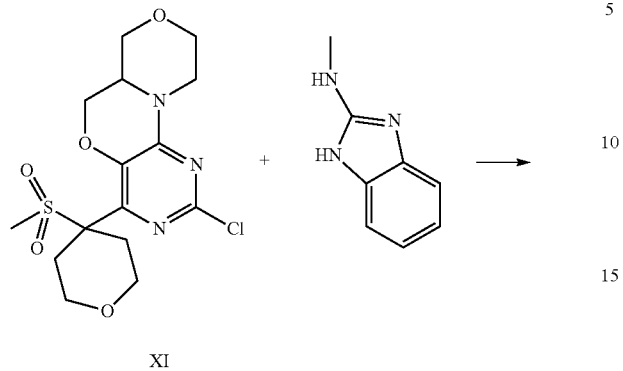

XI

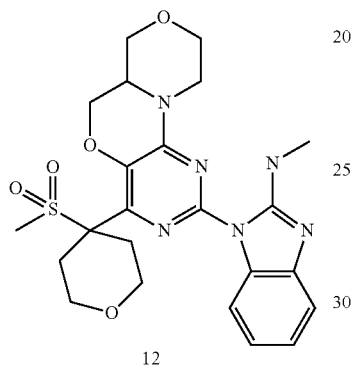

12

Example 12 was synthesized following a similar protocol to the one used for Example 8 from intermediate XI in a mixture of AcCN and DMF.

1H NMR (300 MHz, DMSO) δ 7.96 (d, J=7.9 Hz, 1H), 7.89 (q, J=4.9 Hz, 1H), 7.25 (d, J=7.6 Hz, 1H), 7.07 (t, J=7.5 Hz, 1H), 6.98 (t, J=7.5 Hz, 1H), 4.50-4.31 (m, 2H), 4.07 (d, J=11.7 Hz, 1H), 4.00-3.76 (m, 5H), 3.59 (t, J=10.6 Hz, 1H), 3.32-3.20 (m, 6H), 3.00 (d, J=4.8 Hz, 3H), 2.94 (s, 3H), 2.18-2.06 (m, 2H).

LC-MS1: tR=2.82 min, M+1=501.1.

Example 13

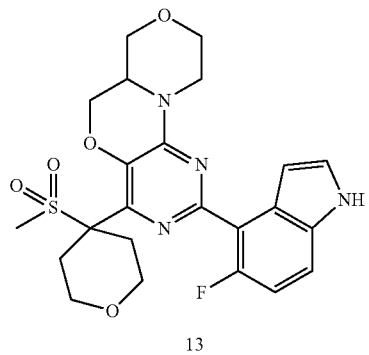

13

Intermediate XXII (80 mg) in THF (3 mL) was treated with TBAF (2 mL; 2 mmol; 1M in THF). After stirring for 1 hour at rt reaction was finished. Then, water was added and the mixture was extracted with DCM, organic phase was dried over MgSO₄, filtered and evaporate affording a residue which was purified by automated chromatography in EtOAc/cyclohexane (from 50% to 75% on EtOAc). Example 13 was recovered as a white solid, (7 mg).

1H NMR (300 MHz, DMSO) δ 11.24 (s, 1H), 7.56-7.30 (m, 2H), 6.97 (dd, J=11.3, 8.8 Hz, 1H), 6.79 (s, 1H), 4.55-4.31 (m, 2H), 4.05-3.74 (m, 6H), 3.53 (t, J=10.5 Hz, 1H), 3.27-3.00 (m, 5H), 2.85 (s, 3H), 2.18-1.94 (m, 3H).

LC-MS1: tR=4.51 min, M+1=489.0.

Intermediate XXII

A mixture of intermediate XI (50 mg), [1-(tert-butyl-dimethyl-silanyl)-5-fluoro-1H-indol-4-yl]boronic acid (45 mg, 0.15 mmol), PdCl₂(PPh₃)₂ (18 mg), 2 M aqueous solution of Na₂CO₃ (0.250 mL), in dioxane (1 mL) was heated in a high pressure tube for 2 h. The dark mixture was filtered off through a Celite pad rinsing with DCM. The filtrate was concentrated in vacuo. The crude was purified by flash column chromatography in SiO₂ eluting with a solvent system of EtOAc/cyclohexane (from 25% to 75% on EtOAc). Required compound)(XII was recovered as white solid, (80 mg).

Example 14

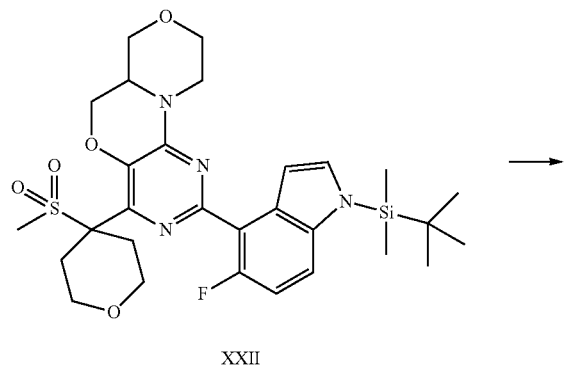

XXII

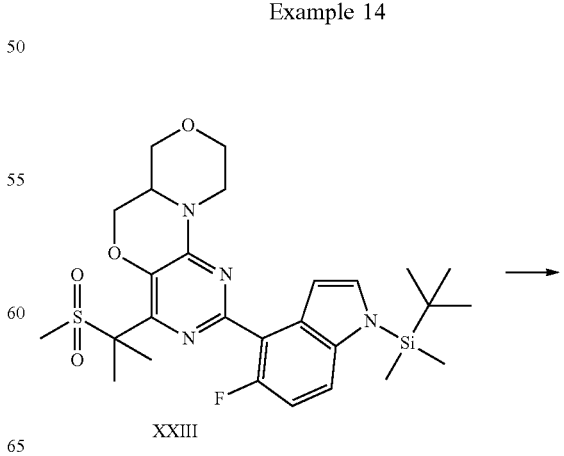

XXIII

Example 16

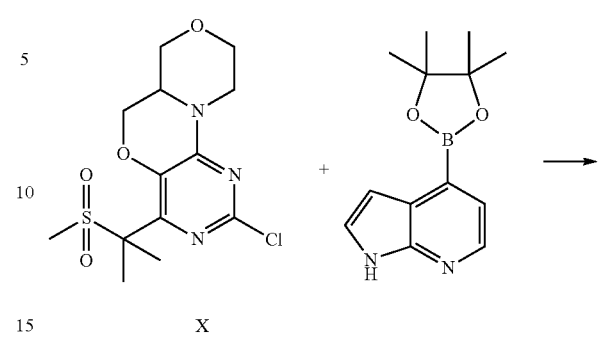

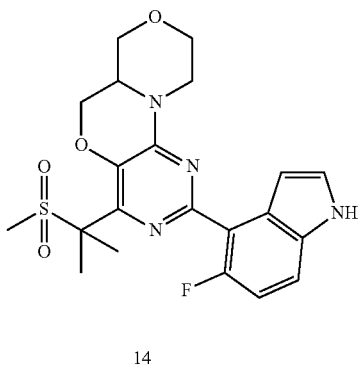

14

Example 14 was synthesized following a similar protocol to the one used for Example 13.

1H NMR (300 MHz, DMSO) δ 11.30 (s, 1H), 7.53-7.45 (m, 2H), 7.04 (dd, J=11.4, 9.0, 1 H), 6.87 (s, 1H), 4.54-4.43 (m, 2H), 4.09-3.78 (m, 4H), 3.58 (t, J=10.9 Hz, 1H), 3.26 (t, J=10.8 Hz, 1H), 3.13 (dt, J=12.9, 3.0 Hz, 1H), 3.03 (s, 3H), 1.90 (s, 3H), 1.88 (s, 3H).

LC-MS1: tR=4.71 min, M+1=447.0.

Intermediate XXIII was synthesized by coupling reaction of X with [1-(tert-butyl-dimethyl-silanyl)-5-fluoro-1H-indol-4-yl]boronic acid using the same protocol to the one used for intermediate XXII.

Example 15

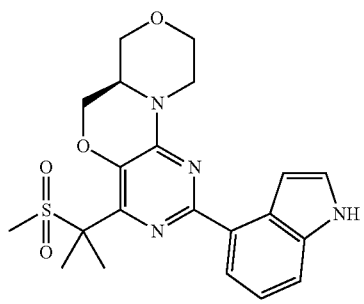

15

Example 15 was synthesized following a similar synthetic route to the one used for Example 1, using as precursor 3(S)-hydroxymethylmorpholine.

LC-MS1: tR=4.88 min, M+1=429.0.

1H NMR (300 MHz, DMSO) δ 11.13 (s, 1H), 7.89 (d, J=7.5 Hz, 1H), 7.41 (d, J=7.8 Hz, 1H), 7.34 (bs, 1H), 7.24 (s, 1H), 7.09 (t, J=7.7 Hz, 1H), 4.53 (d, J=12.2 Hz, 1H), 4.33 (dd, J=10.9, 3.3 Hz, 1H), 3.99 (d, J=8.4 Hz, 1H), 3.93-3.75 (m, 2H), 3.73-3.64 (m, 1H), 3.49 (t, J=10.7 Hz, 1H), 3.23-3.00 (m, 2H), 2.88 (s, 3 H), 1.82 (s, 3H), 1.81 (s, 3H).

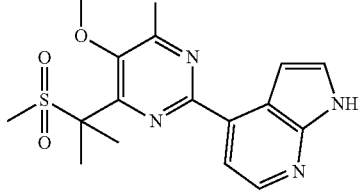

16

A mixture of intermediate X (40 mg, 0.115 mmol), with 4-(4,4,5,5-tetramethyl-1,3,2-dioxaborolan-2-yl)-1H-pyrrolo[2,3-b]pyridine (34 mg, 0.138 mmol), PdCl$_2$(PPh$_3$)$_2$ (12 mg, 0.017 mmol) and 2M aqueous solution of Na$_2$CO$_3$ (0.23 mL) in dioxane (1.2 mL) was heated at reflux in a high pressure tube for 4 h. The dark reaction mixture was cooled down to rt and filtered out through a Celite pad, rinsing with DCM. The filtrate was concentrated in vacuo and the resulting residue was purified by flash column chromatography (SiO$_2$) eluting with a solvent system of EtOAc/cylohexane (from 20% to 50% on EtOAc). Example 16 was recovered as cream solid (31 mg).

LC-MS1 tR=3.606, MS: 430.0 [M+H]+

1H NMR (300 MHz, DMSO) δ11.73 (s, 1H), 8.30 (d, J=5.0 Hz, 1H), 7.88 (d, J=5.0 Hz, 1H), 7.62-7.51 (m, 1H), 7.23 (dd, J=3.3, 1.9 Hz, 1H), 4.59 (d, J=12.0 Hz, 1H), 4.43 (dd, J=10.9, 3.4 Hz, 1H), 4.06 (d, J=8.5 Hz, 1H), 3.97-3.73 (m, 3H), 3.57 (t, J=10.4 Hz, 1H), 3.28-3.10 (m, 2H), 2.95 (s, 3H), 1.90 (s, 3H), 1.88 (s, 3H).

Example 17

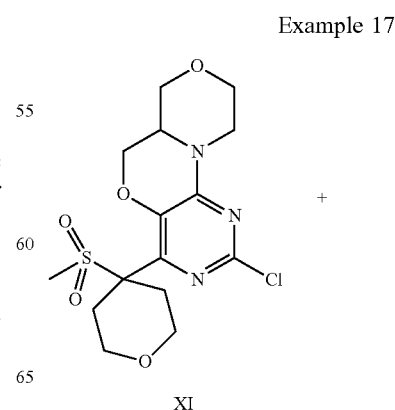

XI

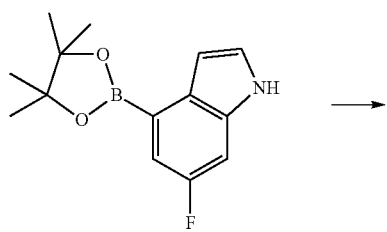

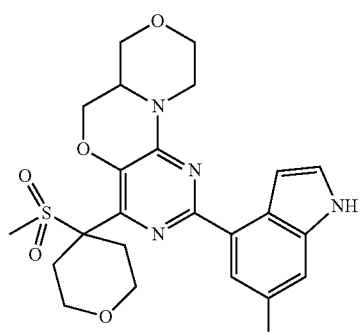

17

Example 17 was synthesized following a similar protocol to the one used for Example 1 by coupling of intermediate XI with indole 6-fluoro-4-boronic acid pinacol ester.

LC-MS1 tR=4.78 min, MS: 489.5 [M+H]+

1H NMR (300 MHz, DMSO) δ 11.22 (s, 1H), 7.65 (d, J=13.7 Hz, 1H), 7.42-7.30 (m, 1H), 7.25-7.12 (m, 2H), 4.54 (d, J=14.8 Hz, 1H), 4.32 (d, J=10.6 Hz, 1H), 4.00 (d, J=11.7 Hz, 1H), 3.95-3.78 (m, 4H), 3.78-3.66 (m, 1H), 3.51 (t, J=10.9 Hz, 1H), 3.22-3.03 (m, 6H), 2.80 (s, 3H), 2.11-2.02 (m, 2H).

Example 18

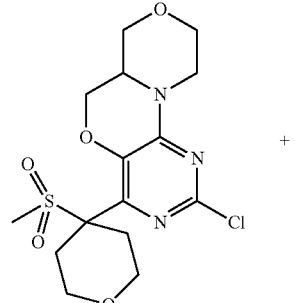

XI

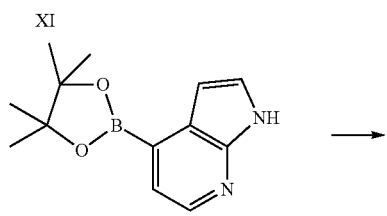

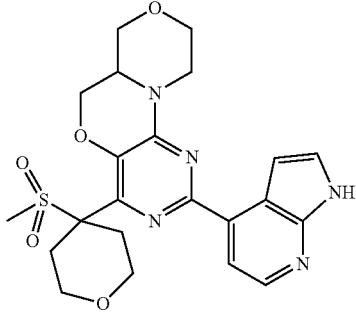

18

Example 18 was synthesized following a similar protocol to the one used for Example 1 by coupling of intermediate XI with 4-(4,4,5,5-tetramethyl-1,3,2-dioxaborolan-2-yl)-1H-pyrrolo[2,3-b]pyridine.

LC-MS1 tR=3.42 min, MS: 472.5 [M+H]+

1H NMR (300 MHz, DMSO) δ 11.75 (s, 1H), 8.29 (d, J=5.0 Hz, 1H), 7.87 (d, J=5.1 Hz, 1H), 7.55 (s, 1H), 7.15 (s, 1H), 4.62 (d, J=12.6 Hz, 1H), 4.41 (dd, J=10.8, 3.2 Hz, 1H), 4.08 (d, J=11.2 Hz, 1H), 4.02-3.76 (m, 5H), 3.59 (t, J=10.7 Hz, 1H), 3.30-3.11 (m, 6H), 2.87 (s, 3H), 2.23-2.07 (m, 2H).

Example 19

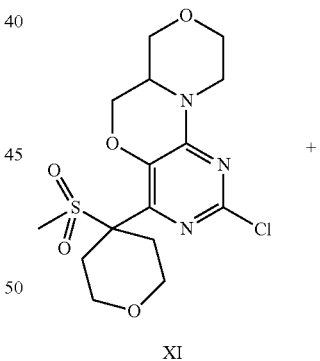

XI

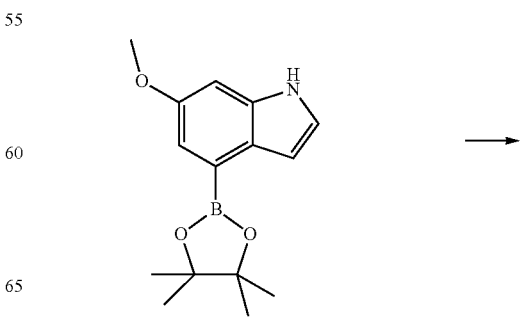

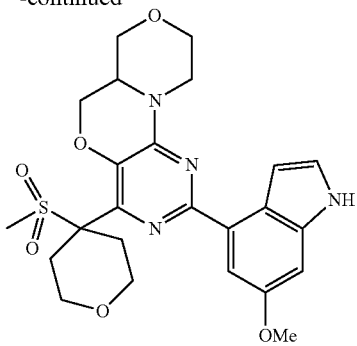

19

Example 19 was synthesized following a similar protocol to the one used for Example 1 by coupling of intermediate XI with 6-methoxy-4-(4,4,5,5-tetramethyl-1,3,2-dioxaborolan-2-yl-1H-indole, CAS: 955979-12-1.

LC-MS1 tR=4.53 min, MS: 501.6 [M+H]+

1H NMR (300 MHz, DMSO) δ 10.96 (s, 1H), 7.53 (s, 1H), 7.22 (s, 1H), 7.08 (s, 1H), 6.97 (s, 1H), 4.56 (d, J=13.6 Hz, 1H), 4.34 (d, J=10.4 Hz, 1H), 4.03 (d, J=11.0 Hz, 1H), 3.98-3.79 (m, 5H), 3.75 (s, 3H), 3.54 (t, J=12.1 Hz, 1H), 3.23-3.05 (m, 6H), 2.81 (s, 3H), 2.18-2.02 (m, 2H).

Example 20

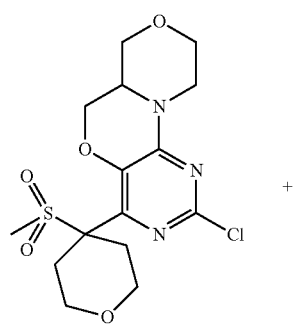

XI

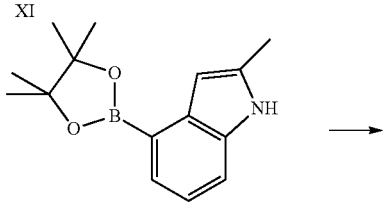

20

Example 20 was synthesized following a similar protocol to the one used for Example 1 by coupling of intermediate XI with 2-methyl-4-(4,4,5,5-tetramethyl-1,3,2-dioxaborolan-2-yl)-1H-indole CAS: 955979-22-3.

LC-MS1 tR=4.77 min MS: 485.6 [M+H]+

1H NMR (300 MHz, DMSO) δ 11.03 (s, 1H), 7.88 (d, J=7.5 Hz, 1H), 7.34 (d, J=7.8 Hz, 1H), 7.05 (t, J=7.7 Hz, 1H), 6.89 (s, 1H), 4.62 (d, J=12.3 Hz, 1H), 4.37 (dd, J=10.8, 3.1 Hz, 1H), 4.07 (d, J=11.3 Hz, 1H), 4.02-3.70 (m, 5H), 3.58 (t, J=11.9 Hz, 1H), 3.31-3.08 (m, 6H), 2.85 (s, 3H), 2.42 (s, 3H), 2.22-2.06 (m, 2H).

Example 21

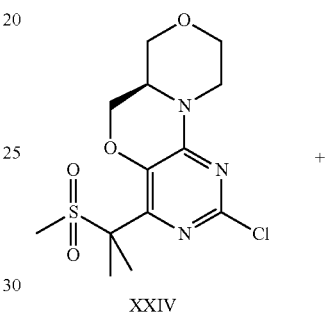

XXIV

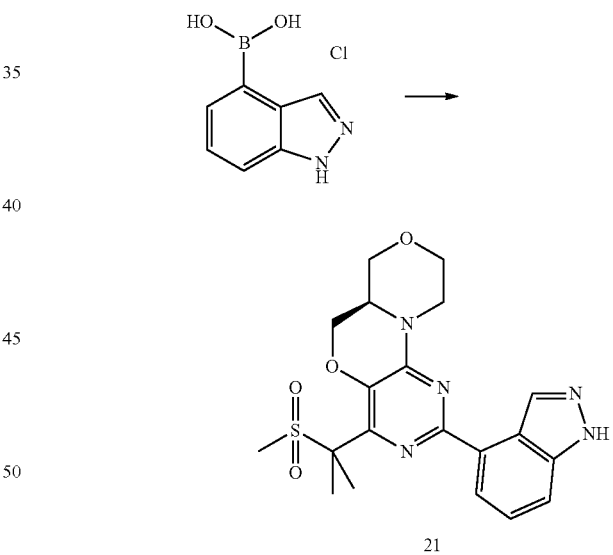

21

Example 21 was synthesized following a similar protocol to the one used for Example 15 by coupling of intermediate XXIV with indazole-4-boronic acid hydrochloride.

LC-MS1: tR=5.169 min, M+1=430.10.

1H NMR (300 MHz, DMSO) δ 13.18 (s, 1H), 8.75 (s, 1H), 8.05 (d, J=7.2 Hz, 1H), 7.63 (d, J=8.2 Hz, 1H), 7.49-7.38 (m, 1H), 4.60 (d, J=12.1 Hz, 1H), 4.41 (dd, J=10.9, 3.3 Hz, 1H), 4.07 (dd, J=11.4, 2.9 Hz, 1H), 3.99-3.71 (m, 3H), 3.77 (t, J=9.4 Hz, 1H), 3.57 (t, J=10.6 Hz, 1H), 3.28-3.10 (m, 2H), 2.96 (s, 3H), 1.90 (s, 3H), 1.88 (s, 3H).

Example 22

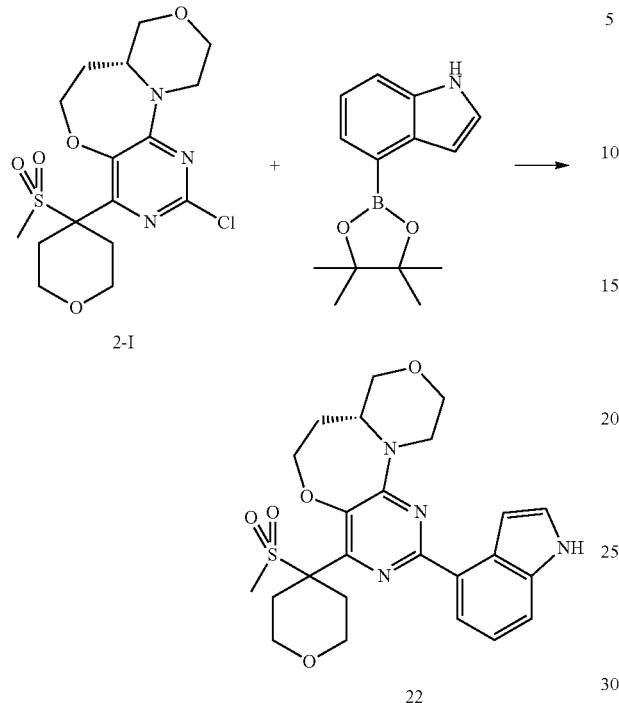

22

A mixture of intermediate 2-I (80 mg), indole-4-boronic acid pinacol ester (60 mg, 0.25 mmol), with PdCl$_2$(dppf) (25 mg) and a 2 aqueous solution of Na$_2$CO$_3$ (0.4 mL, 0.8 mmol) in dioxane (1 mL) was heated in a high pressure tube at 85° C. for 3 h. The dark reaction mixture was filtered through a Celite pad rinsing with DCM. Solvents were removed in vacuo, and the residue was purified by flash column chromatography (Isolute Si II, 5 g) eluting with a solvent system of EtOAc/cyclohexane (from 25% to 100% on EtOAc). The required product was recovered as white solid as compound 22 (8 mg).

LCMS1, tR=4.75 min, MS: 485.2 [M+H]+

1H NMR (300 MHz, DMSO) δ 11.24 (s, 1H), 7.97 (d, J=7.3 Hz, 1H), 7.50 (d, J=8.0 Hz, 1H), 7.43 (t, J=2.6 Hz, 1H), 7.23 (s, 1H), 7.17 (t, J=7.8 Hz, 1H), 4.24 (t, J=5.5 Hz, 2H), 4.11-3.70 (m, 8H), 3.53-3.46 (m, 1H), 3.30-3.09 (m, 4H), 2.85 (s, 3H), 2.24-1.93 (m, 4H).

[α]$_D$=−15 (c 0.204, CHCl$_3$/MeOH 9:1) with an enantiomeric excess of 60% ca.

Intermediate 2-I

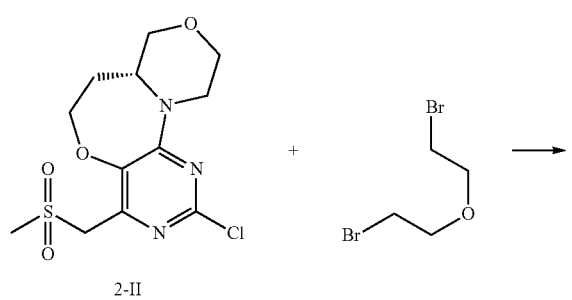

2-I

To a cooled mixture of intermediate 2-II (80 mg) with bis(2-bromoethyl) ether (75 μL, 0.6 mmol) in DMF (4 mL) was added in one pot sodium tert-butoxide (70 mg, 0.7 mmol). The dark brown mixture was stirred at this temperature for 30 min and at rt for 18 h. After that time more tert-butoxide (30 mg) was added to the mixture continuing the stirring for 2 h more. The mixture was quenched by addition of water and extracted three times with EtOAc. The combined organic layers were washed with brine, dried over Na$_2$SO$_4$ and concentrated in vacuo. The required product was recovered as cream-yellow solid of desired product 2-I (80 mg).

Intermediate 2-II

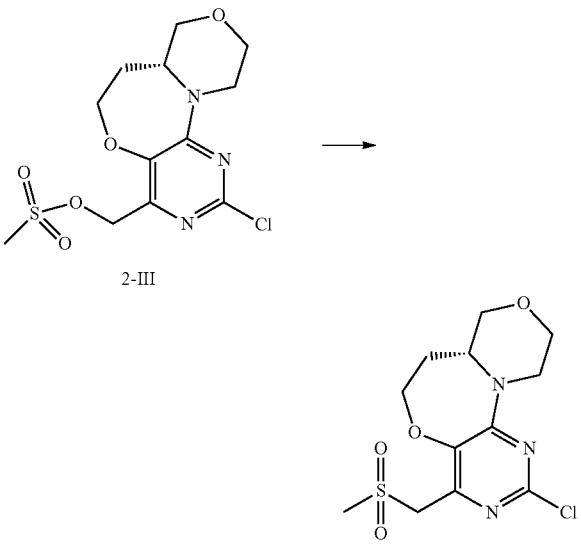

A mixture of intermediate 2-III (210 mg) and sodium methanesulfinate (0.90 mg, 0.89 mmol) in AcCN:DMF (4:1, 2.5 mL) was heated in a high pressure tube at 100° C. for 18 h. The reaction mixture was cooled down to rt, quenched by addition of aqueous 1 M Na$_2$S$_2$O$_3$ and extracted with DCM three times. The combined organic layers were washed with brine (25 mL), dried over Na$_2$SO$_4$ and concentrated in vacuo. The residue intermediate 2-II (165 mg) was used further into next step.

Intermediate 2-III

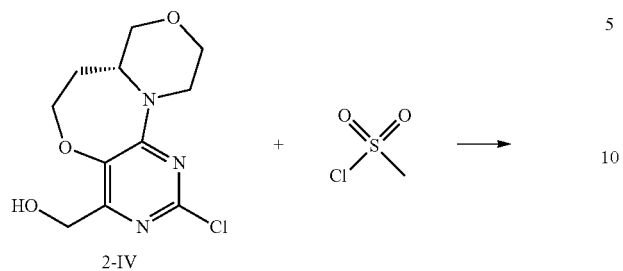

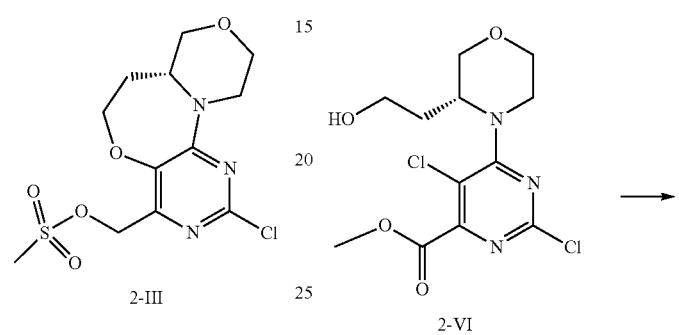

To a mixture of intermediate 2-IV (190 mg) in DCM (10 mL) with TEA (0.150 mL, 1.0 mmol) was added dropwise methanesulfonyl chloride (70 μL, 0.9 mmol). The resulting mixture was stirred at rt for 1 h 30 until staring material was consumed. The reaction was quenched by addition of water and extracted with DCM (3×20 mL). The combined organic layers were washed with brine, dried over $Na_2SO_4$ and concentrated in vacuo. The cream orange crystal solid, intermediate 2-III (210 mg) was used further without additional purification.

Intermediate 3-IV

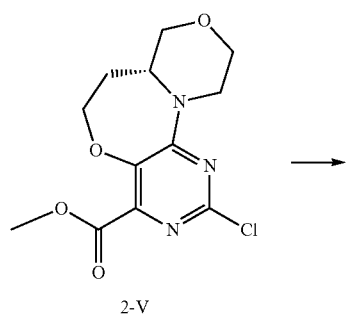

To a cooled solution of intermediate 2-V (0.275 g) in THF (8 mL) was added a 2M solution of $LiBH_4$ in THF (0.6 mL,
0.12 mmol). The resulting mixture was stirred at 0° C. for 30 min and at rt for 2 h. The reaction was quenched by addition of water and extracted with EtOAc three times. The combined organic layers were washed with brine, dried over $Na_2SO_4$ and concentrated in vacuo. The product, intermediate 2-IV, was recovered as cream-orange solid (190 mg) and used further without additional purification.

Intermediate 3-V

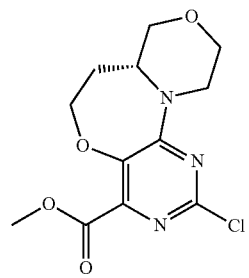

A mixture of intermediate 2-VI (869 mg) with $Cs_2CO_3$ (2.6 mg, 8.1 mmol) in AcCN (120 mL) was heated at reflux (85° C.) for 18 h. The mixture was cooled down to rt and solvents were removed in vacuo. The residue was redissolved in DCM and washed with 1M aqueous HCl (3×25 mL).

The organic phase was washed with brine, dried over $Na_2SO_4$ and concentrated in vacuo, leaving a light orange solid as intermediate 2-V (275 mg) that was used into next step without additional purification.

Intermediate 2-VI

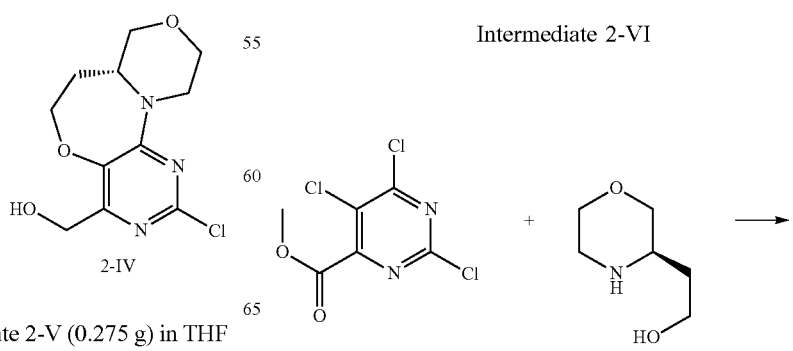

Example 24

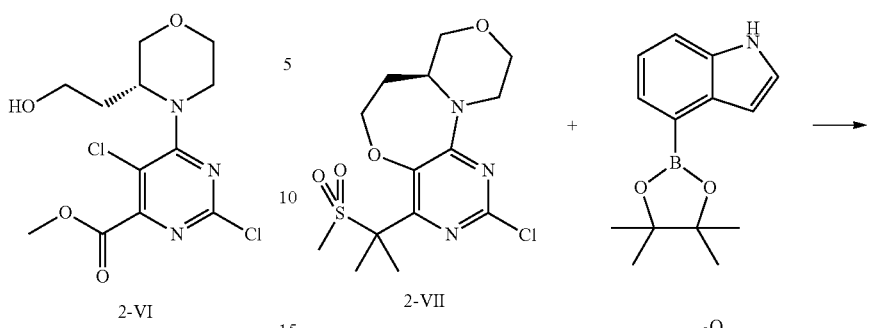

A mixture of intermediate 2-VII (50 mg), indole-4-boronic acid pinacol ester (40 mg, 0.16 mmol), with PdCl$_2$ (dppf) (15 mg) and a 2M aqueous solution of Na$_2$CO$_3$ (0.3 mL, 0.6 mmol) in dioxane (2 mL) was heated in a high pressure tube at 85° C. for 3 h. The dark reaction mixture was cooled down to rt, filtrated through a Celite pad rinsing with DCM and the filtrate was concentrated in vacuo. The crude was purified by flash column chromatography (Isolute Si II 5 g) eluting with a solvent system of EtOAc/cyclohexane (from 50% to 100% on EtOAc). The fractions containing required product were combined and concentrated in vacuo. The title compound was recovered as cream solid which was triturated twice with diethylether and dried in vacuo to obtain desired product example 24 as a white solid (6 mg).

LCMS1, tR=5.01 min, MS: 443.2 [M+H]+

1H NMR (300 MHz, DMSO) δ 11.16 (s, 1H), 7.92 (d, J=7.5 Hz, 1H), 7.43 (d, J=8.0 Hz, 1H), 7.37 (s, 1H), 7.24 (s, 1H), 7.11 (t, J=7.7 Hz, 1H), 4.18 (t, J=5.8 Hz, 2H), 4.00 (d, J=13.0 Hz, 1H), 3.90-3.79 (m, 1H), 3.79-3.66 (m, 3H), 3.61-3.48 (m, 1H), 3.37 (t, J=10.2 Hz, 1H), 2.88 (s, 3H), 2.08-1.89 (m, 2H), 1.84 (s, 6H).

[α]$_D$=+6 (c 0.215, CHCl$_3$/MeOH 9:1) with an enantiomeric excess of 60% ca.

A mixture of methyl 2,5,6-trichloro-4-pyrimidinecarboxylate (700 mg, 2.8 mmol) with (R)-2-(morpholin-3-yl)ethanol hydrochloride (600 mg, 3.5 mmol, 60% enantiomeric excess (ee)) in EtOH (10 mL) and DIPEA (1.5 mL; 8.6 mmol) was heated at reflux for 2 h. The light yellow mixture was cooled down to it and solvents were removed in vacuo. The light yellow oil recovered was redissolved in DCM (60 mL), washed with sat. aq. NaHCO$_3$ (2×50 mL), water (2×50 mL) and brine (50 mL). The organic phase was dried over Na$_2$SO$_4$ and concentrated in vacuo, leaving the required product as light yellow oil, intermediate 2-VI (860 mg) that was used further without additional purification.

Example 23

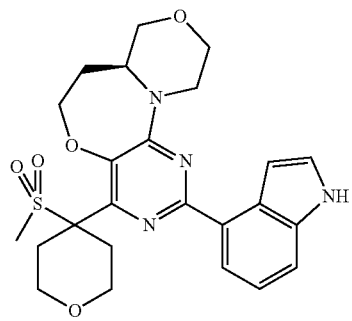

Example 23 was synthesized following same synthetic scheme to the one used for compound 2-1 but using (S)-2-(morpholin-3-yl)ethanol hydrochloride (60% ee) as starting material in step 1.

LCMS1, tR=4.71 min, MS: 485.2 [M+H]+

1H NMR (300 MHz, DMSO) δ 11.24 (s, 1H), 7.97 (d, J=7.4 Hz, 1H), 7.50 (d, J=8.0 Hz, 1H), 7.43 (s, 1H), 7.23 (s, 1H), 7.17 (t, J=7.8 Hz, 1H), 4.24 (t, J=5.4 Hz, 2H), 4.09-3.70 (m, 8H), 3.50 (dd, J=11.3, 7.0 Hz, 1H), 3.30-3.11 (m, 4H), 2.85 (s, 3H), 2.24-1.93 (m, 4H).

[α]$_D$=+8 (c 0.227, CHCl$_3$/MeOH 9:1) with an enantiomeric excess of 60% ca.

Intermediate 2-VII

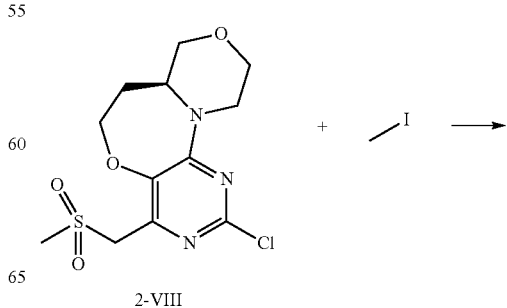

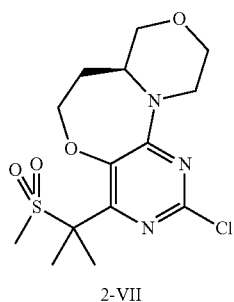

2-VII

To a cooled (0° C.) solution of 2-VIII (80 mg) in DMF (2 mL) was added first sodium tert-butoxide (25 mg, 0.25 mmol) and after 5 min of stirring iodomethane (16 μL, 0.25 mmol). The resulting mixture was stirred for 15 min and a second addition of sodium tert-butoxide (25 mg, 0.25 mmol) and iodomethane (16 μL, 0.25 mmol) was carried out. The mixture was stirred for 2 h and quenched by addition of water. The mixture was extracted with DCM three times. The combined organic layers were washed with brine, dried over $Na_2SO_4$. The crude, intermediate 2-VII (50 mg) was used further into next step without additional purification.

Example 25

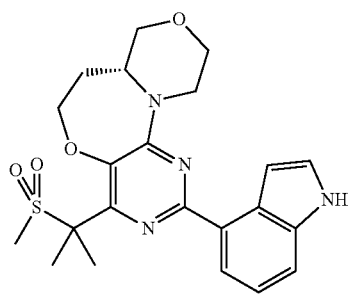

25

The synthetic protocol used for Example 24 was repeated using intermediate XLI in order to obtain example 25.

LCMS1, tR=4.99 min, MS: 443.2 [M+H]+

1H NMR (300 MHz, DMSO) δ 11.23 (s, 1H), 7.98 (d, J=7.4 Hz, 1H), 7.50 (d, J=8.0 Hz, 1H), 7.43 (t, J=2.5 Hz, 1H), 7.31 (s, 1H), 7.17 (t, J=7.7 Hz, 1H), 4.25 (t, J=5.6 Hz, 2H), 4.07 (d, J=13.6 Hz, 1H), 3.97-3.87 (m, 1H), 3.87-3.72 (m, 3H), 3.69-3.56 (m, 1H), 3.44 (t, J=10.3 Hz, 1H), 2.95 (s, 3H), 2.12-1.96 (m, 2H), 1.91 (s, 6H).

$[α]_D$=−6 (c 0.317, CHCl$_3$/MeOH 9:1) with an enantiomeric excess of 60% ca.

Example 26

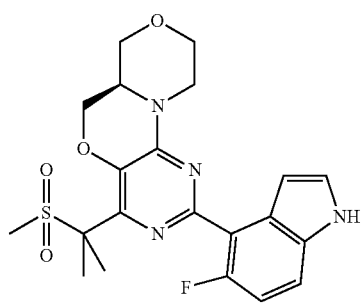

26

Example 26 was synthesized following a similar synthetic route to the one used for example 14, using as precursor 3(S)-hydroxymethylmorpholine.

LC-MS1: tR=4.77 min, MS: =447.1 [M+H]+

1H NMR (300 MHz, DMSO) δ 11.23 (s, 1H), 7.51-7.34 (m, 2H), 6.97 (dd, J=11.2, 8.8 Hz, 1H), 6.80 (s, 1H), 4.49-4.35 (m, 2H), 4.02-3.63 (m, 4H), 3.50-3.37 (m, 1H), 3.21-3.09 (m, 1H), 3.09-2.91 (m, 1H), 2.96 (s, 3H), 1.83 (s, 3H), 1.81 (s, 3H).

Example 27

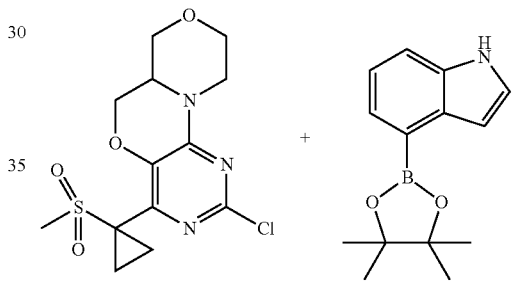

XXV

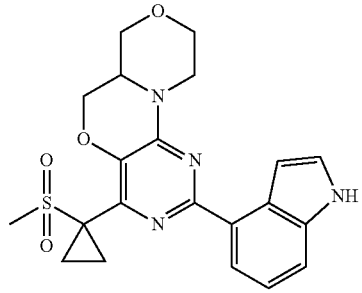

27

A mixture of intermediate XXV (15 mg, 0.043 mmol) with indole-4-boronic acid pinacol ester (13 mg, 0.052 mmol), dichlorobis(triphenylphosphine)palladium(ii) (6 mg, 0.009 mmol) and a 2M aqueous solution of $Na_2CO_3$ (0.1 mL) in dioxane (0.5 mL), was heated in a high pressure tube for 3 h. The dark mixture was cooled down to rt, diluted with water (10 mL) and extracted with EtOAc (2×10 mL). The organic layers were washed with brine, dried over $Na_2SO_4$ and concentrated in vacuo. The crude was purified first by flash column chromatography (Isolute Si II 5 g) eluting with a solvent system of EtOAc/cyclohexane (from 50% to 100% on EtOAc) to obtain 3 mg of final product, Example 27.

LC-MS1: tR=4.08 min M+1=427.1.

1H NMR (300 MHz, DMSO) δ 11.14 (s, 1H), 7.91 (d, J=7.5 Hz, 1H), 7.41 (d, J=8.0 Hz, 1H), 7.35 (bs, 1H), 7.28 (s, 1H), 7.09 (t, J=7.8 Hz, 1H), 4.47 (m, 1H), 4.36 (m, 1H), 3.98 (m, 1H), 3.86 (m, 2H), 3.67 (m, 1H), 3.50 (m, 1H), 3.21-3.01 (m, 2H), 3.02 (s, 3H), 1.64 (bs, 2H), 1.35 (bs, 2H).

Intermediate XXV

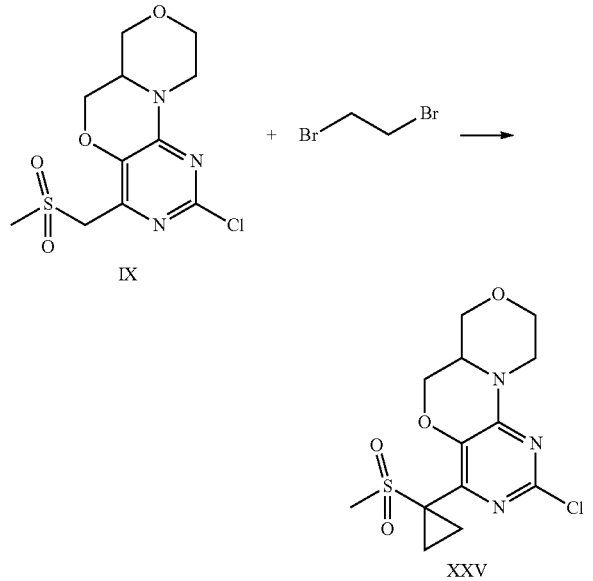

Freshly prepared aqueous NaOH (4N) (0.547 mL) was added to a solution of intermediate IX (70 mg, 0.219 mmol), dibromoethane (0.038 mL, 0.438 mmol) and TBAB (14 mg, 0.044 mmol) in toluene (3 mL). The mixture was stirred at 80° C. in a MW tube for 2 h and at 110° C. (sand bath) in a MW tube for 16 h. After cooling, the reaction mixture was diluted with EtOAc and washed with water and brine. The organic layer was dried over Na₂SO₄ and concentrated in vacuo. The crude product was purified first by flash column chromatography (Isolute Si II 5 g) eluting with a solvent system of EtOAc/cyclohexane (from 20% to 80% on EtOAc) to obtain 15 mg of required intermediate XXV.

Example 28

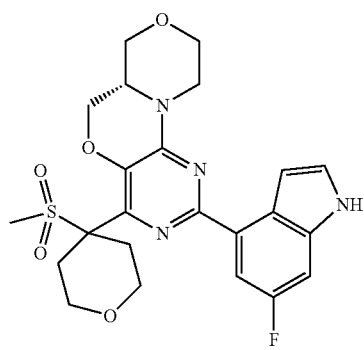

Example 28 was synthesized following a similar synthetic route to the one used for Example 17, using as precursor 3(R)-hydroxymethylmorpholine.
LC-MS1 tR=4.76 min, MS: 489.1 [M+H]⁺

1H NMR (300 MHz, DMSO) δ 11.22 (s, 1H), 7.65 (d, J=13.7 Hz, 1H), 7.42-7.30 (m, 1H), 7.25-7.12 (m, 2H), 4.54 (d, J=14.8 Hz, 1H), 4.32 (d, J=10.6 Hz, 1H), 4.00 (d, J=11.7 Hz, 1H), 3.95-3.78 (m, 4H), 3.78-3.66 (m, 1H), 3.51 (t, J=10.9 Hz, 1H), 3.22-3.03 (m, 6H), 2.80 (s, 3H), 2.11-2.02 (m, 2H).

Example 29

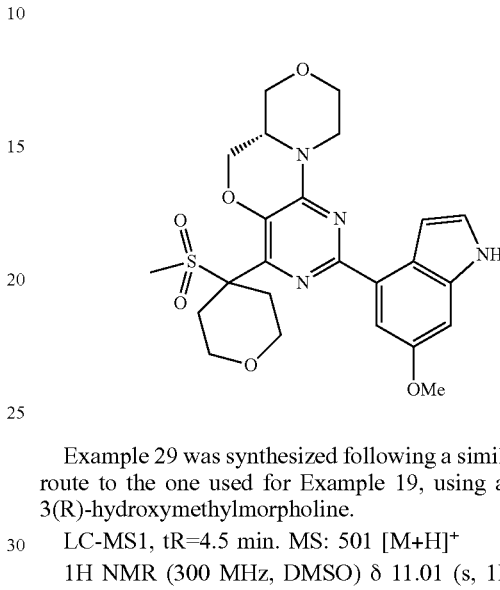

Example 29 was synthesized following a similar synthetic route to the one used for Example 19, using as precursor 3(R)-hydroxymethylmorpholine.
LC-MS1, tR=4.5 min. MS: 501 [M+H]⁺

1H NMR (300 MHz, DMSO) δ 11.01 (s, 1H), 7.57 (d, J=2.2 Hz, 1H), 7.29-7.24 (m, 1H), 7.12 (s, 1H), 7.01 (d, J=1.8 Hz, 1H), 4.60 (d, J=13.1 Hz, 1H), 4.38 (dd, J=10.7, 3.1 Hz, 1H), 4.07 (dd, J=11.4, 2.7 Hz, 1H), 4.00-3.83 (m, 5H), 3.80 (s, 3H), 3.58 (td, J=11.7, 1.9 Hz, 1H), 3.30-3.09 (m, 6H), 2.86 (s, 3H), 2.17-2.03 (m, 2H).

Example 30

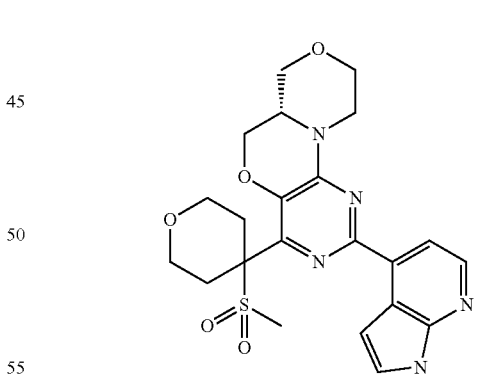

Example 30 was synthesized following a similar synthetic route to the one used for example 18, using as precursor 3(R)-hydroxymethylmorpholine.
LCMS1, tR=3.3 min. MS: 472.5 [m+H]⁺

1H NMR (300 MHz, DMSO) δ 11.69 (s, 1H), 8.23 (d, J=5.0 Hz, 1H), 7.80 (d, J=5.0 Hz, 1H), 7.53-7.37 (m, 1H), 7.14-6.98 (m, 1H), 4.56 (d, J=12.8 Hz, 1H), 4.34 (dd, J=10.8, 3.1 Hz, 1H), 4.01 (dd, J=11.6, 3.0 Hz, 1H), 3.96-3.79 (m, 4H), 3.78-3.67 (m, 1H), 3.52 (t, J=10.7 Hz, 1H), 3.26-3.03 (m, 6H), 2.80 (s, 3H), 2.14-1.95 (m, 2H).

Example 31

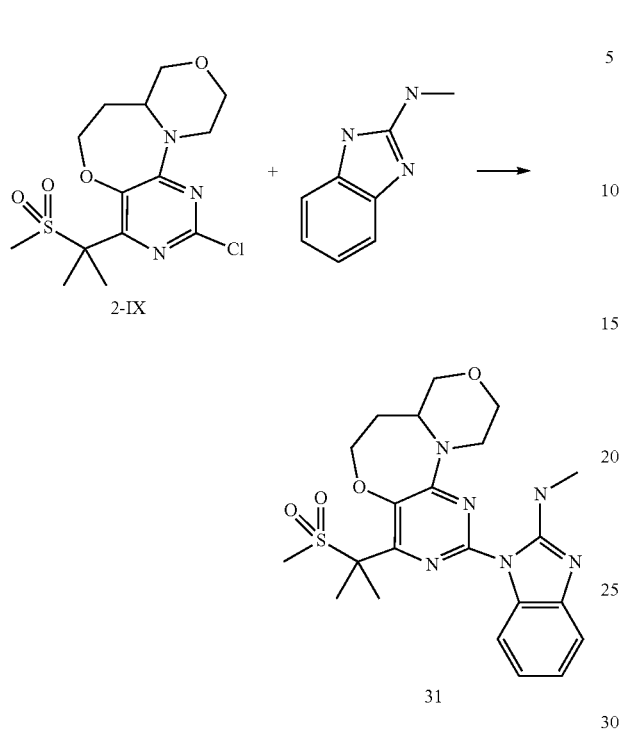

To a suspension of intermediate 2-VII (90 mg, 0.249 mmol) in ACN (1.5 mL) and DMF (0.15 mL) was added N-methyl-1H-1,3-benzodiazol-2-amine (73 mg, 0.497 mmol) and $Cs_2CO_3$ (400 mg, 1.244 mmol). The reaction mixture was heated in a sealed tube at 130° C. for 3 days. On cooling, $H_2O$ (50 mL) was added and the mixture was extracted with EtOAc (2×40 mL). The organics were dried, filtered and evaporated. The residue was purified by flash column chromatography (20% to 80% EtOAc in DCM) and triturated with $Et_2O$ to give the final product 31 as a white solid (50 mg).

LCMS1, tR=3.12 min, MS: 473.2 [M+H]+

1H NMR (300 MHz, DMSO) δ 8.17 (q, J=4.9 Hz, 1H), 8.01 (d, J=7.5 Hz, 1H), 7.25 (d, J=7.3 Hz, 1H), 7.07 (t, J=7.0 Hz, 1H), 6.97 (t, J=7.6 Hz, 1H), 4.26 (m, 2H), 3.99 (m, 3H), 3.87-3.72 (m, 2H), 3.60 (m, 1H), 3.47 (m, 1H), 3.01 (m, 6H), 2.22-1.95 (m, 2H), 1.85 (m, 6H).

Intermediate 2-IX

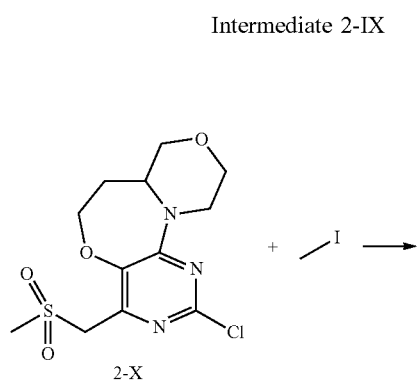

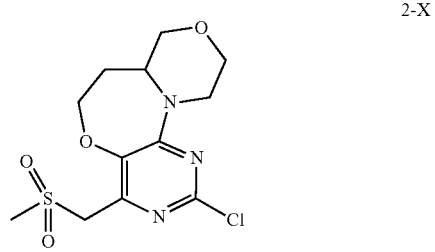 [SMILES: CS(=O)(=O)Cc1nc(Cl)nc2c1OCCC1COCCN21]

2-IX

To a solution of 2-X (90 mg, 0.270 mmol) in DMF (2.2 mL) at 0° C. was added KtBuO (32 mg, 0.566 mmol) and MeI (18 µL). The reaction mixture was stirred at 0° C. for 15 min and KtBuO (32 mg, 0.566 mmol) and MeI (18 pt) were added. The mixture was stirred at rt for 1 h. HCl 1M (20 mL) was added and the mixture was extracted with DCM (3×40 mL). The organics were dried over $Na_2SO_4$, filtered and evaporated. The crude, intermediate 2-IX (100 mg) was used further into next step without additional purification.

Intermediate 2-X

2-X

Intermediate 2-X was synthesized following same synthetic scheme to the one used for intermediate 2-II but using racemic 2-(morpholin-3-yl)ethanol hydrochloride as starting material in step 1.

Example 32

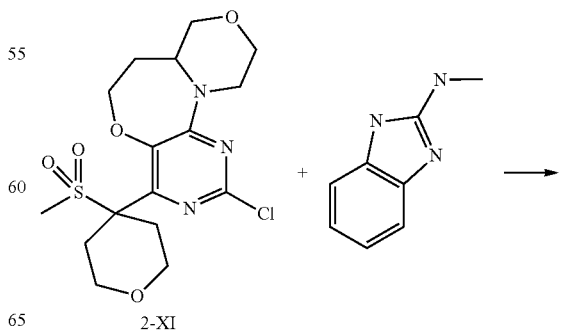

2-XI

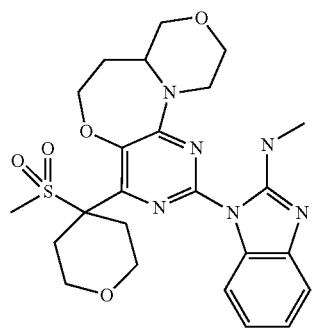

32

To a suspension of intermediate 2-XI (70 mg, 0.173 mmol) in ACN (1.5 mL) and DMF (0.15 mL) was added N-methyl-1H-1,3-benzodiazol-2-amine (51 mg, 0.347 mmol) and Cs₂CO₃ (282 mg, 0.867 mmol). The reaction mixture was heated in a sealed tube at 130° C. for 40 hours. On cooling, H₂O (50 mL) and EtOAc (40 mL) were added. A solid appeared in the interphase, it was filtered and washed with EtOAc and Et₂O to give final product 32 as a white solid (35 mg).

LC-MS1, tR=3.98 min, MS: 515.2 [m+H]⁺

1H NMR (300 MHz, DMSO) δ 7.97 (d, J=7.6 Hz, 1H), 7.88 (q, J=4.9 Hz, 1H), 7.25 (d, J=7.3 Hz, 1H), 7.07 (t, J=7.1 Hz, 1H), 6.98 (t, J=7.6 Hz, 1H), 4.43-4.29 (m, 1H), 4.24 (m, 1H), 4.10-3.76 (m, 8H), 3.56 (m, 1H), 3.46-3.36 (m, 2H), 3.03 (m, 1H), 2.99 (d, J=4.9 Hz, 3H), 2.94 (s, 3H), 2.89 (m, 1H), 2.30-1.96 (m, 4H).

Intermediate 2-XI

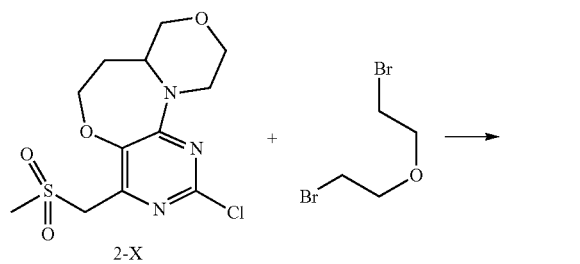

2-X

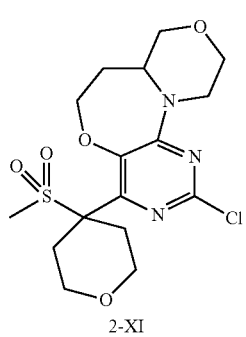

2-XI

To a cooled mixture of intermediate 2-X (280 mg, 0.839 mmol) with bis(2-bromoethyl) ether (265 μL, 2.097 mmol) in DMF (4 mL) was added in one pot sodium tert-butoxide (282 mg, 2.517 mmol). The dark brown mixture was stirred at 0° C. for 30 min and at rt for 20 h. After that time more tert-butoxide (140 mg) was added to the mixture and the stirring was continued for a further 20 h. The mixture was quenched by addition of water (25 mL) and HCl 1M (15 mL) and the mixture was extracted three times with EtOAc (75 mL). The combined organic layers were washed with brine, dried over Na₂SO₄ and concentrated in vacuo. The residue was purified by flash column chromatography (10% to 20% EtOAc/DCM) to give the intermediate product 2-XI as a yellow solid (170 mg).

Example 33

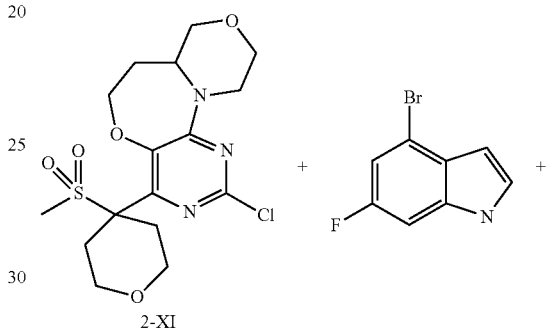

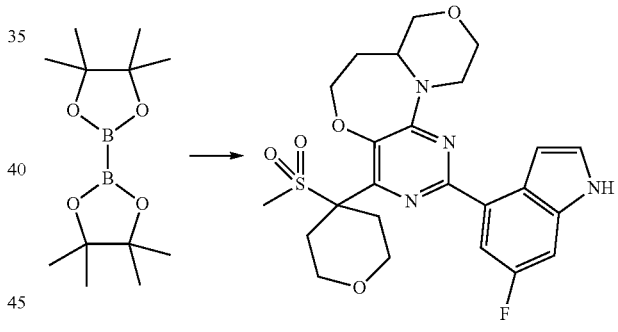

33

A mixture of 4-bromo-6-fluoro-1H-indole (32 mg, 0.149 mmol), bis(pinacolato)diboron (79 mg, 0.309 mmol), KOAc (36 mg, 0.371 mmol) and PdCl₂(dppf) (20 mg, 0.025 mmol) in dioxane (1.3 mL) was heated in a sealed tube at 100° C. for 3 h. On cooling, intermediate 2-XI (50 mg, 0.124 mmol), Pd(PPh₃)₄ (14 mg, 0.012 mmol) and Na₂CO₃ 2M (0.25 mL) were added. The reaction mixture was heated at 100° C. for 20 h. On cooling, the mixture was purified by flash column chromatography (5% to 20% EtOAc in DCM) and triturated with Et₂O to give final compound 33 as a white solid (30 mg).

LC-MS1, tR=4.95 min, MS: 503.2 [M+H]⁺

1H NMR (300 MHz, DMSO) δ 11.32 (s, 1H), 7.74 (d, J=11.4 Hz, 1H), 7.45 (s, 1H), 7.30 (d, J=9.4 Hz, 1H), 7.23 (s, 1H), 4.26 (s, 2H), 4.05-3.71 (m, 8H), 3.52 (m, 1H), 3.56-3.09 (m, 4H), 2.86 (s, 3H), 2.27-1.96 (m, 4H).

Example 34

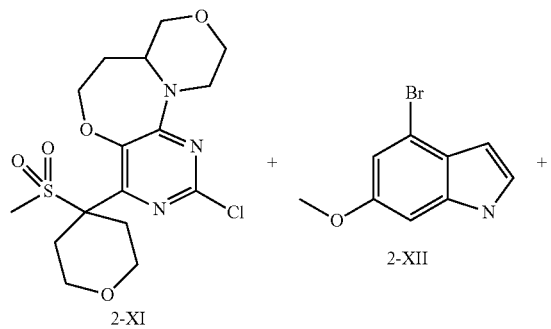

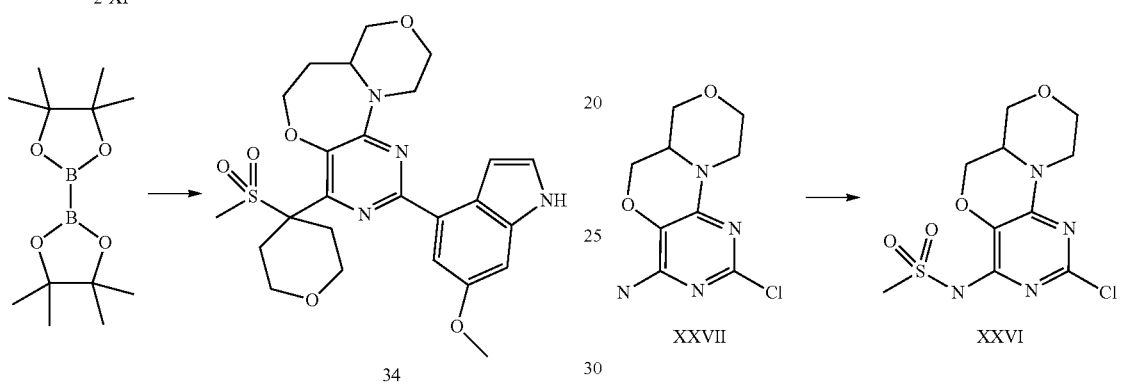

Example 34 was synthesized following a similar protocol to the one used for Example 33 by coupling reaction of compound 2-XII (CAS: 393553-55-4).

LCMS1, tR=4.72 min, MS: 515.2 [M+H]+

1H NMR (300 MHz, DMSO) δ 11.04 (s, 1H), 7.59 (d, J=2.2 Hz, 1H), 7.29 (s, 1H), 7.12 (s, 1H), 7.03 (s, 1H), 4.24 (m, 2H), 4.11-3.79 (m, 8H), 3.79 (s, 3H), 3.56-3.44 (m, 1H), 3.21 (m, 4H), 2.85 (s, 3H), 2.14 (m, 4H).

Example 35

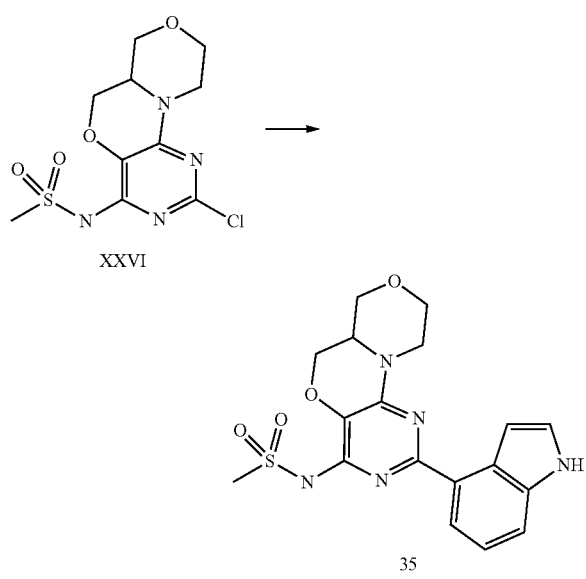

A mixture of intermediate XXVI (40 mg, 0.125 mmol), indole-4-boronic acid pinacol ester (40 mg, 0.162 mmol), PdCl₂(PPh₃)₂ (18 mg, 0.025 mmol) and Na₂CO₃ 2M (0.25 mL) in dioxane (1 mL) was heated in a sealed tube at 100° C. for 4 h. On cooling, the mixture was purified by flash column chromatography (0% to 10% MeOH in DCM) to give the final product 35 as a yellow solid (10 mg).

LC-MS1: tR=4.17 min, M+1=402.5

1H NMR (300 MHz, DMSO) δ 11.11 (s, 1H), 7.85 (d, J=7.5 Hz, 1H), 7.44-7.28 (m, 4H), 7.08 (t, J=7.8 Hz, 1H), 4.38 (m, 1H), 4.30 (m, 1H), 3.96 (m, 1H), 3.84 (m, 2H), 3.53 (m, 2H), 3.34 (s, 4H), 3.22-3.12 (m, 2H), 3.00 (s, 1H).

Intermediate XXVI

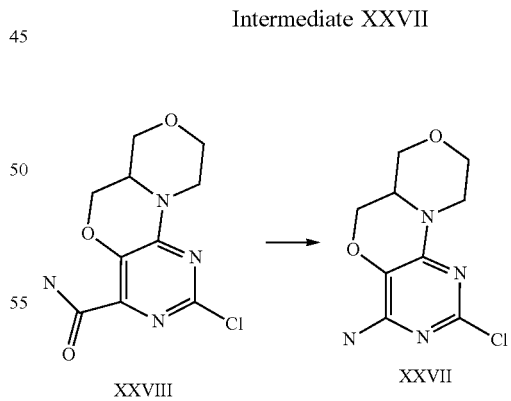

To a solution of intermediate XXVII (30 mg, 0.124 mmol) in DMF (1 mL) was added NaH 60% (12 mg, 0.309 mmol) at 0° C. The mixture was stirred for 20 min and MeSO₂Cl (20 µL, 0.247 mmol) was added. The reaction mixture was allowed to warm to room temperature and stirred for 20 h. After that time more MeSO₂Cl (20 µL, 0.247 mmol) was added and the mixture was stirred for 30 min. Water (20 mL) was added and it was extracted with EtOAc (2×20 mL). The organic layers were dried over Na₂SO₄, filtered and evaporated to give the intermediate product XXVI as orange oil (50 mg).

Intermediate XXVII

A mixture of intermediate XXVIII (50 mg, 0.169 mmol), AcOH (0.5 mL) and H₂O (0.5 mL) was heated in a sealed tube at 100° C. for 30 minutes. On cooling, saturated solution of NaHCO₃ (20 mL) was carefully added and, the mixture was extracted with EtOAc (2×15 mL). The organic layers were dried over Na₂SO₄, filtered and evaporated to give the intermediate product XXVII as white solid (30 mg).

Intermediate XXVIII

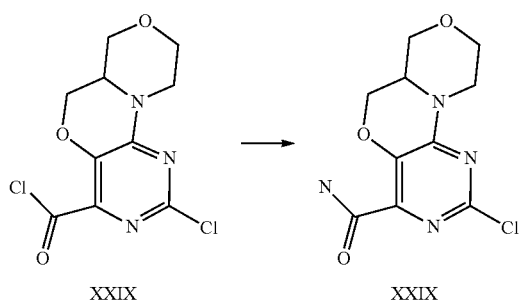

To a suspension of intermediate XXIX (75 mg, 0.259 mmol) in acetone (2 mL) was added a solution of NaN$_3$ (50 mg, 0.776 mmol) in H$_2$O (0.2 mL) dropwise. The reaction mixture was stirred at rt for 1.5 h. Water (5 mL) was added and the mixture was extracted with EtOAc (2×20 mL). The organic layers were dried over Na$_2$SO$_4$, filtered and evaporated to give the intermediate product XXVIII as yellow oily-solid (50 mg).

Intermediate XXIX

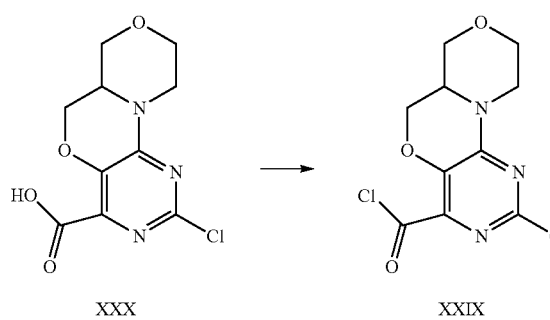

To a suspension of intermediate XXX (70 mg, 0.258 mmol) in DCM (2 mL) was added DMF (1 drop). After 5 min, oxalyl chloride (2 M in DCM) (26 µL) was added at room temperature. After 1 h more oxalyl chloride (2 M in DCM) (0.15 mL) was added. The reaction mixture was stirred at room temperature for 10 min and evaporated to give the intermediate product)(XIX as yellow solid (75 mg).

Intermediate XXX

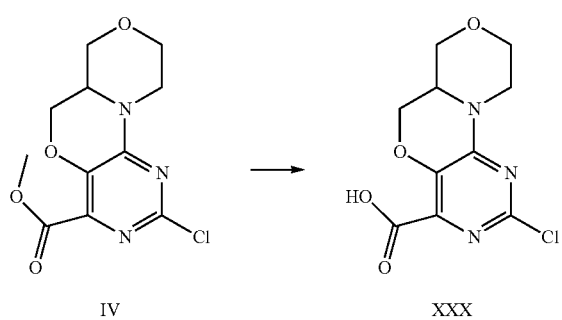

To a suspension of intermediate IV (200 mg, 0.700 mmol) in THF (0.2 mL) was added NaOH 0.5N (1.7 mL, 0.840 mmol). The reaction mixture was stirred at room temperature for 3 h. HCl concentrated was added till pH-4-5 and, the suspension was filtered off and rinsed with H$_2$O to give intermediate XXX as white solid (70 mg). The filtrate was extracted with EtOAc (30 mL) and CHCl$_3$:PrOH (2×30 mL). The organic layers were dried, filtered and evaporated to give intermediate XXX as white solid (130 mg).

Example 36

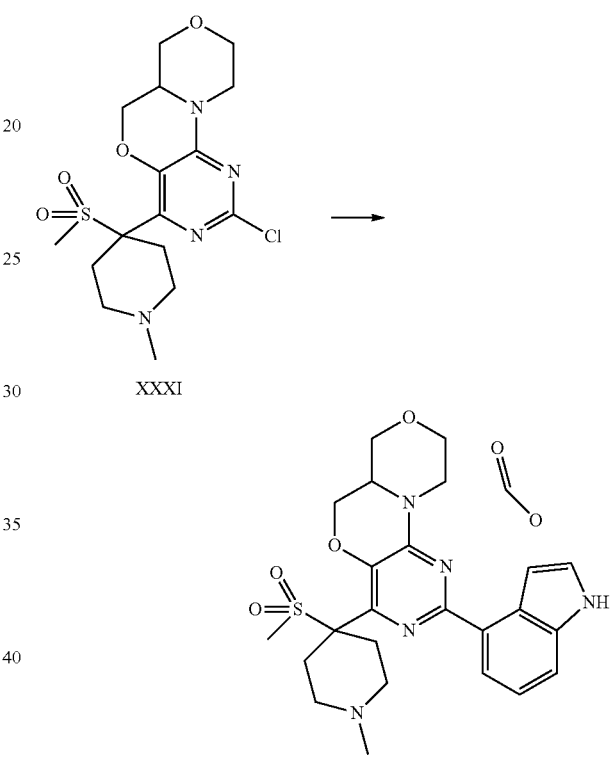

A mixture of intermediate XXXI (30 mg, 0.074 mmol), indole-4-boronic acid pinacol ester (25 mg, 0.1 mmol), PdCl$_2$(PPh$_3$)$_2$ (10 mg, 0.015 mmol), and 2M aqueous solution of Na$_2$CO$_3$ (0.150 mL) in dioxane (1 mL) was heated at 100° C. in a sealed tube under Ar atmosphere. The dark mixture was cooled down to room temperature and filtered through a Celite pad rinsing with DCM. The filtrate was concentrated in vacuo. The residue was purified by flash column chromatography (25% to 100% cyclohexane in EtOAc) and after with 7M NH$_3$ in MeOH/DCM (from 0% to 10%) to give the final product Example 36 as a cream solid (1.5 mg).

LC-MS1: tR=3.55 min, M+1=484.2

1H NMR (300 MHz, DMSO) δ 11.17 (s, 1H), 7.89 (d, J=7.4 Hz, 1H), 7.42 (d, J=7.9 Hz, 1H), 7.39-7.32 (m, 1H), 7.18 (m, 1H), 7.09 (t, J=7.7 Hz, 1H), 4.55 (m, 1H), 4.33 (m, 1H), 4.00 (m, 1H), 3.90-3.64 (m, 4H), 3.59-3.41 (m, 4H), 3.21-2.91 (m, 2H), 2.77 (s, 3H), 1.99 (s, 3H), 1.98-1.88 (m, 2H), 1.78 (m, 2H).

Intermediate XXXI

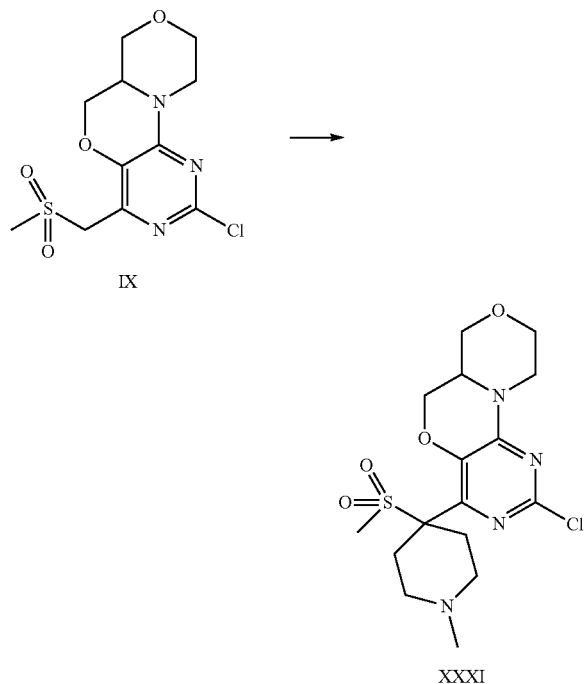

IX

XXXI

To a solution of intermediate IX (50 mg, 0.156 mmol) and mechlorethamine hydrochloride (75 mg, 0.391 mmol) in DMF (3 mL) cooled to 0° C. was added in portions sodium tert-butoxide (75 mg, 0.782 mmol). The resulting mixture was stirred at 0° C. for 30 min and at room temperature for 18 h. After that time more sodium tert-butoxide (70 mg, 0.728 mmol) was added in one pot. The dark resulted mixture was stirred for 1 h, quenched by addition of water, and extracted three times with EtOAc. The combined organic layers were washed with brine, dried over $Na_2SO_4$ and concentrated in vacuo to give intermediate XXXI (30 mg).

Example 37

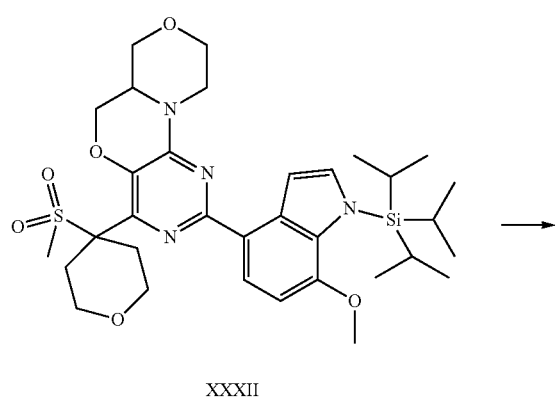

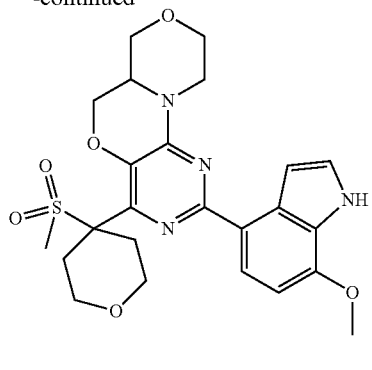

37

To a solution of intermediate XXXII (30 mg, 0.046 mmol) in THF (1 mL) was added a 1 M solution of TBAF in THF (55 μL, 0.055 mmol). The resulting mixture was stirred at rt for 1 h. The reaction was quenched by addition of water and extracted three times with EtOAc. The combined organic layers were washed with brine, dried over $Na_2SO_4$ and concentrated in vacuo. The residue was purified by flash column chromatography (25% to 100% cyclohexane in EtOAc) to give the final product Example 37 as a white solid (4 mg).

LC-MS1: tR=4.68 min, M+1=501.2

1H NMR (300 MHz, DMSO) δ 11.25 (s, 1H), 7.87 (d, J=8.3 Hz, 1H), 7.24 (t, J=2.6 Hz, 1H), 7.14 (s, 1H), 6.67 (d, J=8.3 Hz, 1H), 4.55 (m, 1H), 4.29 (m, 1H), 4.01 (m, 1H), 3.90 (s, 3H), 3.89-3.64 (m, 5H), 3.51 (m, 1H), 3.28-3.09 (m, 6H), 2.79 (s, 3H), 2.13-1.98 (m, 2H).

Intermediate XXXII

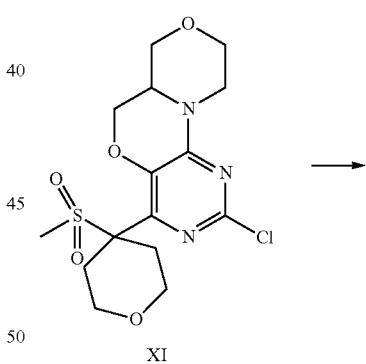

XI

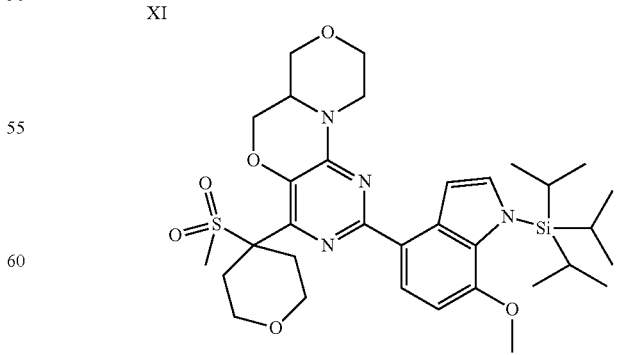

XXXII

A mixture of intermediate XI (50 mg, 0.128 mmol), bis(pinacolato)diboron (81 mg, 0.321 mmol), KOAc (38 mg, 0.385 mmol) and PdCl$_2$(dppf)$_2$ (11 mg, 0.013 mmol) in dioxane (1.5 mL) was heated at 100° C. for 3 h. The dark mixture was cooled down to room temperature and 4-bromo-7-methoxy-1-triisopropylsilanyl-1H-indole (50 mg, 0.154 mmol), Pd(PPh$_3$)$_4$ (13 mg, 0.013 mmol) and 2 M aqueous Na$_2$CO$_3$ (0.2 mL) were added. The resulting mixture was heated in a high pressure tube at 100° C. for 18 h. The dark mixture was cooled down to room temperature and filtered through a Celite pad. The filtrate was concentrated in vacuo. The residue was purified by flash column chromatography (10% to 60% cyclohexane in EtOAc) to give the intermediate XXXII as a cream solid (30 mg).

Example 38

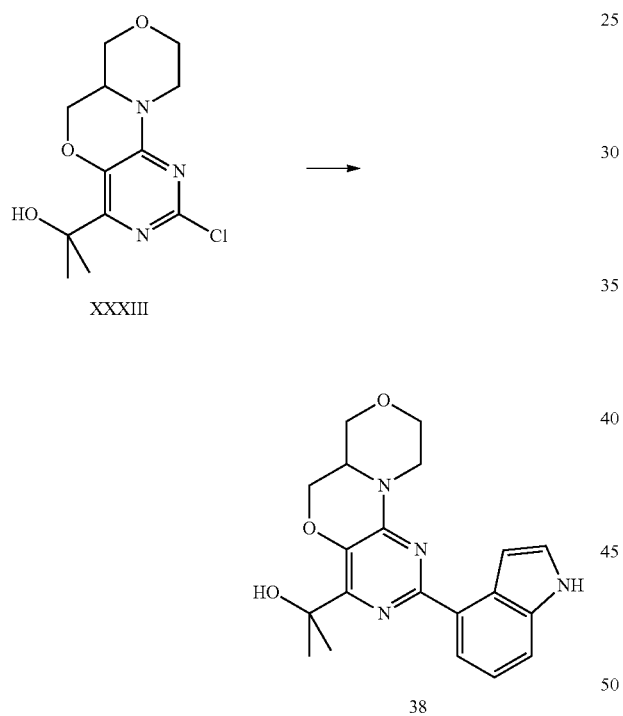

38

A mixture of intermediate XXXIII (45 mg, 0.157 mmol), indole-4-boronic acid pinacol ester (50 mg, 0.205 mmol), PdCl$_2$(PPh$_3$)$_2$ (22 mg, 0.031 mmol) and Na$_2$CO$_3$ 2M (0.32 mL) in dioxane (1 mL) was heated in a sealed tube at 100° C. for 5 h. On cooling, the mixture was purified by flash column chromatography (0% to 5% MeOH in DCM) to give the final product Example 38 as a white solid (10 mg).

LC-MS1: tR=2.87 min, M+1=367.1

1H NMR (300 MHz, DMSO) δ 11.24 (s, 1H), 7.97 (d, J=7.5 Hz, 1H), 7.48 (d, J=8.0 Hz, 1H), 7.44 (t, J=2.7 Hz, 1H), 7.20 (s, 1H), 7.16 (t, J=7.8 Hz, 1H), 5.51 (s, 1H), 4.52 (m, 1H), 4.41 (m, 1H), 4.05 (m, 1H), 3.99-3.86 (m, 2H), 3.72 (s, 1H), 3.57 (m, 1H), 3.17 (m, 3H), 1.51 (s, 6H).

Intermediate XXXIII

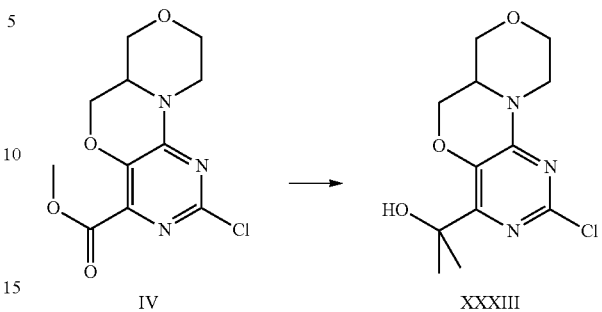

IV           XXXIII

To a suspension of intermediate IV (100 mg, 0.350 mmol) in THF (1.5 mL) at 0° C. was added MeMgBr (3M in Et$_2$O, 0.29 mL, 0.875 mmol) dropwise. The reaction mixture was stirred at 0° C. for 15 min and at room temperature for 1 h. The reaction mixture was poured into saturated solution of NaHCO$_3$ (10 mL) and extracted with EtOAc (2×20 mL). The organic layers were dried over Na$_2$SO$_4$, filtered and evaporated to give the intermediate XXXIII as a yellow solid (95 mg).

Example 39

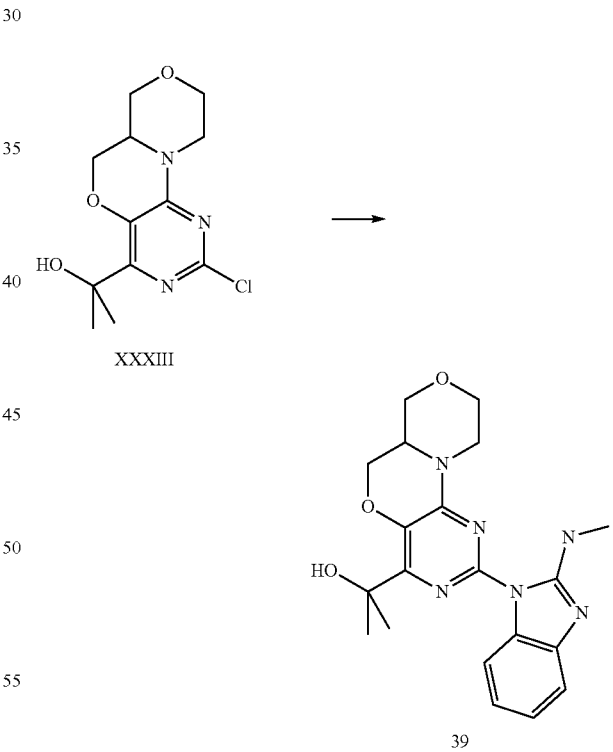

39

To a suspension of intermediate XXXIII (45 mg, 0.157 mmol) in ACN (1 mL) and DMF (0.1 mL) was added N-methyl-1H-1,3-benzodiazol-2-amine (46 mg, 0.315 mmol) and Cs$_2$CO$_3$ (257 mg, 0.787 mmol). The reaction mixture was heated in a sealed tube at 130° C. for 40 h. On cooling, water (35 mL) was added and the mixture was extracted with EtOAc (2×30 mL). The organic layers were dried over Na$_2$SO$_4$, filtered and evaporated. The residue was purified by flash column chromatography (0% to 30% EtOAc in DCM and 0% to 5% MeOH in DCM) to give the final product Example 39 as a white solid (38 mg).

LC-MS1: tR=3.02 min, M+1=397.2

1H NMR (300 MHz, DMSO) δ 8.89 (d, J=4.9 Hz, 1H), 8.14 (d, J=7.5 Hz, 1H), 7.24 (d, J=7.2 Hz, 1H), 7.07 (t, J=7.0 Hz, 1H), 6.97 (t, J=7.1 Hz, 1H), 5.22 (s, 1H), 4.50-4.28 (m, 2H), 4.07 (m, 1H), 4.01-3.90 (m, 1H), 3.86 (m, 1H), 3.79 (m, 1H), 3.58 (m, 1H), 3.23 (m, 2H), 3.05 (m, 3H), 1.52 (s, 5H).

Example 40

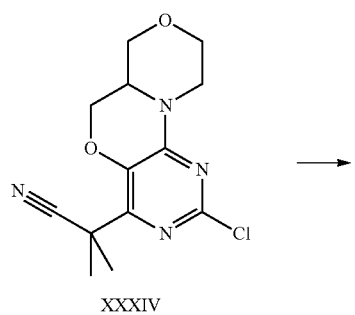

XXXIV

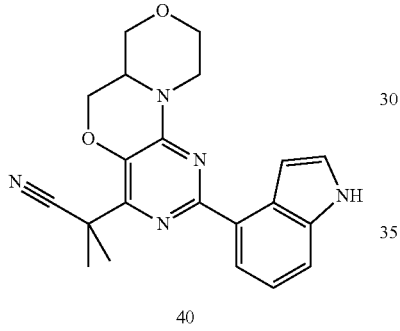

To a degassed mixture of intermediate XXXIV (45 mg, 0.153 mmol), indole-4-boronic acid pinacol ester (50 mg, 0.198 mmol) and 2M aq Na₂CO₃ (0.5 mL) in dioxane (1.5 mL) was added dichlorobis(triphenylphosphine)palladium (ii) (21 mg, 0.031 mmol). The mixture was heated in a close vessel at reflux for 3 h. Water (35 mL) was added and the mixture was extracted with DCM/MeOH 9:1. The organic layers were dried over Na₂SO₄, filtered and evaporated. The residue was purified by flash column chromatography (0% to 6% DCM in MeOH) to give the final product Example 40 (15 mg).

Intermediate XXXIV

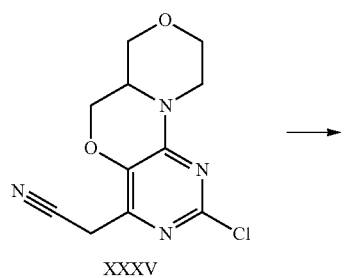

XXXV

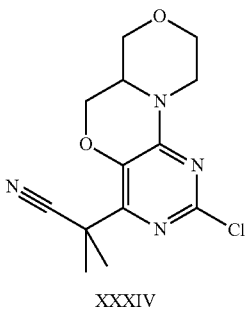

XXXIV

To a mixture of intermediate XXXV (50 mg, 0.187 mmol) and MeI (0.05 mL, 0.803 mmol) in dry DMF (1 mL) at 0° C., NaOtBu (60 mg, 0.562 mmol) was added. The reaction mixture was stirred at room temperature for 2 h. Saturated solution of NaHCO₃ was added and the mixture was extracted with EtOAc. The organic layers were dried over Na₂SO₄, filtered and evaporated to give the intermediate XXXIV (45 mg).

Intermediate XXXV

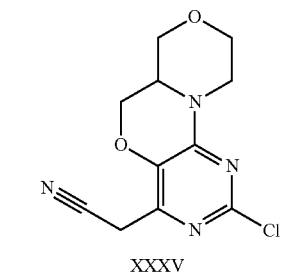

VI

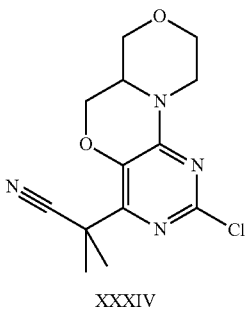

XXXV

To a solution of intermediate VI (200 mg, 0.596 mmol) in DMF (4 mL), NaCN (35 mg, 0.715 mmol) was added at room temperature. The reaction mixture was stirred at room temperature for 2 h. After adding water a solid was filtered off and the filtrate was extracted with EtOAc. The organic layers were dried over Na₂SO₄, filtered and evaporated to give the intermediate XXXV (50 mg).

Example 41

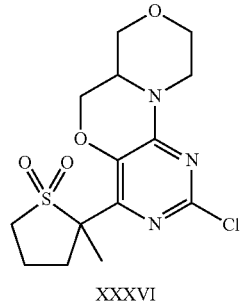

XXXVI

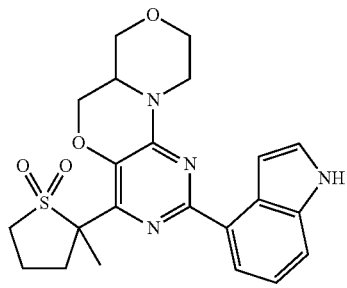

41

A mixture of intermediate XXXVI (134 mg, 0.372 mmol), indole-4-boronic acid pinacol ester (109 mg, 0.447 mmol), PdCl$_2$(PPh$_3$)$_2$ (52 mg, 0.074 mmol) and 2M Na$_2$CO$_3$ aqueous sol (0.745 mL) in 1,4-dioxane (2.55 mL) was heated at 110° C. in a sealed tube in a sea sand bath for 3 hours. On cooling, the reaction mixture was partitioned between H$_2$O and DCM. The aqueous layer was extracted 3 times with DCM. The combined organic layers were dried (Na$_2$SO$_4$), filtered and concentrated. The residue was purified by flash column chromatography, first (0% to 10% MeOH in DCM) and second (0% to 100% EtOAc in cyclohexanes) to give the final product Example 41 as a pale yellow solid (30 mg).

LC-MS: tR=4.92 & 5.00 min, M+1=441.3.

1H NMR (300 MHz, DMSO) δ 11.23 (s, 1H), 8.03 (d, J=7.5 Hz, 1H), 7.49 (d, J=8.0 Hz, 1H), 7.43 (t, J=2.5 Hz, 1H), 7.31 (s, 1H), 7.17 (t, J=7.8 Hz, 1H), 4.57 (m, 1H), 4.43-4.30 (m, 1H), 4.11-3.99 (m, 1H), 3.93 (m, 1H), 3.73 (m, 1H), 3.56 (m, 1H), 3.44-3.32 (m, 2H), 3.28-3.07 (m, 4H), 2.25-2.06 (m, 3H), 1.73 (s, 3H).

Intermediate XXXVI

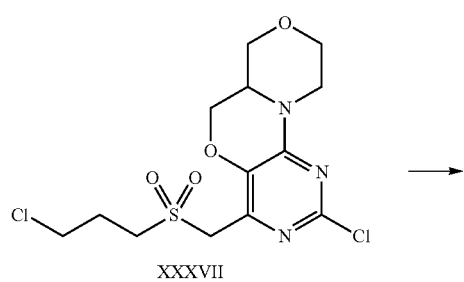

XXXVII

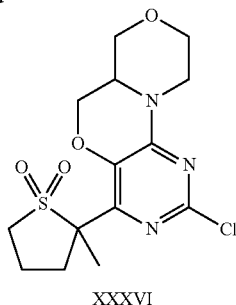

XXXVI

NaOtBu (54 mg, 0.557 mmol) was added to a mixture of intermediate XXXVI (142 mg, 0.371 mmol) in DMF (37 mL) at 0° C. The reaction was stirred at 0° C. for 30 minutes, and at room temperature for 30 additional minutes. An additional amount of NaOtBu (24 mg, 0.248 mmol) was added to the reaction mixture followed by the addition of MeI (0.023 mL, 0.371 mmol) at 0° C. The reaction was stirred at 0° C. for 30 minutes, and then at room temperature for 2 additional hours. Water was added to the reaction mixture and it was extracted with EtOAc (×3). The combined organic layers were dried (Na$_2$SO$_4$), filtered and evaporated to give the intermediate XXXVII (134 mg).

Intermediate XXXVII

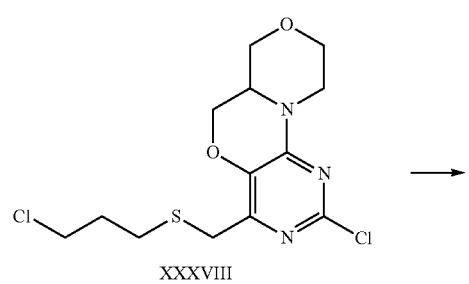

XXXVIII

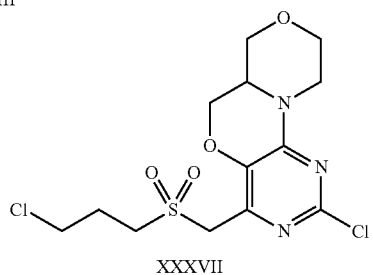

XXXVII

To a mixture of intermediate XXXVIII (209 mg, 0.597 mmol) in dioxane (18.40 mL) and H$_2$O (4.60 mL), mCPBA (113 mg, 0.656 mmol) was added followed by the addition of KMnO$_4$ (127 mg, 0.776 mmol) at room temperature. The reaction was stirred at room temperature for 5 hours. An additional amount of mCPBA (50 mg, 0.290 mmol) and KMnO$_4$ (60 mg, 0.367 mmol) was added to the reaction mixture, and it was stirred at room temperature for 16 hours. An additional amount of mCPBA (20 mg, 0.116 mmol) and KMnO$_4$ (30 mg, 0.184 mmol) was added to the reaction mixture, and it was stirred at room temperature for 3 additional hours. The reaction mixture was quenched with 10% Na$_2$S$_2$O$_3$ aqueous sol and extracted 3 times with EtOAc. The combined organic layers were washed with brine, dried (Na$_2$SO$_4$), filtered and evaporated to give the intermediate XXXV (230 mg).

Intermediate XXXVIII

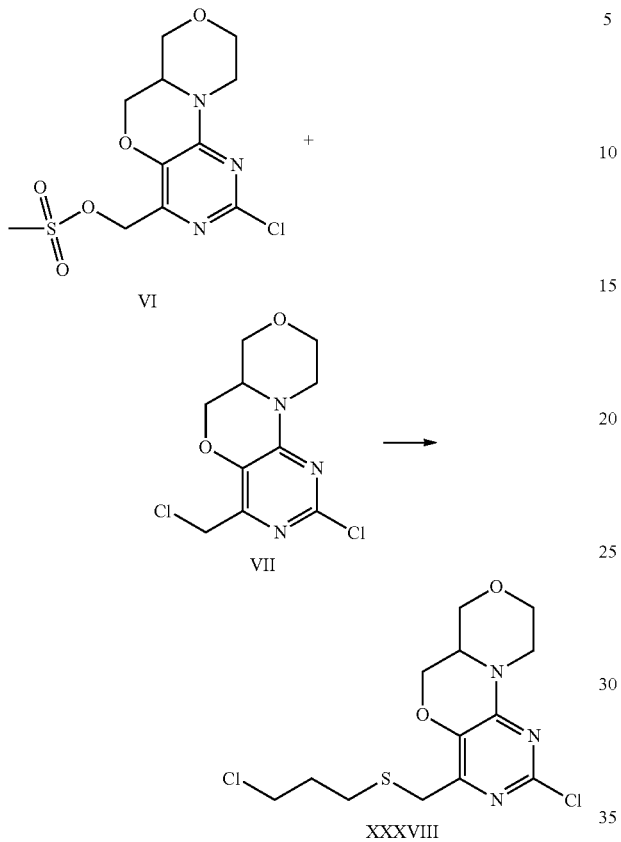

A mixture of intermediates VI and VII (200 mg, 0.596 mmol), 3-chloro-1-propanethiol (79 mg, 0.715 mmol) and DIPEA (0.21 mL, 1.198 mmol) in DCM (11 mL) was heated at 50° C. in a sealed tube in a sea sand bath for 16 hours. An additional amount of 3-chloro-1-propanethiol (40 mg, 0.362 mmol) and DIPEA (0.1 mL, 0.570) were added to the reaction mixture, and it was heated at 50° C. for 72 hours. The reaction was diluted with DCM and washed with a sat NaHCO$_3$ aqueous solution, and with brine. The organic layer was over Na$_2$SO$_4$, filtered and evaporated to give the intermediate XXXVIII (209 mg).

Example 42

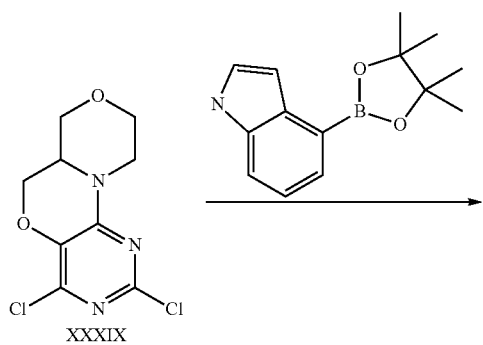

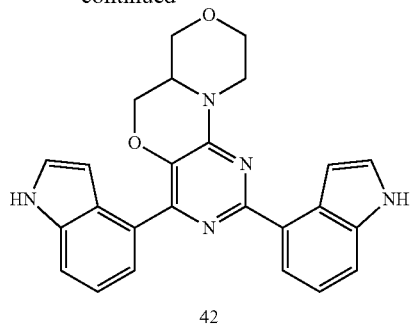

A mixture of intermediate XXXIX (30 mg, 0.114 mmol), indole-4-boronic acid pinacol ester (33 mg, 0.137 mmol), PdCl$_2$(PPh$_3$)$_2$ (12 mg, 0.017 mmol) and Na$_2$CO$_3$ 2M (0.175 mL, 0.343 mmol) in dioxane (0.7 mL) was heated in a sealed tube at 100° C. for 1 hour. On cooling, the mixture was purified by flash column chromatography (0% to 5% MeOH in DCM) to give the final product Example 42 as a white solid (10 mg).

LC-MS: tR=3.34 min, M+1=424.2.

1H NMR (300 MHz, DMSO) δ 11.20 (s, 1H), 11.16 (s, 1H), 8.09 (d, J=7.5 Hz, 1H), 7.48 (t, J=7.3 Hz, 2H), 7.41 (m, 4H), 7.19 (m, 2H), 6.60 (s, 1H), 4.61 (m, 1H), 4.31 (m, 1H), 4.11 (m, 1H), 3.95 (m, 2H), 3.78 (m, 1H), 3.63 (m, 1H), 3.26 (m, 2H).

Intermediate XXXIX

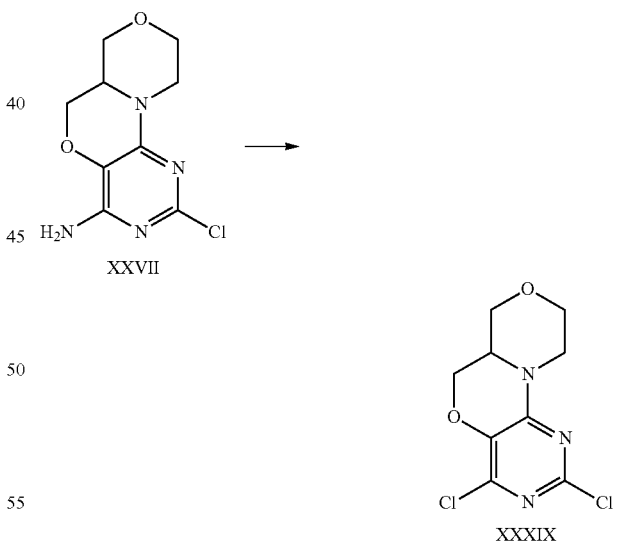

To a solution of intermediate XXVII (100 mg, 0.412 mmol) in DCM (8 mL) was added trimethylchlorosilane (470 μL, 3.709 mmol) dropwise. After stirred at room temperature for 30 minutes, isopentyl nitrite (170 μL, 1.236 mmol) was added dropwise. The reaction mixture was stirred at room temperature for 90 minutes. The mixture was concentrated and the residue was purified by flash column chromatography (0% to 2% MeOH in DCM) to give the intermediate XXVII (65 mg).

Example 43

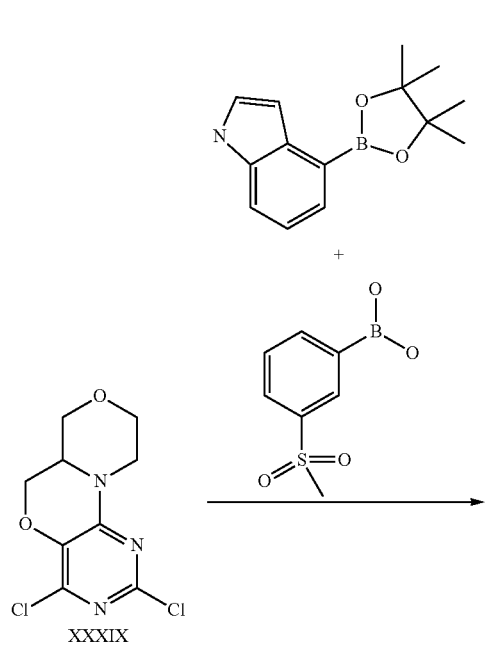

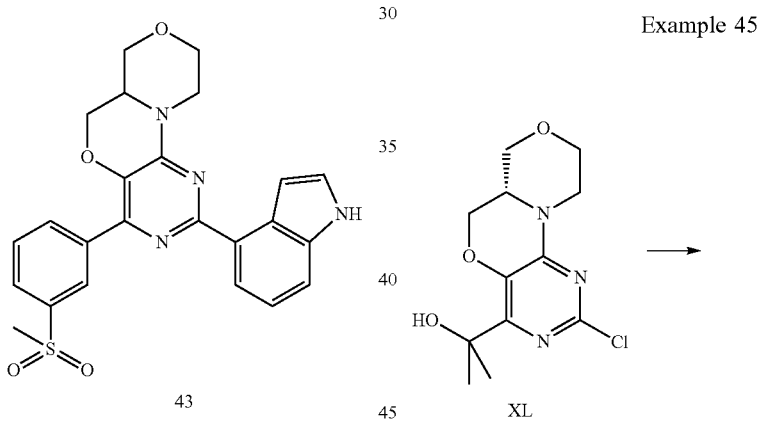

A mixture of intermediate XXXIX (35 mg, 0.134 mmol), indole-4-boronic acid pinacol ester (32 mg, 0.134 mmol), PdCl$_2$(PPh$_3$)$_2$ (14 mg, 0.020 mmol) and Na$_2$CO$_3$ 2 M (0.2 mL) in dioxane (0.8 mL) was heated in a sealed tube at 100° C. for 90 minutes. PdCl$_2$(PPh$_3$)$_2$ (14 mg, 0.020 mmol) and 3-(methylsulfonyl)phenylboronic acid (32 mg, 0.160 mmol) were added and the mixture was heated at 100° C. for 90 minutes. On cooling, the mixture was purified by flash column chromatography, first (0% to 5% MeOH in DCM) and second by prep-HPLC to give Example 43 as a minor product, a white solid (7 mg).

LC-MS: t$_R$=4.89 min, M+1=463.1.

1H NMR (300 MHz, DMSO) δ 11.22 (s, 1H), 8.79 (s, 1H), 8.66 (d, J=7.9 Hz, 1H), 8.52-8.45 (m, 1H), 8.12-8.07 (m, 1H), 8.00 (d, J=8.4 Hz, 1H), 7.76 (t, J=7.8 Hz, 1H), 7.50 (d, J=8.1 Hz, 1H), 7.45-7.33 (m, 2H), 7.19 (t, J=7.7 Hz, 1H), 6.59 (s, 1H), 4.63 (d, J=12.5 Hz, 1H), 4.35 (dd, J=11.1, 3.3 Hz, 1H), 4.08 (d, J=8.7 Hz, 1H), 4.03-3.91 (m, 2H), 3.78 (s, 1H), 3.59 (d, J=11.9 Hz, 1H), 3.26 (s, 3H), 3.14 (s, 1H).

Example 44

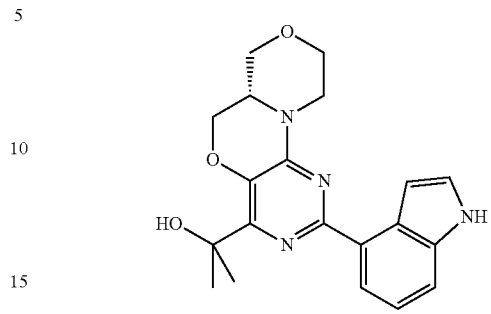

Example 44 was synthesized following a similar synthetic route to that used for Example 38, using as precursor 3(R)-hydroxymethylmorpholine.

LC-MS1, t$_R$=2.92 min. MS: 367.1 [M+H]$^+$

1H NMR (300 MHz, DMSO) δ 11.24 (s, 1H), 7.97 (d, J=6.8 Hz, 1H), 7.55-7.38 (m, 2H), 7.18 (dd, J=14.1, 6.3 Hz, 2H), 5.51 (s, 1H), 4.53 (d, J=11.5 Hz, 1H), 4.42 (dd, J=11.0, 3.3 Hz, 1H), 4.06 (d, J=8.0 Hz, 1H), 3.99-3.86 (m, 2H), 3.72 (s, 1H), 3.57 (t, J=10.5 Hz, 1H), 3.30-3.03 (m, 2H), 1.52 (s, 6H).

Example 45

A mixture of 4-bromo-6-fluoro-1H-indole (36 mg, 0.168 mmol), bis(pinacolato)diboron (90 mg, 0.350 mmol), potassium acetate (41 mg, 0.420 mmol) and PdCl$_2$(dppf) (23 mg, 0.028 mmol) in dioxane (1 mL) was heated in a sealed tube at 100° C. for 3 h. On cooling, intermediate XL (40 mg, 0.140 mmol) in dioxane (1 mL), tetrakis(triphenylphosphine)palladium(0) (16 mg, 0.014 mmol) and $Na_2CO_3$ 2M (0.21 mL) were added. The reaction mixture was heated at 100° C. for 19 h.

On cooling, the mixture was purified by flash column chromatography, first (5% to 10% EtOAc in DCM) and second by prep-HPLC to give the final product Example 45 as a white solid (12 mg).

LC-MS1, $t_R$=4.04 min. MS: 385.2 $[M+H]^+$

1H NMR (300 MHz, DMSO) δ 11.30 (s, 1H), 7.79 (d, J=11.4 Hz, 1H), 7.44 (s, 1H), 7.26 (d, J=15.4 Hz, 2H), 5.34 (s, 1H), 4.47 (dd, J=27.0, 10.9 Hz, 2H), 4.05 (d, J=8.2 Hz, 1H), 3.93 (t, J=10.1 Hz, 2H), 3.72 (s, 1H), 3.58 (s, 1H), 3.20 (dd, J=24.7, 13.8 Hz, 3H), 1.52 (s, 7H).

Intermediate XL

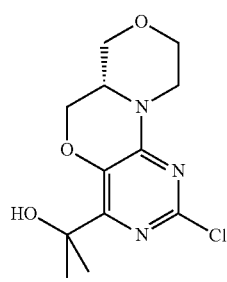

Intermediate XL was synthesized following a similar synthetic route to that used for intermediate XXXIII, using as precursor 3(R)-hydroxymethylmorpholine.

Example 46

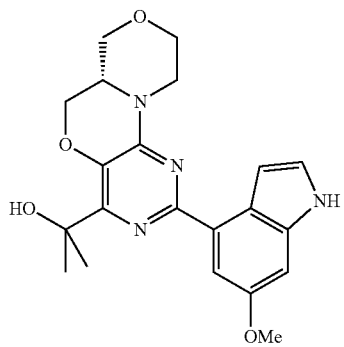

Example 46 was synthesized following a similar synthetic route to the one used for Example 45, by Suzuki coupling of intermediate XL with 4-bromo-6-methoxy-1H-indole in the presence of bis(pinacolato)diboron and palladium catalyst.

LC-MS1, tR=3.38 min. MS: 397.2 $[M+H]^+$

1H NMR (300 MHz, DMSO) δ 11.03 (s, 1H), 7.60 (d, J=2.2 Hz, 1H), 7.29 (s, 1H), 7.10 (s, 1H), 7.02 (s, 1H), 5.44 (s, 1H), 4.59-4.35 (m, 2H), 4.07 (s, 1H), 3.92 (t, J=9.7 Hz, 2H), 3.81 (s, 3H), 3.77-3.65 (m, 1H), 3.57 (s, 1H), 3.22 (s, 2H), 1.52 (s, 6H).

Example 47

Cellular ATR Inhibition Assay

ATR activity is restricted to replicating cells and many of its targets can also be phosphorylated by other PIKKs. These restrictions have limited the development of selective cellular assays in the past. In order to overcome these limitations, a previously developed cellular system in which ATR, and only ATR, can be activated at will in every cell (Toledo et al *Genes Dev.* 22, 297-302 2008) was used. In this system, the addition of 4-hydroxytamoxifen (4-OHT), promotes the nuclear translocation of a fragment of TopBP1 which then activates ATR. The phosphorylation of H2AX that follows 4-OHT addition in these cells is a direct and selective readout of ATR activity, which is not influenced by the rest of PIKKs. This property has been used in the past as a screening platform for compounds with ATR inhibitory capacity (Toledo et al. *Nat Struct Mol Biol* 2011). FIG. 1 illustrates the pipeline to quantify ATR activity with this system, and provides the calculation of $IC_{50}$ for four representative compounds from the current series (compounds of Examples 1, 2, 3 and 11). The cell line used was a clone of the breast cancer cell line MCF7 that stably expresses the ATR activating fragment of TopBP1 (described in Toledo et al *Genes Dev* 2008).

Inhibition of ATR in living cells by compounds of Examples 1, 2, 3 and 11 is shown in FIG. 1. The details are as follows:

(A) The image illustrates the cellular system for ATR activation used in the assays, and which was described in Toledo, L. I., et al. *Genes Dev.* 22, 297-302 (2008). In short, an ATR-activating fragment of the protein TopBP1 is fused to a fragment of the estrogen receptor. The resulting fusion protein is kept in the cytoplasm, but translocates into the nucleus in the presence of 4-hydroxytamoxifen (OHT), where it activates ATR.

(B) OHT-induced activation in this system leads to a generalized phosphorylation of histone H2AX (γH2AX), an ATR target. Importantly, and as described in Toledo, L. I et al. *Genes Dev.* 22, 297-302 (2008), the formation of γH2AX in this system is strictly dependent on ATR, and is not influenced by other related kinases such as DNA-PKs or ATM. The images illustrate the kind of γH2AX signal that is observed with this system. The TopBP1-ER retroviral construct carries an IRES-GFP reporter for the identification of infected cells. Note that every infected (green) cell responds to OHT with a massive formation of γH2AX.

(C) Illustration of the high-throughput microscopy pipeline used for the in cellulo evaluation of ATR inhibitors, as defined in Toledo, L. I. et al. *Nat. Struct. Mol. Biol.* 18, 721-727 (2011). Briefly, TopBP1-ER expressing cells are exposed to OHT for ATR activation in 96 well-plates, and subsequently processed for γH2AX immunofluorescence. The signal is then acquired with an Opera High Throughput Microscope (Perkin Elmer), and the nuclear γH2AX signal is analysed in each well. The average signal in each well is color-coded (black=no signal; red=maximum signal).

(D) Example of how a well-known ATR inhibitor (caffeine), behaves in this cellular assay. On the left, data from the wells of TOPBPI-ER expressing cells with or without OHT (500 nM). On the right, effect of the caffeine on cell exposed to 500 nM OHT. As seen, increasing concentrations of caffeine lead to a gradual decrease in the average nuclear γH2AX signal per well, consistent with ATR inhibition ([caffeine]=0.1, 0.2, 0.5, 1, 2 and 5 mM).

(E) Effect of increasing concentrations of Compound Example 1 and 2 on OHT-induced γH2AX, measured as in (D). (Concentrations: 0.0003, 0.001, 0.003, 0.01, 0.03, 0.1, 0.3, 1 and 3 μM). Duplicates per each condition are shown.

(F) Raw data showing the γH2AX intensity per individual nucleus obtained from the experiment shown in (E), on cells exposed to OHT (500 nM) and increasing concentrations of Compound Example 1. Each dot corresponds to the intensity of γH2AX per individual nucleus. Black bars indicate average values.

(G) Sigmoidal curves representing the data obtained in (E) were used to calculate the $IC_{50}$ values for each compound.

(H) Effect of increasing concentrations of Example 3 and Example 11 on OHT induced γH2AX, measured as in (D). (Concentrations: 0.0003, 0.001, 0.003, 0.01, 0.03, 0.1, 0.3, 1 and 3 µM). Duplicates per each condition are shown.

(J) Raw data showing the γH2AX intensity per individual nucleus obtained from the experiment shown in (H), on cells exposed to OHT (500 nM) and increasing concentrations of Example 11. Each dot corresponds to the intensity of γH2AX per individual nucleus. Black bars indicate average values.

(K) Sigmoidal curves representing the data obtained in (H) were used to calculate the $IC_{50}$ values for each compound.

In addition to the selective system described above, Example compounds presented here were screened for their ability to inhibit intracellular ATR using a western blot assay to detect phosphorylation of the ATR substrate CHK1(S345) in hydroxyurea treated cells. HT29 cells are plated at 500,000 cells per well in 6-well plates in RPMI media (Sigma R6504) supplemented with 10% foetal bovine serum (Sigma F7524), Penicillin/Streptomycin solution diluted 1:100 (Gibco 15070-063), and fungizone (Gibco, 15290-018), and allowed to adhere overnight at 37° C. in 5% $CO_2$. Compounds are then added to the cell media from a final concentration of 10 µM in 3-fold serial dilutions and the cells are incubated at 37° C. in 5% $CO_2$. After 15 min, hydroxyurea (Sigma H8627) is added to a final concentration of 2.5 mM. After 30 min of treatment with hydroxyurea, the cells are washed in PBS, lysed adding 50 µl of in protein lysis buffer (50 mM Tris pH 7.5, 150 mM NaCl, 1% IGEPAL CO-630 (Sigma, Ref. 542334-100G-A), Phospho Stop (Roche, Ref. 04906837001) and Complete Mini EDTA free (Roche, Ref. 11836170001)). The protein content of the lysates was determined by the modified method of Bradford (Sigma, Ref. B6916). The proteins were resolved by SDS-PAGE and transferred to nitrocellulose membrane (VWR International Eurolab, Ref. 732-4007). The membranes were incubated overnight at 4° C. with antibodies specific for total CHK1 (Santa Cruz Biotechnology, sc-8404), phosphoserine-345 CHK1 (Cell Signaling Technology #2348) they were washed and then incubated with IRDye800 conjugated anti-mouse (Pierce/Cultek, 35521) and Alexa Fluor 680 goat anti-rabbit IgG secondary antibodies (Invitrogen, A21076). The bands were visualized and quantified using an Odyssey infrared imaging system (Li-Cor Biosciences). The percentage of phosphorylated CHK1 vs total CHK1 in cells treated with hydroxyurea was taken as hundred percent of phosphorylation. The percentage of CHK1 phosphorylation is finally plotted against concentration for each compound and $EC_{50}$s for intracellular ATR inhibition are calculated using ActivityBase from IDBS.

Biological activity of compounds in ATR cellular assay is represented in the following tables by semi-quantitative results: $EC_{50}$>1 µM (•), 100 nM<$EC_{50}$<1 µM (••) or $EC_{50}$<100 nM (•••).

TABLE 1

| Example | ATR $EC_{50}$ | Example | ATR $EC_{50}$ |
|---|---|---|---|
| 1 | *** | 45 | ** |
| 2 | *** | 46 | ** |
| 3 | *** | 61 | ** |
| 4 | *** | 62 | ** |
| 5 | ** | 63 | *** |
| 6 | ** | 64 | ** |
| 7 | ** | 65 | *** |
| 8 | *** | 66 | ** |
| 9 | ** | 67 | *** |
| 10 | ** | 68 | ** |
| 11 | *** | 69 | ** |
| 12 | ** | 70 | ** |
| 13 | ** | 71 | *** |
| 14 | ** | 72 | ** |
| 15 | ** | 73 | * |
| 16 | ** | 74 | ** |
| 17 | *** | 75 | ** |
| 18 | *** | 76 | * |
| 19 | *** | 77 | *** |
| 20 | ** | 78 | *** |
| 21 | * | 79 | ** |
| 22 | ** | 80 | * |
| 23 | ** | 81 | * |
| 24 | ** | 82 | ** |
| 25 | ** | 83 | ** |
| 26 | * | 86 | * |
| 27 | ** | 87 | * |
| 28 | *** | 92 | *** |
| 29 | *** | 93 | ** |
| 30 | ** | 94 | * |
| 31 | *** | 95 | * |
| 32 | * | 96 | ** |
| 33 | ** | 97 | ** |
| 34 | ** | 101 | ** |
| 35 | * | 102 | * |
| 36 | * | 103 | ** |
| 37 | ** | 105 | ** |
| 38 | ** | 106 | * |
| 39 | ** | 108 | ** |
| 40 | ** | 109 | ** |
| 41 | ** | 110 | * |
| 42 | ** | 112 | ** |
| 43 | ** | 113 | * |
| 44 | ** | 114 | * |

Example 48

Cellular ATR and ATM Inhibition Assay

ATM and ATR have distinct and overlapping responses to DNA damage. They must participate together and responses must be coordinated. Both pathways may be activated by ionizing radiation, and UV. As UV treatment is not practical for use in a high throughput cell assay, the UV mimetic 4NQO (Sigma) was chosen to activate the ATR and ATM DNA damage response pathway.

Chk1, a downstream protein kinase of ATR, has a key role in DNA damage checkpoint control, as well as Chk2 downstream of ATM. Activation of Chk1 involves phosphorylation of Ser317 and Ser345 (regarded as the preferential target for phosphorylation/activation by ATR) and activation of Chk2 implicates phosphorylation of Thr68 (most notably substrate of ATM). This assay measures a decrease in phosphorylation of Chk1 (Ser 345) and Chk1 (Thr 68) in HT29 colon adenocarcinoma cells following treatment with compound and the UV mimetic 4NQO. Compounds at 1 mM were created by diluting in 100% DMSO and then diluted 1:100 into assay media (RPMI, 10% FCS, 1% glutamine). Cells were plated in 6 well Costar plates at $5 \times 10^5$ cells per mL in 2 mL RPMI, 10% FCS, 1% glutamine and grown for 24 hrs. Following addition of compound the cells were incubated for 60 minutes. A final concentration of 3 µM 4NQO (prepared in 100% DMSO) was then added and the cells incubated for a further 60 mins. The cells are lysed and pChk1 Ser345 and pCHK2 Thr68 (Cell Signaling Technology, #2661) versus total CHK1 and CHK2 (Santa Cruz Biotechnology, se-5278) respectively has analysed by western blot as described above. The percentage of phosphorylated CHK1 versus total CHK1 or p-CHK2 versus total CHK2 in cells treated with 4NQO was taken as hundred percent of phosphorylation. The percentage of CHK1 or CHK2 phosphorylation is finally plotted against concentration for each compound and $EC_{50}$s for intracellular ATR inhibition are calculated using ActivityBase from IDBS.

Selectivity of exemplified compounds for ATR over ATM is shown in Table 2.

TABLE 2

| Example | UV mimetic inhibition of CHK1P at 10 µM (%) | UV mimetic inhibition of CHK2P at 10 µM (%) |
| --- | --- | --- |
| 1 | 99 | 0 |
| 2 | 98 | 0 |
| 3 | 98 | 0 |
| 5 | 98 | 0 |
| 8 | 98 | 25 |
| 10 | 95 | 25 |
| ATM inhibitor KU-60019 | 38 | 99 |

Example 49

In Vitro Cell Proliferation Assays

The in vitro potency of the compounds was measured by the cell proliferation assay described above; the CellTiter-Glo® Luminescent Cell Viability Assay, commercially available from Promega Corp., Madison, Wis. This homogeneous assay method is based on the recombinant expression of *Coleoptera* luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al. (1993) *J. Immunol. Meth.* 160:81-88; U.S. Pat. No. 6,602,677). The CellTiterGlo® Assay was conducted in 96 making it amenable to automated high-throughput screening (HTS) (Cree et al. (1995) *AntiCancer Drugs* 6:398-404).

The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 96-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

Example 50

Combination Assay

The combination index (CI) of combinations of certain example compounds and various chemotherapeutic agents in the cell titre in vitro cell proliferation assays may be tested. A combination index score is calculated by the Chou and Talalay method (CalcuSyn software, Biosoft). The strength of synergy is scored using the ranking system of Chou and Talalay: CI less than 0.8 indicates synergy, CI between 0.8 and 1.2 indicates additivity and CI greater than 1.2 indicates antagonism.

The $EC_{50}$ values of representative combinations are also calculated. The individually measured $EC_{50}$ values of the chemotherapeutic agent and the example compounds are compared to the $EC_{50}$ value of the combination. The cell lines are characterized by tumour type. Combination assays are performed as described in: "Pim 1 kinase inhibitor ETP-45299 suppresses cellular proliferation and synergizes with PI3K inhibition". Blanco-Aparicio, et al. *Cancer Lett.* 2011, 300(2), 145-153.

Example 51

PI3K Alpha Activity Assay

The kinase activity was measured by using the commercial ADP Hunter™ Plus assay available from DiscoveRx (#33-016), which is a homogeneous assay to measure the accumulation of ADP, a universal product of kinase activity. The enzyme, PI3K (p110α/p85α was purchased from Carna Biosciences (#07CBS-0402A). The assay was done following the manufacturer recommendations with slight modifications, mainly that the kinase buffer was replace by 50 mM HEPES, pH 7.5, 3 mM $MgCl_2$, 100 mM NaCl, 1 mM EGTA, 0.04% CHAPS, 2 mM TCEP and 0.01 mg/mL BGG. The PI3K was assayed in a titration experiment to determine the optimal protein concentration for the inhibition assay. To calculate the $IC_{50}$ of the compounds, serial 1:5 dilutions of the compounds were added to the enzyme at a fixed concentration (2.5 µg/mL). The enzyme was preincubated with the inhibitor and 30 µM PIP2 substrate (P9763, Sigma) for 5 min and then ATP was added to a final 50 µM concentration. The reaction was carried out for 1 hour at 25° C. Reagent A and B were sequentially added to the wells and plates were incubated for 30 min at 37° C. Fluorescence counts were read in a Victor instrument (Perkin Elmer) with the recommended settings (544 and 580 nm as excitation and emission wavelengths, respectively). Values were normalized against the control activity included for each enzyme (i.e., 100% PI3 kinase activity, without compound). These values were plotted against the inhibitor concentration and were fit to a sigmoid dose—response curve by using the model sigmoidal Four-Parameter Logistc implement for Activity base—software.

Example 52 mTOR Activity Assay

The enzymatic mTOR activity was measured using a LanthaScreen™ kinase activity assay (Invitrogen). The enzyme was purchased from Invitrogen (PV4754), as well as the GFP-labelled substrate (4EBP1-GFP; PV4759) and the Tb-antip4EBP1(pThr46) antibody (PV4757). The assay was performed in 50 Mm HEPES buffer, pH 7.5, containing 1.5 mM $MnCl_2$, 10 mM $MgCl_2$, 1 mM EGTA, 2.5 mM DTT and 0.01% Tween-20. The concentration of the assay components were the following: 0.24 nM mTOR kinase, 400 nM 4EBP1-GFP, 10 mM ATP and serial dilutions of the compound (inhibitor) to be evaluated. After 1 h incubation at room temperature, 20 mM EDTA was used to stop the reaction and terbium-labelled antibody (4 nM) added to detect phosphorylated product. The antibody associates with the phosphorylated product resulting in an increased TR-FRET value. The TR-FRET value (a dimensionless number) was calculated as the ratio of the acceptor signal (GFP, emission at 520 nm) to the donor signal (terbium, emission at 495 nm). Values were plotted against the inhibitor concentration and fitted to a sigmoid dose—response curve using model sigmoidal Four-Parameter Logistc implement for Activity base—software.

Example 53

DNAPK Activity Assay

The kinase activity was measured by using the commercial ADP Hunter™ Plus assay available from DiscoveRx (#90-0083), which is a homogeneous assay to measure the accumulation of ADP, a universal product of kinase activity. The enzyme, DNA-PK was purchased from Promega (#V5811). The assay was done following the manufacturer recommendations with slight modifications: Mainly the kinase buffer was replace by 15 mM HEPES, pH 7.5, 10 mM $MgCl_2$, 20 mM NaCl, 1 mM EGTA, 0.1 mg/mL BGG, 0.02% Tween 20. The DNA-PK was assayed in a titration experiment to determine the optimal protein concentration for the inhibition assay. To calculate the 1050 of the Compounds, serial 1:3 dilutions of the compounds were added to the enzyme at a fixed concentration (2 U/μL). The enzyme was preincubated with the inhibitor and 200 μM DNA substrate and then ATP was added to a final 75 μM concentration. Reaction was carried out for 1 hour at 37° C. Reagent A and B were sequentially added to the wells and plates were incubated for 30 min at RT. Fluorescence counts were read in a EnVision instrument (Perkin Elmer) with the recommended settings (550 and 590 nm as excitation and emission wavelengths, respectively). Values were normalized against the control activity included for each enzyme (i.e., 100% DNA_PK kinase activity, without compound). These values were plotted against the inhibitor concentration and were fit to a sigmoid dose-response curve by using the model sigmoidal Four-Parameter Logistc implement for Activity base—software.

Example 54

AKT Phosphorylation Inhibition (ELISA Assay)

AKT phosphorylation Inhibition. (ELISA assay) may be used as a measure of the PI3K and mTOR activity in cells. Activity is measured as endogenous levels of phospho-Akt1 (Ser473) protein. Osteosarcoma U2OS cells are plated in 96 poly-D-lysine coating tissue culture plates (18.000 cells/well). After the treatment with serial dilutions of the compound during 3 h, the cells are fixed directly in the wells with 4% paraformaldehyde.

After fixing, individual wells go through the same series of steps used for a conventional immunoblot: including blocking with 5% BSA, incubation with 1/1000 of primary antibody-AKT (Ser 74) in PBS containing 5% BSA at 4° C. overnight (Cell Signalling), washing and incubation with second antibody HRP-anti-mouse IgG for 1 h at RT (Amersham). After the addition of SuperSignal ELISA Femto maximum sensitivity chemiluminescent substrate (Pierce) the results are read using a luminescence plate reader (Victor). EC50 values were established for the tested compounds.

Biological activity for selected compounds in the biochemical assay of PI3Kα, mTOR and DNAPK is shown in Table 3.

TABLE 3

| Example | PI3Kα $IC_{50}$ (μM) | mTOR $IC_{50}$ (μM) | DNAPK $IC_{50}$ (μM) |
|---|---|---|---|
| 1 | 1.7 | 0.146 | 17.3 |
| 2 | 13.3 | 2.72 | 25.00 |
| 3 | 4.9 | 1.86 | 25.00 |
| 4 | 2.4 | 0.274 | 10.00 |
| 5 | 14.9 | 0.194 | 25.00 |
| 6 | 4.5 | 0.558 | 4.52 |
| 7 | 6.6 | 1.62 | 10.00 |
| 8 | 2.8 | 0.588 | 1.96 |
| 9 | 2.0 | 3.27 | 25.00 |
| 10 | 11.5 | 10.00 | 10.00 |
| 11 | 1.9 | 0.604 | 1.51 |
| 12 | 50.0 | 10.00 | 10.00 |
| 13 | 21.0 | 10.00 | 10.00 |
| 14 | 7.9 | 2.19 | 10.00 |
| 15 | 1.1 | 0.851 | 2.86 |
| 16 | 0.67 | 0.852 | 2.82 |
| 17 | 6.0 | 2.62 | 10.00 |
| 18 | 8.5 | 10.00 | 10.00 |
| 19 | 5.0 | 1.76 | 10.00 |
| 20 | 10.3 | 1.82 | 25.00 |
| 21 | 0.4 | 5.58 | 4.15 |
| 22 | 50.0 | 10.00 | 25.00 |
| 23 | 50.0 | 10.00 | 6.37 |
| 24 | 19.3 | 1.67 | 10.00 |
| 25 | 23.4 | 0.582 | 10.00 |
| 26 | 2.7 | 10.00 | 10.00 |
| 27 | 2.5 | 0.55 | 25.00 |
| 28 | 4.7 | 0.785 | 25.00 |
| 29 | 3.8 | 0.435 | 25.00 |
| 30 | 2.5 | 4.68 | 25.00 |
| 31 | 6.5 | 0.586 | 1.88 |
| 32 | 50.0 | 3.09 | 10.00 |
| 33 | >10 | 1.93 | 25.00 |
| 34 | 23.3 | 0.808 | 25.00 |
| 35 | 6.95 | 2.35 | 10.00 |
| 36 | 12.5 | 10.00 | 25.00 |
| 37 | 16.9 | 4.4 | 25.00 |
| 38 | 2.39 | 0.275 | 7.21 |
| 39 | 2.17 | 1.24 | 3.18 |
| 40 | 1.67 | 0.279 | 10.00 |
| 41 | 6.9 | 0.381 | 10.00 |
| 42 | 6.55 | 0.412 | 10.00 |
| 43 | 10.6 | >10 | 5.04 |
| 44 | 1.18 | 0.044 | 3.06 |
| 45 | 2.27 | 0.053 | 0.886 |
| 46 | 0.48 | 0.038 | 2.82 |
| 61 | 3.22 | 0.228 | 10.00 |
| 62 | 16.2 | 6.6 | 10.00 |
| 63 | 6.61 | 0.252 | 4.3 |
| 64 | 2.65 | 0.505 | 0.196 |
| 65 | 6.25 | 0.921 | 6.65 |
| 66 | 7.17 | 0.854 | 2.41 |
| 67 | 3.16 | 0.151 | 10.00 |

TABLE 3-continued

| Example | PI3Kα IC$_{50}$ (μM) | mTOR IC$_{50}$ (μM) | DNAPK IC$_{50}$ (μM) |
|---|---|---|---|
| 68 | 7.38 | 2.08 | 10.00 |
| 69 | 1.98 | 0.336 | 4.93 |
| 70 | 0.87 | 0.226 | 0.741 |
| 71 | 1.08 | 0.0993 | 10.00 |
| 72 | 0.82 | 0.0453 | 1.6 |
| 73 | 50.0 | 10.00 | 10.00 |
| 74 | 2.24 | 0.152 | 0.989 |
| 75 | 2.52 | 0.093 | 1.83 |
| 76 | 50.0 | 10.00 | 10.00 |
| 77 | 5.36 | >10 | 10.00 |
| 78 | 4.49 | 0.047 | |
| 79 | 28.6 | 10.00 | 10.00 |
| 80 | 13.1 | 0.501 | 10.00 |
| 81 | 50.0 | 5.55 | 10.00 |
| 82 | 5.6 | 1.59 | 10.00 |
| 83 | 12.2 | 2.47 | 3.11 |
| 86 | 50.0 | 3.41 | 10.00 |
| 87 | 50.0 | 10.00 | 0.21 |
| 92 | 2.75 | 1.24 | 6.15 |
| 93 | 7.44 | 0.117 | 10.00 |
| 94 | 50.0 | 4.48 | 10.00 |
| 95 | 50.0 | 10.00 | 10.00 |
| 96 | 50.00 | 6.08 | 10.00 |
| 97 | 50.0 | 6.8 | 6.8 |
| 101 | 12.6 | 0.227 | 10.00 |
| 102 | 50.0 | 1.82 | 0.10 |
| 103 | 3.16 | 0.058 | 10.00 |
| 105 | 28.9 | 1.99 | 10.00 |
| 106 | 50.0 | 10.00 | 1.16 |
| 108 | 15.4 | 0.579 | 1.75 |
| 109 | 5.69 | 0.224 | 10.00 |
| 110 | 50.0 | 10.00 | 10.00 |
| 112 | 19.5 | 0.235 | 10.00 |
| 114 | 50.00 | 10.00 | 10.00 |

Example 55

Evaluation of the Capacity of the Compounds to Generate Single-Stranded DNA

The main cellular function of ATR is the suppression of RS (Lopez-Contreras, A. J. & Fernandez-Capetillo, O. *DNA Repair (Amst.)* 9, 1249-1255 (2010)). At the molecular level, RS is defined as the accumulation of large patches of single-stranded DNA. In cells, ssDNA is rapidly coated by Replication Protein A (RPA). Therefore, the level of chromatin-bound RPA can be used as a surrogate marker of ssDNA (Toledo, L. I. et al. *Nat. Struct. Mol. Biol.* 18, 721-727 (2011); Lopez-Contreras, A. J. et al. *Journal of Experimental Medicine* (2012). doi:10.1084/jem.20112147).

Figure 2A:
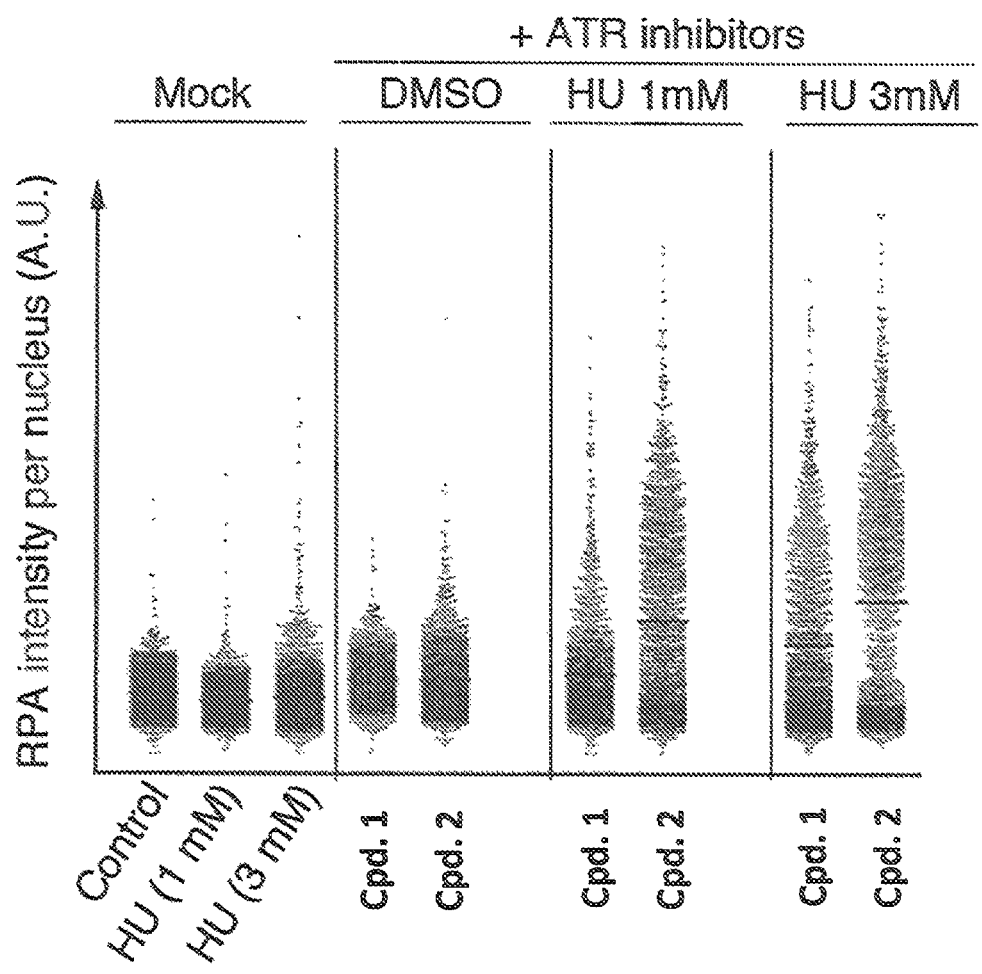
FIG. 2(A) shows the effect of chemical entities Example 1 and Example 2, alone or in combination with hydroxyurea (HU), on the level of chromatin-bound RPA.
Figure 2B:
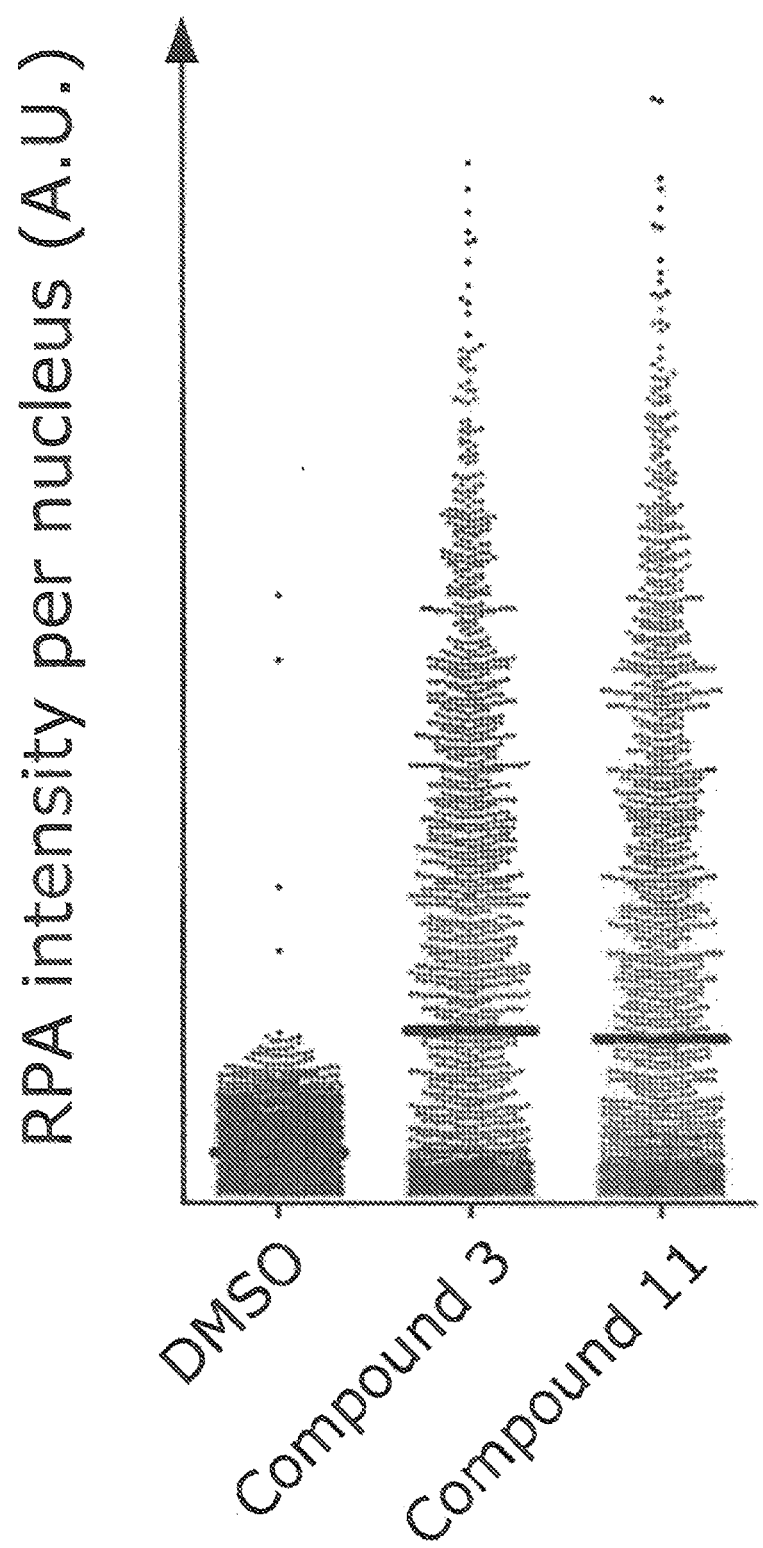
FIG. 2(B) shows the effect of chemical entities Example 3 and Example 11 on the level of chromatin-bound RPA.

The effect of compounds of Examples 1, 2, 3 and 11 on the level of chromatin-bound RPA is shown in FIGS. 2(A) and 2(B). The details are as follows:

(A) FIG. 2(A) shows the effect of Example 1 and Example 2 (1 μM) on the level of chromatin-bound RPA. The compounds were used alone, or in combination with HU, an inhibitor of the ribonucleotide reductase that depletes dNTP pools and is a known inducer of replicative stress. Chromatin-bound RPA was quantified by high-throughput microscopy as described above. Consistent with ATR inhibition, the three compounds can increase chromatin-bound RPA levels, and this activity is greatly exacerbated in the presence of HU.

(B) FIG. 2(B) shows the effect of Example 3 and Example 11 (1 μM) in increasing the levels of chromatin-bound RPA. This was quantified by High-Throughput Microscopy as defined before. Consistent with ATR inhibition, the two compounds can increase chromatin-bound RPA levels.

Example 56

Evaluation of the Activity in Preventing the Collapse of Stalled Replication Forks One of the best-known roles of ATR is preventing the formation of DNA double-stranded breaks (DSB) at stalled replication forks (Lopez-Contreras, A. J. & Fernandez-Capetillo, O. *DNA Repair (Amst.)* 9, 1249-1255 (2010)). To test this activity, two assays were performed (A, B). Both assays demonstrate that compounds of Example 1, Example 2, Example 3 and Example 11 can robustly promote the breakage of HU-stalled replication forks, which is consistent with their ATR inhibitory capacity.

a. In the first assay, U2OS human cells were exposed (or not) to 2 mM of HU to promote the stalling of replication forks. Then, cells were released into media containing 1 μM of compounds Example 1 and Example 2 for 16 h and the DNA content was analysed by flow cytometry measuring the fluorescence intensity of propidium iodide. Control cells were treated with the same volume of DMSO.

The results are shown in FIG. 3(A) for compounds of Examples 1 and 2. The generation of DNA breaks in replicating cells would activate the next cellular checkpoint in G2, leading to cell cycle arrest and an accumulation of cells in the G2 phase. Consistent with this, compounds Example 1 and Example 2 led to an accumulation of cells in the G2 phase, which was greatly enhanced if previously exposed to HU.

The results are shown in FIG. 3(B) for compounds of Examples 3 and 11. Massive generation of DNA breaks in replicating cells would prevent cells to progress through S phase, leading to an accumulation of cells at this stage of the cell cycle. Consistent with this, both compounds led to an intra-S phase accumulation of cells.

b. The generation of DSB deriving from the collapse of stalled forks was also quantified by assessment of the formation of nuclear foci of the DNA repair protein 53BP1. This assessment of ATR inhibition was carried out by methods described in the literature (Toledo et al. *Nat. Struct. Mol. Biol.* 2011). FIG. 4(A) shows the number of 53BP1 foci that were present in cells treated with ATR inhibitors (for Examples 1 and 2) with or without HU as in a. As can be seen in FIG. 4(A), the presence of 1 μM of compound Example 1 or Example 2 led to a massive formation of 53BP1 foci in cells treated with HU (2 mM).

Figure 4B:
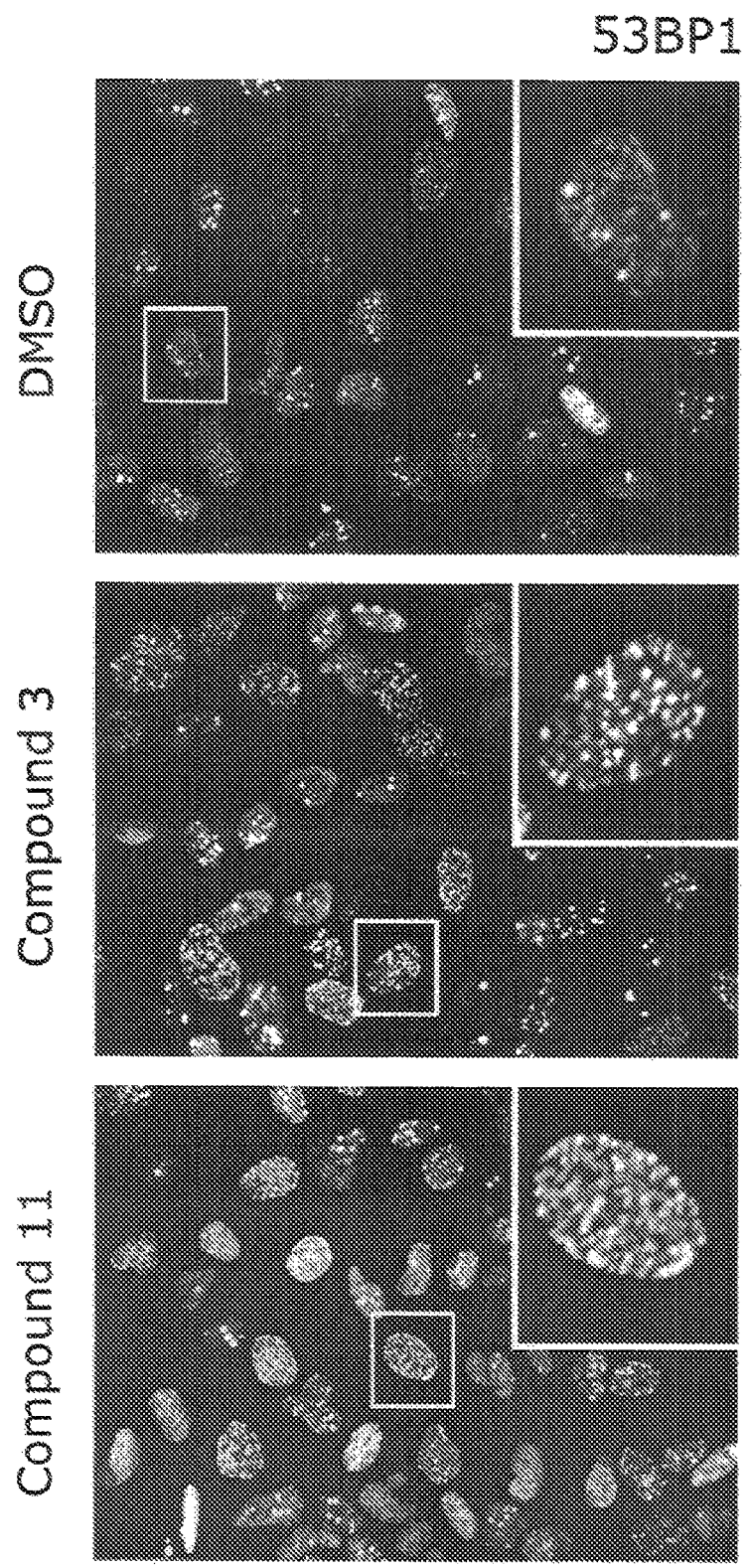
FIG. 4(B) shows the effect of chemical entities Example 3 and Example 11 on the formation of nuclear foci of the DNA repair protein 53BP1.

FIG. 4(B) shows the number of 53BP1 foci that were present in cells treated with ATR inhibitors (for Examples 3 and 11). As seen in the images extracted from cells treated as in a, the presence of 1 μM of Example 3 or Example 11 led to a massive formation of 53BP1 foci. Consistent with their ATR-inhibitory capacity, both assays exemplify that compounds 3 and 11 can robustly promote the stalling and breakage of replication forks.

Example 57 hERG Binding Assay

The hERG gene codes for an ion channel protein located on the heart. It is involved in the coordination of the heart's beating owing its ability to conduct electrical current. Interaction with this hERG channel can cause QT prolongation. This prolongation could lead to ventricular arrhythmias. Therefore, the compounds of the present application were characterized according to the following assay.

Predictor hERG Assay test kits were obtained from Invitrogen (Carlsbad, Calif.). The binding assay was carried out according to the kit instructions. Fluorescence polarization measurements were made using EnVision Microplate Reader from Perkin-Elmer Instruments. Polarization values were calculated automatically using Activity base Software. A description of the assay is published by Piper, et al. *Assay & Drug Dev. Tech.* 6, 213 (2008).

$IC_{50}$ data (in micromolar) for selected compounds is shown in Table 4:

TABLE 4

| Compound | hERG $IC_{50}$ (mM) |
|---|---|
| Ex. 3 | 6 |
| Ex. 11 | 4 |

Example 58

CYP Inhibition Assay

The cytochromes P450 (CYP450) are a superfamily of enzymes that catalyse the oxidative metabolism of a diverse set of hydrophobic chemicals, including most therapeutic drugs. The Luciferase-based P450-Glo assay (Promega, V9770, V9790, V9880, V9890, V9770) employ luminogenic CYP450 probe substrates (Luciferin-IPA, Luciferin-ME, Luciferin-H, Luciferin-BE, Luciferin-ME EGE, Luciferin-H EGE and Luciferin-PPXE) that are derivatives of beetle luciferin, a substrate for luciferase enzymes. The derivatives are not substrates for luciferase but are converted by P450s to luciferin, which in turn reacts with luciferase to produce an amount of light that is directly proportional to the activity of the P450. The assay measures the dose-dependent CYP inhibition by test compounds against recombinant CYP enzymes expressed in insect cells. The CYP reaction is performed by incubating a luminogenic CYP substrate with a CYP enzyme and NADPH regeneration system, then the reconstituted Luciferin Detection Reagent is added. This reagent simultaneously stops the CYP reaction and initiates a glow-type luminescent signal with a half-life greater than 4 hours. The glow-type luciferase reaction produces a stable signal that eliminates the need for strictly timed luminescence detection.

Five CYP isoforms (0.5 pmol) were tested, namely 1A2, 2C9, 2C19, 2D6 and 3A4 (each isoform was assayed in a separate assay plate). Each assay plate contained several compounds at 2 concentrations (10 µM and 1 µM), with 2 replicates at each concentration or a small number of compounds per plate in dose response by duplicate (50, 16.5, 5.4, 1.8, 0.6, 0.2, 0.066, 0.022, 0.007 µM). In addition, each assay plate contained 8 different concentrations of an isoform-specific inhibitor (Furafylline, Sulfaphenazole, N-3-benzylnirvanol, Quinidine and Ketoconazole as inhibitors of CYP 1A2, 2C9, 2C19, 2D6 and 3A4, respectively), with two replicates at each concentration. The test compounds and the reference inhibitors were tested at a final DMSO concentration of 0.5%. The assay plate included also 8 replicates a vehicle control containing 0.5% DMSO/H2O. The membranes containing the CYPs, test compound and the probe substrate were pre-incubated 10 min at 37° C. in the absence of NADPH, NADPH was then added following incubation for 60 minutes at 37° C., the reaction was terminated by the addition of Luciferin detection reagent. After 20 min incubation at 37° C., the assay plate was read in the Envision 2104 Multilable reader. Values were normalized against the control activity included for each CYP. These values were plotted against the inhibitor concentration and were fitted to a sigmoid dose-response curve by using the model sigmoidal Four-Parameter Logistc inplement for Activity base—software.

Time Dependent Inhibition of CYP3A4

Human liver microsomes (0.1 mg/mL) and test compound (0.01, 0.1, 0.4, 1, 4, 10, 50 µM final DMSO concentration 0.2%) or DMSO were either pre-incubated for 30 minutes in the absence and presence of NADPH or underwent a 0 min pre-incubation. Midazolam (2.5 µM) was then added to the incubations. After 5 minutes, methanol was added with internal standards. The samples were analysed by LC/MS/MS to monitor 1'-hydroxymidazolam formation. $IC_{50}$ values were determined.

$IC_{50}$ data (in micromolar units) for five CYP isoforms is shown for selected compounds in Table 5:

TABLE 5

| Compound | P450-1A2 | P450-2C19 | P450-2C9 | P450-2D6 | P450-3A4 |
|---|---|---|---|---|---|
| Ex. 3 | >50 | >50 | >50 | >50 | >50 |
| Ex. 11 | >50 | >50 | 34 | >50 | 39 |

Example 59

Pharmacokinetics

In order to determine what fate of the compounds in vivo, pharmacokinetic studies were carried out using 10-week old BALB-c female mice. Compounds were dissolved in selected vehicles at a concentration calculated in order to administer the dose selected in 0.1 mL. Animals were administered by intravenous and oral route (by gavage), and sacrificed at different time points (n=3 at each time point). Time points are 0.08, 0.25, 0.5, 1, 4 and 8 h for the intravenous branch, and 0.08, 0.16, 0.25, 0.5, 1, 4, 8 and 24 h for oral branch. Blood was collected and processed for plasma which was analysed and quantified by means of tandem mass spectrometry coupled with liquid chromatography. Pharmacokinetic parameters were estimated by fitting the experimental data to a compartmental model using Winnonlin software for pharmacokinetic analysis. The parameters estimated were as follows: area under the curve (AUC); plasmatic half-life of the product (t ½); plasmatic clearance (CI); volume of distribution (Vd); MRT (Mean residence time); bioavailability (F %); Maximum plasma concentration after oral administration (Cmax); Time at which the Cmax occurs (Tmax).

Figure 5:
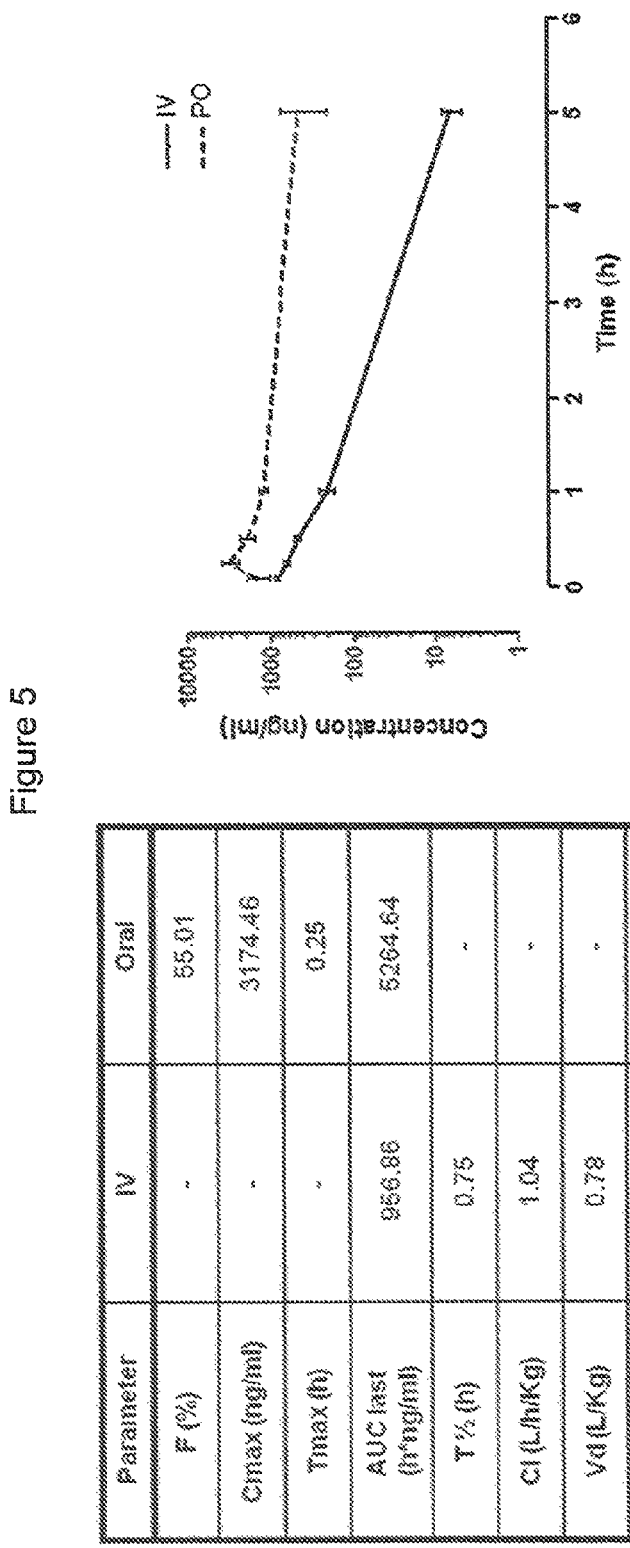
FIG. 5 shows the effect of chemical entity Example 11 on the pharmacokinetic profile.

FIG. 5 shows the pharmacokinetic parameters and profile in Balbc mice after i.v. (1 mg/kg) and p.o. (10 mg/kg) administration of Example 11 formulated in 10% N-Methyl-2-pyrrolidone, 50% polyethylene Glycol 300 and 40% saline solution. Three mice were sacrificed at each time point.

Figure 6:
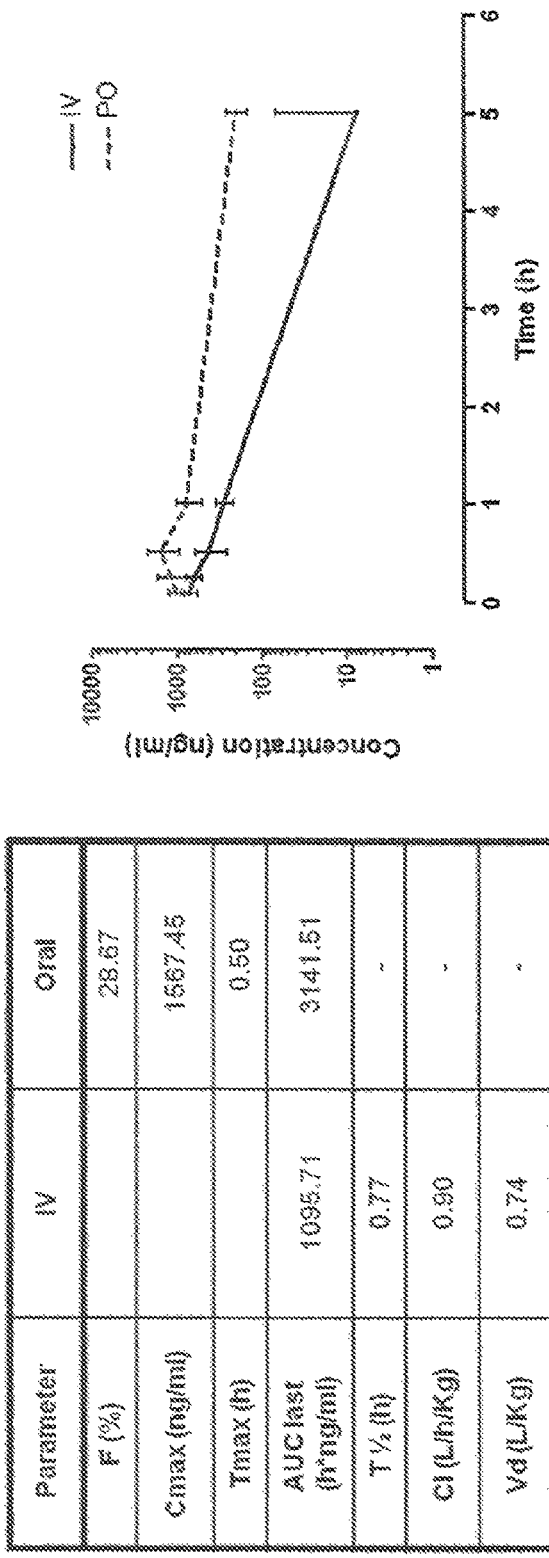
FIG. 6 shows the effect of chemical entity Example 3 on the pharmacokinetic profile.

FIG. 6 shows the pharmacokinetic parameters and profile in Balbc mice after i.v. and p.o. administration of Example 3 formulated in 10% N-Methyl-2-pyrrolidone, 50% polyethylene Glycol 300 and 40% saline solution. Three mice were sacrificed at each time point.

Example 60

In Vivo Efficacy Assessment

The efficacy of compounds of the invention alone or in combination with chemotherapeutics agents were measured in vivo by implanting allografts or xenografts of cancer cells in rodents and treating the tumour-bearing animals with the compounds alone or in combination with chemotherapeutics agents. Variable results were obtained depending on, inter alia, the cell line, the presence or absence of replicative stress or certain mutations in the tumour cells, the sequence of administration of a compound and chemotherapeutic agent, and the dosing regimen.

Figure 7:
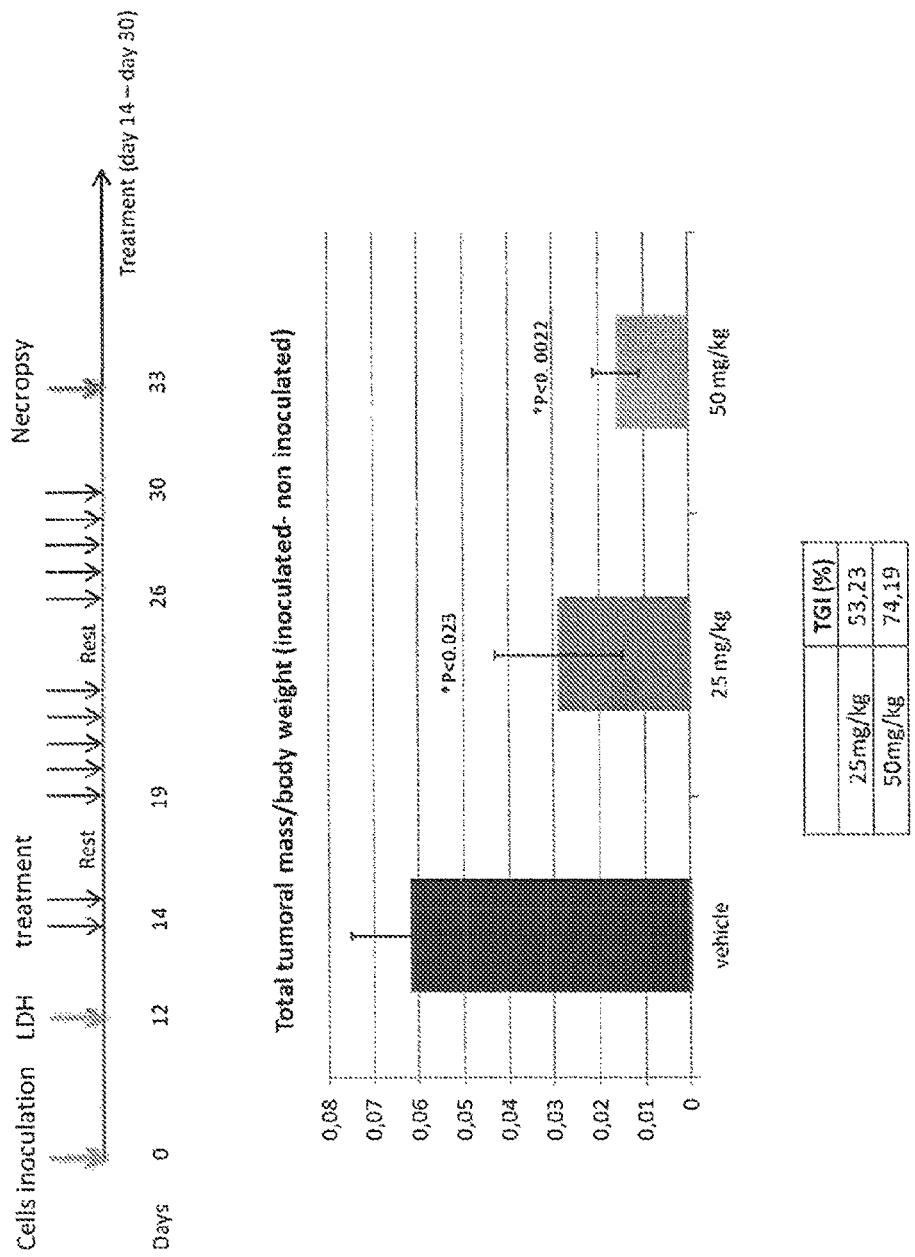
FIG. 7 shows the effect of Example 11 on tumor volume in mice injected intravenously with Eµmyc lymphoma cells.

FIG. 7 shows the tumor volume over 33 days in cohorts of 8-10 weeks old C57BL/6 mice injected intravenously with Eµmyc lymphoma cells. Recipient mice were monitored for tumor formation by the presence of tumoral cells in the blood (LDH measurement), and twice a week by palpation of the pre-scapular and cervical lymph-nodes, once a week by sonography measurement of thoracic lymph-nodes size. Mice were grouped (8 mice per group) and treated orally with vehicle (10% N-Methyl-2-pyrrolidone, 90% plyethylene Glycol 300) and 25 and 50 mg/kg of Example 11 formulated in the same vehicle, once daily, for 2 days a week the first week and 5 days the second and third week. Efficacy of the treatment was done evaluating the relative weight of all tumoral tissues (spleen, salivary lymph-nodes, mammary lymph-nodes, thymus and mesenteric lymph-nodes) versus body weight substrating the relative weight of same normal tissues. Bars represent standard error of the mean (n=8).

Dosing of cohorts commenced on Day 12 after injection of the tumoral cells when all the mice showed an increase in the LDH blood values in respect to non-inoculated mice. Compared to the vehicle control, doses of Example 11 had an effect to delay tumor growth, with increased delay at higher doses. At the lowest dose of 25 mg/kg a tumor growth inhibition (TGI) of 53% was obtained at day 33 compared to vehicle and the highest dose of 50 mg/kg demonstrated a TGI of 74%.

Figure 8:
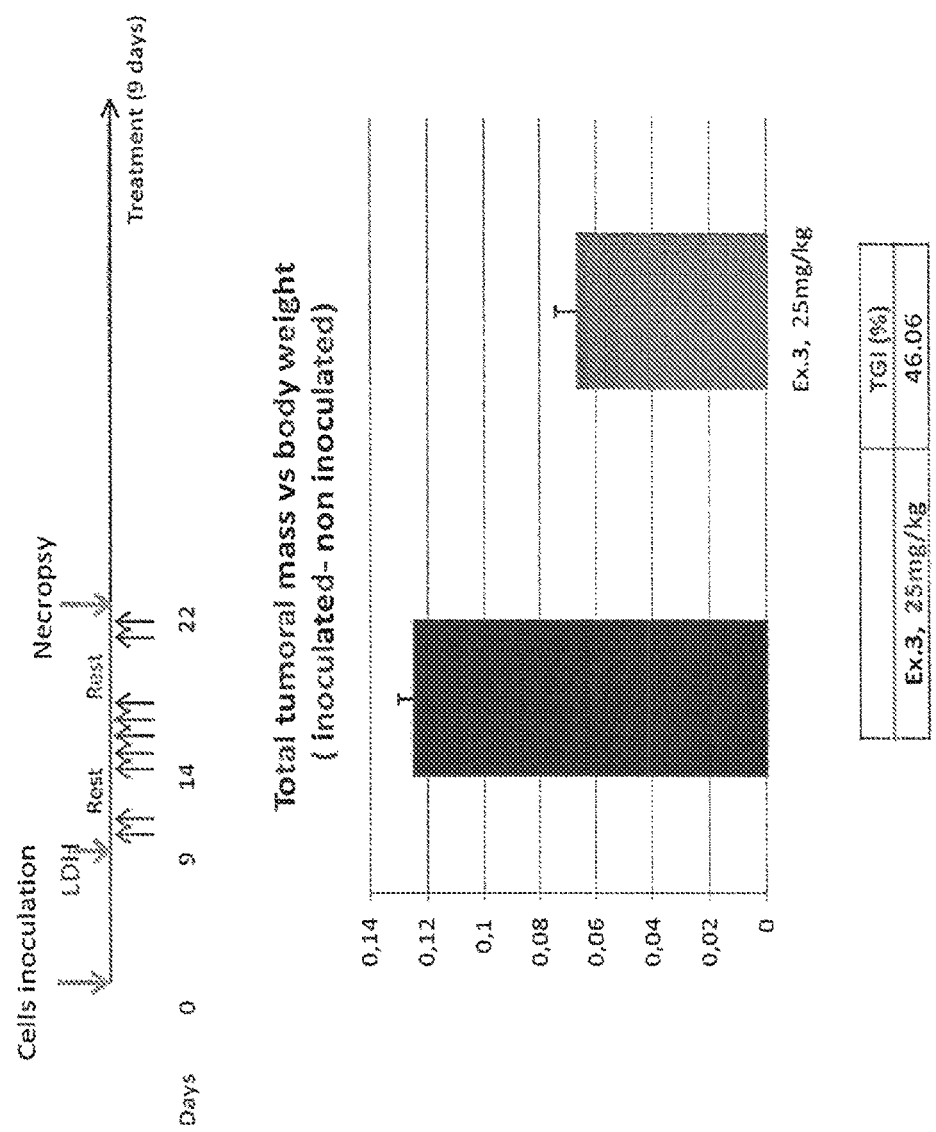
FIG. 8 shows the effect of Example 3 on tumor volume in mice injected intravenously with Eµmyc lymphoma cells.

FIG. 8 shows the tumor volume over 22 days in cohorts of 8-10 weeks old C57BL/6 mice injected intravenously with Eµmyc lymphoma cells and orally dosed once daily (2 days a week the first week, 5 days a week the second week and 2 days a week the third week) for 13 days starting on day 0 with: vehicle (10% N-Methyl-2-pyrrolidone, 90% plyethylene Glycol 300) and 25 mg/kg of Example 3 formulated in the same vehicle (7 mice per group).

Dosing of cohorts commenced on Day 10 after injection of the tumoral cells when all the mice showed an increase in the LDH blood values in respect to a non-inoculated mice. Compared to the vehicle control, dose of Example 3 had an effect to delay tumor growth. At 25 mg/kg a TGI of 46% was obtained at day 23 compared to vehicle.

Example 61

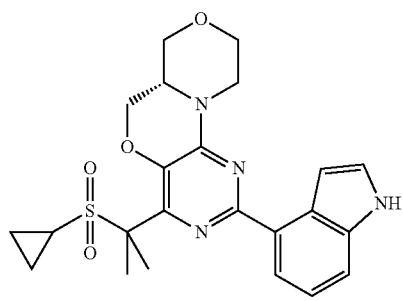

61

Example 61 was synthesized following a similar synthetic route to the one used for Example 4, using as precursor 3(R)-hydroxymethylmorpholine.

LC-MS1: $t_R$=5.26 min, MS: 455.2 [M+H]$^+$.

1H NMR (300 MHz, DMSO) δ 11.20 (s, 1H), 7.98 (d, J=7.4 Hz, 1H), 7.52-7.39 (m, 2H), 7.34 (s, 1H), 7.16 (t, J=7.7 Hz, 1H), 4.59 (d, J=13.0 Hz, 1H), 4.39 (dd, J=10.9, 3.2 Hz, 1H), 4.13-4.00 (m, 1H), 3.99-3.81 (m, 2H), 3.74 (t, J=9.4 Hz, 1H), 3.56 (t, J=10.6 Hz, 1H), 3.19-3.12 (m, 2H), 2.72-2.67 (m, 1H), 1.92 (d, J=3.7 Hz, 6H), 1.01-0.77 (m, 4H).

Example 62

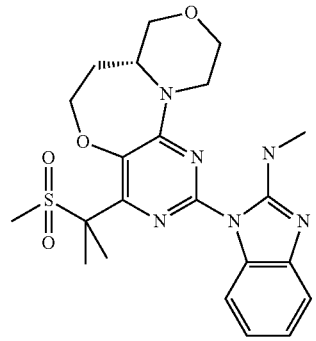

62

Example 62 was synthesized following a same synthetic route to the one used for Example 31, but using intermediate XLI with N-methyl-1H-1,3-benzodiazol-2-amine LC-MS1: $t_R$=2.92 min, MS: 473.3 [M+H]$^+$.

1H NMR (300 MHz, DMSO) δ 8.19-8.14 (q, J=4.7 Hz, 1H), 8.01 (d, J=7.7 Hz, 1H), 7.25 (d, J=7.6 Hz, 1H), 7.07 (td, J=7.6, 1.0 Hz, 1H), 6.97 (td, J=7.8, 1.1 Hz, 1H), 4.33-4.20 (m, 2H), 4.08-3.90 (m, 3H), 3.86-3.75 (m, 2H), 3.60 (ddd, J=12.5, 9.1, 3.4 Hz, 1H), 3.47 (dd, J=11.5, 7.9 Hz, 1H), 3.01 (s, 3H), 3.01 (d, J=4.8 Hz, 3H), 2.21-2.09 (m, 1H), 2.05-1.96 (m, 1H), 1.85 (s, 3H), 1.84 (s, 3H).

Intermediate XLI

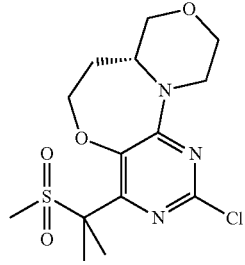

XLI

Intermediate XLI was synthesized following a same synthetic route to the one used for intermediate 2-VII, by alkylation reaction with iodomethane in the presence of tertbutoxide of chiral intermediate 2-II.

Example 63

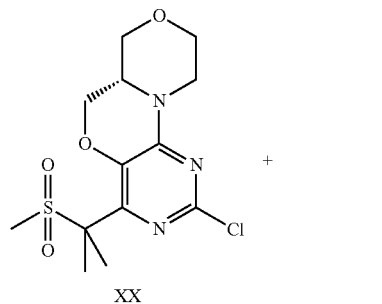

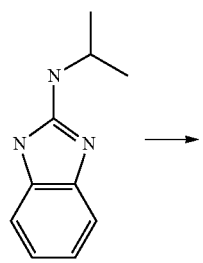

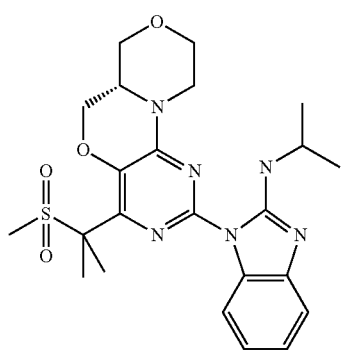

63

A mixture of Intermediate XX (70 mg, 0.2 mmol) in Acetonitrile (1.0 mL) was added (1H-benzoimidazol-2-yl)-isopropyl-amine (65 mg. 0.4) and Cs$_2$CO$_3$ (200 mg, 0.6 mmol). Reaction was heated at 120° C. in a high pressure tube for 6 days. The mixture was cooled down to rt and the solvent was removed in vacuo. The residue was purified by flash column chromatography (Isolute Si II 5), eluting with a solvent system of EtOAc/cyclohexane (from 50% to 100% on EtOAc). The required product was recovered as a white solid, and it was triturated with diethylether. The insoluble solid was filtered out and dried in vacuo (33 mg, 33%).

LC-MS1: tR=3.34 min, MS: 487.2 [M+H]$^+$

1H NMR (300 MHz, DMSO) δ 7.91 (d, J=7.9 Hz, 2H), 7.17 (d, J=7.7 Hz, 1H), 6.99 (t, J=7.5 Hz, 1H), 6.90 (dd, J=11.1, 4.2 Hz, 1H), 4.40-4.23 (m, 2H), 4.17-3.71 (m, 5H), 3.50 (t, J=11.7 Hz, 1H), 3.18 (dd, J=19.4, 8.6 Hz, 2H), 2.94 (s, 3H), 1.78 (s, 3H), 1.76 (s, 3H), 1.20 (d, J=6.4 Hz, 6H).

Intermediate XX

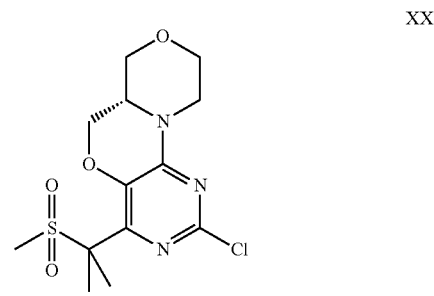 [SMILES: CC(C)(c1nc(Cl)nc2c1OC[C@@H]1COCCN21)S(C)(=O)=O]

Intermediate XX was synthesized following a same synthetic route to the one used for intermediate X, but using as precursor 3(R)-hydroxymethylmorpholine.

Example 64

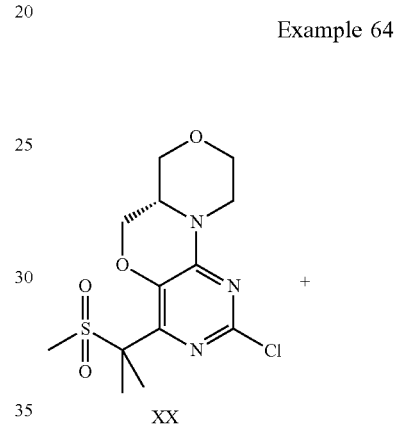

XX

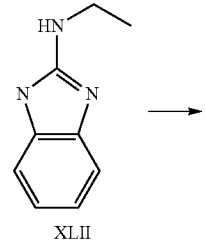

XLII

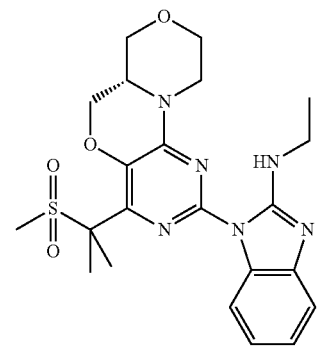

64

A mixture of Intermediate XX (80 mg, 0.2 mmol) in acetonitrile (1.0 mL) was added intermediate XLII (75 mg. 0.4) and Cs$_2$CO$_3$ (225 mg, 0.7 mmol). Reaction was heated at 120° C. in a high pressure tube for 3 days. The mixture was cooled down to rt and diluted with water and EtOAc. The different layers were separated and the organic phase was washed twice with sat. solution of NaHCO₃, once with brine, dried over Na₂SO₄ and concentrated. The residue was purified by flash column chromatography (Isolute Si II 5), eluting with a solvent system of EtOAc/cyclohexane (from 25% to 100% on EtOAc) and re-purified by semi preparative HPLC. The required product was recovered as a white solid.

LC-MS1: tR=3.19 min, MS: 473.2 [M+H]⁺

1H NMR (300 MHz, DMSO) δ 8.09 (t, J=4.1 Hz, 1H), 7.93 (d, J=7.9 Hz, 1H), 7.17 (d, J=7.7 Hz, 1H), 7.00 (t, J=7.7 Hz, 1H), 6.90 (t, J=7.6 Hz, 1H), 4.43-4.25 (m, 2H), 4.00 (dd, J=11.7, 3.6 Hz, 1H), 3.95-3.70 (m, 3H), 3.58-3.32 (m, 3H), 3.22-3.08 (m, 2H), 2.96 (s, 3H), 2.02-1.84 (m, 1H), 1.77 (s, 3H), 1.75 (s, 3H), 1.17 (t, J=7.1 Hz, 3H).

Intermediate XLII

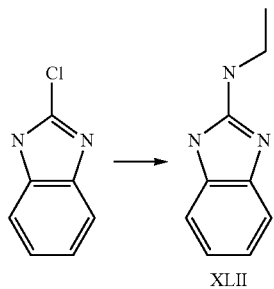

XLII

A mixture of 2-chlorobenzimidazole (150 mg, 0.9 mmol) and ethylamine 70% in water (0.4 mL) in ACN (0.5 mL) was heated under microwave irradiation for 45 min at 160° C. (Biotage, Abs. Level VH). Solvents were removed in vacuo. The crude was suspended in a solvent mixture 1:1 CHCl₃/ iPrOH. The combined organic layers were dried over Na₂SO₄ and concentrated in vacuo, leaving clear oil (75 mg; 65%).

Example 65

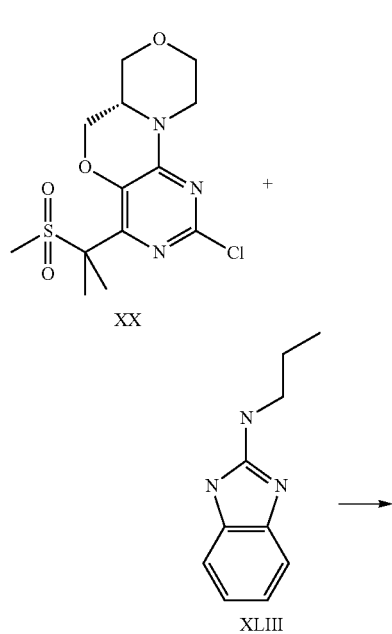

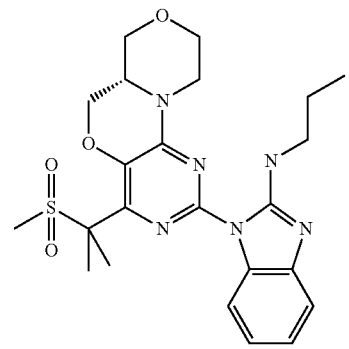

65

A mixture of Intermediate XX (75 mg, 0.2 mmol) in Acetonitrile (2.0 mL) was added intermediate XLIII (76 mg, 0.4) and Cs₂CO₃ (210 mg, 0.6 mmol). Reaction was heated at 115° C. in a high pressure tube for 3 days. The mixture was cooled down to rt and diluted with water and EtOAc. The different layers were separated and the organic phase was washed twice with sat. solution of NaHCO₃, once with brine, dried over Na₂SO₄ and concentrated. The residue was purified by flash column chromatography (Isolute Si II 5), eluting with a solvent system of EtOAc/cyclohexane (from 25% to 100% on EtOAc) and re-purified by semi preparative HPLC. The required product was recovered as a white solid.

LC-MS1: tR=3.32 min, MS: 487.2 [M+H]⁺

1H NMR (300 MHz, DMSO) δ 8.12 (t, J=5.7 Hz, 1H), 7.93 (d, J=7.7 Hz, 1H), 7.17 (d, J=7.6 Hz, 1H), 6.99 (t, J=7.5 Hz, 1H), 6.89 (t, J=7.6 Hz, 1H), 4.42-4.21 (m, 2H), 3.99 (d, J=11.5 Hz, 1H), 3.96-3.69 (m, 3H), 3.50 (t, J=10.6 Hz, 1H), 3.38-3.31 (m, 2H), 3.20-3.13 (m, 2H), 2.95 (s, 3H), 1.77 (s, 3H), 1.75 (s, 3H), 1.59 (dd, J=14.5, 7.3 Hz, 2H), 0.87 (t, J=7.4 Hz, 3H).

Intermediate XLIII

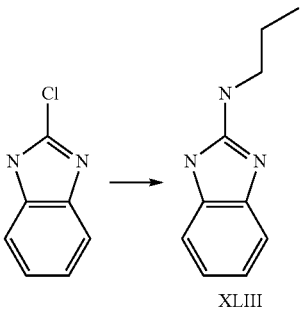

XLIII

A mixture of 2-chlorobenzimidazole (100 mg, 0.6 mmol) and propylamine (0.3 mL, 3.2 mmol) in Acetonitrile (0.4 mL) was heated under microwave irradiation for 50 min at 160° C. (Biotage, Abs. Level VH). Solvents were removed in vacuo, the crude was purified by flash column chromatography (Isolute Si II 5 g) eluting with a solvent system of MeOH/DCM (from 0% to 5% on MeOH). The required final product was recovered as a colourless oil (90 mg; 78%).

Example 66

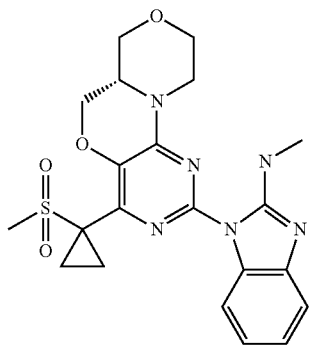

Example 66 was synthesized following a similar protocol to the one used for example 8 from intermediate XLIV in acetonitrile as solvent.

LC-MS1: $t_R$=3.00 min, MS: 457.2 [M+H]$^+$

1H NMR (300 MHz, DMSO) δ 8.14 (q, J=4.3 Hz, 1H), 7.99 (d, J=7.8 Hz, 1H), 7.19 (d, J=7.6 Hz, 1H), 7.01 (t, J=7.5 Hz, 1H), 6.91 (t, J=7.5 Hz, 1H), 4.37 (dd, J=11.0, 3.3 Hz, 1H), 4.26 (d, J=13.0 Hz, 1H), 4.00 (d, J=11.6 Hz, 1H), 3.94-3.82 (m, 2H), 3.82-3.69 (m, 1H), 3.50 (t, J=11.9 Hz, 1H), 3.18 (dd, J=22.2, 11.6 Hz, 2H), 2.99 (s, 3H), 2.97 (d, J=4.8 Hz, 3H), 1.63 (s, 2H), 1.36 (s, 2H).

Intermediate XLIV

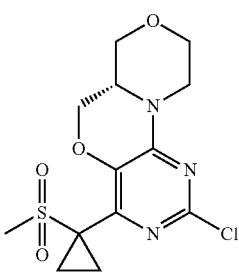

XLIV

Intermediate XLIV was synthesized following a similar protocol to the one used for intermediate XXV using as precursor 3(R)-hydroxymethylmorpholine.

Example 67

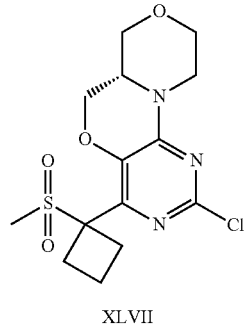

XLVII

+

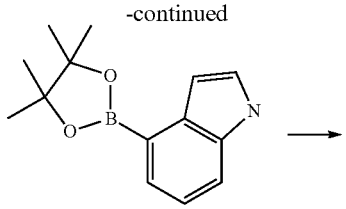

→

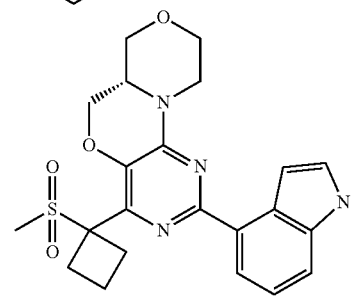

67

A mixture of intermediate XLVII (100 mg, 0.30 mmol), indole-4-boronic acid pinacol ester (81 mg, 0.33 mmol), PdCl$_2$(PdPPh$_3$)$_2$ (20 mg, 0.03) and 0.6 mL of Na$_2$CO$_3$ (2 M aqueous) in dioxane (2.0 mL) was heated at 100° C. for 5 h. The dark mixture was filtered of through a Celite pad rinsing with DCM. The filtrate was concentrated in vacuo and the residue was purified by Biotage flash column chromatography eluting with a solvent system of EtOAc/cyclohexane (from 25% to 75% on EtOAc). The desired product was re-purified by prep HPLC. The required final compound 67 was recovered as a white solid.

LC-MS1: $t_R$=5.05 min, MS: 441.1 [M+H]$^+$

1H NMR (300 MHz, DMSO) δ 11.14 (s, 1H), 7.93 (d, J=7.4 Hz, 1H), 7.41 (d, J=8.0 Hz, 1H), 7.33 (d, J=2.3 Hz, 1H), 7.24 (s, 1H), 7.09 (t, J=7.7 Hz, 1H), 4.49 (d, J=12.9 Hz, 1H), 4.29 (dd, J=10.9, 3.1 Hz, 1H), 3.98 (d, J=11.5 Hz, 1H), 3.87-3.80 (m, 2H), 3.67 (t, J=9.5 Hz, 1H), 3.50 (t, J=10.6 Hz, 1H), 3.23-3.00 (m, 2H), 2.99-2.80 (m, 4H), 2.79 (s, 3H), 2.09-2.07 (m, 1H), 1.85-1.80 (m, 1H).

Intermediate XLVII

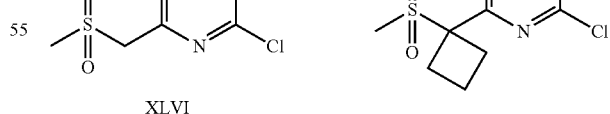

XLVI → XLVII

A mixture of intermediate XLVI (30 mg, 0.1 mmol) 1,3-dibromopropane (22 uL, 0.21 mmol), TBAB (6 mg) and an aqueous 10 M solution of NaOH (0.1 mL) in toluene (1 mL) was heated in a high pressure tube at 110° C. for 18 h. The mixture was cooled down to rt and diluted with EtOAc/water. The different layers were separated and the aqueous phase was extracted twice with EtOAc. The combined organic layers were washed with brine, dried over Na₂SO₄ and concentrated in vacuo. The yellow residue afforded intermediate XLVII.

Intermediate XLVI

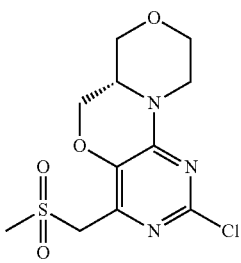

XLVI

Intermediate XLVI was synthesized following a similar protocol to the one used for intermediate IX using as precursor 3(R)-hydroxymethylmorpholine.

Example 68

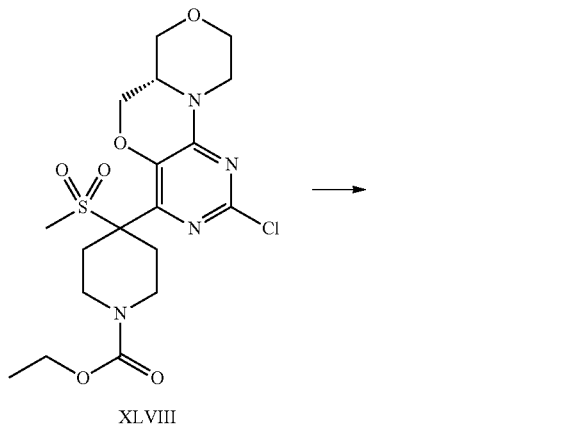

XLVIII

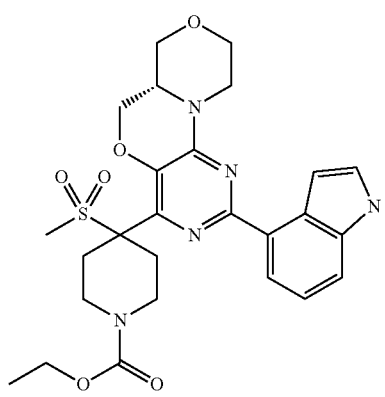

68

A mixture of intermediate XLVIII (110 mg, 0.24 mmol), indole-4-boronic acid pinacol ester (70 mg, 0.28 mmol), PdCl₂(PdPPh₃)₂ (17 mg, 0.02) and 0.5 mL of Na₂CO₃ (2 M aqueous) in dioxane (2.0 mL) was heated at 100° C. for 4 h. The dark mixture was filtered of through a Celite pad rinsing with DCM. The filtrate was concentrated in vacuo and the residue was purified by flash column chromatography (Isolute Si II 5 g) eluting with a solvent system of EtOAc/cyclohexane (from 15% to 100% on EtOAc). The example 68 was recovered as a white solid.

LC-MS1: $t_R$=5.14 min, MS: 542.2 [M+H]⁺

1H NMR (300 MHz, DMSO) δ 11.23 (s, 1H), 7.96 (d, J=7.5 Hz, 1H), 7.49 (d, J=7.9 Hz, 1H), 7.43 (s, 1H), 7.24 (s, 1H), 7.16 (t, J=7.8 Hz, 1H), 4.62 (d, J=12.3 Hz, 1H), 4.39 (dd, J=10.9, 3.2 Hz, 1H), 4.09-3.07 (m, 7H), 3.78 (t, J=10.8 Hz, 1H), 3.57 (t, J=12.8 Hz, 1H), 3.32-3.08 (m, 5H), 2.89 (s, 3H), 2.80 (dd, J=15.3, 11.7 Hz, 1H), 2.06-1.84 (m, 2H), 1.16 (t, J=7.0 Hz, 3H).

Intermediate XLVIII

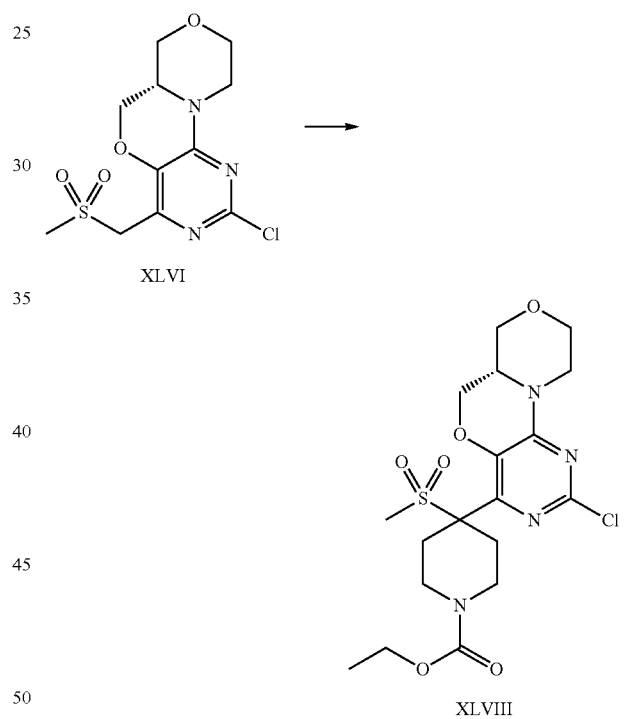

A mixture of intermediate XLVI (200 mg, 0.6 mmol), bis-(2-chloro-ethyl)-carbamic acid esther (335 uL, 1.5 mmol), TBAB (40 mg) and an aqueous 10 M solution of NaOH (0.6 mL) in toluene (2 mL) was heated in a high pressure tube at 110° C. for 18 h. The mixture was cooled down to rt and diluted with water and EtOAc. The different layers were separated and the aqueous layer was extracted with EtOAc twice. The combined organic layers were washed with brine, dried over Na₂SO₄ and concentrated in vacuo. The crude was purified by flash column chromatography (Isolute Si II 10 g) eluting with a solvent system of EtOAc/cyclohexane (from 25 to 75% on EtOAc). The required final compound XLVIII was recovered as cream solid (100 mg, 33%).

Example 69

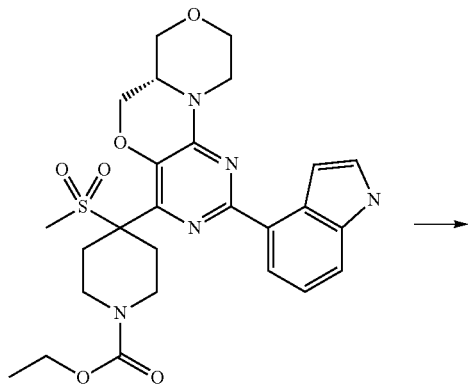

68

A mixture of 68 (60 mg, 0.11 mmol) with LiOH (60 mg, 1.4 mmol) in a solvent mixture of MeOH/2-propanol (1:1, 2 mL) was heated under microwave irradiation for 150 min at 160° C. (Biotage Abs. Level VH). Solvents were removed in vacuo. The crude was purified by flash column chromatography (Isolute Si II 5 g) eluting with a solvent system: first MeOH/DCM (from 0% to 5% on MeOH) and after with NH$_3$ in MeOH/DCM (5% of the solution 7 N NH$_3$ in MeOH). The required final product 69 was recovered as a white solid (15 mg, 28%).

LC-MS1: t$_R$=2.54 min; 2.71 min, MS: 470.2 [M+H]$^+$

1H NMR (300 MHz, DMSO) δ 11.15 (s, 1H), 7.88 (d, J=7.5 Hz, 1H), 7.41 (d, J=7.9 Hz, 1H), 7.35 (s, 1H), 7.19 (s, 1H), 7.09 (t, J=7.7 Hz, 1H), 4.55 (d, J=12.7 Hz, 1H), 4.31 (dd, J=10.5, 2.9 Hz, 1H), 4.00 (d, J=8.6 Hz, 1H), 3.93-3.64 (m, 3H), 3.51 (t, J=11.3 Hz, 1H), 3.19-3.06 (m, 4H), 2.91 (d, J=12.4 Hz, 2H), 2.74 (s, 3H), 2.40-2.33 (m, 2H), 1.94-182 (m, 2H).

Example 70

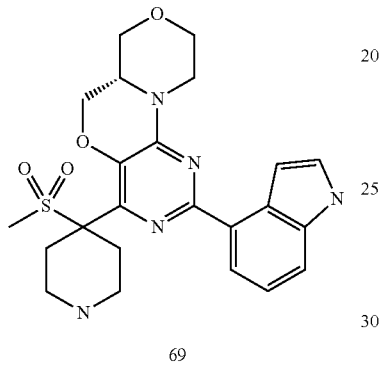

69

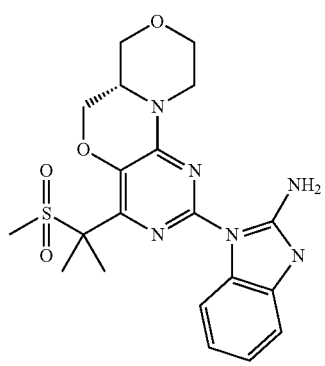

70

The compound 70 was synthesised following a similar synthetic route that the one used for synthesis of Example 11 by reaction of a chiral intermediate XX with 2 aminobenzimidazol (solvent acetonitrile, 130° C. for 3 days).

LC-MS1: t$_R$=2.983 min, MS 445.20 [M+H]$^+$.

1H NMR (300 MHz, DMSO) δ 7.97 (d, J=7.7 Hz, 1H), 7.39 (brs, 2H), 7.18 (d, J=7.5 Hz, 1H), 7.05 (td, J=7.5, 1.0 Hz, 1H), 6.99-6.92 (m, 1H), 4.40 (dt, J=15.1, 7.7 Hz, 2H), 4.05 (dd, J=11.5, 3.2 Hz, 1H), 3.99-3.79 (m, 3H), 3.56 (td, J=11.6, 2.3 Hz, 1H), 3.21 (m, 2H), 3.01 (s, 3H), 1.83 (s, 3H), 1.81 (s, 3H).

Example 71

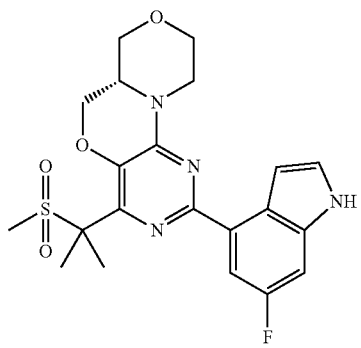

71

The compound 71 was synthesised following a similar synthetic route that the one used for synthesis of Example 1 from coupling reaction of chiral intermediate XX with 6-fluoro indole-4-boronic pinacol ester.

LC-MS1: t$_R$=5.14 min; MS: 447.2 [M+H]$^+$ $^1$H-NMR (300 MHz, DMSO-d6): δ 11.29 (bs, 1H), 7.74 (dd, J=11.4, 2.2 Hz, 1H), 7.43 (bt, J=2.5 Hz, 1H), 7.31 (bs, 1H), 7.26 (dd, J=9.3, 2.2 Hz, 1H), 4.57 (bd, J=12.6 Hz, 1H), 4.40 (dd, J=10.8, 3.3 Hz, 1H), 4.05 (bd, J=11.2 Hz, 1H), 3.96-3.86 (m, 2H), 3.80-3.73 (m, 1H), 3.55 (bt, J=11.2 Hz, 1H), 3.25-3.09 (m, 2H), 2.95 (s, 3H), 1.89 (s, 3H), 1.87 (s, 3H) ppm.

Example 72

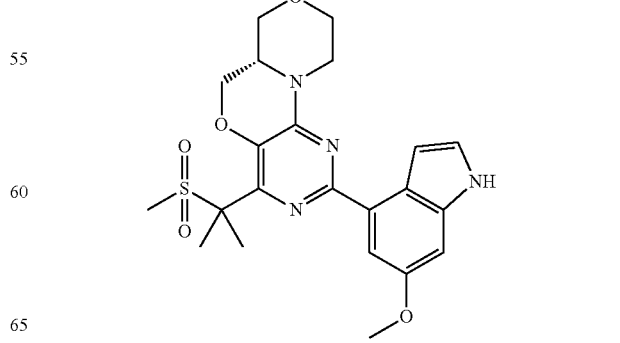

72

The compound 72 was synthesised following a similar synthetic route that the one used for synthesis of Example 1 from coupling reaction of chiral intermediate XX with 6-methoxy indole-4-boronic pinacol ester.

LC-MS1: $t_R$=4.89 min; MS: 459.3 [M+H]$^+$ $^1$H-NMR (300 MHz, DMSO-d6): δ 11.00 (bs, 1H), 7.60 (d, J=2.3 Hz, 1H), 7.27 (bt, J=2.5 Hz, 1H), 7.19 (bs, 1H), 7.00 (d, J=2.3 Hz, 1H), 4.56 (bd, J=12.6 Hz, 1H), 4.39 (dd, J=10.8, 3.3 Hz, 1H), 4.06 (bd, J=11.5 Hz, 1H), 3.96-3.85 (m, 2H), 3.81 (s, 3H), 3.81-3.70 (m, 1H), 3.56 (bt, J=11.6 Hz, 1H), 3.25-3.08 (m, 2H), 2.95 (s, 3H), 1.88 (s, 3H), 1.86 (s, 3H) ppm.

Example 73

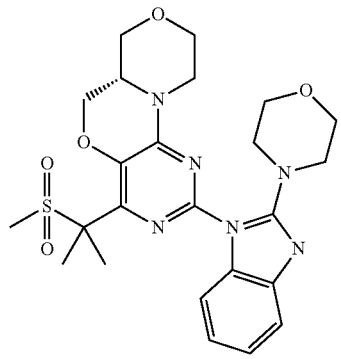

The compound 73 was synthesised following a similar synthetic route that the one used for synthesis of Example 11 by reaction of a chiral intermediate XX with 2-morpholin-4-yl-1H-benzimidazole (solvent acetonitrile, 130° C. for 3 days).

1H NMR (300 MHz, DMSO) δ 7.65 (d, J=7.5 Hz, 1H), 7.38 (d, J=7.5 Hz, 1H), 7.12 (td, J=7.6, 1.1 Hz, 1H), 7.06-6.97 (m, 1H), 4.43 (dd, J=15.6, 8.1 Hz, 2H), 4.06-3.77 (m, 4H), 3.65 (s, 4H), 3.56-3.44 (m, 1H), 3.27-3.07 (m, 6H), 2.99 (s, 3H), 1.83 (s, 3H), 1.81 (s, 3H).

LC-MS1: $t_R$=3.167 min, MS: 515.30 [M+H]$^+$.

Example 74

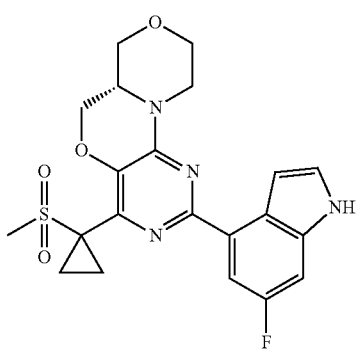

The compound 74 was synthesised following a similar synthetic route that the one used for synthesis of Example 6 from coupling reaction of a chiral intermediate XLIV with 6-fluoro indole-4-boronic pinacol ester.

LCMS 1=$t_R$=4.825 min, MS: 445.2 [M+H]$^+$

1H NMR (300 MHz, DMSO) δ 11.05 (s, 1H), 7.53 (dd, J=11.5, 2.4 Hz, 1H), 7.25-7.16 (m, 1H), 7.13 (s, 1H), 7.04 (dd, J=9.1, 2.1 Hz, 1H), 4.29 (d, J=11.8 Hz, 1H), 4.21 (dd, J=11.0, 3.4 Hz, 1H), 3.89-3.79 (m, 1H), 3.72 (dd, J=13.4, 6.2 Hz, 2H), 3.52 (t, J=9.7 Hz, 1H), 3.34 (dd, J=11.9, 9.2 Hz, 1H), 3.07-2.88 (m, 2H), 2.85 (s, 3H), 1.55-1.43 (m, 2H), 1.20-1.19 (m, 2H).

Example 75

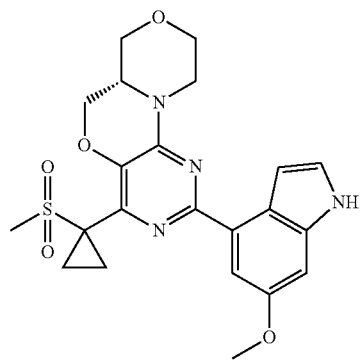

The compound 75 was synthesised following a similar synthetic route that the one used for synthesis of Example 6 from coupling reaction of a chiral intermediate XLIV with 6-methoxy indole-4-boronic pinacol ester.

LCMS 1=$t_R$=4.311 min, MS: 457.1 [M+H]$^+$

1H NMR (300 MHz, DMSO) δ 11.19 (s, 1H), 7.81 (d, J=2.3 Hz, 1H), 7.51-7.35 (m, 2H), 7.20 (d, J=2.1 Hz, 1H), 4.70 (d, J=11.8 Hz, 1H), 4.62 (dd, J=11.0, 3.4 Hz, 1H), 4.25 (d, J=8.5 Hz, 1H), 4.18-4.06 (m, 2H), 4.00 (s, 3H), 3.97-3.86 (m, 1H), 3.75 (t, J=10.7 Hz, 1H), 3.47-3.29 (m, 2H), 3.28 (s, 3H), 1.89 (d, J=3.5 Hz, 2H), 1.61 (d, J=3.8 Hz, 2H).

Example 76

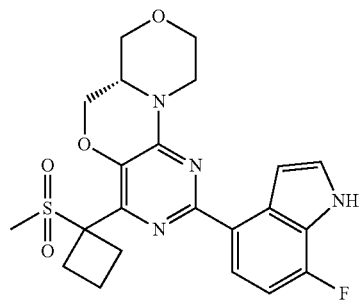

The compound 76 was synthesised following a similar synthetic route that the one used for synthesis of Example 67 from coupling reaction of chiral intermediate XLVII with 7-fluoro indole-4-boronic pinacol ester.

LC-MS1, Rt=6.09 min, MS: 459.1 [M+H]$^+$

1H NMR (300 MHz, DMSO) δ 10.96 (s, 1H), 8.07 (dd, J=8.4, 5.4 Hz, 1H), 7.53 (m, 1H), 6.90 (dd, J=10.1, 8.4 Hz, 1H), 6.58 (dd, J=2.9, 2.3 Hz, 1H), 4.60 (dd, J=13.1, 1.4 Hz, 1H), 4.36 (dd, J=11.0, 3.4 Hz, 1H), 4.03 (dd, J=11.5, 3.2 Hz,

1H), 3.92 (m, 2H), 3.75 (dt, J=9.5, 3.3 Hz, 1H), 3.55 (m, 1H), 3.20 (t, J=10.8 Hz, 1H), 3.11 (td, J=12.8, 3.8 Hz, 1H), 2.94 (m, 4H), 2.89 (s, 3H), 2.18 (m, 1H), 1.87 (m, 1H).

Example 77

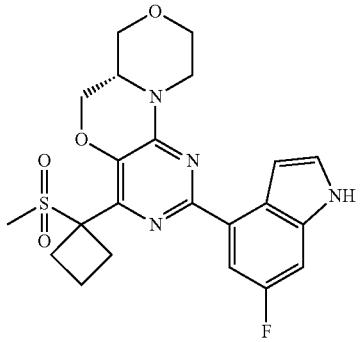

77

The compound 77 was synthesised following a similar synthetic route that the one used for synthesis of Example 67 from coupling reaction of a chiral intermediate XLVII with 6-fluoro indole-4-boronic pinacol ester.

LC-MS1, $t_R$=5.24 min, MS: 459.1 [M+H]$^+$

1H NMR (300 MHz, DMSO) δ 11.28 (s, 1H), 7.77 (dd, J=11.5, 2.4 Hz, 1H), 7.41 (m, 1H), 7.31 (t, J=2.1 Hz, 1H), 7.26 (dd, J=9.2, 2.3 Hz, 1H), 4.55 (dd, J=13.2, 1.5 Hz, 1H), 4.36 (dd, J=10.9, 3.3 Hz, 1H), 4.05 (dd, J=11.5, 3.2 Hz, 1H), 3.92 (m, 2H), 3.75 (m, 1H), 3.56 (td, J=12.1, 2.2 Hz, 1H), 3.15 (m, 2H), 2.95 (m, 4H), 2.86 (s, 3H), 2.14 (m, 1H), 1.88 (m, 1H).

Example 78

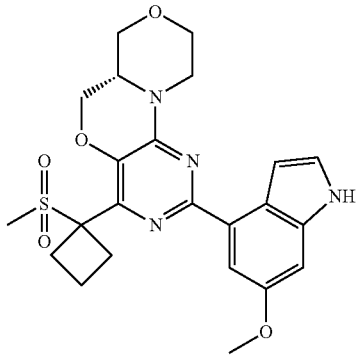

78

The compound 78 was synthesised following a similar synthetic route that the one used for synthesis of Example 67 from coupling reaction of a chiral intermediate XLVII with 6-methoxy indole-4-boronic pinacol ester.

LC-MS1, $t_R$=4.95 min, MS: 471.1 [M+H]$^+$

1H NMR (300 MHz, DMSO) δ 11.00 (s, 1H), 7.63 (d, J=2.4 Hz, 1H), 7.20 (m, 1H), 7.17 (m, 1H), 7.00 (d, J=2.0 Hz, 1H), 4.53 (d, J=11.5 Hz, 1H), 4.35 (dd, J=10.9, 3.3 Hz, 1H), 4.05 (dd, J=11.6, 3.2 Hz, 1H), 3.91 (m, 2H), 3.80 (s, 3H), 3.73 (m, 1H), 3.56 (td, J=11.7, 2.4 Hz, 1H), 3.15 (m, 2H), 2.95 (m, 4H), 2.85 (s, 3H), 2.14 (m, 1H), 1.88 (m, 1H).

Example 79

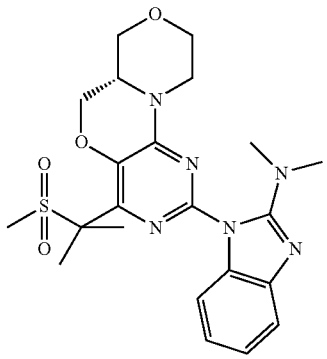

79

The compound 79 was synthesised following a similar synthetic route than the one used for synthesis of Example 11 by reaction of a chiral intermediate XX with 1H-benzimidazol-2-amine, N,N-dimethyl (solvent acetonitrile, 130° C. for 3 days).

LC-MS1: $t_R$=2.820 min, MS: 473.30 [M+H]$^+$.

1H NMR (300 MHz, DMSO) δ 7.51 (d, J=7.9 Hz, 1H), 7.30 (d, J=7.7 Hz, 1H), 7.07 (t, J=7.6 Hz, 1H), 6.94 (t, J=7.6 Hz, 1H), 4.39 (dd, J=25.1, 11.5 Hz, 2H), 4.03-3.87 (m, 3H), 3.82 (t, J=9.1 Hz, 1H), 3.51 (t, J=11.4 Hz, 1H), 3.26-3.17 (m, 1H), 3.11 (dd, J=12.7, 2.8 Hz, 1H), 3.00 (s, 3H), 2.87 (s, 6H), 1.81 (s, 3H), 1.79 (s, 3H).

Examples 80, 81

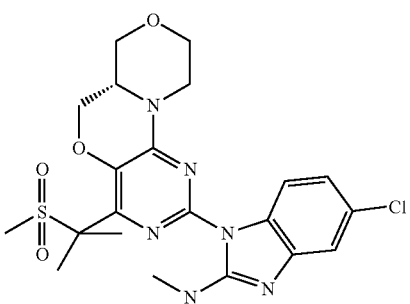

80

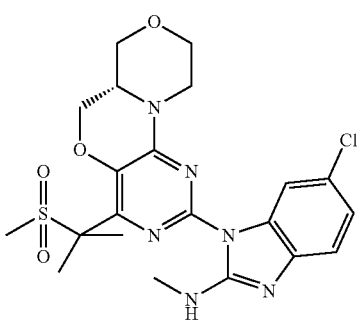

81

The compounds 80 and 81 were synthesised following a similar synthetic route than the one used for synthesis of Example 11 by reaction of a chiral intermediate XX with 5-chloro-N-methyl-1H-1,3-benzodiazol-2-amine.

Example 80

LC-MS1: $t_R$=3.602 min, MS: 493.10 [M+H]$^+$.

1H NMR (300 MHz, DMSO) δ 8.25 (s, 1H), 8.04 (d, J=2.0 Hz, 1H), 7.25 (d, J=8.3 Hz, 1H), 7.12 (d, J=8.3 Hz, 1H), 4.43 (dd, J=10.7, 3.1 Hz, 1H), 4.31 (d, J=13.0 Hz, 1H), 4.07 (dd, J=11.5, 3.4 Hz, 1H), 4.00-3.81 (m, 3H), 3.65-3.54 (m, 1H), 3.30-3.20 (m, 2H), 3.04 (s, 6H), 1.84 (s, 3H), 1.82 (s, 3H).

Example 81

LC-MS 1: $t_R$ =3.651 min, MS 493.10 [M+H]$^+$.

1H NMR (300 MHz, DMSO) δ 8.37 (d, J=4.8 Hz, 1H), 7.96 (d, J=8.5 Hz, 1H), 7.26 (d, J=2.0 Hz, 1H), 6.98 (dd, J=8.5, 2.0 Hz, 1H), 4.42 (dd, J=10.6, 2.9 Hz, 1H), 4.33 (d, J=12.3 Hz, 1H), 4.08-3.78 (m, 4H), 3.56 (dd, J=11.7, 9.6 Hz, 1H), 3.27-3.16 (m, 2H), 3.03 (brs, 6H), 1.82 (s, 3H), 1.80 (s, 3H).

Example 82, 83

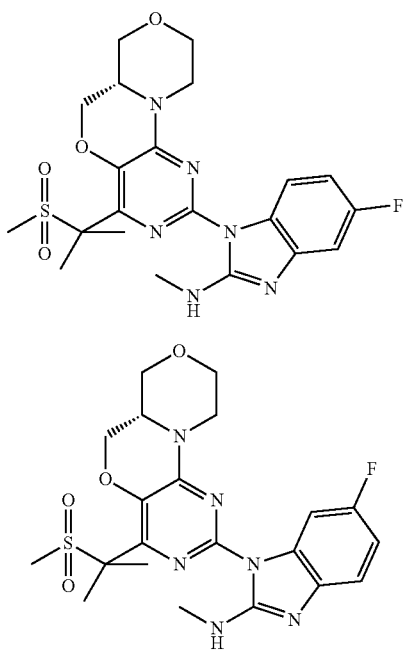

82

83

The compounds 82 and 83 were synthesised following a similar synthetic route than the one used for synthesis of Example 11 by reaction of a chiral intermediate XX with 5-fluoro-N-methyl-1H-1,3-benzodiazol-2-amine.

Example 82

$^1$H-NMR (300 MHz, DMSO-d 6): δ=7.98 (q, J=5.0 Hz, 1H), 7.68 (dd, J=9.9, 2.5 Hz, 1H), 7.12 (dd, J=8.7, 5.1 Hz, 1H), 6.86-6.79 (m, 1H), 4.33 (dd, J=10.8, 4.2 Hz, 1H), 4.23 (bd, J=12.9 Hz, 1H), 3.98 (dd, J=11.7, 3.3 Hz, 1H), 3.89-3.69 (m, 3H), 3.52-3.44 (m, 1H), 3.20-3.07 (m, 2H), 2.94 (s, 3H), 2.91 (d, J=5.0 Hz, 3H), 1.74 (s, 3H), 1.72 (s, 3H) ppm.

LC-MS 1: $t_R$=3.18 min; MS: 477.1[M+H]$^+$

Example 83

$^1$H-NMR (300 MHz, DMSO-d6): δ=8.29 (q, J=4.8 Hz, 1H), 7.97 (dd, J=8.7, 5.1 Hz, 1H), 7.04 (dd, J=9.6, 2.4 Hz, 1H), 6.78 (td, J=8.7, 2.4 Hz, 1H), 4.44-4.34 (m, 2H), 4.09-3.78 (m, 4H), 3.61-3.49 (m, 1H), 3.31-3.16 (m, 2H), 3.03 (s, 3H), 3.02 (d, J=4.8 Hz, 3H), 1.82 (s, 3H), 1.81 (s, 3H) ppm.

LC-MS 1: $t_R$=3.27 min; MS: 477.1 [M+H]$^+$

Example 84, 85

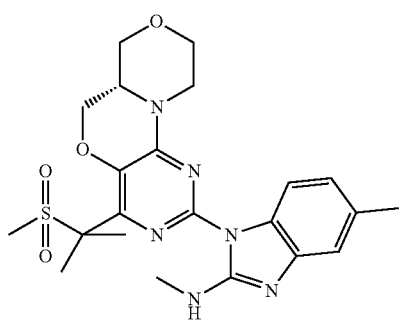

84

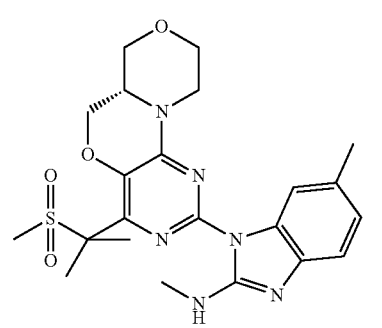

85

The compounds 84 and 85 were synthesised following a similar synthetic route than the one used for synthesis of Example 11 by reaction of a chiral intermediate XX with 5-methyl-N-methyl-1H-1,3-benzodiazol-2-amine.

Examples 86, 87

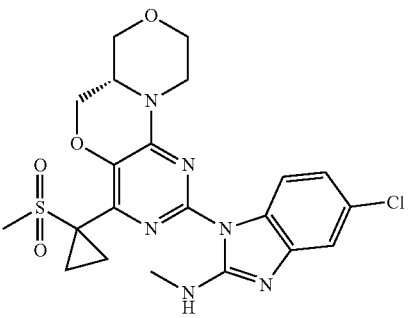

86

-continued

87

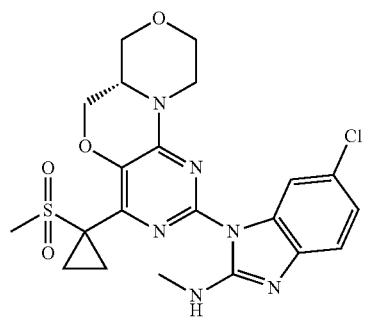

The compounds 86 and 87 were synthesised following a similar synthetic route than the one used for synthesis of Example 66 by reaction of a chiral intermediate XLIV with 5-chloro-N-methyl-1H-1,3-benzodiazol-2-amine.

Example 86

¹H NMR (300 MHz, DMSO) δ 7.98 (d, J=4.9 Hz, 1H), 7.86 (d, J=1.9 Hz, 1H), 7.03 (d, J=8.4 Hz, 1H), 6.90 (dd, J=8.4, 2.0 Hz, 1H), 4.23 (d, J=7.8 Hz, 1H), 4.05 (d, J=12.6 Hz, 1H), 3.86 (d, J=8.1 Hz, 1H), 3.82-3.70 (m, 2H), 3.71-3.53 (m, 1H), 3.38 (dd, J=14.7, 7.9 Hz, 1H), 3.05 (dd, J=19.6, 13.6 Hz, 2H), 2.90-2.79 (m, 6H), 1.48 (s, 2H), 1.21 (s, 2H).

LCMS 1=t$_R$=3.53 min, MS: 491.1[M+H]⁺

Example 87

¹H NMR (300 MHz, DMSO) δ 8.34 (d, J=4.8 Hz, 1H), 8.03 (d, J=8.5 Hz, 1H), 7.27 (d, J=2.0 Hz, 1H), 6.99 (dd, J=8.5, 2.1 Hz, 1H), 4.44 (dd, J=10.9, 3.3 Hz, 1H), 4.31 (d, J=12.5 Hz, 1H), 4.05 (d, J=8.0 Hz, 1H), 4.01-3.89 (m, 2H), 3.89-3.73 (m, 1H), 3.57 (t, J=11.8 Hz, 1H), 3.29-3.13 (m, 2H), 3.10-3.00 (m, 6H), 1.69 (s, 2H), 1.42 (s, 2H).

LCMS 1: t$_R$=3.59 min, MS: 491.1 [M+H]⁺

Example 88, 89

88

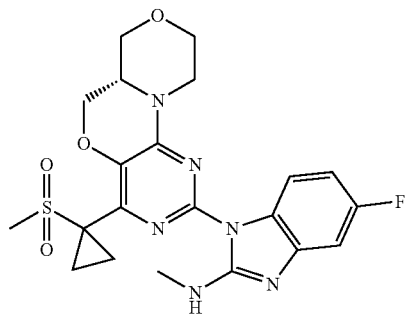

89

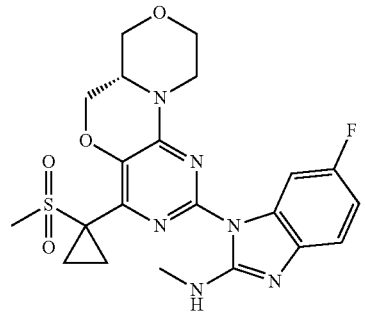

The compounds 88 and 89 were synthesised following a similar synthetic route than the one used for synthesis of Example 66 by reaction of a chiral intermediate XLIV with 5-fluoro-N-methyl-1H-1,3-benzodiazol-2-amine.

Example 90, 91

90

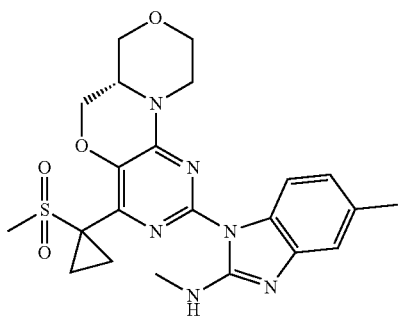

91

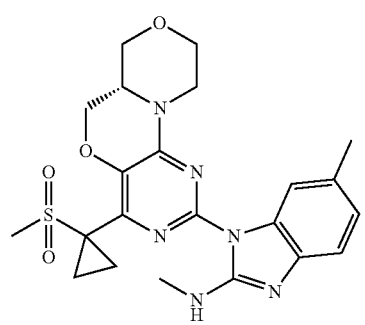

The compounds 90 and 91 were synthesised following a similar synthetic route than the one used for synthesis of Example 66 by reaction of a chiral intermediate XLIV with 5-methyl-N-methyl-1H-1,3-benzodiazol-2-amine.

Examples 92

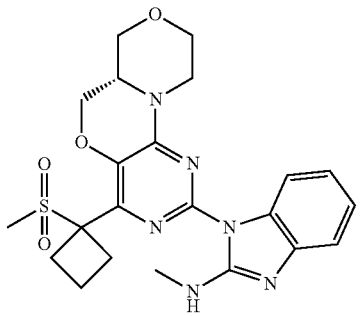

92

The compound 92 was synthesised following a similar synthetic route than the one used for synthesis of Examples 90, 91 by reaction of a chiral intermediate XLVII with N-methyl-1H-1,3-benzodiazol-2-amine.

1H NMR (300 MHz, DMSO) δ 8.12 (d, J=4.9 Hz, 1H), 8.05 (d, J=7.4 Hz, 1H), 7.25 (d, J=6.9 Hz, 1H), 7.07 (m, 1H), 6.98 (dd, J=11.5, 3.8 Hz, 1H), 4.36 (m, 2H), 4.06 (m, 1H), 3.93 (dd, J=10.9, 8.4 Hz, 2H), 3.83 (m, 1H), 3.58 (t, J=10.5 Hz, 1H), 3.22 (t, J=10.8 Hz, 2H), 3.01 (d, J=4.8 Hz, 3H), 2.91 (s, 3H), 2.85 (m, 4H), 2.16 (dd, J=19.0, 10.1 Hz, 1H), 1.90 (m 1H).

LCMS1: $t_R$=3.19 min; MS=471.0 [M+H]$^+$.

Example 93

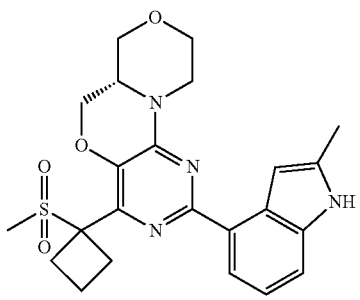

93

The compound 93 was synthesised following a similar synthetic route that the one used for synthesis of Example 67 from coupling reaction of chiral intermediate XLVII with 2-methyl indole-4-boronic pinacol ester.

LC-MS1, Rt=5.13 min, MS: 455.1 [M+H]$^+$

1H NMR (300 MHz, DMSO) δ 11.02 (s, 1H), 7.95 (dd, J=7.6, 0.8 Hz, 1H), 7.33 (d, J=7.9 Hz, 1H), 7.05 (t, J=7.7 Hz, 1H), 7.00 (s, 1H), 4.55 (dd, J=13.0, 1.3 Hz, 1H), 4.34 (dd, J=11.0, 3.3 Hz, 1H), 4.05 (dd, J=11.4, 3.0 Hz, 1H), 3.90 (m, 2H), 3.73 (t, J=9.6 Hz, 1H), 3.56 (dd, J=12.0, 9.1 Hz, 1H), 3.21 (t, J=10.8 Hz, 1H), 3.12 (m, 1H), 2.97 (m, 4H), 2.85 (s, 3H), 2.41 (s, 3H), 2.13 (m, 1H), 1.88 (m, 1H).

Examples 94, 95

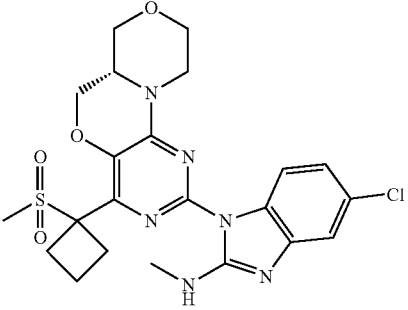

94

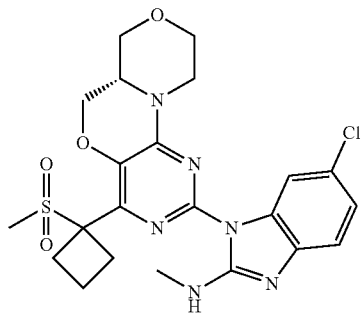

95

The compounds 94 and 95 were synthesised following a similar synthetic route than the one used for synthesis of Examples 90, 91 by reaction of a chiral intermediate XLVII with 5-chloro-N-methyl-1H-1,3-benzodiazol-2-amine.

Example 94

1H NMR (300 MHz, DMSO) δ 8.24 (q, J=4.7 Hz, 1H), 8.02 (d, J=8.5 Hz, 1H), 7.27 (d, J=2.1 Hz, 1H), 6.99 (dd, J=8.5, 2.1 Hz, 1H), 4.37 (dd, J=11.0, 3.5 Hz, 1H), 4.32 (d, J=11.8 Hz, 1H), 4.05 (d, J=8.2 Hz, 1H), 3.93 (m, 2H), 3.81 (m, 1H), 3.57 (t, J=10.5 Hz, 1H), 3.22 (t, J=10.9 Hz, 2H), 3.02 (d, J=4.8 Hz, 3H), 2.91 (s, 3H), 2.84 (m, 4H), 2.16 (dd, J=19.2, 10.0 Hz, 1H), 1.89 (s, 1H). LCMS1: $t_R$=3.88 min; MS=505.1 [M+H]$^+$ Example 95

1H NMR (300 MHz, DMSO) δ 8.11 (d, J=4.9 Hz, 1H), 8.07 (d, J=2.1 Hz, 1H), 7.24 (d, J=8.4 Hz, 1H), 7.10 (dd, J=8.4, 2.1 Hz, 1H), 4.38 (dd, J=11.0, 3.3 Hz, 1H), 4.26 (d, J=11.6 Hz, 1H), 4.07 (dd, J=11.6, 3.4 Hz, 1H), 3.94 (dd, J=11.0, 8.2 Hz, 2H), 3.83 (m, 1H), 3.59 (td, J=12.0, 2.6 Hz, 1H), 3.25 (m, 2H), 3.02 (d, J=4.8 Hz, 3H), 2.91 (s, 3H), 2.85 (m, 4H), 2.17 (m, 1H), 1.90 (m, 1H). $t_R$=3.81 min; MS=505.0 [M+H]$^+$

Example 96, 97

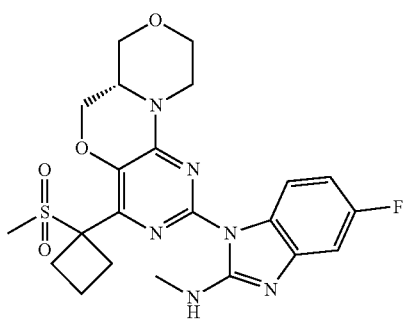

96

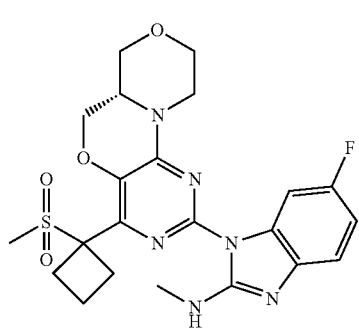

97

The compounds 96 and 97 were synthesised following a similar synthetic route than the one used for synthesis of Examples 90, 91 by reaction of a chiral intermediate XLVII with 5-fluoro-N-methyl-1H-1,3-benzodiazol-2-amine.

Example 96

1H NMR (300 MHz, DMSO) δ 8.03 (q, J=4.4 Hz, 1H), 7.82 (dd, J=10.1, 2.6 Hz, 1H), 7.22 (dd, J=8.6, 5.1 Hz, 1H), 6.92 (m, 1H), 4.38 (dd, J=10.9, 3.3 Hz, 1H), 4.28 (d, J=12.8 Hz, 1H), 4.08 (dd, J=11.6, 3.4 Hz, 1H), 3.94 (m, 2H), 3.81 (m, 1H), 3.58 (m, 1H), 3.24 (m, 2H), 3.00 (d, J=4.8 Hz, 3H), 2.91 (s, 3H), 2.84 (m, 4H), 2.17 (dd, J=19.7, 9.2 Hz, 1H), 1.90 (m, 1H).

LC-MS1, Rt=3.36 min, MS=489.1[M+H]$^+$

Example 97

1H NMR (300 MHz, DMSO) δ 8.24 (q, J=4.7 Hz, 1H), 8.02 (dd, J=8.8, 5.2 Hz, 1H), 7.05 (dd, J=9.8, 2.6 Hz, 1H), 6.78 (m, 1H), 4.36 (m, 2H), 4.06 (dd, J=11.7, 3.3 Hz, 1H), 3.93 (t, J=10.0 Hz, 2H), 3.81 (m, 1H), 3.58 (m, 1H), 3.22 (t, J=10.8 Hz, 2H), 3.02 (d, J=4.8 Hz, 3H), 2.91 (s, 3H), 2.85 (m, 4H), 2.17 (m, 1H), 1.89 (m, 1H).

LC-MS1, Rt=3.46 min, MS=489.1[M+H]$^+$

Example 98, 99

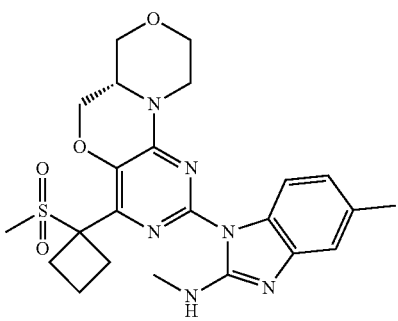

98

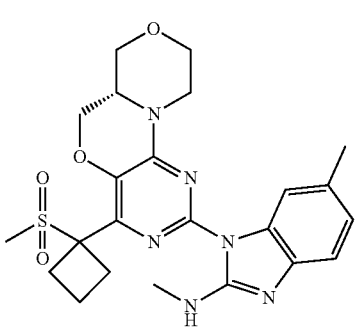

99

The compounds 98 and 99 were synthesised following a similar synthetic route than the one used for synthesis of Examples 90, 91 by reaction of a chiral intermediate XLVII with 5-methyl-N-methyl-1H-1,3-benzodiazol-2-amine.

Example 100

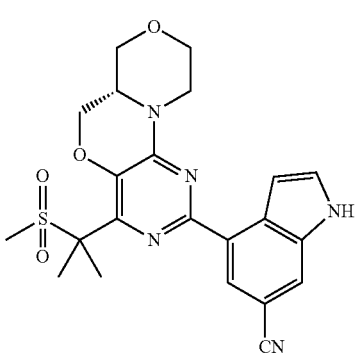

100

The compound 100 was synthesised following a similar synthetic route that the one used for synthesis of Example 1 from coupling reaction of a chiral intermediate XX with 6-cyano indole-4-boronic pinacol ester.

Example 101

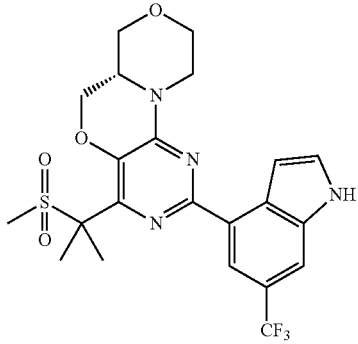

The compound 101 was synthesised following a similar synthetic route that the one used for synthesis of Example 1 from coupling reaction of chiral intermediate XX with 6-trifluoromethyl indole-4-boronic pinacol ester.

$^1$H-NMR (300 MHz, DMSO-d6): δ 11.68 (bs, 1H), 8.18 (bs, 1H), 7.81 (bs, 1H), 7.69 (bt, J=2.7, 1H), 7.43 (bs, 1H), 4.55 (bd, J=11.7 Hz, 1H), 4.41 (dd, J=11.1, 3.6 Hz, 1H), 4.07 (dd, J=11.4, 3 Hz, 1H), 3.97-3.88 (m, 2H), 3.81-3.73 (m, 1H), 3.61-3.52 (m, 1H), 3.25-3.11 (m, 2H), 2.95 (s, 3H), 1.89 (s, 3H), 1.88 (s, 3H) ppm.

LC-MS 1: $t_R$=5.65 min; MS=497.2 [M+H]$^+$

Example 102

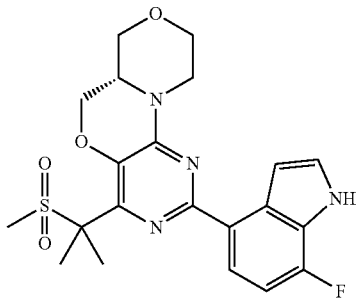

The compound 102 was synthesised following a similar synthetic route that the one used for synthesis of Example 1 from coupling reaction of chiral intermediate XX with 7-fluoro indole-4-boronic pinacol ester.

$^1$H-NMR (300 MHz, DMSO-d6): δ=11.45 (bs, 1H), 8.06 (dd, J=8.4, 5.4 Hz, 1H), 7.52 (bt, J=2.7 Hz, 1H), 6.91 (dd, J=10.2, 8.4 Hz, 1H), 6.60 (bt, J=2.7 Hz, 1H), 4.63 (bd, J=11.7 Hz, 1H), 4.43 (dd, J=10.8, 3.3 Hz, 1H), 4.06-3.89 (m, 3H), 3.82-3.73 (m, 1H), 3.60-3.52 (m, 1H), 3.21 (t, J=10.8, 1H), 3.16-3.02 (m, 1H), 3.05 (s, 3H), 1.88 (s, 3H), 1.87 (s, 3H) ppm.

LC-MS 1: $t_R$=5.98 min; MS=447.1 [M+H]$^+$

Example 103

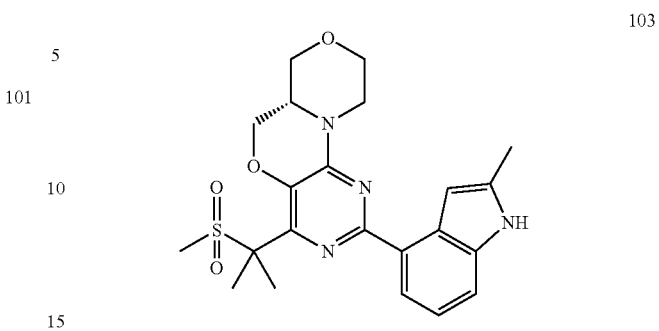

The compound 103 was synthesised following a similar synthetic route that the one used for synthesis of Example 1 from coupling reaction of chiral intermediate XX with 2-methyl indole-4-boronic pinacol ester.

$^1$H-NMR (300 MHz, DMSO-d6): δ 11.00 (bs, 1H), 7.87 (d, J=7.6 Hz, 1H), 7.30 (d, J=7.6 Hz, 1H), 7.02 (t, J=7.6 Hz, 1H), 6.96 (bs, 1H), 4.56 (bd, J=12.0 Hz, 1H), 4.36 (dd, J=10.8, 3.5 Hz, 1H), 4.03 (bd, J=11.6 Hz, 1H), 3.93-3.82 (m, 2H), 3.76-3.68 (m, 1H), 3.53 (bt, J=11.6 Hz, 1H), 3.22-3.05 (m, 2H), 2.92 (s, 3H), 2.39 (s, 3H), 1.86 (s, 3H), 1.84 (s, 3H) ppm.

LC-MS1: $t_R$=5.12 min; MS: 443.0 [M+H]$^+$

Example 104

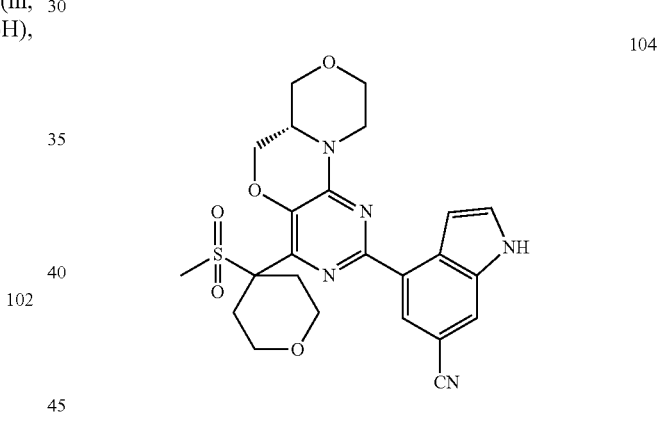

The compound 104 was synthesised following a similar synthetic route than the one used for synthesis of Example 3 by coupling reaction of a chiral intermediate XII with 6-cyano indole-4-boronic acid pinacol ester.

Example 105

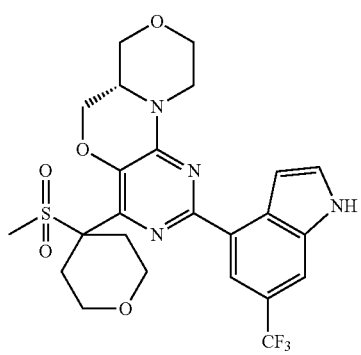

The compound 105 was synthesised following a similar synthetic route than the one used for synthesis of Example 3 by coupling reaction of a chiral intermediate XII with 6-trifluoromethyl indole-4-boronic acid pinacol ester.

1H NMR (300 MHz, DMSO) δ 11.69 (s, 1H), 8.15 (s, 1H), 7.81 (s, 1H), 7.69 (t, J=2.7 Hz, 1H), 7.34 (s, 1H), 4.58 (d, J=12.0 Hz, 1H), 4.39 (m, 1H), 4.08 (d, J=11.4 Hz, 1H), 3.93 (m, 4H), 3.79 (m, 1H), 3.58 (t, J=10.6 Hz, 1H), 3.27-3.13 (m, 6H), 2.88 (s, 3H), 2.10 (m, 2H).

LCMS1: $t_R$=5.39 min; MS=539.2 [M+H]$^+$.

Example 106

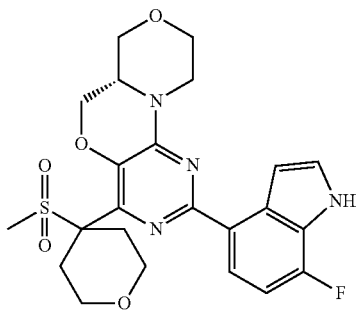

The compound 106 was synthesised following a similar synthetic route than the one used for synthesis of Example 3 by coupling reaction of chiral intermediate XII with 7-fluoro indole-4-boronic acid pinacol ester.

1H NMR (300 MHz, DMSO) δ 11.04 (s, 1H), 8.00 (dd, J=8.3, 5.3 Hz, 1H), 7.52 (d, J=2.6 Hz, 1H), 6.91 (dd, J=10.1, 8.4 Hz, 1H), 6.59 (m, 1H), 4.66 (d, J=13.2 Hz, 1H), 4.39 (dd, J=10.9, 3.3 Hz, 1H), 4.04 (d, J=11.5 Hz, 1H), 3.93 (m, 4H), 3.79 (m, 1H), 3.58 (t, J=10.5 Hz, 1H), 3.24 (m, 4H), 3.07 (d, J=13.7 Hz, 2H), 2.93 (s, 3H), 2.14 (m, 2H).

LCMS1: $t_R$=5.62 min; MS=489.1 [M+H]$^+$.

Example 107

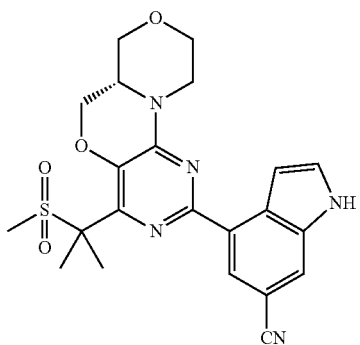

The compound 107 was synthesised following a similar synthetic route that the one used for synthesis of Example 6 from coupling reaction of a chiral intermediate XLIV with 6-cyano indole-4-boronic pinacol ester.

Example 108

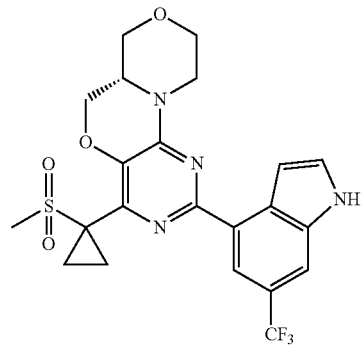

The compound 108 was synthesised following a similar synthetic route that the one used for synthesis of Example 6 from coupling reaction of a chiral intermediate XLIV with 6-trifluoromethyl indole-4-boronic pinacol ester.

$^1$H NMR (300 MHz, DMSO) δ 11.68 (s, 1H), 8.20 (d, J=1.4 Hz, 1H), 7.81 (s, 1H), 7.69 (t, J=2.7 Hz, 1H), 7.47 (s, 1H), 4.46 (dd, J=18.7, 7.6 Hz, 2H), 4.08 (d, J=8.2 Hz, 1H), 4.02-3.90 (m, 2H), 3.83-3.68 (m, 1H), 3.57 (t, J=10.6 Hz, 1H), 3.32-3.13 (m, 2H), 3.08 (s, 3H), 1.77-1.67 (m, 2H), 1.44-1.43 (m, 2H).

LCMS 1=$t_R$ 5.38 min; MS=495.1 1 [M+H]$^+$.

Example 109

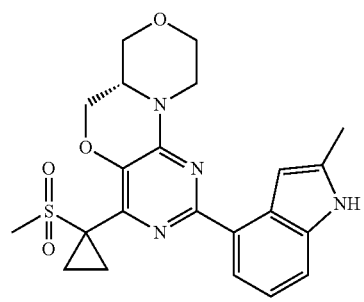

The compound 109 was synthesised following a similar synthetic route that the one used for synthesis of Example 6 from coupling reaction of a chiral intermediate XLIV with 2-methyl indole-4-boronic pinacol ester.

LCMS 1=tR=4.141 min, MS: 441.1 [M+H]$^+$

1H NMR (300 MHz, DMSO) δ 10.80 (s, 1H), 7.70 (dd, J=7.5, 0.9 Hz, 1H), 7.11 (d, J=7.9 Hz, 1H), 6.90-6.69 (m, 2H), 4.30 (d, J=11.8 Hz, 1H), 4.19 (dd, J=11.0, 3.3 Hz, 1H), 3.83 (dd, J=14.5, 5.1 Hz, 1H), 3.78-3.65 (m, 2H), 3.51 (t, J=9.7 Hz, 1H), 3.34 (dd, J=12.0, 9.2 Hz, 1H), 3.08-2.91 (m, 2H), 2.87 (s, 3H), 2.20 (s, 3H), 1.54-1.46 (m, 2H), 1.20-1.17 (m, 2H).

Example 110

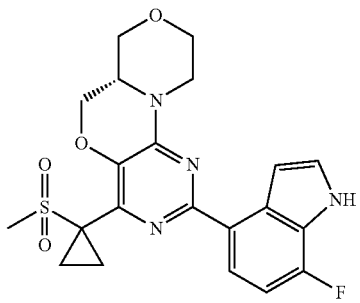

The compound 110 was synthesised following a similar synthetic route that the one used for synthesis of Example 6 from coupling reaction of a chiral intermediate XLIV with 7-fluoro indole-4-boronic pinacol ester.

$^1$H NMR (300 MHz, DMSO) δ 11.17 (s, 1H), 8.10 (dd, J=8.4, 5.4 Hz, 1H), 7.61-7.50 (m, 1H), 6.92 (dd, J=10.1, 8.4 Hz, 1H), 6.64-6.56 (m, 1H), 4.59 (d, J=11.4 Hz, 1H), 4.44 (dd, J=11.0, 3.5 Hz, 1H), 4.11-3.87 (m, 3H), 3.85-3.70 (m, 1H), 3.85-3.68 (m, 1H), 3.56 (t, J=10.5 Hz, 1H), 3.32-3.10 (m, 2H), 3.08 (s, 3H), 1.79-1.70 (m, 2H), 1.51-1.42 (m, 2H).

LCMS 1=Rt=5.77 min, MS=445.1 [M+H]$^+$

Example 111

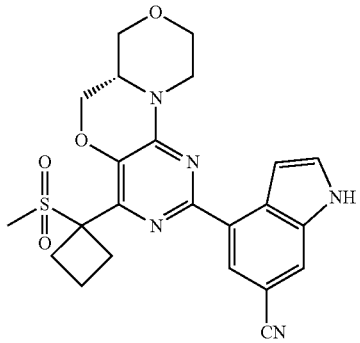

The compound 111 was synthesised following a similar synthetic route that the one used for synthesis of Example 67 from coupling reaction of chiral intermediate XLVII with 6-cyano indole-4-boronic pinacol ester.

Example 112

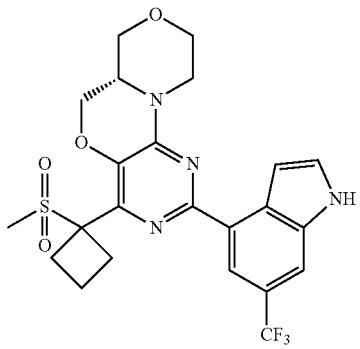

The compound 112 was synthesised following a similar synthetic route that the one used for synthesis of Example 67 from coupling reaction of chiral intermediate XLVII with 6-trifluoromethyl indole-4-boronic pinacol ester.

LC-MS1, Rt=5.74 min, MS=509.1 [M+H]$^+$

1H NMR (300 MHz, DMSO) δ 11.67 (s, 1H), 8.22 (d, J=1.2 Hz, 1H), 7.81 (d, J=0.5 Hz, 1H), 7.68 (m, 1H), 7.43 (s, 1H), 4.51 (d, J=11.4 Hz, 1H), 4.36 (m, 1H), 4.05 (m, 1H), 3.94 (m, 2H), 3.75 (m, 1H), 3.57 (m, 1H), 3.21 (m, 2H), 2.95 (m, 4H), 2.86 (s, 3H), 2.13 (m, 1H), 188 (m, 1H).

Examples 113 and 114

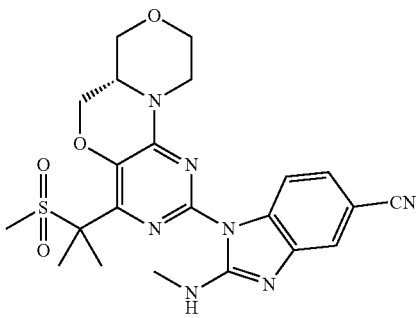

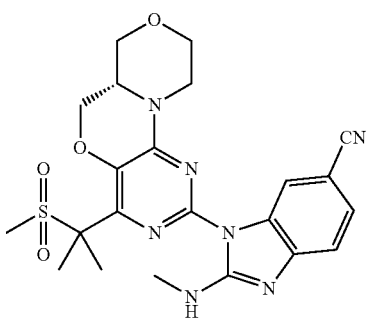

The compounds 113 and 114 were synthesised following a similar synthetic route than the one used for synthesis of Example 11 by reaction of a chiral intermediate XX with 5-carbonitrile-N-methyl-1H-1,3-benzodiazol-2-amine.

Example 113

1H NMR (300 MHz, DMSO) δ 8.36 (d, J=4.8 Hz, 1H), 8.22 (s, 1H), 7.45 (d, J=8.3 Hz, 1H), 7.31 (d, J=8.2 Hz, 1H), 4.37 (dd, J=10.8, 3.1 Hz, 1H), 4.26 (d, J=11.7 Hz, 1H), 4.07-3.71 (m, 4H), 3.53 (t, J=10.7 Hz, 1H), 3.25-3.12 (m, 2H), 3.00 (d, J=4.8 Hz, 3H), 2.97 (s, 3H), 1.76 (d, J=5.2 Hz, 6H).

LCMS1: Rt 4.01 min; MS=483.9 [M+H]$^+$

Example 114

1H NMR (300 MHz, DMSO) δ 8.25 (d, J=4.8 Hz, 1H), 8.05 (d, J=8.3 Hz, 1H), 7.61 (s, 1H), 7.33 (dd, J=8.3, 1.5 Hz, 1H), 4.48-4.19 (m, 2H), 4.11-3.72 (m, 4H), 3.50 (t, J=10.7 Hz, 1H), 3.30-3.14 (m, 2H), 2.97 (d, J=2.9 Hz, 3H), 1.75 (d, J=5.0 Hz, 6H).

LCMS1: Rt 3.78 min; MS: 483.9 [M+H]$^+$

The invention claimed is:

1. A chemical compound of formula (I)

(I)

wherein
R₁ is selected from aryl or heteroaryl;
R₂ is selected from $NR_3SO_2R_3$, alkyl, cycloalkyl, aryl and heteroaryl;
wherein R₃ is independently selected at each occurrence from H, alkyl optionally substituted by 1, 2 or 3 halo atoms, cycloalkyl optionally substituted by 1, 2 or 3 halo atoms and heterocycloalkyl optionally substituted by 1, 2 or 3 halo atoms; and
m is 1 or 2;
alkyl is a linear saturated hydrocarbon having up to 10 carbon atoms ($C_1$-$C_{10}$) or a branched saturated hydrocarbon of between 3 and 10 carbon atoms ($C_3$-$C_{10}$);
cycloalkyl is a mono- or bi-cyclic saturated $C_3$-$C_{10}$ hydrocarbon, which may optionally be fused to an aryl group; or cycloalkyl is adamantyl;
heterocycloalkyl is a C-linked or N-linked 3-10 membered saturated mono- or bi-cyclic ring, which contains 1, 2, 3 or 4 ring heteroatoms independently selected from N, S and O, wherein an N or S atom in the ring may be substituted with oxygen to form an N-oxide, sulfoxide or sulfone group;
aryl is phenyl, biphenyl or naphthyl; and
heteroaryl is a 5, 6, 9 or 10, 12, 13 or 14 membered mono-, bi- or tri-cyclic aromatic ring, which may contain 1, 2, 3 or 4 ring heteroatoms independently selected from N, S and O;
and pharmaceutically acceptable salts, solvates and stereoisomers thereof.

2. The chemical compound as claimed in claim 1, wherein when any of R₁, R₂ and R₃ is selected from alkyl, cycloalkyl, heterocycloalkyl, aryl and heteroaryl, then
said alkyl, heterocycloalkyl and cycloalkyl may optionally be substituted at each occurrence with 1, 2, 3, 4 or 5 substituents, wherein the substituents are independently selected from halo, OH, CN, $COOR_4$, $CF_3$, $NR_4R_4$, $NR_4COR_4$, $(NR_4)_nSO_2R_4$, wherein n is 0 or 1, alkyl optionally substituted by 1, 2 or 3 halo atoms, cycloalkyl optionally substituted by 1, 2 or 3 halo atoms, O-alkyl optionally substituted by 1, 2 or 3 halo atoms, and wherein two substituents on a single atom may be taken together with the atom to which they are attached to form a cyclic structure selected from cycloalkyl and heterocycloalkyl optionally substituted by 1, 2 or 3 groups selected from halo, $C(O)C_1$-$C_4$ alkyl, $C(O)O$—($C_1$-$C_4$ alkyl) and $C_1$-$C_4$ alkyl optionally substituted with 1, 2 or 3 halo atoms;
said aryl and heteroaryl may be optionally substituted at each occurrence with 1, 2, 3, 4 or 5 substituents independently selected from halo, OH, CN, $COOR_4$, $CF_3$, $NR_4R_4$, $NR_4COR_4$, $(NR_4)_nSO_2R_4$, wherein n is 0 or 1, $NHR_5$, alkyl optionally substituted by 1, 2 or 3 halo atoms, O-alkyl optionally substituted by 1, 2 or 3 halo atoms, cycloalkyl optionally substituted by 1, 2 or 3 halo atoms, and heterocycloalkyl optionally substituted by 1, 2 or 3 halo atoms;
R₄ is independently selected at each occurrence from H, alkyl, aryl, heteroaryl, cycloalkyl and heterocycloalkyl, wherein alkyl, aryl, heteroaryl, cycloalkyl and heterocycloalkyl is optionally substituted by 1, 2 or 3 substituents selected from halo, alkyl, O-alkyl, $N(C_1$-$C_4$alkyl)_2$, $N(C_1$-$C_4$alkyl)$COC_1$-$C_4$alkyl, or the R₄ groups are taken together with the atom(s) to which they are attached to form a heterocycloalkyl, optionally substituted by 1, 2 or 3 halo atoms or, where a substituent comprising an R₄ group is present on an alkyl, cycloalkyl or heterocycloalkyl, the R₄ group may be taken together with a substituent on that alkyl, cycloalkyl or heterocycloalkyl to form a heterocycloalkyl optionally substituted by 1, 2 or 3 halo atoms; and
R₅ is independently selected from COalkyl, COaryl or COheteroaryl.

3. The chemical compound as claimed in claim 1, wherein R₁ is selected from wherein
R₆ is selected from halo and H;
R₇, R₈ and R₉ are each independently selected from H; halo; CN; $R_{10}$; and $OR_{10}$;
wherein $R_{10}$ is ($C_1$-$C_6$)alkyl optionally substituted with 1, 2 or 3 halo atoms;
R₁₁ is selected from H, $R_{10}$, $NR_4R_4$ and $NR_4COR_4$;
wherein R₄ is independently selected at each occurrence from H or alkyl optionally substituted by 1, 2 or 3 halo atoms, or the R₄ groups are taken together with the atom(s) to which they are attached to form heterocycloalkyl, optionally substituted by 1, 2 or 3 halo atoms; and
R₁₂ is selected from H, halo, $OR_{10}$ or $R_{10}$.

4. The chemical compound as claimed in claim 3, wherein R₆ is selected from H and halo;

$R_7$, $R_8$ and $R_9$ are selected from H, halo, CN, $O(C_1-C_6)$ alkyl and $(C_1-C_6)$alkyl optionally substituted by one or more halo atoms;

$R_{11}$ is selected from H, $(C_1-C_6)$alkyl, $NR_4R_4$ and $NR_4COR_4$; and $R_{12}$ is selected from H, halo, $(C_1-C_6)$alkyl and $O(C_1-C_6)$ alkyl.

5. The chemical compound as claimed in claim 3, wherein $R_6$, $R_7$, $R_8$, $R_9$ and $R_{12}$ are H; and $R_{11}$ is selected from $(C_1-C_6)$alkyl, $NR_4R_4$ and $NR_4COR_4$.

6. The chemical compound as claimed in claim 3, wherein $R_6$, $R_8$, $R_9$, $R_{11}$ and $R_{12}$ are H; and $R_7$ is selected from halo, CN, $O(C_1-C_6)$alkyl, and $(C_1-C_6)$alkyl optionally substituted by 1, 2 or 3 halo atoms.

7. The chemical compound as claimed in claim 3, wherein $R_6$, $R_7$, $R_8$, $R_9$, $R_{11}$ and $R_{12}$ are H.

8. . The chemical compound as claimed in claim 1, wherein $R_2$ is selected from $NR_3SO_2R_3$, alkyl and cycloalkyl;

wherein alkyl and cycloalkyl is substituted with at least one substituent selected from $(NR_4)_nSO_2R_4$, wherein n is 0 or 1, OH and CN; and wherein alkyl and cycloalkyl is further optionally substituted with 1 or 2 substituents independently selected from halo, CN, $COOR_4$, $CF_3$, $(C_1-C_6)$alkyl optionally substituted by 1, 2 or 3 halo atoms, cycloalkyl optionally substituted by 1, 2 or 3 halo atoms, and $O(C_1-C_6)$ alkyl optionally substituted by 1, 2 or 3 halo atoms, or with 2 substituents on a single atom that are taken together with the atom to which they are attached to form a cyclic structure selected from cycloalkyl and heterocycloalkyl optionally substituted by 1, 2 or 3 groups selected from halo, $C_1-C_4$ alkyl, $C(O)C_1-C_4$ alkyl and $C(O)O$—$C_1-C_4$ alkyl.

9. The chemical compound as claimed in claim 8, wherein $R_2$ is $(CH_2)_pC(R_{13})_2(CH_2)_qQ$, wherein Q is $(NR_4)_nSO_2R_4$, OH or CN, wherein p and q are independently 0, 1 or 2, and wherein (i) $R_{13}$ is independently selected at each occurrence from the group consisting of H and $(C_1-C_4)$alkyl, or (ii) one $R_{13}$ is selected from the group consisting of H and $(C_1-C_4)$ alkyl or the other $R_{13}$ is taken together with $R_4$, if present, to form a 3-6 membered heterocycloalkyl optionally substituted by 1, 2 or 3 halo atoms, or (iii) the $R_{13}$ groups are taken together with the carbon to which they are attached form a cyclic structure selected from $(C_3-C_6)$cycloalkyl and 3-6 membered heterocycloalkyl, optionally substituted by 1, 2 or 3 groups selected from halo, $C_1-C_4$ alkyl, $C(O)C_1-C_4$ alkyl and $C(O)O$—$C_1-C_4$ alkyl.

10. The chemical compound as claimed in claim 9, wherein both $R_{13}$ groups are H, wherein both $R_{13}$ groups are methyl or wherein the $R_{13}$ groups are taken together with the carbon to which they are attached form cyclopropanyl, cyclobutyl, tetrahydropyranyl, piperidinyl, N-ethoxycarbonylpiperidinyl or N-methylpiperidinyl.

11. The chemical compound as claimed in claim 10, wherein Q is $SO_2R_4$.

12. The chemical compound as claimed in claim 1, wherein when m is 1 the mandatory chiral centre in the chemical entity of formula (I) is in the (S) configuration and wherein when m is 2 the mandatory chiral centre in the chemical entity of formula (I) is in the (R) configuration.

13. The chemical compound as claimed in claim 1, selected from the group consisting of:

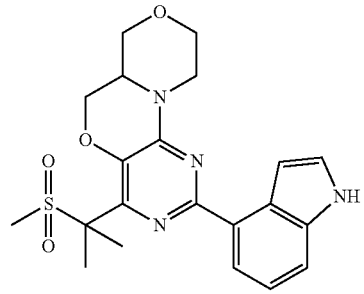

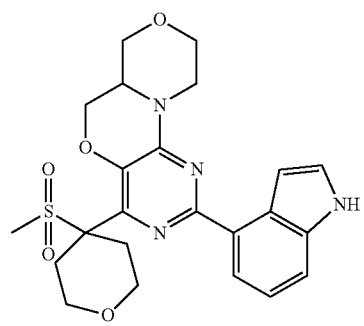

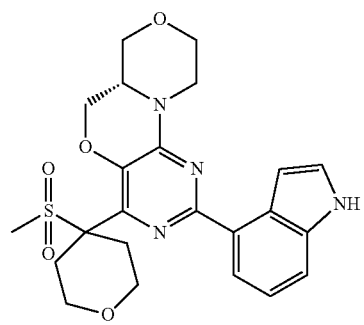

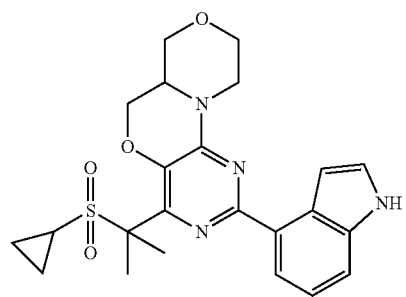

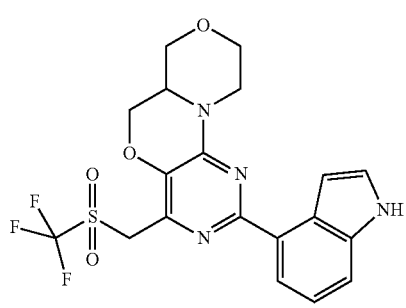

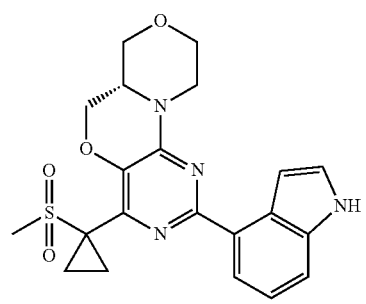
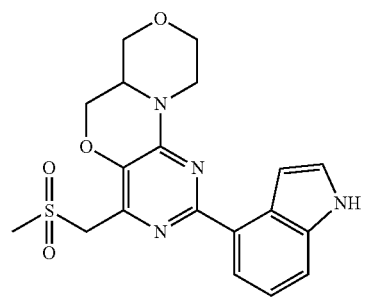
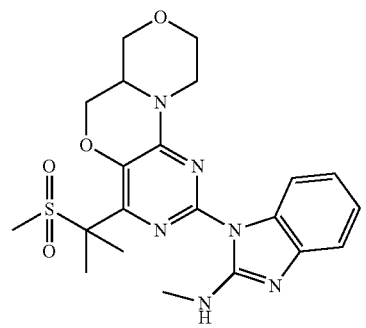
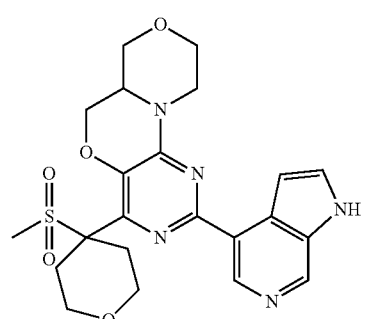
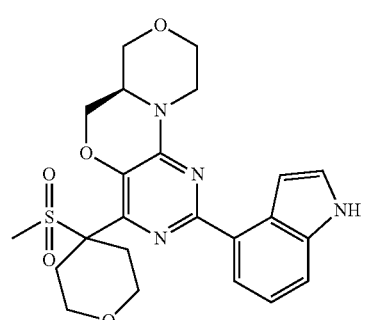
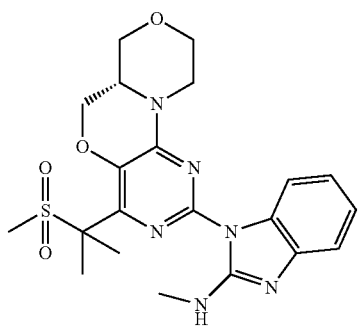
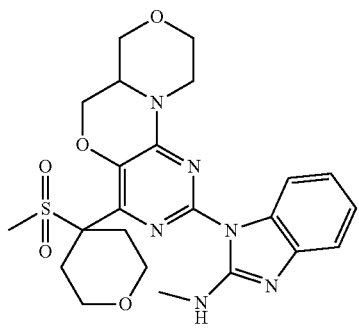
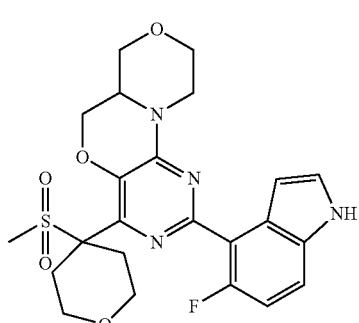
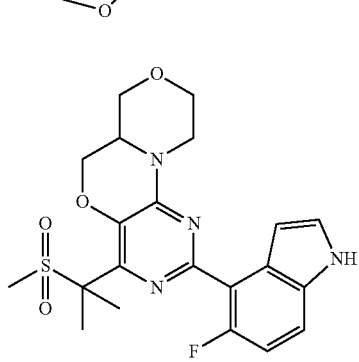
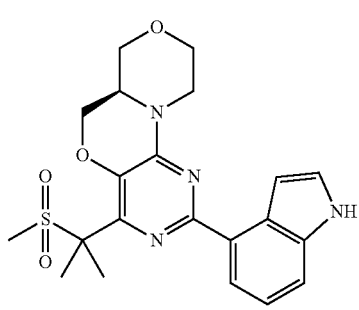

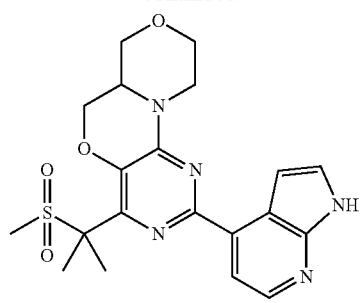
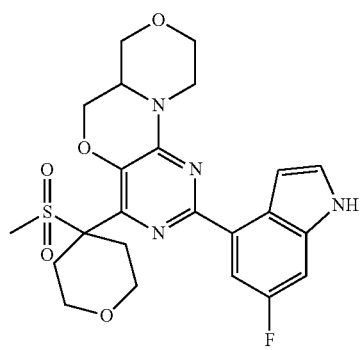
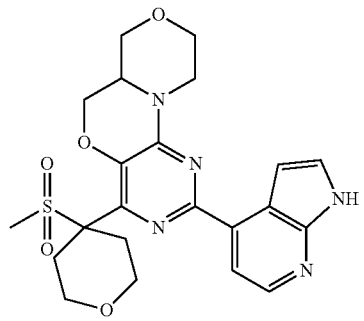
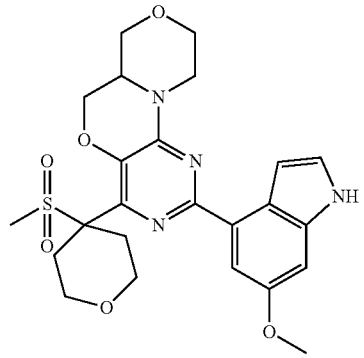
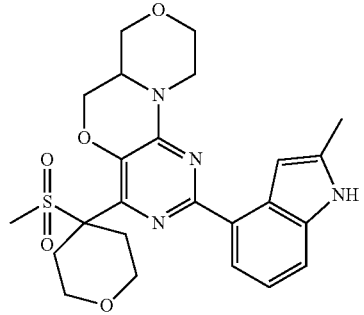
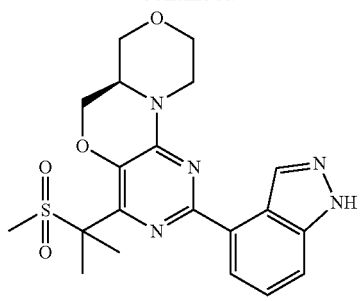
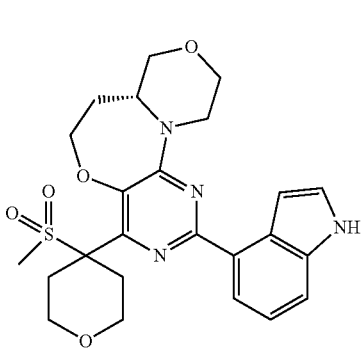
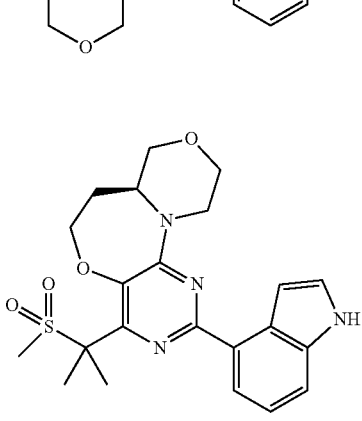
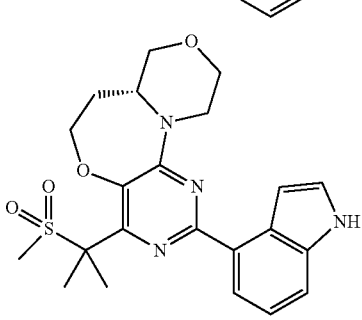
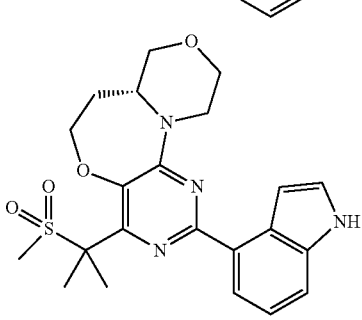

-continued
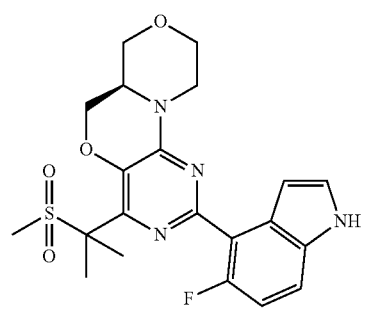
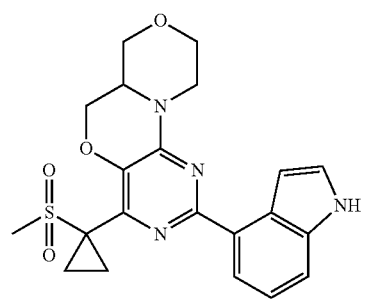
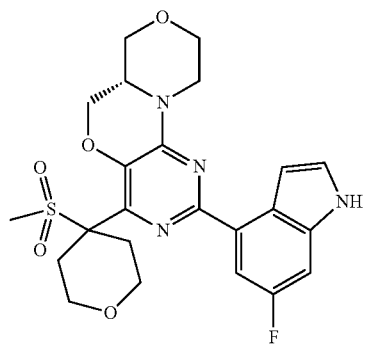
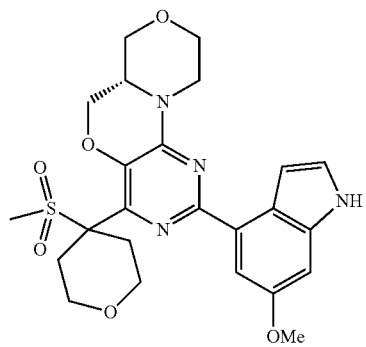
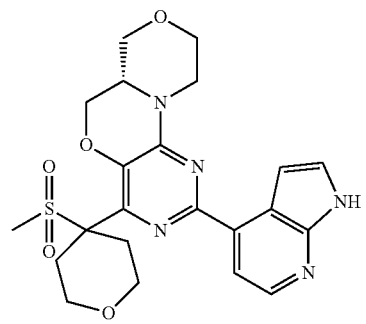
-continued
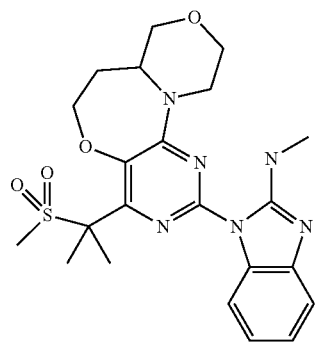
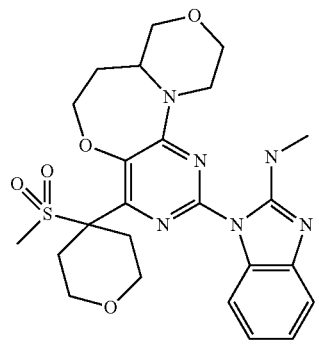
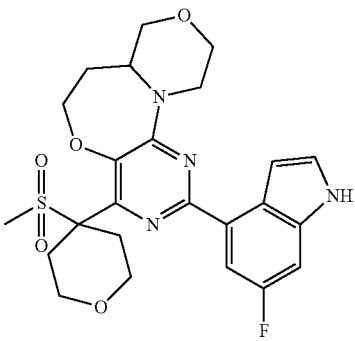
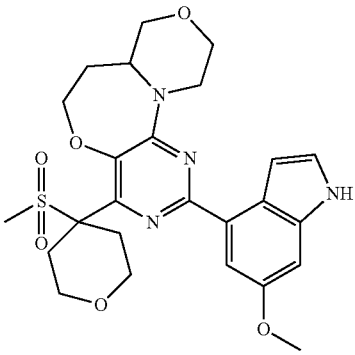
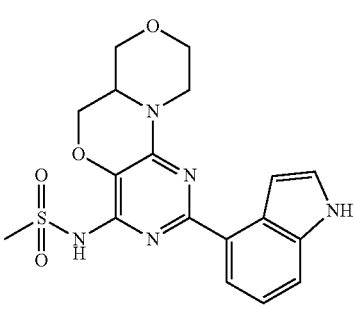

145
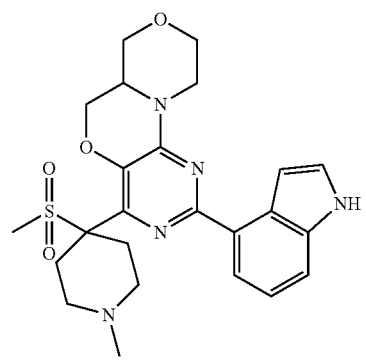
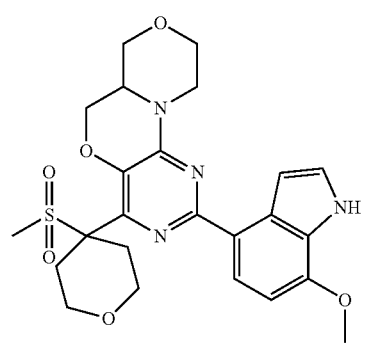
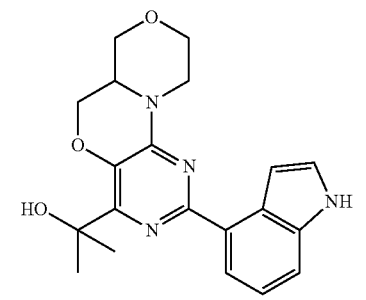
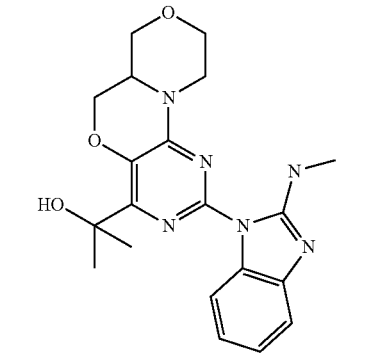
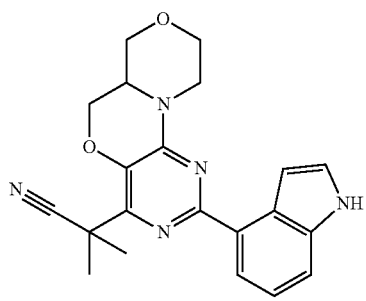
146
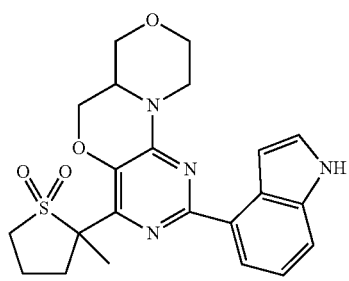
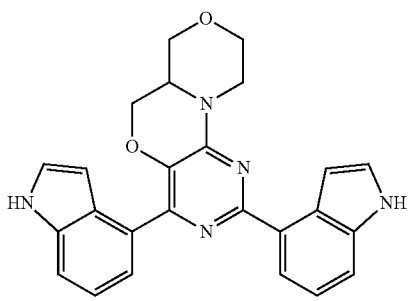
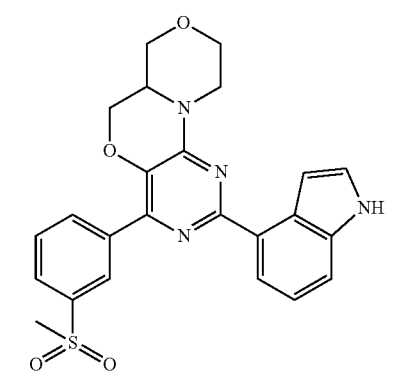
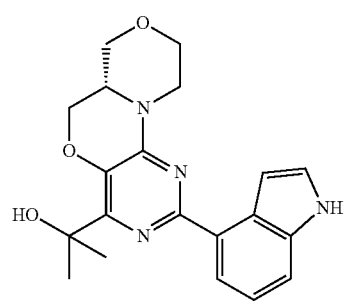
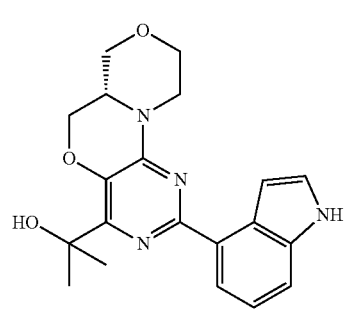

147
-continued
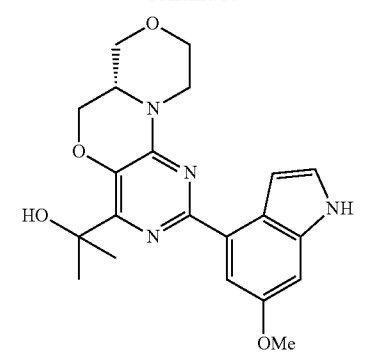
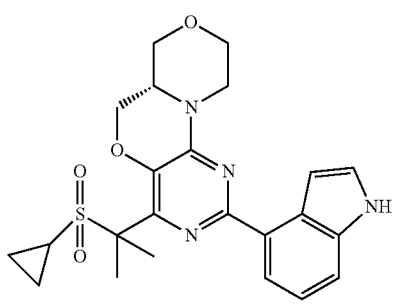
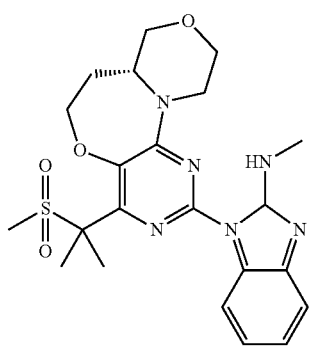
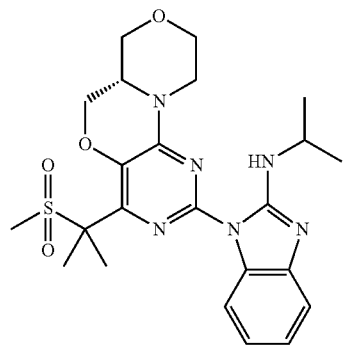
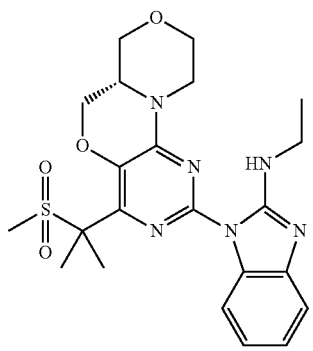
148
-continued
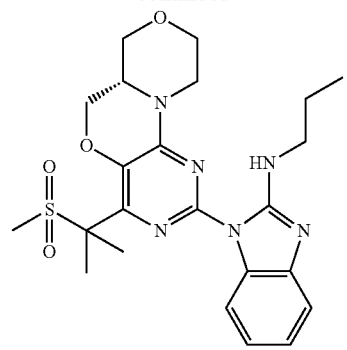
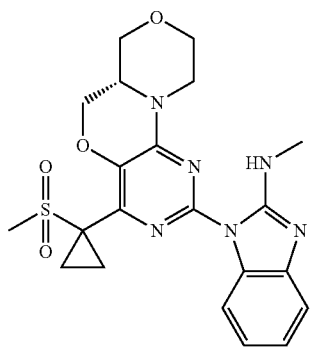
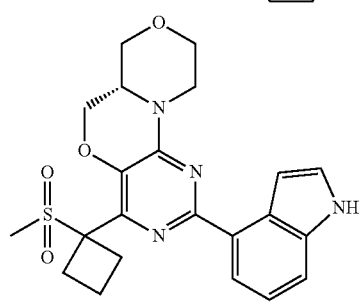
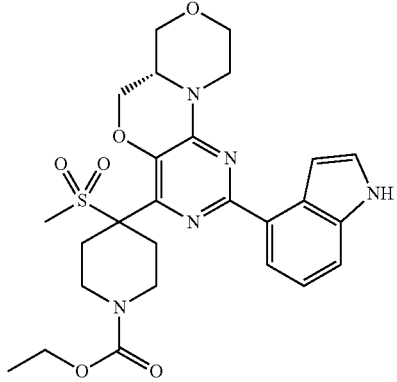
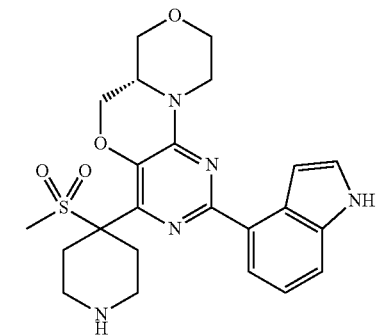

149
-continued
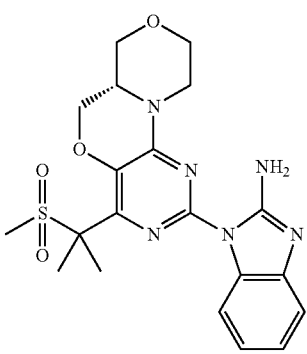
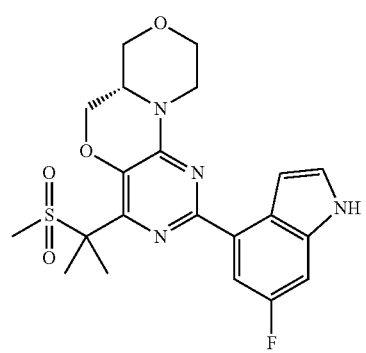
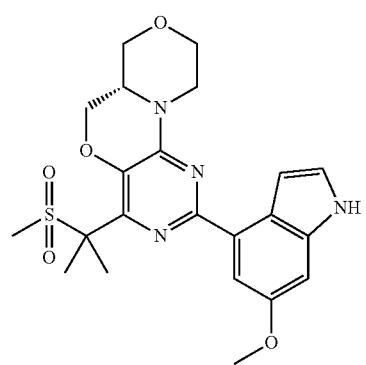
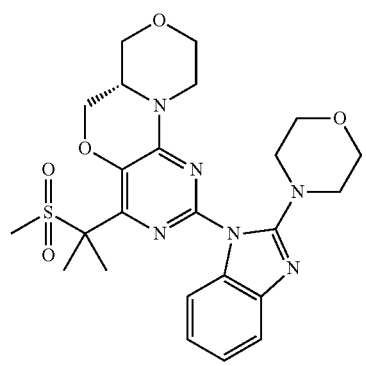
150
-continued
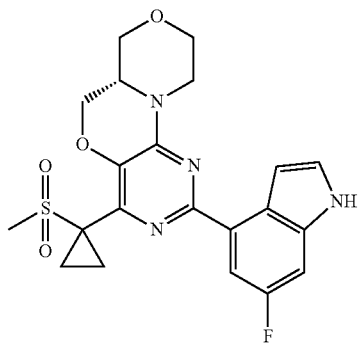
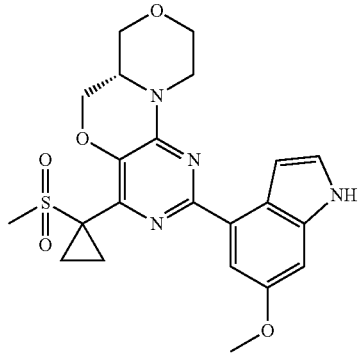
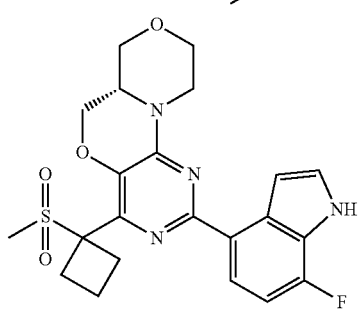
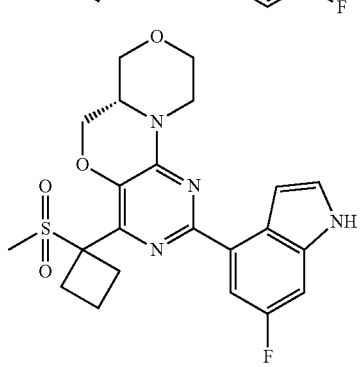
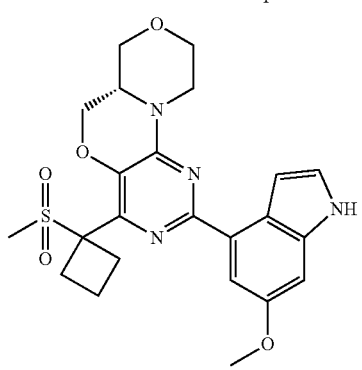

151
-continued
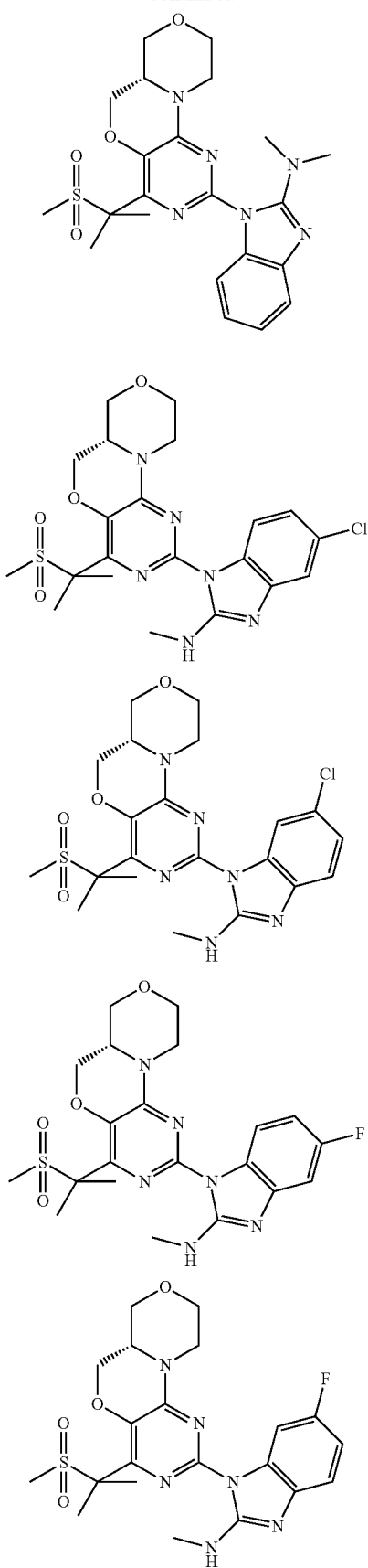
152
-continued
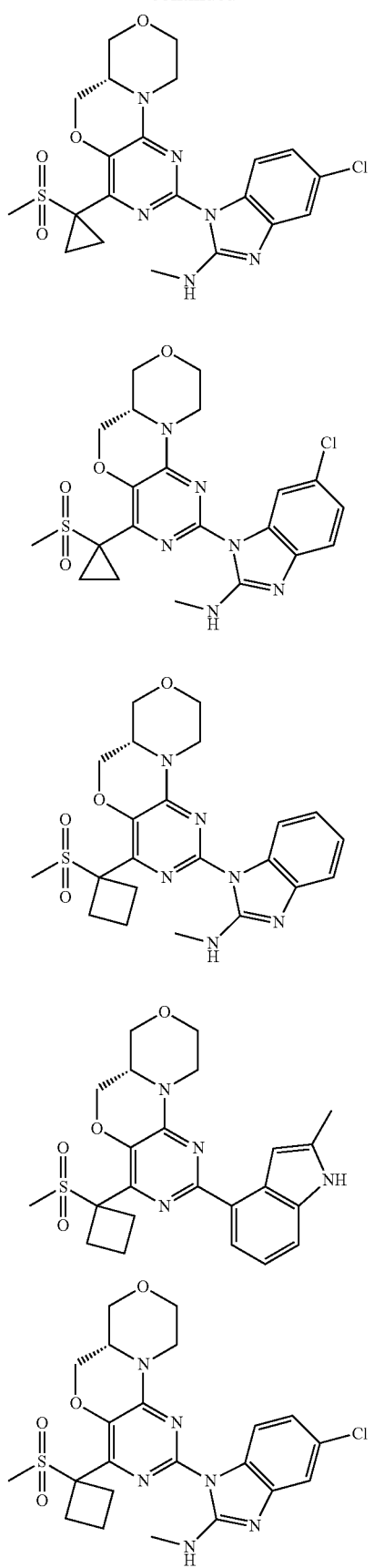

153
-continued
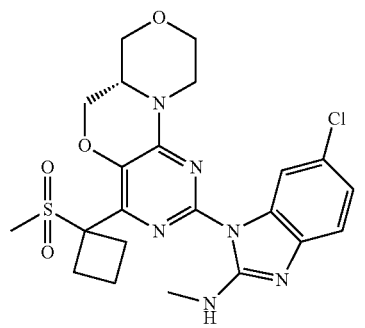
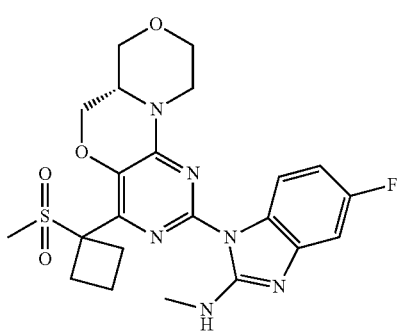
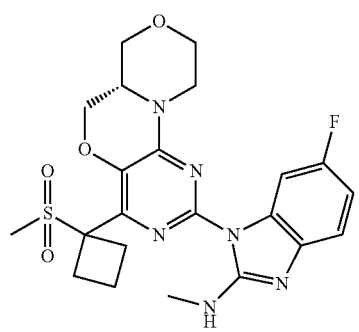
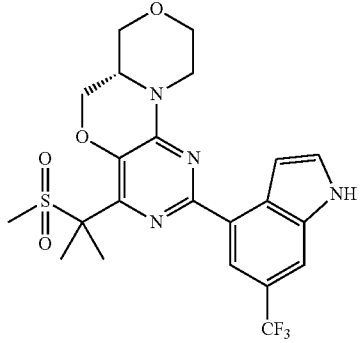
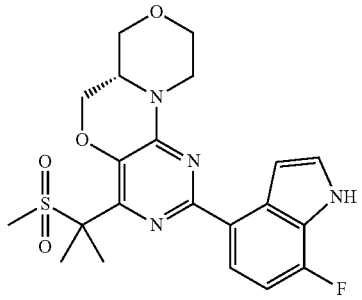
154
-continued
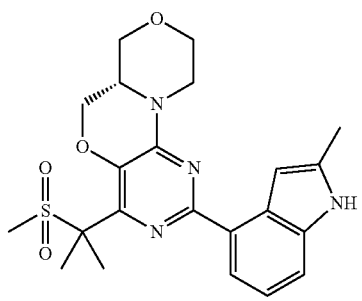
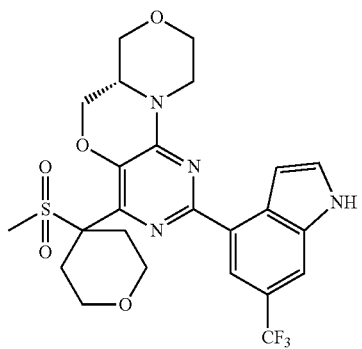
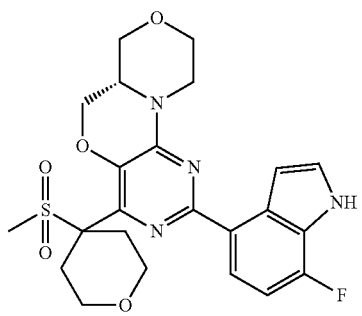
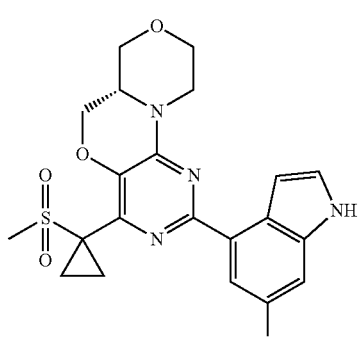
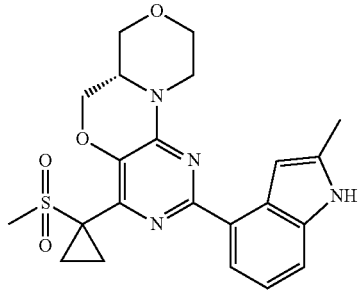

-continued

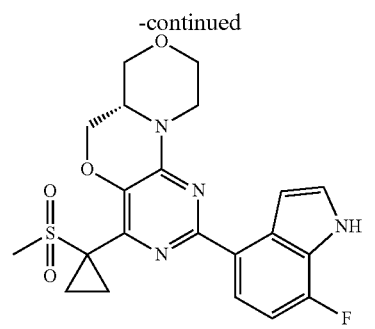
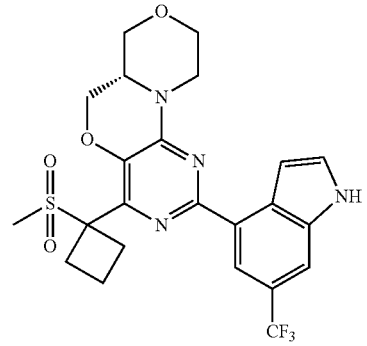
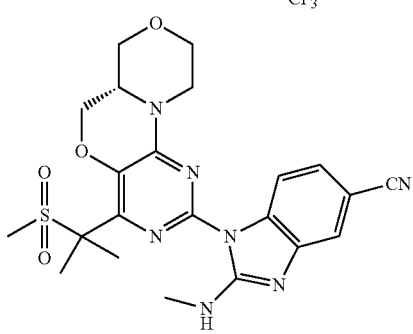

-continued

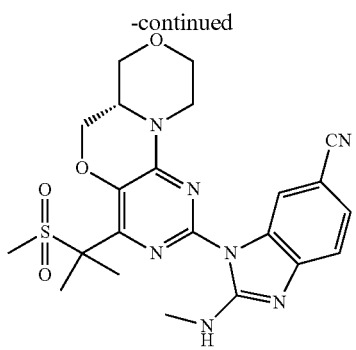

and pharmaceutically acceptable salts, solvates and stereoisomers thereof.

14. A pharmaceutical composition comprising a chemical compound as claimed in claim 1 and a pharmaceutically acceptable carrier, diluent or excipient.

15. A method of a disease or condition in which ATR activity is implicated comprising administration to a subject in need thereof a therapeutically effective amount of a chemical compound as claimed in claim 1, wherein the disease or condition in which ATR activity is implicated is cancer.

16. The method of claim 15, wherein the disease or condition in which ATR activity is implicated is endometrial cancer, colon cancer or stomach cancer.

17. A combination product comprising:
(A) a chemical compound as claimed in claim 1; and
(B) another therapeutic agent that is useful in the treatment of cancer and/or a proliferative disease,
wherein each of components (A) and (B) is formulated in admixture with a pharmaceutically-acceptable adjuvant, diluent or carrier.

* * * * *

UNITED STATES PATENT AND TRADEMARK OFFICE
CERTIFICATE OF CORRECTION

PATENT NO. : 9,453,031 B2
APPLICATION NO. : 14/774294
DATED : September 27, 2016
INVENTOR(S) : Joaquín Pastor Fernández et al.

Page 1 of 1

It is certified that error appears in the above-identified patent and that said Letters Patent is hereby corrected as shown below:

In the Claims:

At column 156, claim number 15, line number 21, please replace "A method of a disease or condition in which ATR" with ---A method of treatment of a disease or condition in which ATR---

Signed and Sealed this
Fifteenth Day of November, 2016

Michelle K. Lee
*Director of the United States Patent and Trademark Office*